US010174120B2

(12) United States Patent
Buckanovich et al.

(10) Patent No.: US 10,174,120 B2
(45) Date of Patent: *Jan. 8, 2019

(54) METHODS AND COMPOSITIONS FOR TREATING SOLID TUMORS AND ENHANCING TUMOR VACCINES

(71) Applicant: THE TRUSTEES OF THE UNIVERSITY OF PENNSYLVANIA, Philadelphia, PA (US)

(72) Inventors: Ronald J Buckanovich, Ann Arbor, MI (US); George Coukos, Wynnewood, PA (US); Andrea Facciabene, Philadelphia, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/001,241

(22) Filed: Jan. 20, 2016

(65) Prior Publication Data
US 2016/0368996 A1 Dec. 22, 2016

Related U.S. Application Data

(63) Continuation of application No. 12/076,759, filed on Mar. 21, 2008, now Pat. No. 9,289,426.

(60) Provisional application No. 60/907,138, filed on Mar. 22, 2007, provisional application No. 60/907,091, filed on Mar. 21, 2007.

(51) Int. Cl.
C07K 16/28 (2006.01)
A61K 31/506 (2006.01)
A61K 31/7105 (2006.01)
G01N 33/574 (2006.01)
A61K 38/06 (2006.01)
C12N 15/113 (2010.01)
C12Q 1/6886 (2018.01)

(52) U.S. Cl.
CPC ........ C07K 16/2869 (2013.01); A61K 31/506 (2013.01); A61K 31/7105 (2013.01); A61K 38/06 (2013.01); C12N 15/1138 (2013.01); C12Q 1/6886 (2013.01); G01N 33/57484 (2013.01); G01N 33/57492 (2013.01); C07K 2317/76 (2013.01); C12N 2310/11 (2013.01); C12N 2310/14 (2013.01); C12N 2320/30 (2013.01); C12Q 2600/106 (2013.01); C12Q 2600/158 (2013.01); G01N 2333/70525 (2013.01); G01N 2333/726 (2013.01)

(58) Field of Classification Search
None
See application file for complete search history.

(56) References Cited

U.S. PATENT DOCUMENTS

| 6,545,048 B1* | 4/2003 | Patterson | A61K 38/06 514/16.1 |
| 7,566,452 B1* | 7/2009 | Schneider | C07K 14/57536 424/156.1 |
| 2004/0138121 A1* | 7/2004 | Gulati | A61K 31/00 514/13.3 |
| 2006/0204478 A1* | 9/2006 | Harats | A61K 31/198 424/93.2 |

OTHER PUBLICATIONS

Buckanovich et al, J Clin Onco, 2006 ASCO meeting abs No. 2524, Jun. 2006.*
Lahav et al, PNAS, 96:11496-500, 1999).*
Buckanovich et al., Endothelin B receptor mediates the endothelial barrier to T cell homing to tumors and disables immune therapy, Nature Medicine, vol. 14, No. 1, Jan. 2008, p. 28-36.
Brandes et al., Proc. Natl. Acad. Sci. USA, 2000; 97:9747-9752.
Butcher et al., Lymphocyte trafficking and regional immunity, Adv. Immunol. 72, 209-53, 1999.
Barlow et al., Enteric nervous system progenitors are coordinately controlled by the G protein-coupled receptor EDNRB and the receptor tyrosine kinase RET, Neuron 40, 905-16, 2003.
Chung et al., Interaction and Inhibitory Cross-Talk between Endothelin and ErbB Receptors in the Adult Heart, Molecular Pharmacolgy Fast Forward, Published on Mar. 1, 2007 as doi:10.1124/mol.106.027599.
Caudy AA et al., Genes & Devel, 16:2491-96.
Davis ID et al., Blood dendritic cells generated with Flt3 ligand and CD40 ligand prime CD8+ T cells efficiently in cancer patients, J. Immunother., Sep.-Oct. 2006, 29(5):499-511.
Dasgupta et al., Endothelin receptor antagonists—an overview., Curr. Med. Chem., Mar. 2002, 9(5):549-75.
Dingemanse et al.,Entry-into-humans study with tezosentan, an intravenous dual endothelin receptor antagonist., J. Cardiovasc Pharmacol., Jun. 2002, 39(6):795-802.
Dumeule et al., Brain endothelial cells as pharmacological targets in brain tumors, Molecular Neurobiology 30, 157-83, 2004.
Eerola et al., Tumour infiltrating lymphocytes in relation to tumour angiogenesis, apoptosis and prognosis in patients with large cell lung carcinoma, Lung Cancer 26, 73-83, 1999.
Ernstoff, Self-Recognition and Tumor Response to Immunotherapy, J. Clin. Oncol. 23, 5875-5877, 2005.

(Continued)

Primary Examiner — Lei Yao
(74) Attorney, Agent, or Firm — Mark S. Cohen; Pearl Cohen Zedek Latzer Baratz LLP

(57) ABSTRACT

The present invention provides methods of treating and enhancing efficacy of immunotherapy for a solid tumor in a subject, comprising the step of contacting the subject with a compound or composition that modulates the expression or activity of ETRB, ET-1, ICAM-1, or another protein found herein to play a role in homing of T cells to a solid tumor. The present invention also provides methods of prognosticating a solid tumor in a subject, comprising the step of measuring an expression level of a protein found herein to play a role in homing of T cells to a solid tumor, or a nucleotide molecule encoding same.

2 Claims, 23 Drawing Sheets

Specification includes a Sequence Listing.

(56) References Cited

OTHER PUBLICATIONS

Freeman et al., Peripheral blood T lymphocytes and lymphocytes infiltrating human cancers express vascular endothelial growth factor: a potential role for T cells in angiogenesis, Cancer Research 55, 4140-5, 1995.
Furchgott et al., FASEB J., Endothelium-derived relaxing and contracting factors, 1989; 3:2007-2018.
Fleming et al., NO: the primary EDRF .,J. Mol. Cell. Cardiol., 1999; 31:5-14.
Guruli et al., Function and Survival of dendritic cells depend on endothelin-1 and endothelin receptor autocrine loops, Blood 104, 2107-15, 2004.
Grimshaw et al., A role for endothelin-2 and its receptors in breast tumor cell invasion, Cancer Research 64, 2461-8, 2004.
Hess et al., Human CD4+ T cells present within the microenvironment of human lung tumors are mobilized by the local and sustained release of IL-12 to kill tumors in situ by indirect effects of IFN-gamma, Journal of Immunology 170, 400-12, 2003.
Ignarro et al., Endothelium-derived relaxing factor produced and released from artery and vein is nitric oxide.,Proc. Natl. Acad. Sci. USA, 1987; 84:9265-9269.
Kapadia et al., CTLA-4 Blockade: Autoimmunity as Treatment, J. Clin. Oncol., 23, 8926-8928, 2005.
Kataki et al., Tumor infiltrating lymphocytes and macrophages have a potential dual role in lung cancer by supporting both host-defense and tumor progression, Journal of Laboratory & Clinical Medicine, 140, 320-8, 2002.
Kruger et al., Temporally distinct requirements for endothelin receptor B in the generation and migration of gut neural crest stem cells, Neuron 40, 917-29, 2003.
Morse et al., Recent developments in therapeutic cancer vaccines, Nature Clinical Practice Oncology 2, 108-13, 2005.
Mapara et al., Tolerance and Cancer: Mechanisms of Tumor Evasion and Strategies for Breaking Tolerance, J. Clin. Oncol. 22, 1136-1151, 2004.
Naito et al., CD8+ T cells infiltrated within cancer cell nests as a prognostic factor in human colorectal cancer, Cancer Research 58, 3491-4, 1998.
Naz et al., Novel human prostate-specific cDNA: molecular cloning, expression, and immunobiology of the recombinant protein, Biochem. Biophys. Res. Commun., 297:1075-84.
Neilsen PE, Curr. Opin. Struct. Biol. 9:353-57.
Pawelec G., Tumour escape: antitumour effectors too much of a good thing?, Cancer Immunology, Immunotherapy 53, 262-74, 2004.
Pages et al., Effector memory T cells, early metastasis, and survival in colorectal cancer, New England Journal of Medicine 353, 2654-66, 2005.
Peoples et al., Clinical trial results of a HER2/neu (E75) Vaccine to prevent recurrence in high-risk breast cancer patients, J. Clin. Oncol. 23, 7536-7545, 2005.
Rossi et al., The biology of chemokines and their receptors, Annu. Rev. Immunol. 18, 217-42, 2000.
Salani et al., Endothelin-1 induces an angiogenic phenotype in cultured endothelial cells and stimulates neovascularization in vivo, American Journal of Pathology 157, 1703-11, 2000.
Sampaio et al., Role of endothelins on lymphocyte accumulation in allergic pleurisy, Journal of Leukocyte Biology 67, 189-95, 2000.
Sencer et al., Anti-tumor vaccine adjuvant effects of IL-2 liposomes in mice immunized against MCA-102 sarcoma, European Cytokine Network 2, 311-8, 1991.
Sato et al., Intraepithelial CD8+ tumor-infiltrating lymphocytes and a high CD8+/regulatory T cell ratio are associated with favorable prognosis in ovarian cancer, Proceedings of the National Academy of Sciences of the United States of America 102, 18538-43, 2005.
ST Croix et al., Genes expressed in human tumor endothelium, Science 289, 1197-202, 2000.
Vanhoutte et al., Vascular biology. Old-timer makes a comeback. ,Nature, 1998; 396:213, 215-216.
Wulfing et al., Expression of endothelin-1, endothelin-A, and endothelin-B receptor in human breast cancer and correlation with long-term follow-up, Clinical Cancer Research 9, 4125-31, 2003.
Zimmermann et al., Endothelin receptor antagonists and cerebral vasospasm, Clin. Auton. Res., Jun. 2004, 14(3):143-5.
Zhang et al., Intratumoral T cells, recurrence, and survival in epithelial ovarian cancer, New England Journal of Medicine 348, 203-13, 2003.
Caudy AA et al., "Fragile X-related protein and VIG associate with the RNA interference machinery" Genes & Development 16:2491-96 (2002).
Naz et al., Novel human prostate-specific cDNA: molecular cloning, expression, and immunobiology of the recombinant protein, Biochemical and Biophysical Research Communication 297 (2002):1075-1084.
Neilsen PE, Current Opinion in Structural Biology (1999) 9:353-357.
Mitchell et al., "The cytotoxic T cell response to peptide analogs of the HLA-A*0201-restricted MUC1 signal sequence epitope M1.2", Cancer Immunol. Immunother. 2006.
Lahav et al., PNAS 1999, 96: 11496-500.
Buckanovich et al., J. Clin. Onco. 2006, ASCO Meeting abs. No. 2524, 2006.
Benencia et al., Cancer Biology and Therapy 5: 7 867-875, 2006.

* cited by examiner

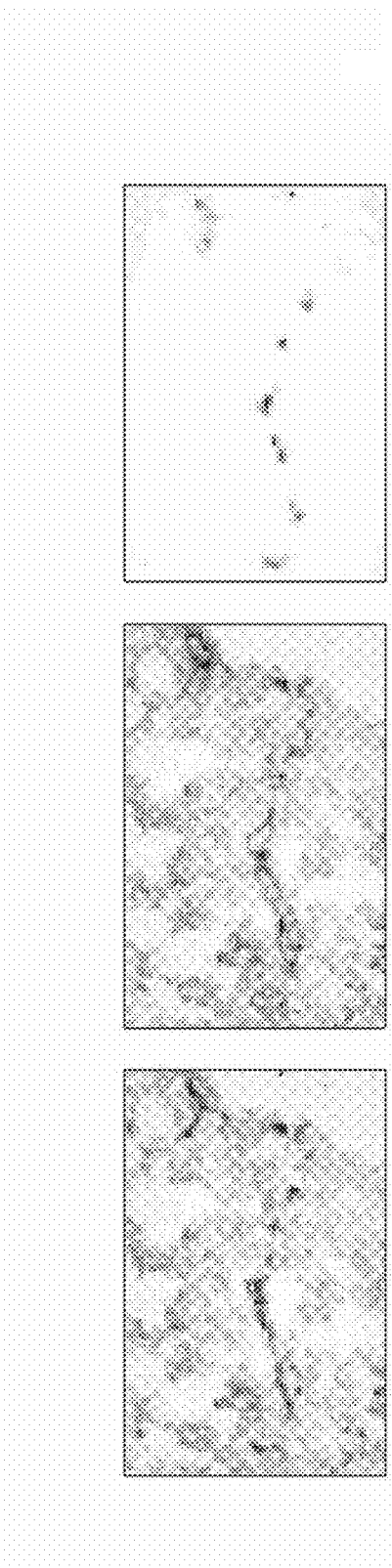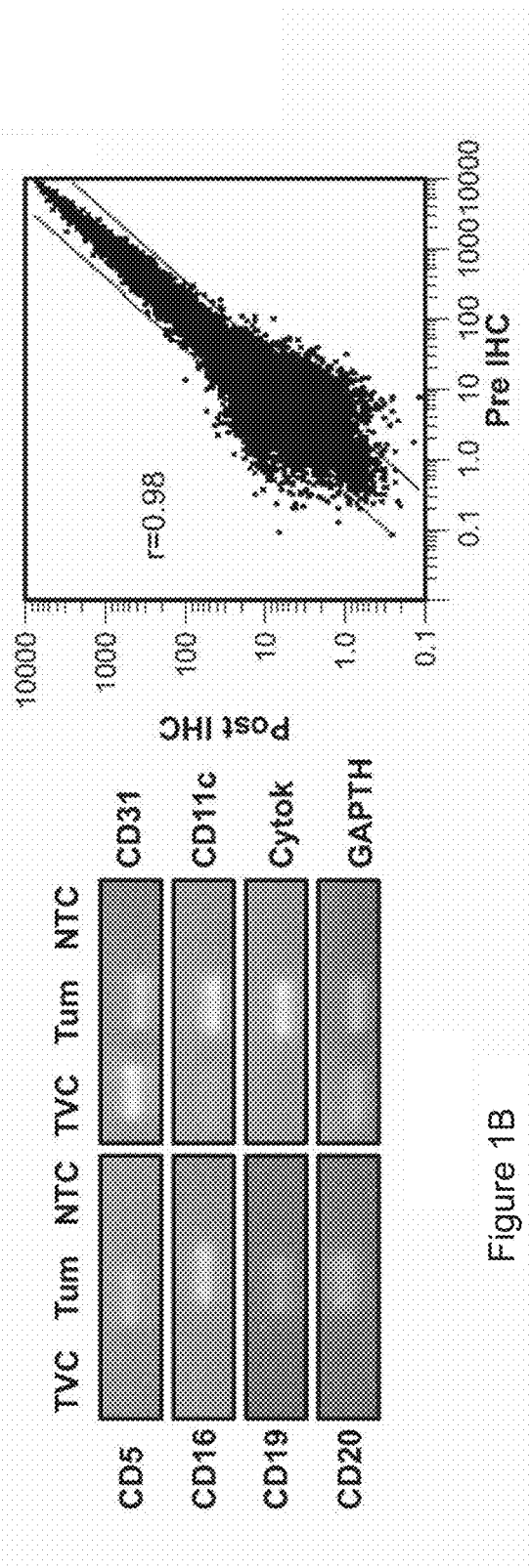

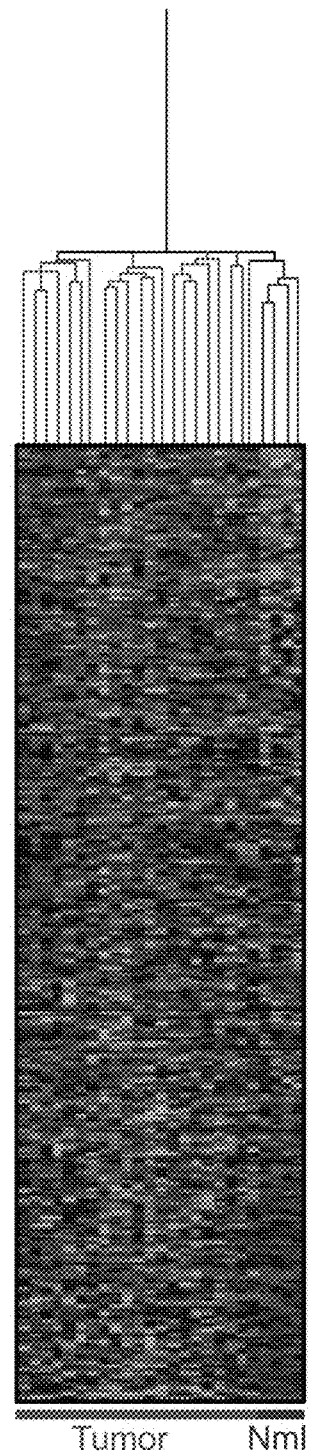
Figure 1D-A

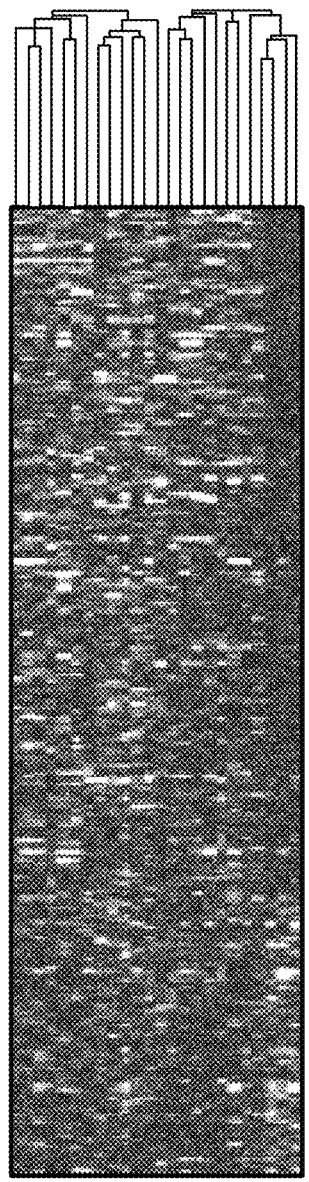
Figure 1D-B

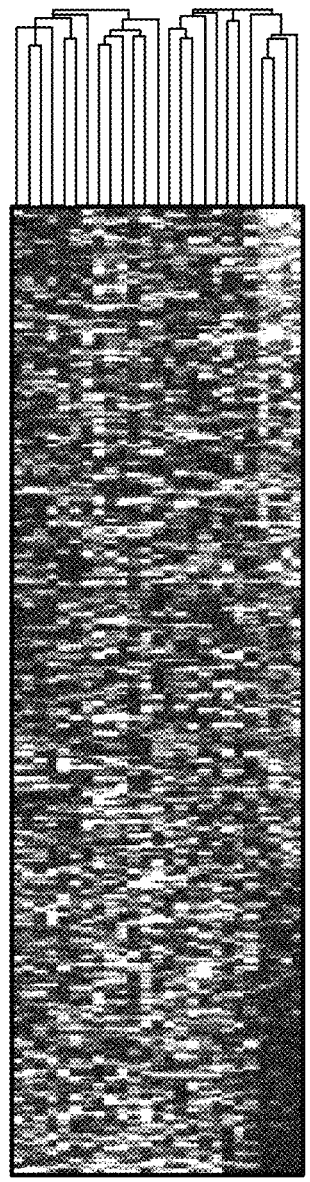
Figure 1D-C

| Normal Tissue | n | Adican | C11005 | COL11A1 | DR6 | EGFL5 | FAX1 | FZRL1 | FZ10 | GPMGB | LZTS1 | OLFML2B | STC2 |
|---|---|---|---|---|---|---|---|---|---|---|---|---|---|
| Adipose Tissue | 10 | 333 | 11 | 14 | 267 | 89 | 34 | 16 | 18 | 54 | 25 | 122 | 16 |
| Adrenal Gland Cortex | 4 | 358 | 20 | 20 | 60 | 13 | 42 | 10 | 14 | 87 | 25 | 56 | 14 |
| Bone Marrow | 5 | 70 | 10 | 16 | 84 | 19 | 22 | 9 | 12 | 31 | 26 | 35 | 14 |
| Bronchus | 3 | 256 | 18 | 63 | 387 | 24 | 35 | 33 | 21 | 84 | 22 | 73 | 18 |
| Cerebellum | 9 | 33 | 19 | 17 | 143 | 16 | 61 | 7 | 16 | 1408 | 21 | 30 | 13 |
| Cerebral Cortex | 9 | 37 | 40 | 40 | 335 | 17 | 71 | 7 | 12 | 2517 | 47 | 36 | 12 |
| Cerebrum | 43 | 39 | 41 | 39 | 340 | 18 | 76 | 9 | 14 | 3027 | 46 | 34 | 14 |
| Cervix | 4 | 693 | 57 | 13 | 110 | 26 | 61 | 12 | 42 | 244 | 20 | 153 | 18 |
| Colon Cecum | 3 | 445 | 14 | 15 | 147 | 15 | 23 | 62 | 16 | 324 | 21 | 46 | 15 |
| Coronary Artery | 3 | 162 | 14 | 15 | 184 | 15 | 53 | 8 | 13 | 263 | 25 | 130 | 20 |
| Endometrium | 4 | 231 | 43 | 28 | 204 | 52 | 141 | 16 | 39 | 121 | 24 | 294 | 14 |
| Esophagus | 4 | 194 | 12 | 19 | 315 | 28 | 28 | 99 | 155 | 111 | 27 | 38 | 13 |
| Heart Atrium | 4 | 159 | 14 | 15 | 117 | 15 | 23 | 12 | 11 | 163 | 23 | 60 | 24 |
| Heart Entricle | 3 | 170 | 26 | 16 | 109 | 16 | 29 | 8 | 12 | 97 | 25 | 36 | 18 |
| Kidney Cortex | 4 | 107 | 74 | 13 | 390 | 14 | 32 | 94 | 10 | 35 | 22 | 30 | 22 |
| Kidney Medulla | 4 | 197 | 122 | 14 | 313 | 16 | 33 | 121 | 12 | 117 | 21 | 31 | 16 |
| Liver | 4 | 76 | 8 | 14 | 73 | 16 | 25 | 12 | 12 | 16 | 21 | 26 | 12 |
| Lung | 3 | 173 | 6 | 12 | 170 | 151 | 31 | 12 | 14 | 157 | 23 | 90 | 30 |
| Lymph Nodes | 4 | 111 | 13 | 11 | 382 | 15 | 25 | 10 | 17 | 71 | 26 | 63 | 13 |
| Mammary Gland | 3 | 340 | 20 | 14 | 221 | 298 | 36 | 17 | 16 | 116 | 33 | 96 | 47 |
| Medulla | 9 | 40 | 62 | 36 | 538 | 24 | 63 | 8 | 14 | 3154 | 24 | 36 | 13 |
| Mid brain | 107 | 47 | 53 | 41 | 405 | 20 | 69 | 8 | 15 | 2792 | 39 | 48 | 14 |
| Myometrium | 5 | 209 | 25 | 12 | 138 | 16 | 32 | 7 | 15 | 60 | 22 | 95 | 13 |
| Nipple Cross-section | 4 | 505 | 7 | 21 | 137 | 18 | 79 | 165 | 57 | 229 | 29 | 73 | 53 |
| Oral Mucosa | 4 | 370 | 9 | 14 | 506 | 25 | 45 | 59 | 218 | 60 | 30 | 81 | 13 |
| Ovary | 4 | 116 | 9 | 29 | 89 | 16 | 84 | 17 | 14 | 34 | 23 | 48 | 16 |
| Pharyngcal Mucosa | 4 | 375 | 9 | 16 | 556 | 31 | 51 | 39 | 247 | 73 | 29 | 62 | 15 |
| Pituitary Gland | 8 | 63 | 86 | 36 | 116 | 24 | 29 | 11 | 17 | 116 | 28 | 29 | 19 |
| Prostate Gland | 3 | 188 | 202 | 14 | 207 | 20 | 38 | 35 | 46 | 234 | 21 | 37 | 15 |
| Salivary Gland | 4 | 216 | 79 | 20 | 97 | 18 | 26 | 31 | 20 | 111 | 21 | 40 | 13 |
| Saphenous Vein | 3 | 365 | 9 | 16 | 103 | 19 | 39 | 22 | 21 | 67 | 26 | 281 | 27 |
| Skeletal Muscle | 5 | 61 | 33 | 18 | 67 | 17 | 29 | 8 | 11 | 25 | 31 | 50 | 29 |
| Spinal Cord | 8 | 50 | 26 | 38 | 792 | 27 | 100 | 10 | 11 | 5203 | 22 | 30 | 19 |
| Spleen | 4 | 175 | 11 | 15 | 75 | 15 | 63 | 13 | 11 | 203 | 20 | 25 | 25 |
| Stomach | 11 | 510 | 24 | 16 | 326 | 20 | 25 | 45 | 17 | 195 | 24 | 49 | 15 |
| Testes | 3 | 42 | 18 | 30 | 77 | 15 | 21 | 7 | 12 | 16 | 37 | 183 | 14 |
| Thyroid Gland | 4 | 415 | 377 | 13 | 69 | 15 | 22 | 33 | 19 | 58 | 20 | 153 | 21 |
| Tongue | 8 | 176 | 12 | 17 | 324 | 21 | 40 | 23 | 63 | 52 | 24 | 51 | 14 |
| Tonsil | 3 | 176 | 10 | 14 | 276 | 24 | 36 | 13 | 38 | 28 | 21 | 69 | 14 |
| Trachea | 3 | 372 | 24 | 47 | 585 | 31 | 38 | 40 | 27 | 88 | 21 | 50 | 14 |
| Trigeminal Ganglia | 8 | 130 | 78 | 77 | 305 | 87 | 35 | 8 | 19 | 1871 | 34 | 173 | 13 |
| Urethra | 3 | 912 | 106 | 17 | 445 | 33 | 23 | 31 | 69 | 297 | 23 | 304 | 24 |
| Vagina | 4 | 915 | 121 | 14 | 189 | 37 | 45 | 31 | 75 | 259 | 20 | 93 | 15 |
| Vulva | 4 | 1309 | 15 | 16 | 226 | 38 | 33 | 70 | 108 | 126 | 32 | 69 | 18 |

Figure 1E-A

| Tumor Tissue | II | | | | | | | | | | | | |
|---|---|---|---|---|---|---|---|---|---|---|---|---|---|
| Adrenal Gland | 2 | 370 | 22 | 103 | 924 | 31 | 143 | 744 | 12 | 54 | 53 | 639 | 127 |
| Bladder | 14 | 418 | 21 | 220 | 1513 | 100 | 86 | 240 | 10 | 66 | 22 | 122 | 45 |
| Brain | 2 | 123 | 14 | 216 | 280 | 100 | 173 | 106 | 32 | 5616 | 26 | 60 | 37 |
| Breast | 183 | 1281 | 29 | 671 | 368 | 99 | 115 | 105 | 20 | 158 | 28 | 325 | 588 |
| Cervix | 9 | 830 | 38 | 805 | 584 | 130 | 92 | 251 | 119 | 116 | 20 | 208 | 47 |
| Colon | 125 | 614 | 18 | 309 | 590 | 47 | 53 | 709 | 48 | 66 | 24 | 176 | 78 |
| Corpus Uteri | 7 | 649 | 124 | 488 | 396 | 1042 | 157 | 324 | 352 | 757 | 39 | 574 | 184 |
| Endometrium | 42 | 544 | 152 | 220 | 575 | 172 | 184 | 288 | 131 | 209 | 26 | 100 | 138 |
| Esophagus | 2 | 630 | 7 | 141 | 306 | 24 | 44 | 146 | 8 | 22 | 3 | 95 | 39 |
| Kidney | 91 | 183 | 30 | 35 | 562 | 19 | 108 | 355 | 11 | 60 | 29 | 194 | 269 |
| Liver | 15 | 903 | 21 | 389 | 712 | 76 | 93 | 453 | 25 | 63 | 27 | 213 | 98 |
| Lung | 61 | 867 | 29 | 512 | 824 | 273 | 80 | 238 | 79 | 144 | 26 | 244 | 100 |
| Omendum | 30 | 1309 | 101 | 1210 | 399 | 326 | 208 | 229 | 134 | 218 | 25 | 294 | 114 |
| Ovary | 91 | 582 | 123 | 299 | 536 | 186 | 196 | 378 | 125 | 169 | 28 | 142 | 129 |
| Pancreas | 4 | 885 | 19 | 403 | 846 | 35 | 73 | 312 | 12 | 1045 | 23 | 377 | 93 |
| Prostate | 17 | 173 | 180 | 17 | 389 | 19 | 54 | 268 | 18 | 232 | 22 | 54 | 43 |
| Recto Sigmoid | 32 | 761 | 22 | 443 | 591 | 68 | 77 | 759 | 42 | 82 | 26 | 259 | 62 |
| Small Intestine | 8 | 226 | 36 | 153 | 347 | 53 | 70 | 272 | 47 | 217 | 70 | 85 | 55 |
| Stomach | 6 | 742 | 85 | 35 | 584 | 28 | 79 | 561 | 26 | 624 | 53 | 102 | 32 |
| Testis | 1 | 86 | 11 | 16 | 565 | 17 | 85 | 12 | 10 | 381 | 76 | 214 | 46 |
| Thyroid | 10 | 352 | 141 | 88 | 207 | 41 | 48 | 198 | 18 | 114 | 19 | 83 | 45 |
| Vulva | 3 | 1047 | 12 | 1349 | 435 | 96 | 149 | 506 | 65 | 318 | 21 | 228 | 49 |

Figure 1E-B

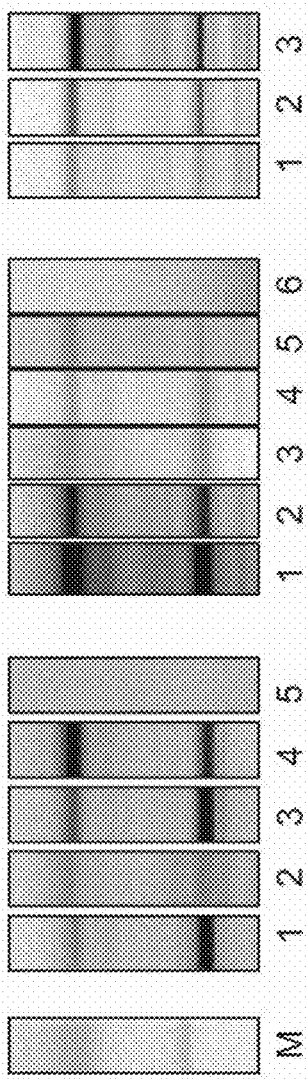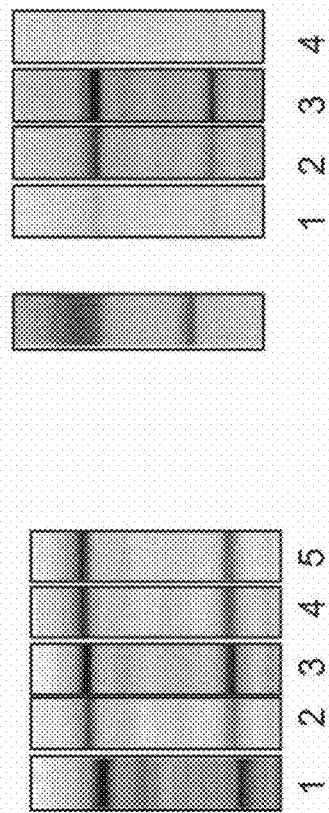

| \multicolumn{3}{c}{Higher in TEC from TIL - Tumors} | \multicolumn{3}{c}{Higher in TEC from TIL + Tumors} |

| Fold Change | Common Name | Genbank Acc | Fold Change | Common Name | Genbank Acc |
|---|---|---|---|---|---|
| 3.627 | MEG3 | AI291123 | 5.412 | C3 | NM_000064 |
| 2.886 | SEC61G | NM_014302 | 3.746 | | AW262311 |
| 2.873 | KIAA1609 | AA195124 | 3.455 | ZNFN1A5 | BF056303 |
| 2.82 | ACTR6 | NM_022496 | 3.141 | LOC283663 | AI926479 |
| 2.784 | | AK026659 | 3.096 | IGLJ3 | X57812 |
| 2.746 | ATP9A | AB014511 | 2.872 | ZNF521 | AK021452 |
| 2.665 | | R38110 | 2.831 | | AK000119 |
| 2.642 | NCOA1 | BF576458 | 2.682 | CALD1 | BF063186 |
| 2.584 | WIT-1 | NM_015855 | 2.678 | CYP1B1 | NM_000104 |
| 2.539 | | AI343000 | 2.65 | EIF5B | BG261322 |
| 2.513 | MSI2 | BE220026 | 2.618 | | AA903710 |
| 2.502 | ETRB | NM_000115 | 2.587 | HSPC056 | BF942281 |
| 2.473 | PAPSS2 | AW299958 | 2.576 | FLJ32949 | AI039361 |
| 2.372 | ALDOA | NM_000034 | 2.48 | CFLAR | AI634046 |
| 2.372 | ZNF423 | AW149417 | 2.467 | | N54783 |
| 2.358 | ENPP2 | L35594 | 2.457 | FLJ10330 | N32872 |
| 2.344 | HSU79266 | NM_013299 | 2.455 | C18orf14 | NM_024781 |
| 2.34 | KIAA0146 | D63480 | 2.45 | | AI417595 |
| 2.316 | | AI300126 | 2.448 | GBP1 | AW014593 |
| 2.279 | EMX2 | AI478455 | 2.438 | | AA417078 |
| 2.273 | MYBL1 | AW592266 | 2.427 | SFRS1 | AA046439 |
| 2.27 | MPHOSPH9 | X98258 | 2.426 | NICAL | NM_022765 |
| 2.267 | | AI083578 | 2.419 | NOL7 | NM_016167 |
| 2.233 | ETRB | M74921 | 2.41 | MYCBP2 | AA488899 |
| 2.214 | | H37807 | 2.382 | ESR1 | NM_000125 |
| 2.212 | | AI800895 | 2.382 | | AI683805 |
| 2.17 | TAF3 | AI123516 | 2.356 | ADRBK2 | AI651212 |
| 2.148 | SLC1A4 | BF340083 | 2.348 | | AW954199 |
| 2.141 | HES1 | BE973687 | 2.346 | SCAP2 | NM_003930 |
| 2.135 | DLK1 | U15979 | 2.328 | STK3 | NM_006281 |
| 2.122 | SGCB | U29586 | 2.324 | AKAP10 | AU147278 |

Figure 3B

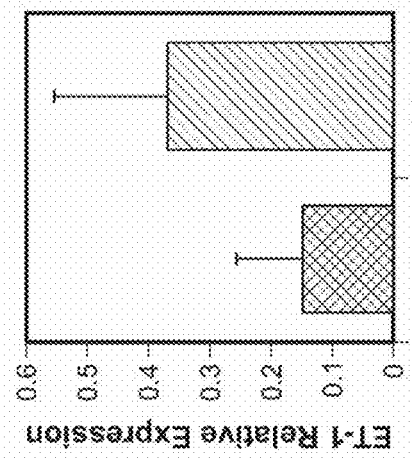
Figure 5C
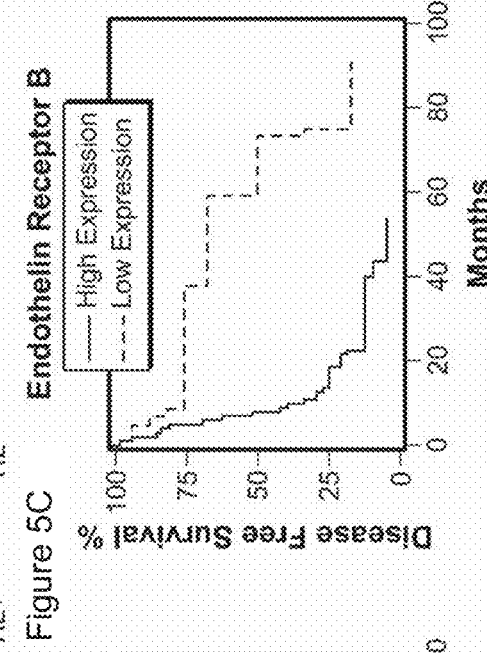
Figure 6A
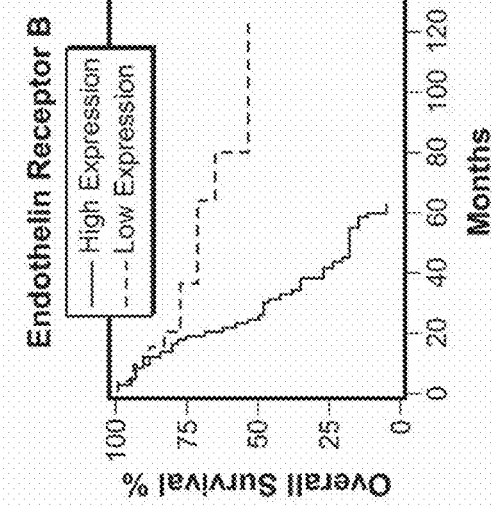

METHODS AND COMPOSITIONS FOR TREATING SOLID TUMORS AND ENHANCING TUMOR VACCINES

CROSS REFERENCE TO RELATED APPLICATIONS

This application is a continuation of U.S. patent application Ser. No. 12/076,759 filed Mar. 21, 2008, now U.S. Pat. No. 9,289,426, which claims priority from U.S. Provisional Patent Applications 60/907,091, filed Mar. 21, 2007 and 60/907,138, filed Mar. 22, 2007, both of which are incorporated herein by reference in their entirety.

STATEMENT REGARDING FEDERALLY SPONSORED RESEARCH OR DEVELOPMENT

The invention described herein was supported in whole or in part by grants from The National Institutes of Health (Grant No. R01 CA098951, P50-CA083638, K12-HD43459, and D43-TW00671). The government has certain rights in the invention.

FIELD OF INVENTION

The present invention provides methods of treating and enhancing efficacy of immunotherapy for a solid tumor in a subject, comprising the step of contacting the subject with a compound or composition that modulates the expression or activity of ETRB, ET-1, ICAM-1, or another protein found herein to play a role in homing of T cells to a solid tumor. The present invention also provides methods of prognosticating a solid tumor in a subject, comprising the step of measuring an expression level of a protein found herein to play a role in homing of T cells to a solid tumor, or a nucleotide molecule encoding same.

BACKGROUND OF THE INVENTION

Clinical studies have demonstrated the potential of cancer immune therapy using adoptively transferred T cells or tumor vaccines. Although these have achieved marked response in some patients, they have fallen short of expectations in others. The success of cell-mediated immune rejection mechanisms depends in part on the ability of effector cells to adequately infiltrate tumors. Yet, the mechanisms governing homing of effector cells into tumors remain poorly understood. Specifically, the role of endothelium in T cell homing to tumors has not been elucidated to date.

Evidence exists that a variety of solid human tumors, including melanoma, gastrointestinal, breast, lung and ovarian cancer, are spontaneously infiltrated by T cells. Within each tumor type, the intensity of tumor-infiltrating T cells may vary significantly, and brisk T cell infiltrate has been associated with improved prognosis. For example, T cells infiltrating tumor islets (intraepithelial T cells) are detected only in a select group of patients in ovarian cancer. These patients exhibit markedly improved progression-free and overall survival, a finding recently confirmed by others.

Methods for improving cancer vaccine immunotherapy are urgently needed in the art.

SUMMARY OF THE INVENTION

The present invention provides methods of treating and enhancing efficacy of immunotherapy for a solid tumor in a subject, comprising the step of contacting the subject with a compound or composition that modulates the expression or activity of ETRB, ET-1, ICAM-1, or another protein found herein to play a role in homing of T cells to a solid tumor. The present invention also provides methods of prognosticating a solid tumor in a subject, comprising the step of measuring an expression level of a protein found herein to play a role in homing of T cells to a solid tumor, or a nucleotide molecule encoding same.

In one embodiment, provided herein is a method of treating a solid tumor in a subject, comprising the step of contacting the subject with a compound or composition that reduces an activity of an Endothelin B receptor (ETRB), thereby treating a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In one embodiment, provided herein is a method of enhancing an efficacy of an immunotherapy for a solid tumor in a subject, comprising the step of contacting the subject with a compound or composition that reduces an activity of an ETRB, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of treating a solid tumor in a subject, comprising the step of contacting the subject with a compound or composition that reduces an expression of an ETRB, thereby treating a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of enhancing an efficacy of an immunotherapy for a solid tumor in a subject, comprising the step of contacting the subject with a compound or composition that reduces an expression of an ETRB, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of treating a solid tumor in a subject, comprising the step of contacting the subject with a compound or composition that reduces an expression of a protein selected from Musashi 2, delta-like 1, Hairy/Enhancer of Split 1, MEG3, SEC61G, KIAA1609, ACTR6, clone LNG00414, ATP9A, IMAGE: 23539, NCOA1, WIT1, PAPSS2, ALDOA, ZNF423, ENPP2, HSU79266, KIAA0146, IMAGE:1902075, EMX2, MYBL1, IMAGE:1660792, IMAGE:191524, IMAGE: 2365035, TAF3, SLC1A4, and SGCB, thereby treating a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of enhancing an efficacy of an immunotherapy for a solid tumor in a subject, comprising the step of contacting the subject with a compound or composition that reduces an expression of a protein selected from Musashi 2, delta-like 1, Hairy/Enhancer of Split 1, MEG3, SEC61G, KIAA1609, ACTR6, clone LNG00414, ATP9A, IMAGE:23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of treating a solid tumor in a subject, comprising the step of contacting the subject with a compound or composition that reduces an activity of a protein selected from Musashi 2, delta-like 1, Hairy/Enhancer of Split 1, MEG3, SEC61G, KIAA1609, ACTR6, clone LNG00414, ATP9A, IMAGE:23539, NCOA1, WIT1, PAPSS2, ALDOA, ZNF423, ENPP2, HSU79266, KIAA0146, IMAGE:1902075, EMX2, MYBL1, IMAGE:1660792, IMAGE:191524, IMAGE:2365035, TAF3, SLC1A4, and SGCB, thereby treating a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of enhancing an efficacy of an immunotherapy for a solid tumor in a subject, comprising the step of comprising the step of contacting the subject with a compound or composition that reduces an activity of a protein selected from Musashi 2, delta-like 1, Hairy/Enhancer of Split 1, MEG3, SEC61G, KIAA1609, ACTR6, clone LNG00414, ATP9A, IMAGE: 23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of treating a solid tumor in a subject, comprising the step of contacting the subject with a compound or composition that increases an expression of a protein selected from CASP8 and FADD-like apoptosis regulator (CFLAR) protein; estrogen receptor alpha (ESR1); caldesmin-1; adrenergic receptor B2 (ADRBK2); IMAGE:2755380, ZNFN1A5, LOC283663, IGLJ3, ZNF521, COL05405, CYP1B1, EIF5B, IMAGE:1518332, HSPCO56, FLJ32949, IMAGE: 244300, FLJ10330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10, thereby treating a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of enhancing an efficacy of an immunotherapy for a solid tumor in a subject, comprising the step of contacting the subject with a compound or composition that increases an expression of a protein selected from CFLAR; ESR1; caldesmin-1, ADRBK2; IMAGE:2755380, ZNFN1A5, LOC283663, IGLJ3, ZNF521, COL05405, CYP1B1, EIF5B, IMAGE: 1518332, HSPCO56, FLJ32949, IMAGE:244300, F1110330, C18orf14, IMAGE:2115041, GBP1, IMAGE: 731714, SFRS1, NICAL, NOL7, MYCBP2, IMAGE: 2275600, ADRBK2, EST366269, SCAP2, STK3, and AKAP10, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of treating a solid tumor in a subject, comprising the step of contacting the subject with a compound or composition that increases an activity of a protein selected from CFLAR; ESR1; caldesmin-1, ADRBK2; IMAGE:2755380, ZNFN1A5, LOC283663, IGLJ3, ZNF521, COL05405, CYP1B1, EIF5B, IMAGE:1518332, HSPCO56, FLJ32949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10, thereby treating a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of enhancing an efficacy of an immunotherapy for a solid tumor in a subject, comprising the step of contacting the subject with a compound or composition that increases an activity of a protein selected from CFLAR; ESR1; caldesmin-1, ADRBK2; IMAGE:2755380, ZNFN1A5, LOC283663, IGLJ3, ZNF521, COL05405, CYP1B1, EIF5B, IMAGE: 1518332, HSPCO56, FLJ32949, IMAGE:244300, F1110330, C18orf14, IMAGE:2115041, GBP1, IMAGE: 731714, SFRS1, NICAL, NOL7, MYCBP2, IMAGE: 2275600, ADRBK2, EST366269, SCAP2, STK3, and AKAP10, thereby enhancing an efficacy of an immunotherapy for a solid tumor in a subject. In another embodiment, the solid tumor is a solid tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of enhancing an efficacy of an immunotherapy for a solid tumor in a subject, comprising the step of contacting the subject with a compound or composition that reduces an expression or activity of an endothelin-1 (ET-1) protein, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. In another embodiment, a cancer cell of the tumor is contacted by the compound or composition. Each possibility represents a separate embodiment of the present invention.

In another embodiment, provided herein is a method of enhancing an efficacy of an immunotherapy for a solid tumor in a subject, comprising the step of contacting the subject with a compound or composition that reduces an interaction between an ETRB and ET-1, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. In another embodiment, a cancer cell of the tumor is contacted by the compound or composition. Each possibility represents a separate embodiment of the present invention.

In another embodiment, provided herein is a method of identifying a subject with a solid tumor likely to benefit from a chemotherapy prior to a oncologic surgery, the method comprising the steps of (a) measuring an expression level of an Endothelin B receptor (ETRB) or a nucleotide molecule encoding an Endothelin B receptor (ETRB) in the solid tumor; and (b) comparing the expression level to a reference standard, whereby, if the expression level is higher than the reference standard, then the subject is likely to benefit from the chemotherapy prior to the oncologic surgery. In another embodiment, the chemotherapy is a neoadjuvant chemotherapy. In another embodiment, the oncologic surgery is a debulking surgery. In another embodiment, the surgery is a cytoreductive surgery. In another embodiment, the surgery is a palliative surgery. In another embodiment, the surgery is a supportive surgery. Each possibility represents a separate embodiment of the present invention. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of prognosticating a solid tumor in a subject, the method comprising the steps of (a) measuring an expression level of an ETRB or a nucleotide molecule encoding an ETRB in the solid tumor; and (b) comparing the expression level to a reference standard, whereby, if the expression level is higher than the reference standard, then the prognosis is less favorable than a subject for whom the expression level is lower than or equal to the reference standard. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of identifying a subject with a solid tumor likely to benefit from an immunotherapy, the method comprising the steps of (a) measuring an expression level of an ETRB or a nucleotide molecule encoding an ETRB in the solid tumor; and (b) comparing the expression level to a reference standard, whereby, if the expression level is lower than the reference standard, then the subject is likely to benefit from an immunotherapy. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of enhancing an efficacy of an immunotherapy for a solid tumor in a subject, comprising the step of contacting the subject with a compound or composition that increases an expression or activity of an intercellular adhesion molecule 1 (ICAM-1) protein, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

BRIEF DESCRIPTION OF THE FIGURES

The invention will be better understood from a reading of the following detailed description taken in conjunction with the drawings in which like reference designators are used to designate like elements, and in which FIG. 1: FIG. 1A. Immuno-LCM steps. Left panel: Rapid IHC for CD31 allows prompt identification of vasculature in ovarian cancer frozen sections. Middle panel: Tissue section after LCM of CD31$^+$ cells. Right panel: captured tumor vascular cells. FIG. 1B. RT-PCR analysis of lineage-specific markers in RNA from tumor vascular cells (TVC) isolated with immuno-LCM, whole tumor (Tum) or a no template control (NTC). FIG. 1C. Scatter plot and correlation value of amplified RNA from unstained tissue (Pre IHC) versus RNA amplified after IHC optimized as in Table 1 (Post IHC). FIG. 1D. Part 1. Heat map condition tree developed using a hierarchical clustering algorithm, excluding all genes where the difference between the means of the tumor and normal vascular samples was less than its standard error. FIG. 1E, part 2: Red color shown alone. FIG. 1F, part 3: Green color shown alone. FIGS. 1G and 1H. Archived Gene Expression Datasets. Data used for expression of the TVM in normal and tumor tissue samples; also available in the Gene Expression Omnibus (GEO; National Center for Biotechnology Information [NCBI]) with series numbers GSE3526 and GSE2109, respectively. All CEL-files were similarly processed using the Robust Multi-array Average (RMA) algorithm.

FIG. 2. Quality of total RNA isolated from 8 μm frozen ovarian cancer tissue sections through different methodologies and analyzed by Agilent Bioanalyzer (FIG. 2A-FIG. 2E), quantitative real-time PCR (FIG. 2F) or Affymetrix U133A arrays (FIG. 2G). FIG. 2A. RNA distribution profiles following fixation with different fixatives. (Lanes: 1, ethanol; 2, methanol; 3, acetone; 4, acetic acid+ethanol; 5, paraformaldehyde). FIG. 2B. RNA profiles after isolation without immunostaining (Lane 1) or following IHC with or without RNAse inhibitor. (Lanes: 2, RNA Protector; 3, Placental RNAse inhibitor; 4, SuperRNASin; 5, RNA Protector+SuperRNASin; 6, no RNAse inhibitor. FIG. 2C. RNA profiles after different immunostaining procedures. (Lanes: 1, IHC using DAB; 2, IHC using AEC; 3, immunofluorescence). FIG. 2D. Time course demonstrating RNA stability after IHC performed with procedure optimized as in Table 1. (Lanes: 1, 0 min; 2, 30 min; 3, one hr; 4, two hrs; 5, three hrs). FIG. 2E. RNA profiles following different RNA isolation methods. (Lanes: 1, Arcturus kit; 2, Stratagene kit; 3, modified Trizol; 4, Zymo kit).

FIG. 3. Vascular cells from ITC(+) and ITC(−) tumors cluster separately. FIG. 3B. List of genes differentially expressed.

FIG. 4. qRT-PCR confirmation of differential mRNA expression.

FIG. 5. Confirmation of Protein Expression. FIG. 5C. A bar graph showing Endothelin-1 (ET-1) mRNA expression in ovarian cancer with or without TIL (n=16 each, mean±SD, p=0.26).

FIG. 6. FIG. 6A. ETRB as a Biomarker for Poor Prognosis in Ovarian Cancer. Disease-free and overall survival curves from a panel of 61 stage III epithelial ovarian cancer patients based upon ITC status (+) vs (−) and based upon high or low ETRB mRNA expression level as determined by qRTPCR.

FIG. 7. ETRB inhibition restricts tumor growth and increases overall survival in vaccinated animals.

FIG. 9.

DETAILED DESCRIPTION OF THE INVENTION

Figure 2F:
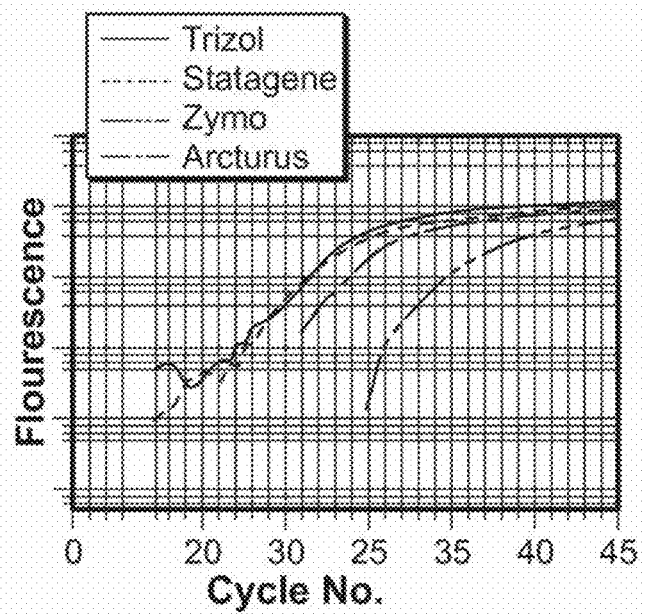
FIG. 2F. qRT-PCR for β-actin transcripts with RNA purified with the indicated RNA purification protocols.

The present invention provides methods of treating and enhancing efficacy of immunotherapy for a solid tumor in a subject, comprising the step of contacting the subject with a compound or composition that modulates the expression or activity of ETRB, ET-1, ICAM-1, or another protein found herein to play a role in homing of T cells to a solid tumor. The present invention also provides methods of prognosticating a solid tumor in a subject, comprising the step of measuring an expression level of a protein found herein to play a role in homing of T cells to a solid tumor, or a nucleotide molecule encoding same.

In one embodiment, provided herein is a method of treating a solid tumor in a subject, comprising the step of contacting the subject with a compound or composition that reduces an activity of an Endothelin B receptor (ETRB), thereby treating a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In one embodiment, provided herein is a method of enhancing an efficacy of an immunotherapy for a solid tumor in a subject, comprising the step of contacting the subject with a compound or composition that reduces an activity of an ETRB, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of treating a solid tumor in a subject, comprising the step of contacting the subject with a compound or composition that reduces an expression of an ETRB, thereby treating a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of enhancing an efficacy of an immunotherapy for a solid tumor in a subject, comprising the step of contacting the subject with a compound or composition that reduces an expression of an ETRB, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of treating a solid tumor in a subject, comprising the step of contacting the subject with a compound or composition that reduces an expression of a protein selected from Musashi 2, delta-like 1, Hairy/Enhancer of Split 1, MEG3, SEC61G, KIAA1609, ACTR6, clone LNG00414, ATP9A, IMAGE:23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB, thereby treating a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of enhancing an efficacy of an immunotherapy for a solid tumor in a subject, comprising the step of contacting the subject with a compound or composition that reduces an expression of a protein selected from Musashi 2, delta-like 1, Hairy/Enhancer of Split 1, MEG3, SEC61G, KIAA1609, ACTR6, clone LNG00414, ATP9A, IMAGE:23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of treating a solid tumor in a subject, comprising the step of contacting the subject with a compound or composition that reduces an activity of a protein selected from Musashi 2, delta-like 1, Hairy/Enhancer of Split 1, MEG3, SEC61G, KIAA1609, ACTR6, clone LNG00414, ATP9A, IMAGE:23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB, thereby treating a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of enhancing an efficacy of an immunotherapy for a solid tumor in a subject, comprising the step of comprising the step of contacting the subject with a compound or composition that reduces an activity of a protein selected from Musashi 2, delta-like 1, Hairy/Enhancer of Split 1, MEG3, SEC61G, KIAA1609, ACTR6, clone LNG00414, ATP9A, IMAGE:23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of treating a solid tumor in a subject, comprising the step of contacting the subject with a compound or composition that increases an expression of a protein selected from CASP8 and FADD-like apoptosis regulator (CFLAR) protein; estrogen receptor alpha (ESR1); caldesmin-1; adrenergic receptor B2 (ADRBK2); C3, IMAGE:2755380, ZNFN1A5, LOC283663, IGLJ3, ZNF521, COL05405, CYP1B1, EIF5B, IMAGE:1518332, HSPCO56, FLJ32949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10, thereby treating a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of enhancing an efficacy of an immunotherapy for a solid tumor in a subject, comprising the step of contacting the subject with a compound or composition that increases an expression of a protein selected from CFLAR; ESR1; caldesmin-1, ADRBK2; C3, IMAGE:2755380, ZNFN1A5, LOC283663, IGLJ3, ZNF521, COL05405, CYP1B1, EIF5B, IMAGE:1518332, HSPCO56, FLJ32949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10, thereby enhancing an efficacy of an immunotherapy for a solid tumor in a subject. In another embodiment, the solid tumor is an ovarian tumor. In another embodiment, the solid tumor is an epithelial ovarian tumor.

In another embodiment, the solid tumor is any other type of solid tumor known in the art. In another embodiment, the tumor is contacted by the compound or composition. Each possibility represents a separate embodiment of the present invention.

In another embodiment, provided herein is a method of treating a solid tumor in a subject, comprising the step of contacting the subject with a compound or composition that increases an activity of a protein selected from CFLAR; ESR1; caldesmin-1, ADRBK2; C3, IMAGE:2755380, ZNFN1A5, LOC283663, IGLJ3, ZNF521, COL05405, CYP1B1, EIF5B, IMAGE:1518332, HSPCO56, F1132949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10, thereby treating a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of enhancing an efficacy of an immunotherapy for a solid tumor in a subject, comprising the step of contacting the subject with a compound or composition that increases an activity of a protein whereby the compound is or the composition comprises CFLAR. In another embodiment, the compound is ESR1. In another embodiment, the compound is caldesmin-1. In another embodiment, the compound is ADRBK2. In another embodiment, the compound is C3. In another embodiment, the compound is IMAGE:2755380. In another embodiment, the compound is ZNFN1A5. In another embodiment, the compound is LOC283663. In another embodiment, the compound is IGLJ3. ZNF521. In another embodiment, the compound is COL05405. In another embodiment, the compound is CYP1B1. In another embodiment, the compound is EIF5B. In another embodiment, the compound is IMAGE. In another embodiment, the compound is 1518332. In another embodiment, the compound is HSPCO56. In another embodiment, the compound is F1132949. In another embodiment, the compound is IMAGE:244300. In another embodiment, the compound is F1110330. In another embodiment, the compound is C18orf14. In another embodiment, the compound is IMAGE:2115041. In another embodiment, the compound is GBP1. In another embodiment, the compound is IMAGE:731714. In another embodiment, the compound is SFRS1. In another embodiment, the compound is NICAL. In another embodiment, the compound is NOL7. In another embodiment, the compound is MYCBP2. In another embodiment, the compound is IMAGE:2275600. In another embodiment, the compound is ADRBK2. In another embodiment, the compound is EST366269. In another embodiment, the compound is SCAP2. In another embodiment, the compound is STK3. In another embodiment, the compound is AKAP10. Thereby enhancing an efficacy of an immunotherapy for a solid tumor in a subject. In another embodiment, the solid tumor is a solid tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In one embodiment the compound used in the compositions described herein for increasing the activity of a protein selected is CFLAR, or ESR1; caldesmin-1, ADRBK2; C3, IMAGE:2755380, ZNFN1A5, LOC283663, IGLJ3, ZNF521, COL05405, CYP1B1, EIF5B, IMAGE:1518332, HSPCO56, F1132949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, AKAP10, or their combination in other discrete embodiments of the compounds used in the methods and compositions provided herein.

In another embodiment, provided herein is a method of enhancing an efficacy of an immunotherapy for a solid tumor in a subject, comprising the step of contacting the subject with a compound or composition that reduces an expression or activity of an endothelin-1 (ET-1) protein, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. In another embodiment, a cancer cell of the tumor is contacted by the compound or composition. Each possibility represents a separate embodiment of the present invention.

In another embodiment, provided herein is a method of enhancing an efficacy of an immunotherapy for a solid tumor in a subject, comprising the step of contacting the subject with a compound or composition that reduces an interaction between an ETRB and ET-1, thereby enhancing an efficacy of an immunotherapy for a solid tumor in a subject. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. In another embodiment, a cancer cell of the tumor is contacted by the compound or composition. Each possibility represents a separate embodiment of the present invention.

In another embodiment, provided herein is a method of identifying a subject with a solid tumor likely to benefit from a chemotherapy prior to a oncologic surgery, the method comprising the steps of (a) measuring an expression level of an Endothelin B receptor (ETRB) or a nucleotide molecule encoding an Endothelin B receptor (ETRB) in the solid tumor; and (b) comparing the expression level to a reference standard, whereby, if the expression level is higher than the reference standard, then the subject is likely to benefit from the chemotherapy prior to the oncologic surgery. In another embodiment, the ETRB level is measured in a tumor endothelial cell (TEC) or TEC population of the tumor. In another embodiment, the chemotherapy is a neoadjuvant chemotherapy. In another embodiment, the oncologic surgery is a debulking surgery. In another embodiment, the surgery is a cytoreductive surgery. In another embodiment, the surgery is a palliative surgery. In another embodiment, the surgery is a supportive surgery. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of identifying a subject with a solid tumor likely to benefit from a chemotherapy prior to a oncologic surgery, the method comprising the steps of (a) measuring an expression level of an ET-1 or a nucleotide molecule encoding an ET-1 in the solid tumor; and (b) comparing the expression level to a reference standard, whereby, if the expression level is higher than the reference standard, then the subject is likely to benefit from the chemotherapy prior to the oncologic surgery. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of identifying a subject with a solid tumor likely to benefit from a chemotherapy prior to a oncologic surgery, the method comprising the steps of (a) measuring an expression level in the solid tumor of a protein selected from Musashi 2, delta-like 1, Hairy/Enhancer of Split 1, MEG3, SEC61G, KIAA1609, ACTR6, clone LNG00414, ATP9A, IMAGE: 23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB; or a nucleotide molecule encoding a protein selected from Musashi 2, delta-like 1, Hairy/Enhancer of Split 1, MEG3, SEC61G, KIAA1609, ACTR6, clone LNG00414, ATP9A, IMAGE: 23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB; and (b) comparing the expression level to a reference standard, whereby, if the expression level is higher than the reference standard, then the subject is likely to benefit from the chemotherapy prior to the oncologic surgery. In another embodiment, the expression level is measured in a TEC or TEC population of the tumor. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of identifying a subject with a solid tumor likely to benefit from a chemotherapy prior to a oncologic surgery, the method comprising the steps of (a) measuring an expression level in the solid tumor of a protein selected from CFLAR; ESR1; caldesmin-1, ADRBK2; C3, IMAGE:2755380, ZNFN1A5, LOC283663, IGLJ3, ZNF521, COL05405, CYP1B1, EIF5B, IMAGE:1518332, HSPCO56, FLJ32949, IMAGE: 244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10 or a nucleotide molecule encoding a protein selected from CFLAR; ESR1; caldesmin-1, ADRBK2; C3, IMAGE:2755380, ZNFN1A5, LOC283663, IGLJ3, ZNF521, COL05405, CYP1B1, EIF5B, IMAGE:1518332, HSPCO56, FLJ32949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10; and (b) comparing the expression level to a reference standard, whereby, if the expression level is lower than the reference standard, then the subject is likely to benefit from the chemotherapy prior to the oncologic surgery. In another embodiment, the expression level is measured in a TEC or TEC population of the tumor. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, "chemotherapy" refers to neoadjuvant chemotherapy. In another embodiment, the term refers to any other type of chemotherapy known in the art. In another embodiment, "oncologic surgery" refers to a debulking surgery. In another embodiment, the surgery is a cytoreductive surgery. In another embodiment, the surgery is a palliative surgery. In another embodiment, the surgery is a supportive surgery. Each possibility represents a separate embodiment of the present invention.

In another embodiment, provided herein is a method of prognosticating a solid tumor in a subject, the method comprising the steps of (a) measuring an expression level of an ETRB or a nucleotide molecule encoding an ETRB in the solid tumor; and (b) comparing the expression level to a reference standard, whereby, if the expression level is higher than the reference standard, then the prognosis is less favorable than a subject for whom the expression level is lower than or equal to the reference standard. In another embodiment, the ETRB level is measured in a TEC or TEC population of the tumor. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of prognosticating a solid tumor in a subject, the method comprising the steps of (a) measuring an expression level of an ET-1 or a nucleotide molecule encoding an ET-1 in the solid tumor; and (b) comparing the expression level to a reference standard, whereby, if the expression level is higher than the reference standard, then the prognosis is less favorable than a subject for whom the expression level is lower than or equal to the reference standard. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of prognosticating a solid tumor in a subject, the method comprising the steps of (a) measuring an expression level in the solid tumor of a protein selected from Musashi 2, delta-like 1, Hairy/Enhancer of Split 1, MEG3, SEC61G, KIAA1609, ACTR6, clone LNG00414, ATP9A, IMAGE: 23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB; or a nucleotide molecule encoding a protein selected from Musashi 2, delta-like 1, Hairy/Enhancer of Split 1, MEG3, SEC61G, KIAA1609, ACTR6, clone LNG00414, ATP9A, IMAGE: 23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB; and (b) comparing the expression level to a reference standard, whereby, if the expression level is higher than the reference standard, then the prognosis is less favorable than a subject for whom the expression level is lower than or equal to the reference standard. In another embodiment, the expression level is measured in a TEC or TEC population of the tumor. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of providing a prognosis on treatment of a subject having a solid tumor, the method comprising the steps of (a) measuring an expression level in the solid tumor of a protein selected from CFLAR; ESR1; caldesmin-1, ADRBK2; C3, IMAGE:2755380, ZNFN1A5, LOC283663, IGLJ3, ZNF521, COL05405, CYP1B1, EIF5B, IMAGE:1518332, HSPCO56, FLJ32949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10; or a nucleotide molecule encoding a protein selected from CFLAR; ESR1; caldesmin-1, ADRBK2; C3, IMAGE: 2755380, ZNFN1A5, LOC283663, IGLJ3, ZNF521, COL05405, CYP1B1, EIF5B, IMAGE:1518332, HSPCO56, FLJ32949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10; and (b) comparing the expression level to a reference standard, whereby, if the expression level is higher than the reference standard, then the prognosis is more favorable than a subject for whom the expression level is lower than or equal to the reference standard. In another embodiment, the expression level is measured in a TEC or TEC population of the tumor. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of identifying a subject with a solid tumor likely to benefit from an immunotherapy, the method comprising the steps of (a) measuring an expression level of an ETRB or a nucleotide molecule encoding an ETRB in the solid tumor; and (b) comparing the expression level to a reference standard, whereby, if the expression level is lower than the reference standard, then the subject is likely to benefit from an immunotherapy. In another embodiment, the method identifies a subject likely to benefit from immunotherapy in the absence of BQ788. In another embodiment, a subject exhibiting a high ETRB expression level is a candidate for immunotherapy in conjunction with BQ788. In another embodiment, the expression level is measured in a TEC or TEC population of the tumor. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of identifying a subject with a solid tumor likely to benefit from an immunotherapy, the method comprising the steps of (a) measuring an expression level of an ET-1 or a nucleotide molecule encoding an ET-1 in the solid tumor; and (b) comparing the expression level to a reference standard, whereby, if the expression level is lower than the reference standard, then the subject is likely to benefit from an immunotherapy. In another embodiment, the method identifies a subject likely to benefit from immunotherapy in the absence of BQ788. In another embodiment, a subject exhibiting a high ET-1 expression level is a candidate for immunotherapy in conjunction with BQ788. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of identifying a subject with a solid tumor likely to benefit from an immunotherapy, the method comprising the steps of (a) measuring an expression level in the solid tumor of a protein selected from Musashi 2, delta-like 1, Hairy/Enhancer of Split 1, MEG3, SEC61G, KIAA1609, ACTR6, clone LNG00414, ATP9A, IMAGE:23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB; or a nucleotide molecule encoding a protein selected from Musashi 2, delta-like 1, Hairy/Enhancer of Split 1, MEG3, SEC61G, KIAA1609, ACTR6, clone LNG00414, ATP9A, IMAGE: 23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB; and (b) comparing the expression level to a reference standard, whereby, if the expression level is lower than the reference standard, then the subject is likely to benefit from an immunotherapy. In another embodiment, the method identifies a subject likely to benefit from immunotherapy in the absence of BQ788. In another embodiment, a subject exhibiting a high expression level is a candidate for immunotherapy in conjunction with BQ788. In another embodiment, the expression level is measured in a TEC or TEC population of the tumor. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of identifying a subject with a solid tumor likely to benefit from an immunotherapy, the method comprising the steps of (a) measuring an expression level in the solid tumor of a protein selected from CFLAR; ESR1; caldesmin-1, ADRBK2; C3, IMAGE:2755380, ZNFN1A5, LOC283663, IGLJ3, ZNF521, COL05405, CYP1B1, EIF5B, IMAGE:1518332, HSPCO56, FLJ32949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10; or a nucleotide molecule encoding a protein selected from CFLAR; ESR1; caldesmin-1, ADRBK2; C3, IMAGE: 2755380, ZNFN1A5, LOC283663, IGLJ3, ZNF521, COL05405, CYP1B1, EIF5B, IMAGE:1518332, HSPCO56, FLJ32949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10; and (b) comparing the expression level to a reference standard, whereby, if the expression level is lower than the reference standard, then the subject is likely to benefit from an immunotherapy. In another embodiment, the method identifies a subject likely to benefit from immunotherapy in the absence of BQ788. In another embodiment, a subject exhibiting a high expression level is a candidate for immunotherapy in conjunction with BQ788. In another embodiment, the expression level is measured in a TEC or TEC population of the tumor. In another embodiment, the solid tumor is an ovarian tumor. In another embodiment, the solid tumor is an epithelial ovarian tumor. In another embodiment, the solid tumor is any other type of solid tumor known in the art. Each possibility represents a separate embodiment of the present invention.

In another embodiment, provided herein is a method of enhancing an efficacy of an immunotherapy for a solid tumor in a subject, comprising the step of contacting the subject with a compound or composition that increases an expression of an intercellular adhesion molecule 1 (ICAM-1) protein, thereby enhancing an efficacy of an immunotherapy for a solid tumor in a subject. In another embodiment, the tumor is contacted with the compound or composition. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of enhancing an efficacy of an immunotherapy for a solid tumor in a subject, comprising the step of contacting the subject with a compound or composition that increases an activity of an ICAM-1 protein, thereby enhancing an efficacy of an immunotherapy for a solid tumor in a subject. In another embodiment, the tumor is contacted with the compound or composition. In another embodiment, the solid tumor is an ovarian tumor. In another embodiment, the solid tumor is an epithelial ovarian tumor. In another embodiment, the solid tumor is any other type of solid tumor known in the art. In another embodiment, the tumor is contacted by the compound or composition. Each possibility represents a separate embodiment of the present invention.

In another embodiment, provided herein is a method of inhibiting tumor growth in a subject, comprising the step of administering to the subject a compound or composition that decreases the expression or activity of a protein selected from ETRB, ET-1, Musashi 2, delta-like 1, Hairy/Enhancer of Split 1, MEG3, SEC61G, KIAA1609, ACTR6, clone LNG00414, ATP9A, IMAGE:23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB, thereby inhibiting tumor growth in a subject.

In another embodiment, provided herein is a method of inhibiting tumor growth in a subject, comprising the step of administering to the subject a compound or composition that increases the expression or activity of a protein selected from CFLAR; ESR1; caldesmin-1, ADRBK2; C3, IMAGE:2755380, ZNFN1A5, LOC283663, IGLJ3, ZNF521, COL05405, CYP1B1, EIF5B, IMAGE:1518332, HSPCO56, FLJ32949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10, thereby inhibiting tumor growth in a subject.

In another embodiment, a method of the present invention is performed following oncologic surgery. In another embodiment, the method is performed following debulking surgery. In another embodiment, the method is performed following administration of chemotherapy. Each possibility represents a separate embodiment of the present invention.

In another embodiment, provided herein is a method of inhibiting growth of metastases in a subject, comprising the step of administering to the subject a compound or composition that decreases the expression or activity of a protein selected from ETRB, ET-1, Musashi 2, delta-like 1, Hairy/Enhancer of Split 1, MEG3, SEC61G, KIAA1609, ACTR6, clone LNG00414, ATP9A, IMAGE:23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB, thereby inhibiting growth of metastases in a subject.

In another embodiment, provided herein is a method of inhibiting growth of metastases in a subject, comprising the step of administering to the subject a compound or composition that increases the expression or activity of a protein selected from CFLAR; ESR1; caldesmin-1, ADRBK2; C3, IMAGE:2755380, ZNFN1A5, LOC283663, IGLJ3, ZNF521, COL05405, CYP1B1, EIF5B, IMAGE:1518332, HSPCO56, FLJ32949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10, thereby inhibiting growth of metastases in a subject.

In another embodiment, provided herein is a method of abrogating tolerance of a subject to a tumor, comprising the step of administering to the subject a compound or composition that decreases the expression or activity of a protein selected from ETRB, ET-1, Musashi 2, delta-like 1, Hairy/Enhancer of Split 1, MEG3, SEC61G, KIAA1609, ACTR6, clone LNG00414, ATP9A, IMAGE:23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB, thereby abrogating tolerance of a subject to a tumor.

In another embodiment, provided herein is a method of abrogating tolerance of a subject to a tumor, comprising the step of administering to the subject a compound or composition that increases the expression or activity of a protein selected from CFLAR; ESR1; caldesmin-1, ADRBK2; C3, IMAGE:2755380, ZNFN1A5, LOC283663, IGLJ3, ZNF521, COL05405, CYP1B1, EIF5B, IMAGE:1518332, HSPCO56, FLJ32949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10, thereby abrogating tolerance of a subject to a tumor.

In another embodiment, provided herein is a method of increasing T cell homing to a tumor, comprising the step of administering to the subject a compound or composition that decreases the expression or activity of a protein selected from ETRB, ET-1, Musashi 2, delta-like 1, Hairy/Enhancer of Split 1, MEG3, SEC61G, KIAA1609, ACTR6, clone LNG00414, ATP9A, IMAGE:23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB, thereby increasing T cell homing to a tumor.

In another embodiment, provided herein is a method of increasing T cell homing to a tumor, comprising the step of administering to the subject a compound or composition that increases the expression or activity of a protein selected from CFLAR; ESR1; caldesmin-1, ADRBK2; C3, IMAGE:2755380, ZNFN1A5, LOC283663, IGLJ3, ZNF521, COL05405, CYP1B1, EIF5B, IMAGE:1518332, HSPCO56, FLJ32949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10, thereby increasing T cell homing to a tumor.

In another embodiment, provided herein is a method of increasing T cell retention in a tumor islet, comprising the step of administering to the subject a compound or composition that decreases the expression or activity of a protein selected from ETRB, ET-1, Musashi 2, delta-like 1, Hairy/Enhancer of Split 1, MEG3, SEC61G, KIAA1609, ACTR6, clone LNG00414, ATP9A, IMAGE:23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB, thereby increasing T cell retention in a tumor islet.

In another embodiment, provided herein is a method of increasing T cell retention in a tumor islet, comprising the step of administering to the subject a compound or composition that increases the expression or activity of a protein selected from CFLAR; ESR1; caldesmin-1, ADRBK2; C3, IMAGE:2755380, ZNFN1A5, LOC283663, IGLJ3, ZNF521, COL05405, CYP1B1, EIF5B, IMAGE:1518332, HSPCO56, F1132949, IMAGE:244300, F1110330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10, thereby increasing T cell retention in a tumor islet.

In another embodiment, provided herein is an isolated CD8+ cell or cell population isolated from a vaccinated BQ-788-treated animal. In another embodiment, the CD8+ cell or cell population is isolated from a tumor of a vaccinated BQ-788-treated animal. In another embodiment, provided herein is a method of isolating a tumor-antigen specific T cell, comprising the step of administering an Endothelin antagonist to a tumor-bearing animal. In another embodiment, the Endothelin antagonist is an ETRB antagonist. In another embodiment, the Endothelin antagonist is BQ-788. In another embodiment, the Endothelin antagonist is any other type of Endothelin antagonist known in the art. Each possibility represents a separate embodiment of the present invention.

In another embodiment, provided herein is an isolated CD8+ cell or cell population isolated from an animal that has been treated with a compound or composition the decreases the expression or activity of a protein selected from ET-1, Musashi 2, delta-like 1, Hairy/Enhancer of Split 1, MEG3, SEC61G, KIAA1609, ACTR6, clone LNG00414, ATP9A, IMAGE:23539, NCOA1, WIT1, PAPSS2, ALDOA, ZNF423, ENPP2, HSU79266, KIAA0146, IMAGE:1902075, EMX2, MYBL1, MPHOSPH9, IMAGE:1660792, IMAGE:191524, IMAGE:2365035, TAF3, SLC1A4, and SGCB. In another embodiment, the CD8+ cell or cell population is isolated from a tumor of the animal. In another embodiment, provided herein is a method of isolating a tumor-antigen specific T cell, comprising the step of administering the compound or composition to a tumor-bearing animal. Each possibility represents a separate embodiment of the present invention.

In another embodiment, provided herein is an isolated CD8+ cell or cell population isolated from an animal that has been treated with a compound or composition the increases the expression or activity of a protein selected from CFLAR; ESR1; caldesmin-1, ADRBK2; C3, IMAGE:2755380, ZNFN1A5, LOC283663, IGLJ3, ZNF521, COL05405, CYP1B1, EIF5B, IMAGE:1518332, HSPCO56, F1132949, IMAGE:244300, FLJ10330, C18orf14, IMAGE:2115041, GBP1, IMAGE:731714, SFRS1, NICAL, NOL7, MYCBP2, IMAGE:2275600, ADRBK2, EST366269, SCAP2, STK3, and AKAP10, thereby increasing T cell retention in a tumor islet. In another embodiment, the CD8+ cell or cell population is isolated from a tumor of the animal. In another embodiment, provided herein is a method of isolating a tumor-antigen specific T cell, comprising the step of administering the compound or composition to a tumor-bearing animal. Each possibility represents a separate embodiment of the present invention.

The animal used in methods and compositions of the present invention is, in another embodiment, a mouse. In another embodiment, the animal is a rodent. In another embodiment, the animal is any animal used for research purposes. In another embodiment, the animal is any other suitable animal known in the art.

In another embodiment, provided herein is a method of enhancing the effectiveness of a tumor immunotherapy in a subject, comprising the step of administering to the subject a composition that reduces the expression or activity of RGC32, thereby enhancing the effectiveness of a tumor immunotherapy in a subject.

In another embodiment, provided herein is a method of enhancing the effectiveness of a tumor immunotherapy in a subject, comprising the step of administering to the subject a composition that reduces the expression or activity of VE-Cadherin, thereby enhancing the effectiveness of a tumor immunotherapy in a subject.

In another embodiment, provided herein is a method of enhancing the effectiveness of a tumor immunotherapy in a subject, comprising the step of inhibiting an ETRB-mediated pathway, thereby enhancing the effectiveness of a tumor immunotherapy in a subject. In another embodiment, the pathway is an intracellular pathway. In another embodiment, the pathway is an extracellular pathway. In another embodiment, the production of nitric oxide (NO) is inhibited. In another embodiment, the production of extracellular $Ca^{2+}$ is inhibited. In another embodiment, the production of prostacyclin is inhibited. In another embodiment, the production of endothelium-derived hyperpolarizing factor is inhibited. In another embodiment, the ETRB pathway that is inhibited is a G-protein-coupled receptor (GPCR) pathway. In another embodiment, the pathway involves activation of phospholipase C by the GPCR. In another embodiment, the pathway involves generation of inositol triphosphate from the phospholipase C. In another embodiment, the pathway involves generation of diacylglycerol from the phospholipase C. In another embodiment, the inositol triphosphate stimulates calcium release. In another embodiment, the diacylglycerol causes protein kinase C activation. In another embodiment, the ETRB pathway that is a phospholipase D pathway. In another embodiment, diacylglycerol is generated by the phospholipase D activation. In another embodiment, phospholipase A2 is stimulated by the phospholipase D activation. In another embodiment, arachidonic acid is released following phospholipase A2 stimulation. In another embodiment, the Na+/H+ exchanger is activated by the phospholipase D. In another embodiment, a tyrosine kinase is activated by the phospholipase D. In another embodiment, a MAP kinase is activated by the phospholipase D. Each possibility represents a separate embodiment of the present invention.

Endothelin receptor-activated pathways are well known in the art, and are described for example, in Ignarro et al (Ignarro L J, Buga G M, Wood K S, Byrns R E, Chaudhuri G. Proc Natl Acad Sci USA. 1987; 84:9265-9269); Furchgott et al (Furchgott R F, Vanhoutte P M. FASEB J. 1989; 3:2007-2018); Fleming et al (Fleming I, Busse R. J Mol Cell Cardiol. 1999; 31:5-14); Vanhoutte et al (Vanhoutte P M.

Nature. 1998; 396:213, 215-216); and Brandes et al (Brandes R P, Schmitz-Winnenthal F H, Feletou M, Godecke A, Huang P L, Vanhoutte P M, Fleming I, Busse R. Proc Natl Acad Sci USA. 2000; 97:9747-9752). Each possibility represents a separate embodiment of the present invention.

In another embodiment of methods of the present invention, the compound or composition is brought into contact with the solid tumor. In another embodiment, a tumor endothelial cells (TEC) of the solid tumor is contacted. In another embodiment, an endothelial cell of the solid tumor contacted. In another embodiment, wherein an ovarian tumor is the target, the ovarian tumor is contacted. In another embodiment, a TEC of the ovarian tumor is contacted. In another embodiment, an endothelial cell of the ovarian tumor contacted. In another embodiment, the compound or composition is administered systemically. In another embodiment, the compound or composition is administered directly to the tumor. In another embodiment, the compound or composition is administered in the vicinity of the tumor. Each possibility represents a separate embodiment of the present invention.

In another embodiment of methods of the present invention, the subject has received an immunotherapy. In another embodiment, the subject is currently receiving an immunotherapy. In another embodiment, the subject is slated to receive an immunotherapy. "Currently receiving" refers, in another embodiment, to a subject between doses of an immunotherapy regimen. In another embodiment, the term refers to a subject that has received or will receive a dose of the immunotherapy regimen on the same day as the method of the present invention is performed. In another embodiment, the subject receives a dose of the immunotherapy regimen in the same week as the method of the present invention is performed. In another embodiment, the subject receives a dose of the immunotherapy regimen simultaneously with performing a method of the present invention. Each possibility represents a separate embodiment of the present invention.

"Immunotherapy" refers, in another embodiment, to a vaccine therapy. In another embodiment, the term refers to direct vaccination of the subject. In another embodiment, the term refers to passive vaccination of the subject. In another embodiment, the term refers to transfer to the subject of a population of cells comprising anti-tumor antigen-specific T cells. In another embodiment, the population of cells is from a donor. In another embodiment, the population of cells is from the subject. In another embodiment, the population of cells is expanded ex vivo. In another embodiment, the anti-tumor antigen-specific T cells in the population of cells are expanded ex vivo.

In another embodiment, the term refers to cytokine treatment. In another embodiment, the term refers to interferon treatment. In another embodiment, the term refers to growth factor treatment. In another embodiment, the term refers to antibody therapy. In another embodiment, the term refers to therapy with a compound that modulates T cell activity. In another embodiment, the term refers to therapy with an adjuvant. In another embodiment, the term refers to adoptive lymphocyte therapy. In another embodiment, the term refers to cellular immunotherapy. In another embodiment, the term refers to toll-like receptor therapy. In another embodiment, the term refers to any therapeutic method that utilizes an immune mechanism.

Each type of immunotherapy represents a separate embodiment of the present invention.

Methods for ex vivo immunotherapy are well known in the art and are described, for example, in Davis I D et al (Blood dendritic cells generated with Flt3 ligand and CD40 ligand prime CD8+ T cells efficiently in cancer patients. J Immunother. 2006 September-October; 29(5):499-511) and Mitchell M S et al (The cytotoxic T cell response to peptide analogs of the HLA-A*0201-restricted MUC1 signal sequence epitope, M1.2. Cancer Immunol Immunother. 2006 Jul. 28). Each method represents a separate embodiment of the present invention.

In another embodiment, "immunotherapy" comprises the steps of (a) inducing ex vivo, from human blood cells obtained from a donor, formation and proliferation of human CTL that recognize a malignant cell of the cancer; and (b) infusing the human CTL into the subject.

The anti-ETRB compound of methods and compositions of the present invention is, in another embodiment, BQ788. In another embodiment, the compound is Bosentan (Tracleer™). In another embodiment, the compound is tezosentan. In another embodiment, the compound is Pergolide. In another embodiment, the compound is any other anti-ETRB compound known in the art. In another embodiment, the compound is a general inhibitor of Endothelin receptors. In another embodiment, the compound is specific for ETRB. In another embodiment, the compound preferentially inhibits ETRB over other Endothelin receptors. In another embodiment, the compound is an antibody. In another embodiment, the compound is an anti-ETRB antibody.

In another embodiment, the dose of BQ788 is below that used to inhibit angiogenesis.

Various embodiments of dosage ranges of BQ788 can be used, in another embodiment, in methods of the present invention. In one embodiment, the dosage is in the range of 1-80 mg/day. In another embodiment, the dosage is in the range of 5-80 mg/day. In another embodiment the dosage is in the range of 20-80 mg/day. In another embodiment the dosage is in the range of 20-60 mg/day. In another embodiment the dosage is in the range of 40-60 mg/day. In another embodiment the dosage is in a range of 45-60 mg/day. In another embodiment the dosage is in the range of 15-25 mg/day. In another embodiment the dosage is in the range of 55-65 mg/day. In one embodiment, the dosage is 20 mg/day. In another embodiment, the dosage is 40 mg/day. In another embodiment, the dosage is 60 mg/day. In another embodiment, the dosage is 80 mg/day.

In another embodiment, the dosage is 20 μg. In another embodiment, the dosage is 10 μg. In another embodiment, the dosage is 30 μg. In another embodiment, the dosage is 40 μg. In another embodiment, the dosage is 60 μg. In another embodiment, the dosage is 80 μg. In another embodiment, the dosage is 100 μg. In another embodiment, the dosage is 150 μg. In another embodiment, the dosage is 200 μg. In another embodiment, the dosage is 300 μg. In another embodiment, the dosage is 400 μg. In another embodiment, the dosage is 600 μg. In another embodiment, the dosage is 800 μg. In another embodiment, the dosage is 1000 μg. In another embodiment, the dosage is 1500 μg. In another embodiment, the dosage is 2000 μg.

In another embodiment, the dosage is 10 μg/BQ788/dose. In another embodiment, the dosage is 20 μg/BQ788/dose. In another embodiment, the dosage is 30 μg/BQ788/dose. In another embodiment, the dosage is 40 μg/BQ788/dose. In another embodiment, the dosage is 60 μg/BQ788/dose. In another embodiment, the dosage is 80 μg/BQ788/dose. In another embodiment, the dosage is 100 μg/BQ788/dose. In another embodiment, the dosage is 150 μg/BQ788/dose. In another embodiment, the dosage is 200 μg/BQ788/dose. In another embodiment, the dosage is 300 µg/BQ788/dose. In another embodiment, the dosage is 400 µg/BQ788/dose. In another embodiment, the dosage is 600 µg/BQ788/dose. In another embodiment, the dosage is 800 µg/BQ788/dose. In another embodiment, the dosage is 1000 µg/BQ788/dose. In another embodiment, the dosage is 1500 µg/BQ788/dose. In another embodiment, the dosage is 2000 µg/BQ788/dose.

In another embodiment, the BQ788 is administered systemically at 1 of the above doses. In another embodiment, the BQ788 is administered intra-tumorally at 1 of the above doses. Each possibility represents a separate embodiment of the present invention.

In another embodiment of methods and compositions of the present invention, the compound used to reduce expression of a protein is an antisense molecule. In another embodiment, the compound is an RNA inhibitory molecule. In another embodiment, the compound is any other type of compound known in the art that is capable of reducing expression of a protein or its transcript. Each possibility represents a separate embodiment of the present invention.

The step of "decreasing" the expression of a protein in a method of the present invention comprises, in another embodiment, directly decreasing the protein level. In another embodiment, the step comprises inhibiting transcription of the nucleotide molecule (e.g. mRNA) encoding the protein. In another embodiment, the step comprises inhibiting translation of the mRNA. In another embodiment, the step comprises inducing, enhancing, or increasing degradation of the mRNA. In another embodiment, the step comprises inducing, enhancing, or increasing degradation of the protein itself. In another embodiment, the step comprises any other method of decreasing the expression of a gene or protein that is known in the art. Each possibility represents a separate embodiment of the present invention.

In another embodiment, a method of the present invention comprises the use of a bivalent antibody that binds to both a therapeutic compound and a protein identified in the present invention. In another embodiment, the polyvalent antibody is conjugated to both a tumoricidal compound and a protein identified in the present invention. Each possibility represents a separate embodiment of the present invention.

In another embodiment, an anti-cancer agent is conjugated to a ligand that binds a protein identified in the present invention or a nucleotide encoding same and administered to the subject. In another embodiment, the ligand is an antibody. In another embodiment, the ligand is a complementary nucleotide molecule. In another embodiment, the ligand is a small molecule. In another embodiment, the ligand is any other type of molecule known in the art capable of binding a protein identified in the present invention or a nucleotide encoding same. Each possibility represents a separate embodiment of the present invention.

The anti-cancer agent utilized in methods and compositions of the present invention is, in another embodiment, a radioactive isotope. In another embodiment, the anti-cancer agent is a cytotoxic agent. In another embodiment, the anti-cancer agent is a cytotoxic drug. In another embodiment, the anti-cancer agent is a nucleic acid molecule. In another embodiment, the anti-cancer agent is an antisense molecule. In another embodiment, the anti-cancer agent is an RNA inhibitory molecule. In another embodiment, the anti-cancer agent is an anti-tumor agent. In another embodiment, the anti-cancer agent is a cytotoxic virus. In another embodiment, the anti-cancer agent is a cytotoxic pathogen. In another embodiment, the anti-cancer agent is a nanosphere. In another embodiment, the nanosphere is loaded with a cytotoxic compound. In another embodiment, the nanosphere is loaded with a chemotherapy drug. In another embodiment, the nanosphere is loaded with a toxin. In another embodiment, the nanosphere is loaded with an anti-cancer compound. In another embodiment, the anti-cancer agent is a nanoparticle. In another embodiment, the anti-cancer agent is an engineered T cell. In another embodiment, the anti-cancer agent is an engineered cytotoxic cell. In another embodiment, the anti-cancer agent is any other type of engineered molecule known in the art. In another embodiment, the anti-cancer agent is any other agent used in cancer therapy. In another embodiment, the anti-cancer agent is any other type of anti-cancer agent known in the art. Each possibility represents a separate embodiment of the present invention.

In one embodiment, virions whose tail tube major subunit (V) proteins are modified with a cyclizable Arg-Gly-Asp (RGD) peptide are able to transfect tumor cells at a significant frequency. Phage-mediated transfection with virions whose tail tube major subunit (V) proteins are modified with a cyclizable Arg-Gly-Asp (RGD) capable of expressing the compounds described herein are used in one embodiment with the compositions described herein for the treatment methods provided.

"Engineered T cell" refers, in another embodiment, to a T cell designed to recognize a cell containing or expressing a molecule of interest. In another embodiment, the molecule of interest is a TVM of the present invention. In another embodiment, the term refers to a T cell with redirected specificity (T-bodies) for a TVM. In another embodiment, an engineered T cell of the present invention expresses a ligand that binds to or interacts with a TVM. In another embodiment, the engineered T cell exhibits specific activity against a TVC.

In another embodiment, an engineered T cell of the present invention expresses a chimeric immunoreceptor (CIR) directed against a TVM. In another embodiment, the CIR contains a bi-partite signaling module. In another embodiment, the extracellular module of the CIR is a single chain variable fragment (scFv) antibody that binds or interacts with a TVM. In another embodiment, the intracellular module of the CIR contains a costimulatory domain. In another embodiment, the costimulatory domain is a 4-1BB domain. In another embodiment, the costimulatory domain is a TCR domain. In another embodiment, the CIR contains both a 4-1BB domain and a TCR domain.

In another embodiment, an engineered T cell of the present invention is expanded in culture. In another embodiment, an engineered T cell of the present invention is activated in culture.

Each type of engineered T cell represents a separate embodiment of the present invention.

"Cytotoxic virus" refers, in another embodiment, to a virus capable of lysing a cell. In another embodiment, the term refers to a virus capable of lysing a tumor cell. In another embodiment, the virus is a recombinant virus that has been engineered to exhibit a characteristic favorable for anti-tumor activity. In another embodiment, the virus is wild-type, other than is conjugation to an antibody or ligand of the present invention. In another embodiment, the virus is an attenuated virus. Each possibility represents a separate embodiment of the present invention.

In another embodiment, the cytotoxic agent or anti-tumor agent is concentrated in the solid tumor. In another embodiment, the cytotoxic agent or anti-tumor agent is targeted to the solid tumor. In another embodiment, concentration of the cytotoxic agent or anti-tumor agent induces cytotoxicity in a tumor cell of the solid tumor. Each possibility represents a separate embodiment of the present invention.

Endothelin antagonists are well known in the art, and are described, for example, in Dasgupta et al (Dasgupta F, Mukherjee A K, Gangadhar N. Curr Med Chem. 2002 March; 9(5):549-75); Dingemanse et al (Dingemanse J, Clozel M, van Giersbergen P L. J Cardiovasc Pharmacol. 2002 June; 39(6):795-802); and Zimmermann et al (Zimmermann M, Seifert V. Clin Auton Res. 2004 June; 14(3):143-5). Each possibility represents a separate embodiment of the present invention.

The ETRB of methods and compositions of the present invention has, in another embodiment, the sequence: MQPPPSLCGRALVALVLACGLSRIWGEERGFPP-DRATPLLQTAEIMTPPTKTLWPKGSNA SLARSLAPA-EVPKGDRTAGSPPRTISPPPCQGPIEIKETFKYINTVVS-CLVFVLGIIGNSTLLRIIYKN KCMRNGPNILIASLALGDLLHIVIDIPINVYKLLAED-WPFGAEMCKLVPFIQKASVGITVLSLCALS IDRYRAVASWSRIKGIGVPKWTAVEIVLIWVVSVV-LAVPEAIGFDIITMDYKGSYLRICLLHPVQK TAFMQ-FYKTAKDWWLFSFYFCLPLAITAFFYTLMTCEML-RKKSGMQIALNDHLKQRREVAKTV FCLVLVFALCWLPLHLSRILKLTLYNQNDPNRCELLS-FLLVLDYIGINMASLNSCINPIALYLVSKR FKNCFK-SCLCCWCQSFEEKQSLEEKQSCLKFKANDHGYDN-FRSSNKYSSS (SEQ ID No: 1; GenBank Accession # M74921). In another embodiment, the ETRB is a homologue of SEQ ID No: 1. In another embodiment, the ETRB is a variant of SEQ ID No: 1. In another embodiment, the ETRB is an isomer of SEQ ID No: 1. In another embodiment, the ETRB is a proteolytic product of SEQ ID No: 1. In another embodiment, the ETRB is a precursor of SEQ ID No: 1. Each possibility represents a separate embodiment of the present invention.

In another embodiment, the ETRB has a sequence set forth in 1 of the following GenBank Accession Numbers: NM_000115, NM_003991, AB209198, E07650, BC014472, S75587, S44866, or S75586. In another embodiment, the ETRB is a homologue of 1 of the above GenBank Accession Numbers. In another embodiment, the ETRB is a variant of 1 of the above GenBank Accession Numbers. In another embodiment, the ETRB is an isomer of 1 of the above GenBank Accession Numbers. In another embodiment, the ETRB is a proteolytic product of 1 of the above GenBank Accession Numbers. In another embodiment, the ETRB is a precursor of 1 of the above GenBank Accession Numbers. In another embodiment, the ETRB is encoded by a nucleotide sequence set forth in 1 of the above GenBank Accession Numbers. Each possibility represents a separate embodiment of the present invention.

The ET-1 of methods and compositions of the present invention has, in another embodiment, the sequence: MDYLLMIFSLLFVACQGAPETAVLGAELSAV-GENGGEKPTPSPPWRLRRSKRCSCSSLM DKECVY-FCHLDIIWVNTPEHVVPYGLGSPRSKRALENLLPT-KATDRENRCQCASQKDKKCWNFC QAGKELRAEDIMEKDWNNHKKGKDCSKLGKKCIY-QQLVRGRKIRRSSEEHLRQTRSETMRNSV KSSFHDP-KLKGNPSRERYVTHNRAHW (SEQ ID No: 2; GenBank Accession # NM_001955). In another embodiment, the ET-1 is a homologue of SEQ ID No: 2. In another embodiment, the ET-1 is a variant of SEQ ID No: 2. In another embodiment, the ET-1 is a isomer of SEQ ID No: 2. In another embodiment, the ET-1 is a proteolytic product of SEQ ID No: 2. In another embodiment, the ET-1 is a precursor of SEQ ID No: 2. Each possibility represents a separate embodiment of the present invention.

In another embodiment, the ET-1 has a sequence set forth in 1 of the following GenBank Accession Numbers: DQ496112, DQ890981, AK226096, BC009720, BC036851. In another embodiment, the ET-1 is a homologue of 1 of the above GenBank Accession Numbers. In another embodiment, the ET-1 is a variant of 1 of the above GenBank Accession Numbers. In another embodiment, the ET-1 is an isomer of 1 of the above GenBank Accession Numbers. In another embodiment, the ET-1 is a proteolytic product of 1 of the above GenBank Accession Numbers. In another embodiment, the ET-1 is a precursor of 1 of the above GenBank Accession Numbers. In another embodiment, the ET-1 is encoded by a nucleotide sequence set forth in 1 of the above GenBank Accession Numbers. Each possibility represents a separate embodiment of the present invention.

Methods for measuring the expression level of a protein or nucleotide (e.g. mRNA) molecule are well known in the art. In another embodiment, the method comprises a polymerase chain reaction (PCR; see Experimental Examples herein). In another embodiment, the method comprises use of an antibody. In another embodiment, the method is Western blotting. In another embodiment, the method is an antibody ELISA kit. In another embodiment, the method is an RT-PCR kit. In another embodiment, the method is an RNA isolation kit. In another embodiment, the means is a cDNA synthesis kit. In another embodiment, the method is any other method of measuring the expression level of a protein or nucleotide that is known in the art. Each possibility represents a separate embodiment of the present invention.

In another embodiment, a protein or nucleotide molecule of the present invention is homologous to a peptide disclosed herein. The terms "homology," "homologous," etc, when in reference to any protein or peptide, refer, in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

Homology is, in another embodiment, determined by computer algorithm for sequence alignment, by methods well described in the art. For example, computer algorithm analysis of nucleic acid sequence homology can include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 1-90 of greater than 70%. In another embodiment, "homology" refers to identity to a sequence selected from SEQ ID No: 1-90 of greater than 72%. In another embodiment, "homology" refers to identity to one of SEQ ID No: 1-90 of greater than 75%. In another embodiment, "homology" refers to identity to a sequence selected from SEQ ID No: 1-90 of greater than 78%. In another embodiment, "homology" refers to identity to one of SEQ ID No: 1-90 of greater than 80%. In another embodiment, "homology" refers to identity to one of SEQ ID No: 1-90 of greater than 82%. In another embodiment, "homology" refers to identity to a sequence selected from SEQ ID No: 1-90 of greater than 83%. In another embodiment, "homology" refers to identity to one of SEQ ID No: 1-90 of greater than 85%. In another embodiment, "homology" refers to identity to one of SEQ ID No: 1-90 of greater than 87%. In another embodiment, "homology" refers to identity to a sequence selected from SEQ ID No: 1-90 of greater than 88%. In another embodiment, "homology" refers to identity to one of SEQ ID No: 1-90 of greater than 90%. In another embodiment, "homology" refers to identity to one of SEQ ID No: 1-90 of greater than 92%. In another embodiment, "homology" refers to identity to a sequence selected from SEQ ID No: 1-90 of greater than 93%. In another embodiment, "homology" refers to identity to one of SEQ ID No: 1-90 of greater than 95%. In another embodiment, "homology" refers to identity to a sequence selected from SEQ ID No: 1-90 of greater than 96%. In another embodiment, "homology" refers to identity to one of SEQ ID No: 1-90 of greater than 97%. In another embodiment, "homology" refers to identity to one of SEQ ID No: 1-90 of greater than 98%. In another embodiment, "homology" refers to identity to one of SEQ ID No: 1-90 of greater than 99%. In another embodiment, "homology" refers to identity to one of SEQ ID No: 1-90 of 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). In other embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

Protein and/or peptide homology for any AA sequence listed herein is determined, in another embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and, in another embodiment, employ the use of the Smith and Waterman algorithms, and/or global/local or BLOCKS alignments for analysis, for example. Each method of determining homology represents a separate embodiment of the present invention.

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA is, in one embodiment, in the form of a tRNA (transfer RNA). In another embodiment, the RNA is snRNA (small nuclear RNA). In another embodiment, the RNA is rRNA (ribosomal RNA). In another embodiment, the RNA is mRNA (messenger RNA). In another embodiment, the RNA is anti-sense RNA. In another embodiment, the RNA is small inhibitory RNA (siRNA). In another embodiment, the RNA is micro RNA (miRNA). In another embodiment, the RNA is a ribozyme. In another embodiment, the RNA is agRNA (antigenic RNA). "agRNA" refers, in another embodiment, to a double stranded RNA capable of interacting with mRNA and silencing gene transcription. The use of siRNA and miRNA has been described (Caudy A A et al, Genes & Devel 16: 2491-96 and references cited therein). DNA can be, in other embodiments, in form of plasmid DNA, viral DNA, linear DNA, or chromosomal DNA, or derivatives of these groups. In addition, these forms of DNA and RNA can be single, double, triple, or quadruple stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001, Sambrook and Russell, eds.) and Methods in Enzymology: Methods for molecular cloning in eukaryotic cells (2003; Purchio and G. C. Fareed, eds.). Each nucleic acid derivative represents a separate embodiment of the present invention.

In another embodiment, provided herein is a kit comprising a reagent utilized in performing a method of the present invention. In another embodiment, provided herein is a kit comprising a composition, tool, or instrument of the present invention.

"Contacting," in another embodiment, refers to directly contacting the target cell with a composition of the present invention. In another embodiment, "contacting" refers to indirectly contacting the target cell with a composition of the present invention. Each possibility represents a separate embodiment of the present invention. In another embodiment, the composition of the present invention is carried in the subjects' bloodstream to the target cell. In another embodiment, the composition is carried by diffusion to the target cell. In another embodiment, the composition is carried by active transport to the target cell. In another embodiment, the composition is administered to the subject in such a way that it directly contacts the target cell. Each possibility represents a separate embodiment of the present invention.

Pharmaceutical Compositions and Methods of Administration

Pharmaceutical compositions containing compositions of the present invention can be, in another embodiment, administered to a subject by any method known to a person skilled in the art, such as parenterally, paracancerally, transmucosally, transdermally, intramuscularly, intravenously, intradermally, subcutaneously, intra-peritonealy, intra-ventricularly, intra-cranially, intra-vaginally or intra-tumorally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the pharmaceutical compositions are administered by intravenous, intra-arterial, or intramuscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Suitable topical formulations include gels, ointments, creams, lotions, drops and the like. In another embodiment, for topical administration, the compositions are prepared and applied as solutions, suspensions, or emulsions in a physiologically acceptable diluent with or without a pharmaceutical carrier.

In another embodiment, the active compound is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprises binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents(e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions influence, in another embodiment, the physical state, solubility, stability, rate of in vivo release, and rate of in vivo clearance.

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the active agents are converted into a solution, suspension, or emulsion, if desired with the substances customary and suitable for this purpose, for example, solubilizers or other substances.

Each of the above additives, excipients, formulations and methods of administration represents a separate embodiment of the present invention.

In one embodiment, the term "administering" refers to bringing a subject in contact with an activecompound of the present invention. In another embodiment, administration is accomplished in vitro, i.e. in a test tube. In another embodiment, administration is accomplished in vivo, i.e. in cells or tissues of a living organism. Each possibility represents a separate embodiment of the present invention.

In one embodiment, the methods of the present invention comprise administering an active composition or compound of the present invention as the sole active ingredient. However, also encompassed within the scope of the present invention are methods for chemotherapy that comprise administering the active composition or compound in combination with one or more therapeutic agents (e.g. anti-tumor agents or cancer chemotherapy agents).

EXPERIMENTAL DETAILS SECTION

Materials and Experimental Methods

Tissues

Stage-III epithelial ovarian cancer and ductal breast cancer specimens were collected at the University of Turin, Italy, following informed consent, from previously untreated patients. Additional ovarian cancer specimens, and normal ovaries were collected at the University of Pennsylvania Medical Center after obtaining written informed consent under Institutional Review Board (IRB)-approved protocols. Malignant mesothelioma (n=3), non-small cell lung carcinoma (n=3) (provided by Dr. Steven M. Albelda) and malignant melanoma (n=3) (provided by Dr. David Elder) were collected after obtaining written informed consent under IRB-approved protocols. A panel of normal human tissues (FIG. 3) was provided by the Cooperative Human Tissue Network. All specimens were processed in compliance with HIPAA requirements.

Reagents

Antibody against human CD31 (BD Pharmingen) followed by secondary antibodies (Vector, Burlingame, Calif.) were diluted (1:10) in PBS containing RNA Protector (1:10, Roche, Basel, Switzerland). Streptavidin conjugate and AEC chromagen (Dako, Carpenteria, Calif.) were diluted in PBS containing RNA Protector. Laser Capture Microdissection (LCM) was performed using Microcut (MMI, Glattbrugg, Switzerland), employing less than three hours per slide.

RNA Isolation

In order to increase RNA yield, dissected samples were treated with pre-digested proteinase-K. RNA was isolated using TRIzol reagent microprotocol (Gibco, Carlsbad, Calif.). Glycogen carrier (20 μg) was utilized to increase RNA yield in all protocols. RNA integrity and quantity were assayed using the Bioanalyzer (Agilent, Foster City, Calif.).

RNA Amplification

RNA was amplified using Messageamp® (Ambion, Austin, Tex.), with the following modifications: First-strand synthesis was performed at 42° C. (2 hours), then 48° C. (10 min). After second-strand synthesis, RNA was transcribed at 37° C. (12 hours); T7-polymerase and RNAse inhibitor were added and transcription was continued for 12 more hours. After 2 rounds of amplification, cRNA was biotin-labeled (12-24 hours, ENZO RNA labeling kit, Farmingdale, N.Y.) and purified using RNA cleanup (Qiagen, Valencia, Calif.).

Arrays

Immunohistochemistry-guided laser capture microdissection was performed from 24 epithelial ovarian cancers (EOC) with or without (12 each) intratumoral T cells (ITC). CD31 positive cells with a vascular morphology were isolated and RNA extracted using TRIzol. RNA was amplified using the Ambion MessageAmp kit, and hybridized to the U133a and U133B human genome arrays from Affymetrix.

Array Analysis

Genes were identified that were present in at least 1 of the 29 samples analyzed; and only those genes that demonstrated at least a 1.5-fold increase or decrease in relative expression between ITC(+) and ITC(−) tumor vascular cells were further analyzed. Using hierarchical clustering, a gene tree was generated using the resulting list of differentially genes. Molecules were identified that were present in vascular cells from at least 9 of 14 ITC(+) tumors and upregulated by at least 2-fold compared to ITC(−) vascular cells. Similarly, molecules were identified that were present in vascular cells from at least 6 of 11 ITC (−) tumors and 2-fold upregulated compared to ITC(+) tumor vascular cells using Genespring software (Agilent Technologies, Santa Clara, Calif.). Quantitative PCR (qPCR) and Western blot of 60 EOC tumors was used to confirm over-expression of Endothelin B receptor (ETRB) in ITC(−) tumors.

qRT-PCR qRT-PCR was performed using primers to the 3′ end of transcripts spanning intron-exon boundaries whenever possible for 35 cycles using Sybergreen® (ABI, Foster City, Calif.), with primers at 150 nM concentrations. Primers were 18-24 nucleotides and were designed to have a TM of 59-61° C. All transcripts were confirmed using 3% agarose gel electrophoresis. Gene expression was normalized against β-actin in all studies unless stated otherwise.

Immunostaining

For validation studies, immunohistochemistry (IHC) was performed using the VECTASTAIN ABC® kit (Vector, Burlingame, Calif.). All primary antibodies were incubated for one hour. Immuno-reaction was visualized with 3,3′-diaminobenzidine (Vector). All staining steps were performed at room temperature.

Bioinformatic and Statistical Analyses

Statistical significance for mRNA expression differences between tissue types was determined using a two-tailed Student's t-Test. Pearson's correlation was used to determine linearity of arrays performed with one versus two rounds of amplification or before and after immuno-LCM. Analyses of expression profiles were performed using Genespring software (Agilent); all samples were normalized with the median defined as 1.0. A heat map condition tree was developed using a hierarchical clustering algorithm (Genespring®) excluding all genes where the difference between the means of the tumor and normal vascular samples was less than its standard error. Descriptive statistics were performed with the SPSS® statistics software package (SPSS, IL, USA). The algorithm for the nonparametric method based on the ranks of the expression level for tumor and normal samples was developed in SAS 9.1.

Optimization of Immunostaining

To procure highly purified tumor vasculature, a rapid and reliable immuno-LCM protocol was established for microarray applications. Different fixation conditions were tested, including −20° C. acetone; 70% ethanol:10% acetic acid (1:1 vol:vol); methanol; or 4% paraformaldehyde. Fixation with acetone or ethanol-based fixatives resulted in the greatest RNA yield (FIG. 2A). Acetic acid:ethanol fixation did not enable optimal IHC visualization of select target proteins. Acetone fixation was chosen for all further experiments.

Next, immunostaining was optimized. RNA isolated from tissue sections after standard IHC using LSAB (Dako) or Vectastain (Vector) showed near-complete degradation (FIG. 2B-6). We thus developed an ultra-fast IHC protocol with increased concentrations of reagents. High concentrations of RNAse inhibitor were added to all aqueous solutions. The choice of RNAse inhibitor was critical for RNA integrity. RNA Protector® (Roche) was found to be superior to placental RNAse inhibitor (Stratagene) or SuperRNAsin® (Ambion), leading to two-fold increase in RNA yield and integrity (FIG. 2B). Combining RNAse inhibitors reduced the efficacy of RNA Protector. Addition of RNA Protector to IHC allowed for 90% preservation of RNA integrity, based upon comparison of ribosomal RNA ratios determined using the Agilent Bioanalyzer.

Next detection systems were compared. AEC chromagen resulted in 40% greater RNA yield than DAB. Immunofluorescence resulted in 100% increased RNA yield compared to AEC (FIG. 1C), but contaminating cells were poorly identifiable without counterstaining, as assessed by qRT-PCR detection of the T-cell marker CD3-c. Furthermore, fluorescence quenching limited LCM time. Thus, AEC IHC was used for subsequent experiments.

In addition, the effect of LCM time on RNA yield and integrity was examined. Leaving immunostained tissue sections at room temperature for up to three hours before RNA was isolated had no significant impact on the quality or quantity of RNA isolated (FIG. 1D).

Optimization of RNA Purification.

RNA amplification methods (Arcturus Picopure kit, Stratagene microRNA isolation kit, Zymo mini RNA isolation kit and the modified TRIzol method for less than $10^5$ cells) were compared for RNA yield and quality after immuno-LCM. Arcturus Picopure gave the highest RNA yield for tissues stained with hematoxylin alone, but not following IHC (FIG. 2E). The protocol from ZYMO also resulted in low RNA yield. Conversely, the Stratagene micro RNA isolation kit and the modified TRIzol method gave significantly better and similar yields by quantification with the Agilent Bioanalyzer.

RNA quality was tested by qRT-PCR of GADPH and β-actin transcripts in total RNA procured from $1\times10^6$ cells microdissected and processed as in Table 2. GADPH or β-actin transcripts were detected at similar levels in RNA isolated with the modified TRIzol method using phase-lock tubes (Eppendorf, Hamburg, Germany) or with the Stratagene micro RNA isolation kit. Arcturus picopure and ZYMO RNA isolation kits were 10-fold and 256-fold less sensitive, respectively (FIG. 2F).

The resulting protocol, requiring approximately 25 minutes for IHC, proved successful for numerous antibodies (Table 1). While some antibodies required longer incubation times (up to 15 minutes), there was no loss of RNA yield or integrity. Staining was quite specific, even with high concentrations of antibody. The protocol was reproducibly able to capture 500,000 μm² of tumor vascular cells in 3 hours of microdissection and recover ~20 ng total RNA. RNA was reproducibly amplified to 15 μg of biotin-labeled cRNA.

Optimization of RNA Amplification

Figure 2G:
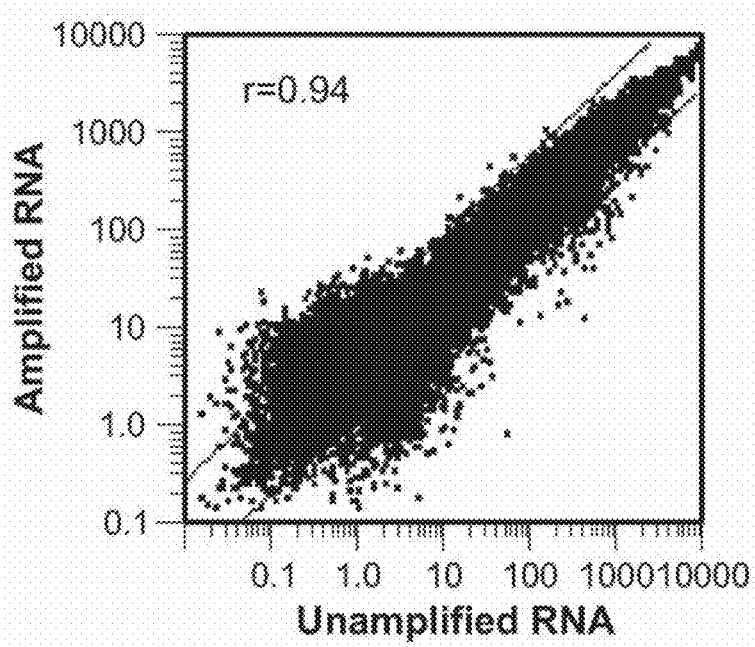
FIG. 2G. Scatter plots and correlation values of amplified RNA (y-axis) to unamplified total tumor RNA (x-axis).

The linearity of amplifications using Ambion MessageAmp® was tested by comparing the gene expression profile of 10 μg unamplified whole tumor RNA to amplified 6, 24 or 60 ng of the same RNA. Transcriptional profiling was performed using Affymetrix U133 chips. Correlation between unamplified RNA and 24 or 60 ng input RNA was high ($r^2$=0.93 and 0.94, respectively) (FIG. 2G). Correlation was lower with 6 ng input RNA ($r^2$=0.87). High correlation was found between gene expression profiles from amplifications of input. RNA procured from the same tumor performed within the same experiment (intra-assay, $r^2$=0.99) or in different experiments (inter-assay, $r^2$=0.97). Immuno-LCM had no impact on expression profile (FIG. 1C).

TABLE 1

List of antibodies tested, company and clone used in the study as indicated. Success with staining using the rapid IHC protocol for LCM following fixation in acetone or acetic acid/ethanol (AA/EtOH) is reported on the side for tested antibodies. (—), poor stain, (*) fair stain, () good stain, (*) excellent stain. ND, not determined.

| Antibody | Company | Clone | Acetone | AA/EtOH |
|---|---|---|---|---|
| Biot hCD45 | BD Pharm | H130 | *** | — |
| Biot hCD31 | Ancell | 158-2B3 | *** | ** |
| Biot hCD31 | Caltag | MBC 78.2 | ** | ** |
| hCD31 | Dako | JC70A | ** | ** |
| Biot CD146 | Chemicon | MAB16985B | *** | *** |
| CytoKeratin | Dako | AO575 | * | — |
| Biot hCD3 | BD Pharm | UCHT1 | *** | — |
| Fitc hCD31 | BD Pharm | WM59 | *** | *** |
| SMA-α-Cy3 | Sigma | 1A4 | ND | ND |
| FOLH1 | Zymed | ZMD.80 | ND | ND |
| STC2 | Genway | A22017 | ND | ND |
| Biot CD74 | BD Pharm | Mb741 | ND | ND |
| AML-1 | Active Motif | Polyclonal | ND | ND |
| hCD34-PE | BD Pharm | 581 | ND | ND |
| F-Spon | Abcam | Ab14271-50 | ND | ND |
| Lrp4 | Abcam | Ab13388-25 | ND | ND |
| Endothelial Lipase | Cayman Chemical | Polyclonal | ND | ND |

The optimized Immuno-LCM protocol is summarized in Table 2.

TABLE 2

Summary of Immuno-LCM Protocol

| | |
|---|---|
| Tumor | Freshly cut 8 μm sections of snap frozen tumor |
| IHC** | Fix in −20° C. Acetone - 4 min |
| | Incubate with primary Ab 1:10 - 5 min |
| | Incubate with 3x biotinylated anti-mouse Ab (Vector) - 5 min. |
| | Brief wash in PBS |
| | 2.5X Streptavidin-biotin amplification (DAKO) - 5 min |
| | Brief wash in PBS |
| | AEC (DAKO) stain - 3 to 5 min |
| | Brief wash in PBS |
| | Stain with dilute hematoxylin |
| | Rinse |
| | (**All steps with 1:10 RNAse Protector) |
| LCM | Dry tissue sections with hair dryer - 1 min |
| | Microdissect cells - up to 3 hours |
| RNA isolation | Treat with Proteinase K (10 μg/ml) - 8 min |
| | Extract RNA with TRIzol in phase lock gel - 1 hour |
| RNA Amplification | Use Ambion MessageAmp ® |

During the optimization of RNA isolation and amplification methodology, it was found that the immuno-LCM procedure had minimal impact on RNA integrity (FIG. 2A-F) or gene expression profiling (FIGS. 1C and 2G).

The absence of tumor cell and lymphocyte lineage-specific markers was confirmed in immuno-LCM purified TECs by RT-PCR and quantitative real-time polymerase chain reaction (qRT-PCR).

ETRB as an Ovarian Carcinoma Biomarker

RNA was isolated from 61 snap-frozen advanced stage (III and IV) EOC specimens collected from previously untreated patients undergoing debulking surgery. Quantitative PCR was used to assay ETRB expression. The Wilcoxon rank-sum test was used to compare ENDR expression among groups defined by ITC and debulking. The survival curves were estimated using the Kaplan-Meier procedure. Hazard ratios for ENDR expression were obtained from Cox proportional hazard models and presented with their 95% confidence intervals.

BQ788 as a Tumor Vaccine Adjuvant

Two injections of 5×10 $6^{th}$ UV irradiated ID8 ovarian cancer cells were injected sub-cutaneously in C57Bl6 mice one week apart. Vaccinated mice and non-vaccinated controls were injected with 5×10$^6$ ID8 cells in the flank with 300 ml matrigel or intraperitoneally. Tumors were allowed to grow for 2 or 5 weeks as indicated, and then treated with intraperitoneal injections of BQ-788 (300 mcg) or control peptide for 2 weeks.

FACS analysis was performed using APC-CD45 (BD Pharmingen), PE-anti CD3, FITC anti CD4, and Biotin anti-CD8 coupled with streptavid PE-Cy7.

IHC was performed using the Vectastain kit (Vector) mouse anti-ETRB (Abcam 1922-225), anti ADRBK2 (AbCAM, rabbit polyclonal), anti-ESRalpha (Genetex 1D5). Western blots were performed using the anti-ETRB 1:200 and HRP anti-rabbit secondary (Santa Cruz Biotechnology).

Cell Culture

Human vascular endothelial cells (HUVEC) were grown to 70% confluence in EBM media then treated with 50 nM Endothelin receptor B inhibitor BQ-788 (American peptide), or 2.5 nm Endothelin alone or in the presence of either 50 nm Endothelin receptor A inhibitor BQ123 (American peptide), or 50 nM Endothelin receptor B inhibitor BQ-788. Alternatively cells were treated with BQ-788 alone. Media was changed every 48 hrs for a total of 6 days. After 6 days cells were harvested for RNA, flow cytometry or incubated activated T cells. T cells were activated for 48 hours with either 5 ng/ml PMA (ref) or CD3 and CD28 beads. After activation T cells were labeled with CFSE and then incubated with pretreated endothelial cells for 2 hours with shaking. Cells were then washed 3× with PBS and adhesions was determined using a fluorescent plate reader.

EXAMPLE 1

Figure 3A:
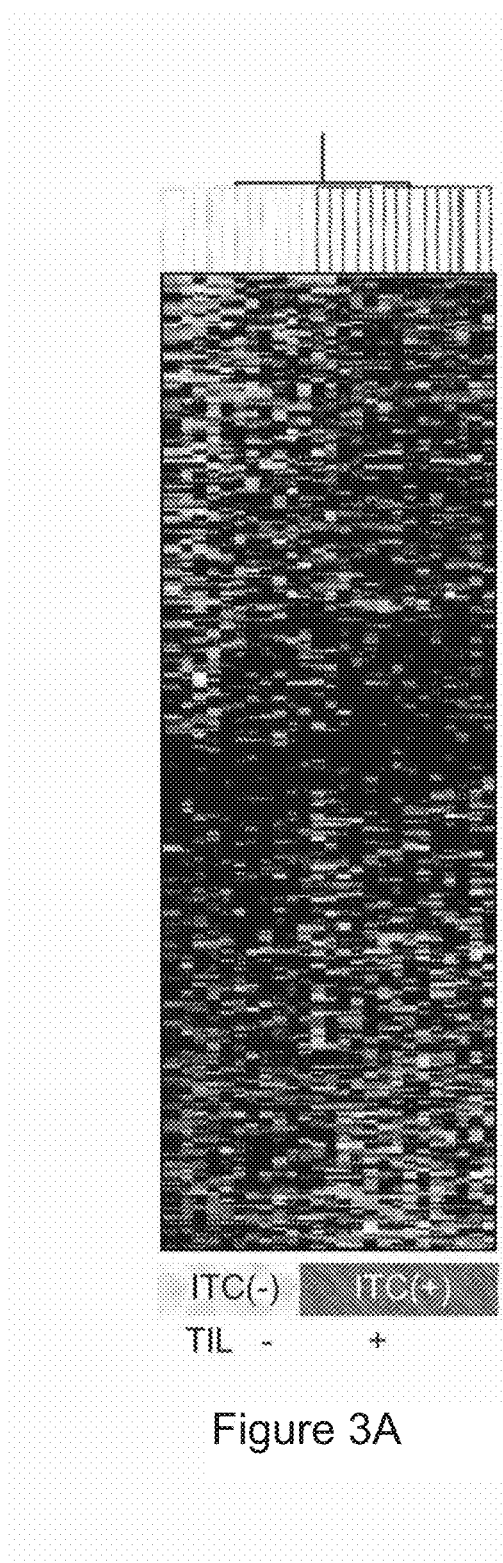
FIG. 3A. Condition tree and heat map based on vascular cell RNA expression from normal vasculature (Blue), ITC(−) tumor vascular cells (Yellow) and ITC(+) tumor vascular cells (Red). Samples were classified using a list of genes previously identified to classify tumor versus normal vascular cells and then sorted based on high expression in ITC(+) versus ITC(−) vascular samples.

Identification of Distinct Endothelial Profiles in Tumors Containing or Lacking Intraepithelial T Cells Immunohistochemistry-guided laser capture microdissection (immuno-LCM) coupled with RNA amplification and genome-wide transcriptional profiling was utilized to analyze high-quality RNA from highly purified tumor endothelial cells. In preparatory experiments, 21 tumor endothelial cells (TEC) and 4 normal ovarian endothelial cell (EC) specimens were analyzed and to identify genes that are specifically expressed in tumor endothelium. In the present experiment, TEC samples were divided into ovarian tumors with brisk intraepithelial (IE) T cell (n=14) and tumors lacking altogether IE T cells (n=11), and unsupervised hierarchical clustering was performed using 17,920 genes (after elimination of all genes wherein the difference between TEC and normal endothelial cell means was less than the standard error of the difference in the means). TECs of tumors with IE T cells were accurately classified from TECs of tumors lacking IE T cells, demonstrating a clear difference in molecular profiles (FIG. 3). When unsupervised hierarchical clustering included also profiles of normal EC, TEC from tumors lacking IE T cells clustered closely with normal EC.

Among genes differentially expressed (>2.5-fold) between the 2 types of TEC (FIG. 3), genes that were upregulated in TEC from tumors lacking IE T cells included the endothelin receptor B (ETRB); the RNA binding protein homolog Musashi 2 (MSI2); and 2 members of the Notch signaling pathway, delta-like 1 and Hairy/Enhancer of Split 1, while genes that were upregulated in TECs of tumors harboring IE T cells included the complement component 3 (C3); the apoptosis regulator CFLAR; the estrogen receptor alpha (ESR1); and the adrenergic receptor B2 (ADRBK2). Thus, expression profiling distinguished TECs from tumors with or without IE T cells and identified TEC molecules specifically associated with the absence of IE T cells.

The genes identified are set forth in Table 3:

| Fold change | Common name and/or Gene Symbol | GenBank Accession Number/SEQ ID Number | |
|---|---|---|---|
| Genes upregulated in ITC⁻ TVC | | | |
| 3.627 | MEG3 (Maternally expressed 3) | AI291123; AB032607; BC036882; BC036882; BC062783; AJ413186; AK055725; AK057522; AK092504; AK092707; AK124580; AK127864 | 3-4 |
| 2.886 | SEC61G (Sec61 gamma subunit) | NM_014302; BC009480; BC051840; NM_014302; AF086539; | 5 |
| 2.873 | KIAA1609 | AA195124; BC023251 | 6-7 |
| 2.82 | ACTR6 (ARP6 actin-related protein 6 homolog) | NM_022496; BC015107; AB038229; AF212251; AK023495; AK023684; AK124075 | 8 |
| 2.784 | FLJ23006 fis, clone LNG00414 | AK026659 | 9 |
| 2.746 | ATP9A (ATPase, Class II, type 9A) | AB014511; AF086357; AK025559; BC016044; BC036759; AB014511; NM_006045 | 10-11 |
| 2.665 | IMAGE: 23539 | R38110 | 12 |
| 2.642 | NCOA1 (Nuclear receptor coactivator 1) | BF576458; AJ000881; AJ000882; U59302 | 13-14 |
| 2.584 | Wilms tumor upstream neighbor 1 (WIT1) | NM_015855; BC002734 | 15 |
| 2.539 | IMAGE: 1909757 | AI343000 | 16 |

-continued

| Fold change | Common name and/or Gene Symbol | GenBank Accession Number/SEQ ID Number | |
|---|---|---|---|
| 2.513 | MSI2 (Musashi homolog 2) | BE220026; BC017560; AK093888 | 17-18 |
| 2.502 | ETRB | NM_000115; AB209198; D90402; S57283 | 19 |
| 2.473 | PAPSS2 (3'-phosphoadenosine 5'-phosphosulfate synthase 2) | AW299958; AF091242 | 20-21 |
| 2.372 | aldolase A, fructose-bisphosphate (ALDOA) | NM_000034 | 22 |
| 2.372 | ZNF423 (Zinc finger protein 423) | AW149417; NM_015069 | 23-24 |
| 2.358 | ENPP2 (Ectonucleotide pyrophosphatase/phosphodiesterase 2 (autotaxin)) | L35594; BC034961; AK124910; AK130313; D45421; NM_001040092; NM_006209 | 25 |
| 2.344 | HSU79266 (a.k.a. SAC3D1; SAC3 domain containing 1) | NM_013299; BC007448; U79266 | 26 |
| 2.34 | KIAA0146 | D63480 | 27 |
| 2.316 | IMAGE: 1902075 | AI300126 | 28 |
| 2.279 | EMX2 (Empty spiracles homolog 2) | AI478455; NM_004098; AF301598; BC010043; AK055041 | 29-30 |
| 2.273 | MYBL1; (V-myb myeloblastosis viral oncogene homolog (avian)-like 1) | AW592266; X66087 | 31-32 |
| 2.27 | MPHOSPH9 | X98258 | 33 |
| 2.267 | IMAGE: 1660792 | AI083578 | 34 |
| 2.233 | ETRB | M74921 | 35 |
| 2.214 | IMAGE: 191524 | H37807 | 36 |
| 2.212 | IMAGE: 2365035 | AI800895 | 37 |
| 2.17 | TAF3 (TAF3 RNA polymerase II, TATA box binding protein (TBP)-associated factor, 140 kDa) | AI123516; AL117661; BC028077 BC062352 | 38-39 |
| 2.148 | SLC1A4 (Solute carrier family 1 (glutamate/neutral amino acid transporter), member 4) | BF340083; BC026216; NM_003038 | 40-41 |
| 2.141 | HES1 (Hairy and enhancer of split 1) | BE973687; BC039152; NM_005524; AF264785; AK000415 | 42-43 |
| 2.135 | DLK1 (Delta-like 1 homolog) | U15979; BC007741; BC013197; BC014015; NM_001032997; NM_003836 | 44 |
| 2.122 | SGCB (Sarcoglycan, beta (43 kDa dystrophin-associated glycoprotein) | U29586; BC020709 | 45 |
| | Genes upregulated in ITC$^+$ TVC | | |
| 5.412 | complement component 3 (C3) | NM_000064 | 46 |
| 3.746 | IMAGE: 2755380 | AW262311 | 47 |
| 3.455 | ZNFN1A5 (a.k.a. IKZF5 (IKAROS family zinc finger 5 (Pegasus)) | BF056303; AK023288; AK055507 | 48-49 |
| 3.141 | LOC283663 | AI926479; AL713736; AK090515; AK097083; AK123700 | 50-51 |
| 3.096 | IGLJ3 (Human rearranged immunoglobulin lambda light chain mRNA) | X57812; BC012159; BC015833; BC018749; BC020233; BC020236; BC022098; BC022823 | 52 |
| 2.872 | ZNF521 (Zinc finger protein 521), | AK021452; AL117615; BC032869 | 53 |
| 2.831 | clone COL05405 | AK000119 | 54 |
| 2.682 | CALD1 (Caldesmon 1) | BF063186; BC040354; NM_004342; NM_033138-140; AB062484; AJ223812; BC015839; BX538339; BX648808 | 55-56 |
| 2.678 | cytochrome P450, family 1, subfamily B, polypeptide 1 (CYP1B1) | NM_000104; NM_000104; U03688 | 57 |
| 2.65 | EIF5B (Eukaryotic translation initiation factor 5B) | BG261322; BC032639; AJ006412; AL133563; AB018284; AJ006776; AK091864; NM_015904 | 58-59 |
| 2.618 | IMAGE: 1518332 | AA903710 | 60 |
| 2.587 | HSPC056 (a.k.a. ARMC8; Armadillo repeat containing 8), | BF942281; BC032661; BC041699 | 61-62 |
| 2.576 | FLJ32949 (a.k.a. DPY19L2 (Dpy-19-like 2 (C. elegans)) | AI039361; AL833344; NM_173812; AY358792 | 63-64 |
| 2.48 | CFLAR (CASP8 and FADD-like apoptosis regulator) | AI634046; Y14040; AF005775 | 65-66 |

-continued

| Fold change | Common name and/or Gene Symbol | GenBank Accession Number/SEQ ID Number | |
|---|---|---|---|
| 2.467 | IMAGE: 244300 | N54783 | 67 |
| 2.457 | FLJ10330/PRPF38B (PRP38 pre-mRNA processing factor 38 (yeast) domain containing B) | N32872; BC007757; BC009453; BC040127; BC107801 | 68-69 |
| 2.455 | C18orf14 | NM_024781; BC007757; BC009453; BC040127; BC107801 | 70 |
| 2.45 | IMAGE: 2115041 | AI417595 | 71 |
| 2.448 | GBP1/GBP3 (Guanylate binding protein 3) | AW014593; AB208912; M55542; NM_002053 | 72-73 |
| 2.438 | IMAGE: 731714 | AA417078 | 74 |
| 2.427 | SFRS1 (Splicing factor, arginine/serine-rich 1 (splicing factor 2, alternate splicing factor)), | AA046439; BC010264; NM_006924; AB062124; AB209558 | 75-76 |
| 2.426 | NICAL; MICAL1 (Microtubule associated monoxygenase, calponin and LIM domain containing 1) | NM_022765; BC009972; BC042144; BC052983; AB048948; AK025392; BC036514; AK021999; AK024500; AK160384 | 77 |
| 2.419 | NOL7 | NM_016167; BC062683; BC023517; AF172066 | 78 |
| 2.41 | MYCBP2 (MYC binding protein 2) | AA488899; AF075587; BX647202; AB020723; AK092651; NM_015057 | 79-80 |
| 2.382 | estrogen receptor 1 (ESR1) | NM_000125 | 81 |
| 2.382 | IMAGE: 2275600 | AI683805 | 82 |
| 2.356 | ADRBK2 (Adrenergic, beta, receptor kinase 2) | AI651212; BC029563; BC063545; AK055687; AK123767 | 83-84 |
| 2.348 | EST366269 MAGE resequences | AW954199 | 85 |
| 2.346 | SCAP2/SKAP2 (Src kinase associated phosphoprotein 2) | NM_003930; BC036044 | 86 |
| 2.328 | Homo sapiens serine/threonine kinase 3 (STE20 homolog, yeast) (STK3) | NM_006281; BC010640; AKI31363; U26424 | 87 |
| 2.324 | AKAP10 (A kinase (PRKA) anchor protein 10) | AU147278; BC017055; | 88-89 |

EXAMPLE 2

Validation of Endothelial Genes Associated with IE T-Cells

Figure 4A:
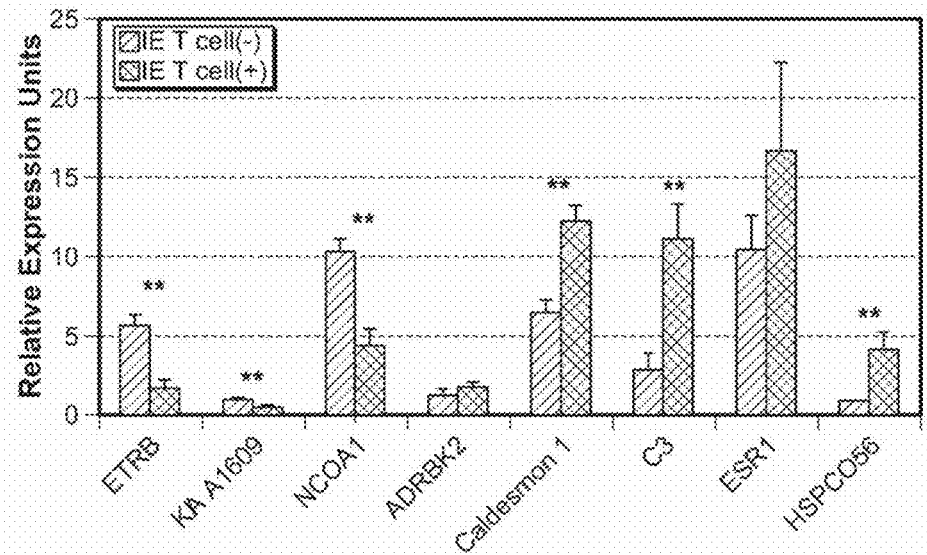
FIG. 4A. qRT-PCR of whole tumor RNA for the indicated genes from 28 stage III epithelial ovarian cancers 16 ITC(+) and 12 ITC(−).
Figure 4B:
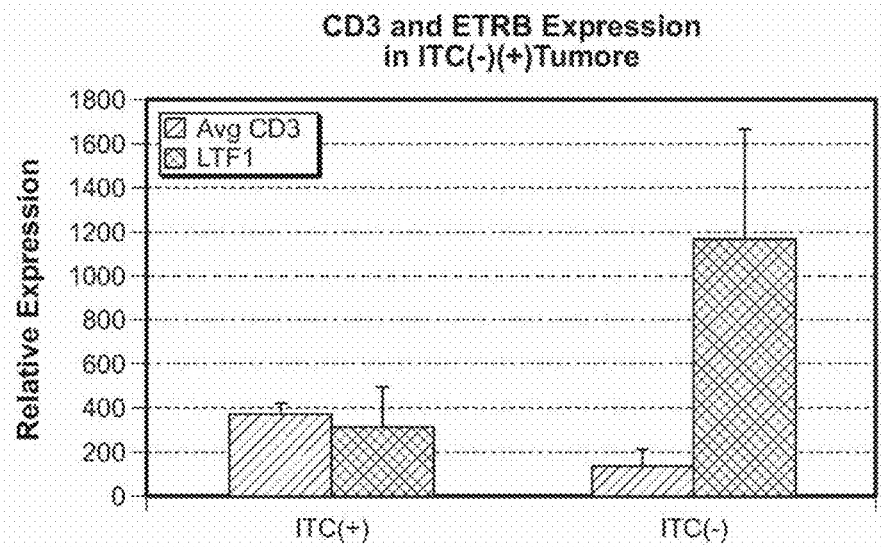
FIG. 4B. qRT-PCR for the indicated genes on FACS isolated tumor endothelial cells from 4 ITC(+) and 3 ITC(−) tumors. ** indicates statistically significant difference between samples with $p<0.05$.

All of the above genes were detected in whole tumor RNA from a different set of tumors (n=28) (FIG. 4A) as well as in CD146+ VE-cadherin+ CD45− TEC freshly immuno-purified by FACS from advanced ovarian cancers (n=7). Overexpression of ETRB, KIAA1609, and NCOA in tumors lacking IE T cells (n=12) was confirmed by qRT-PCR (4.3-fold and 2.2-fold respectively, p<0.05). Furthermore, ETRB, KIAA1609, and NCOA were significantly overexpressed by qRT-PCR in TEC from tumors lacking IE T cells (all, p<0.0x; n=3) (FIG. 4). Furthermore, overexpression of C3, caldesmin-1, HSPCO56, ADRBK2, and ESR1 in tumors exhibiting IE T cells was confirmed by qRT-PCR (all p<0.05; n=16) (FIG. 4A). C3, caldesmin-1, HSPC036, ADRBK2, and ESR1 were significantly overexpressed by qRT-PCR also in TEC from tumors harboring IE T cells (t-test; n=4) (FIG. 4B). Thus, association of specific endothelial genes with the presence or absence of IE T cells was confirmed by qRT-PCR.

EXAMPLE 3

Overexpression of ETRB and its Ligand, Et-1, Associate with Lack of IE T-Cells ETRB was consistently associated with absence of IE T cells in human ovarian cancer; thus, expression of this protein in ovarian cancer and its function in T cell homing were examined further. Consistent with the results above, ETRB protein was detected by IHC in ovarian tumor vasculature and stromal cells, but not in tumor cells. IHC revealed higher expression of endothelial ETRB in tumors lacking IE T cells relative to tumors harboring T cells. The endothelial location of ESR1 and ADRBK2 was validated by IHC with available antibodies.

Figure 5A:
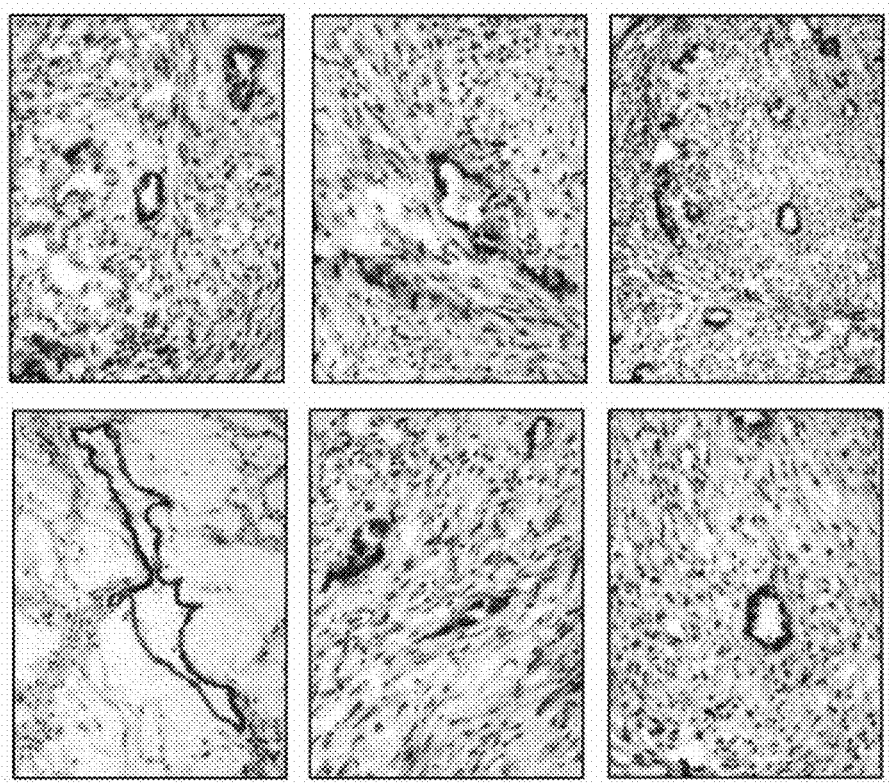
FIG. 5A. Immunohistochemistry for $ET_BR$, confirming protein expression in tumor vascular cells from epithelial ovarian cancer.
Figure 5B:
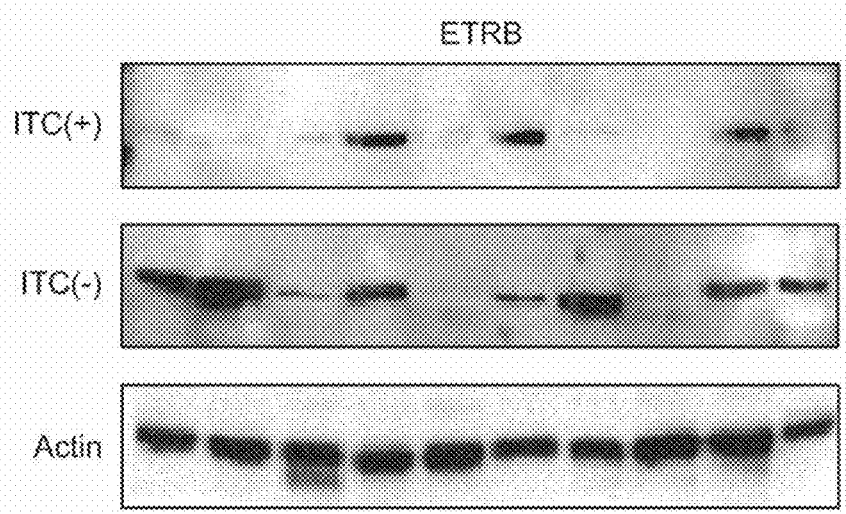
FIG. 5B. Western blot analysis demonstrating increase ETRB protein ITC(−) tumors as compared to ITC(+) tumors (Left panels) and increased ETRB expression in ITC(+) poor prognosis tumors (overall survival<36 months) (right panels).

ETRB protein was further quantified by Western blotting in ovarian cancer samples (n=40); it was detected at lower levels in the 20 tumors harboring IE T cells, but was robustly expressed in 16 of 20 tumors lacking IE T cells (FIG. 5). Among tumors with IE T cells, those expressing ETRB were associated with lower density of IE T cells compared to tumors lacking IE T cells as assessed by CD3 IHC as well as CD3-epsilon mRNA levels. Thus, increased expression of ETRB by tumor endothelium is associated with absence or paucity of IE T cells.

Expression of the ligand of ETRB, endothelin-1 (ET-1), was examined in ovarian cancer. ET-1 expression was restricted to tumor islets. To test whether ET-1 is expressed by tumor cells, ET-1 mRNA levels in highly purified tumor cells procured by immuno-LCM were quantified. Strong expression of ET-1 in vivo was documented in tumor cells isolated from 10 ovarian cancers. Further, ET-1 expression was significantly higher in tumors lacking IE T cells relative to tumors harboring IE T cells. Collectively, these data show that over-expression of ETRB by tumor endothelium and its ligand ET-1 by tumor cells is associated with abrogation of T cell infiltration in tumor islets. Further, these findings show that a molecular crosstalk occurs between tumor cells and tumor endothelium that predicts lack of T cell homing to tumors and show an important role of the ET-1/ETRB axis in controlling T cell trafficking in tumors.

EXAMPLE 4

ETRB Overexpression Predicts Poor Outcome in Ovarian Cancer

Figure 6B:
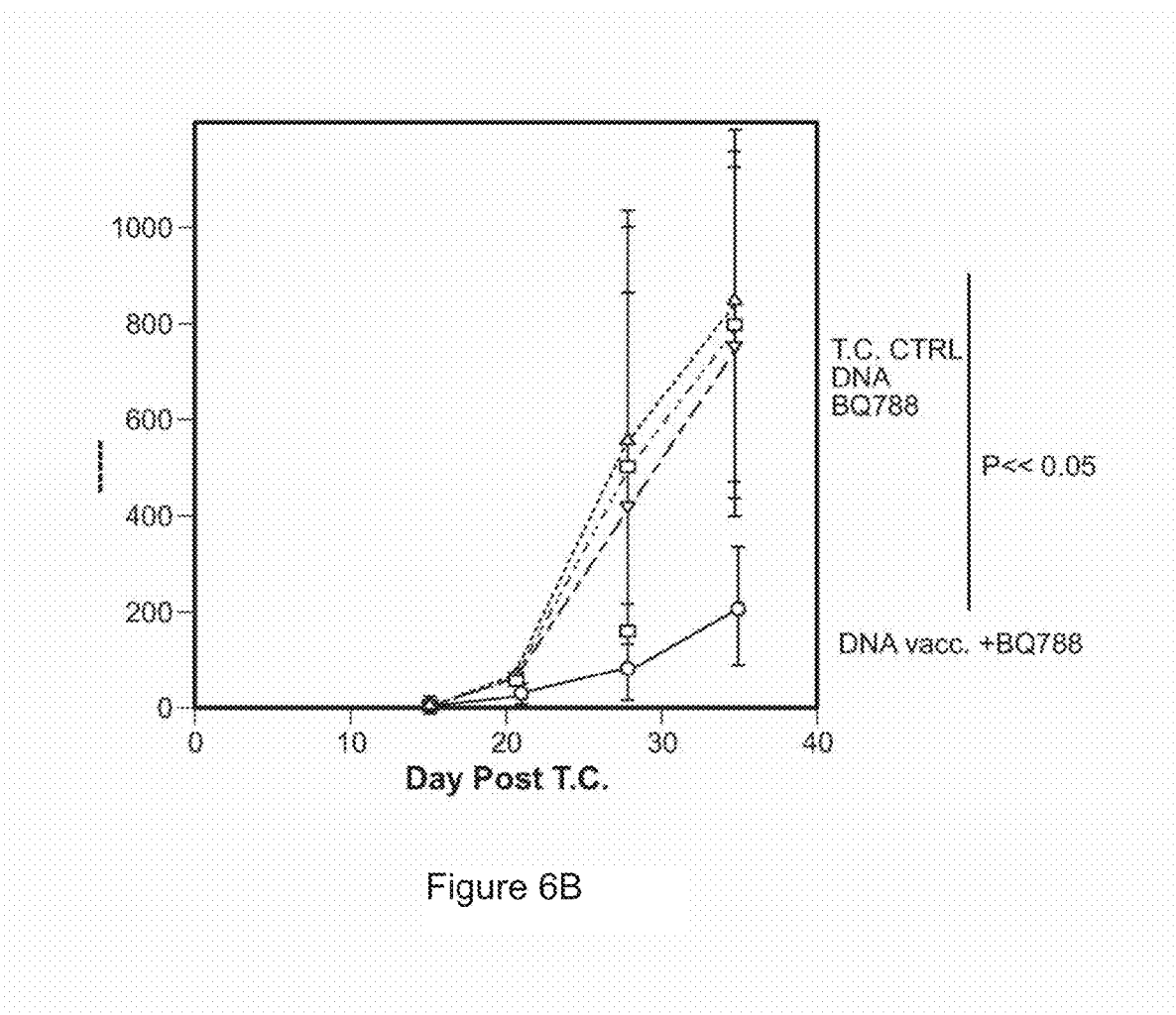
FIG. 6B. A graph showing the impact of treatment with BQ-788, starting at 2 or at 5 weeks, on tumor growth.

IE T cell infiltration is a strong predictor of clinical outcome in ovarian cancer. To determine whether ETRB overexpression is predictive of poor outcome in ovarian cancer, ETRB expression was quantified by qRT-PCR in 62 EOC specimens (38 with and 23 lacking IE T-cells) and patients were stratified into groups. There were significant differences in the distributions of both overall survival and disease-free survival, according to high and low expression of ETRB ($p<0.001$); the five-year overall survival rate was 41% for patients whose tumors exhibited higher ETRB expression versus 100% for those whose tumors exhibited the lowest expression ETRB EOC patients (FIG. 6). In univariate analysis, the hazard ratio for lowest ETRB-expressing group was 0.05 for overall survival (95% CI 0-0.42, $p<=0.005$) and 0.15 for disease-free survival compared to the highest group (95% CI 0.04-0.56, $p<=0.005$). High expression of ETRB strongly correlated with absence of IE T-cells.

EXAMPLE 5

Endothelial ETRB Regulates T Cell Trafficking

Materials and Experimental Methods

The murine epithelial ovarian cancer cell line ID8, syngeneic to C57BL/6 mice was cultured in DMEM supplemented with 4% FBS, 13 ITS media supplement (bovine insulin (5 mg/L), human transferrin (5 mg/L), and sodium selenite (5 mg/L); Sigma), and antibiotics.

Flank and Orthotopic, Intraperitoneal ID8 Models

Female C57BL/6 mice (8 weeks of age) were injected 3 times i.p. with $1 \times 10^6$ UV-treated, apoptotic ID8 ovarian cancer cells (resuspended in 500 microliter (mcL) DMEM without supplements) in the flank. For the orthotopic, intraperitoneal model, mice were injected i.p. with $5 \times 10^6$ ID8 cells.

Results

Figure 7A:
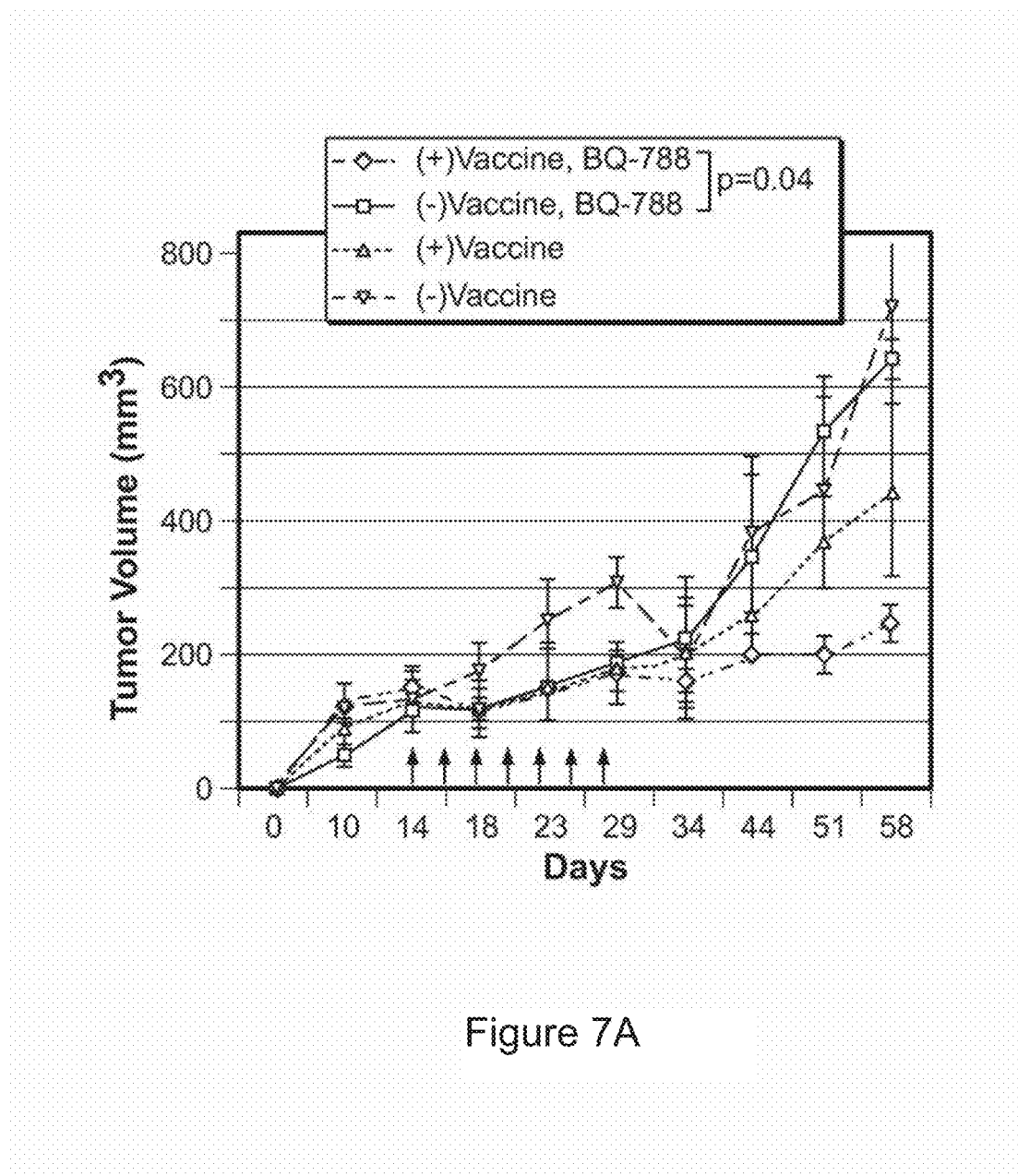
FIG. 7A and FIG. 7B. Tumor growth curves for ID8 tumors injected in the flank of animals treated with either no therapy (Vaccine−), anti-tumor vaccine and control protein therapy (Vaccine+), no vaccine and BQ788 therapy, or vaccine and BQ788 therapy. Arrows indicate time of BQ788 or control protein administration at either 2 weeks (FIG. 7A) or 5 weeks after tumor engraftment (FIG. 7B).
Figure 7B:
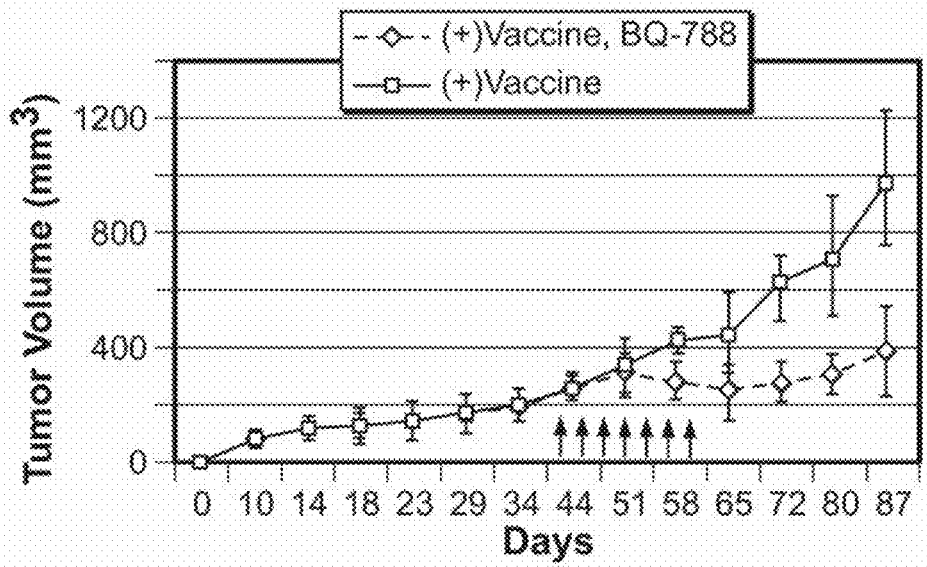
Figure 7C:
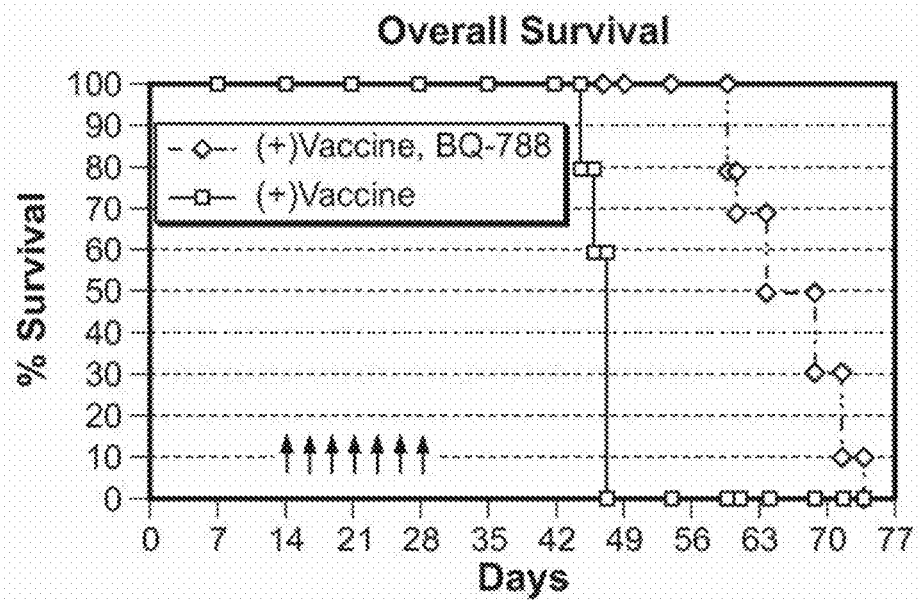
FIG. 7C. Overall survival curves of animals injected with intraperitoneal ID8 cells, which received either anti-tumor vaccine+control protein therapy (Vaccine+) or vaccine+BQ788 therapy. BQ788 therapy was initiated two weeks after injection of intraperitoneal ID8 cells.
Figure 8A:
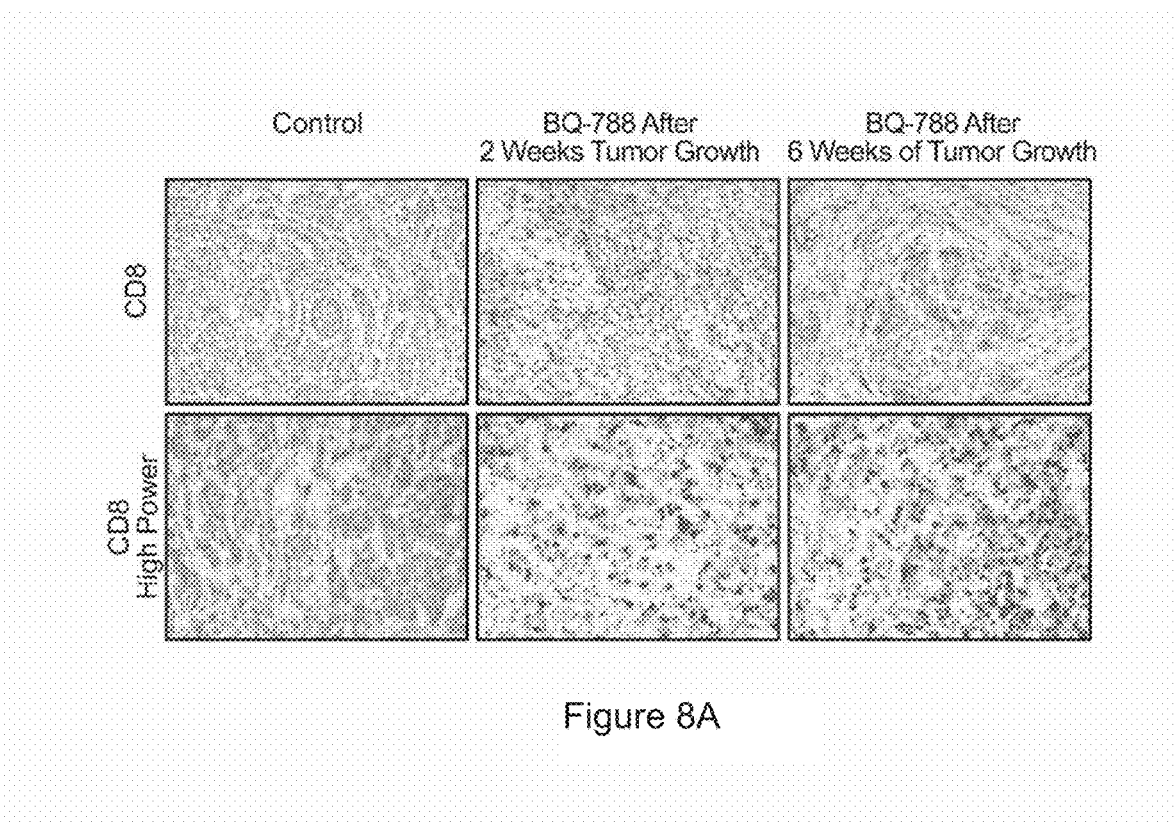
FIG. 8A. IHC demonstrating few intratumoral CD8 positive cells in vaccinated control animals (left panels) but significant numbers of $CD8^+$ T cells after early or delayed administration of BQ788 (middle and left panels).
Figure 8B:
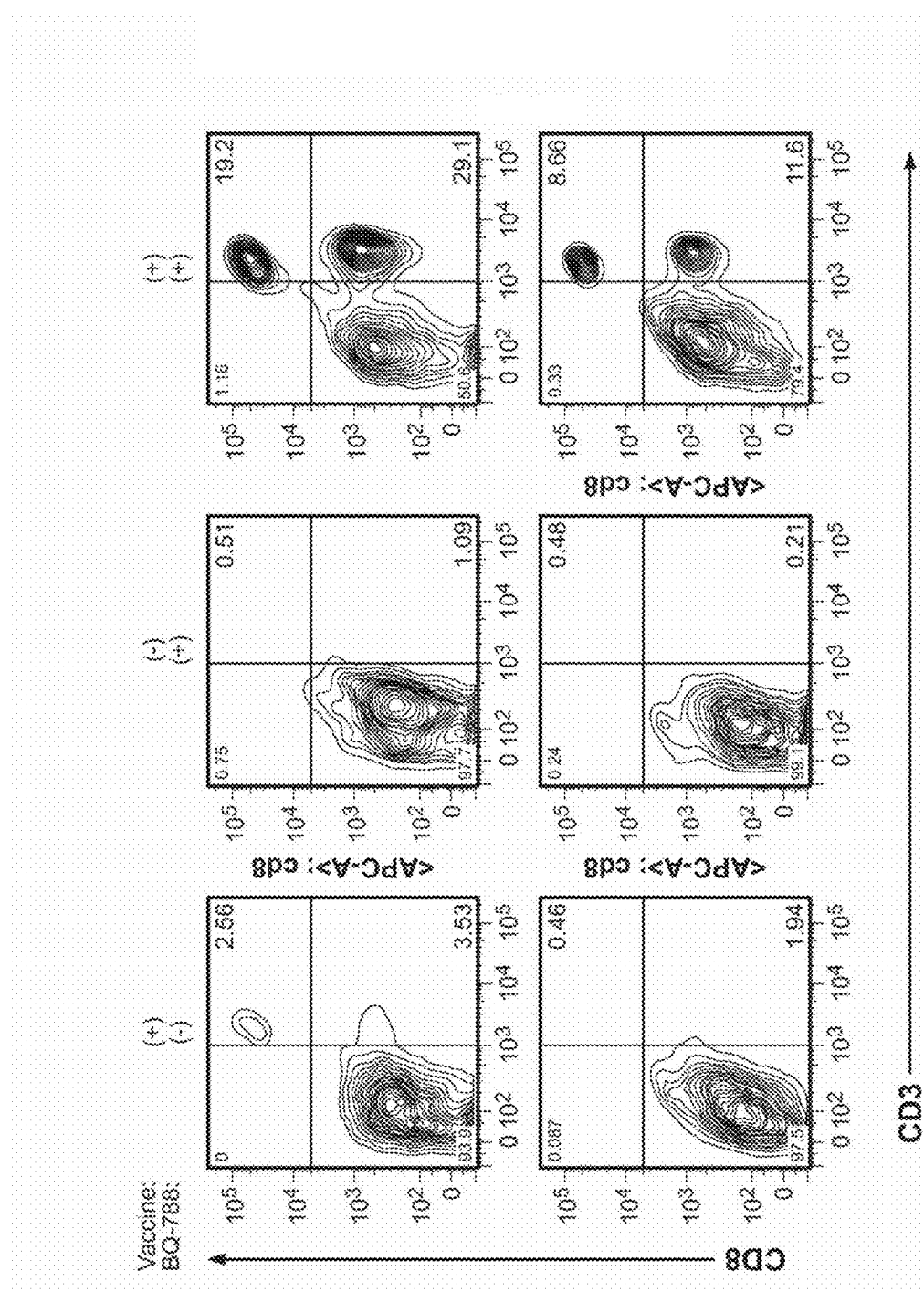
FIG. 8B FACS analysis demonstrating increased numbers of $CD3^+$, $CD8^+$ T cells in BQ788 treated animals as compared to control animals.
Figure 8C:
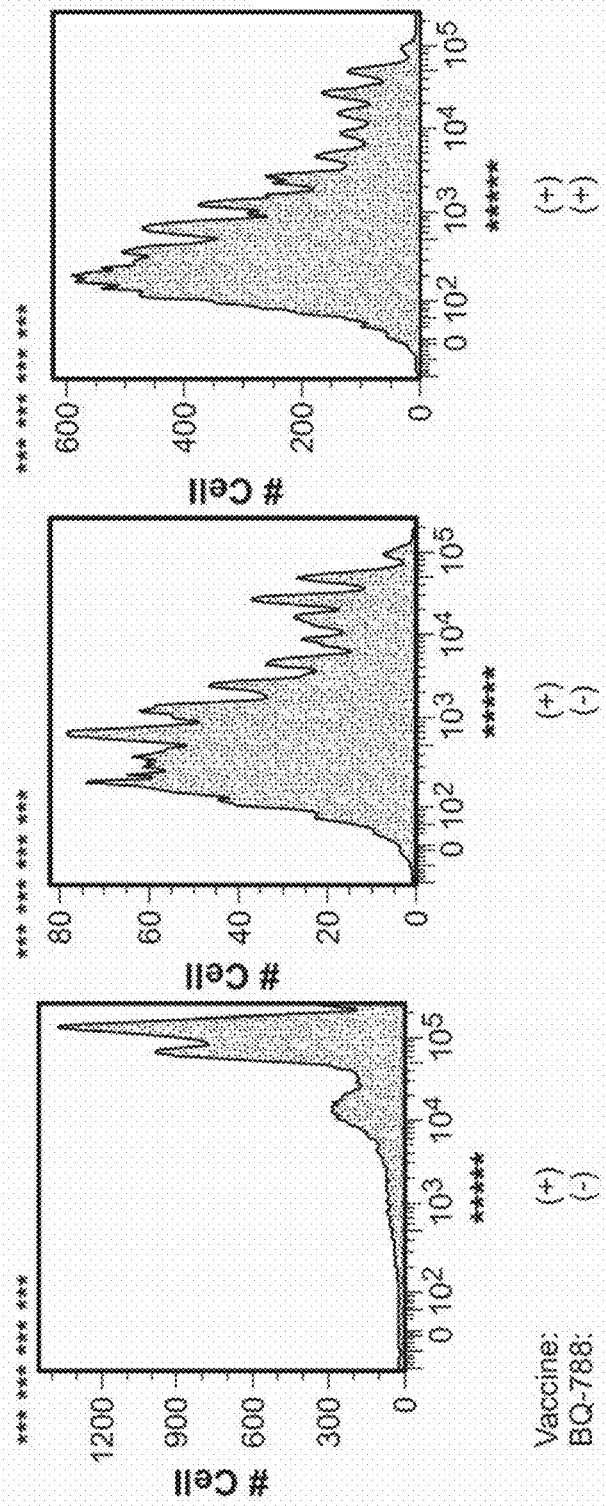
FIG. 8C. T cell proliferation assay in response to ID8 pulsed dendritic cells from vaccinated-BQ788 treated animals or controls.
Figure 8D:
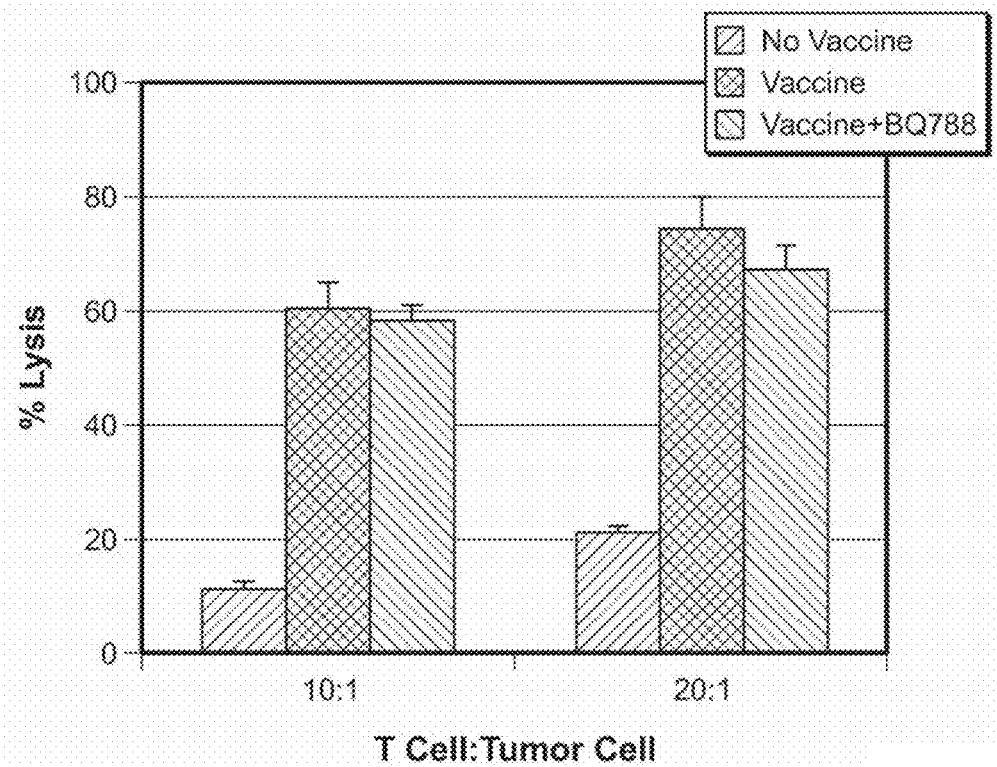
FIG. 8D. Cytotoxic T lymphocyte assay demonstrating the ability of $CD8^+$ splenocytes from vaccinated control and BQ788 vaccinated animals to lyse ID8 cells.
Figure 8E:
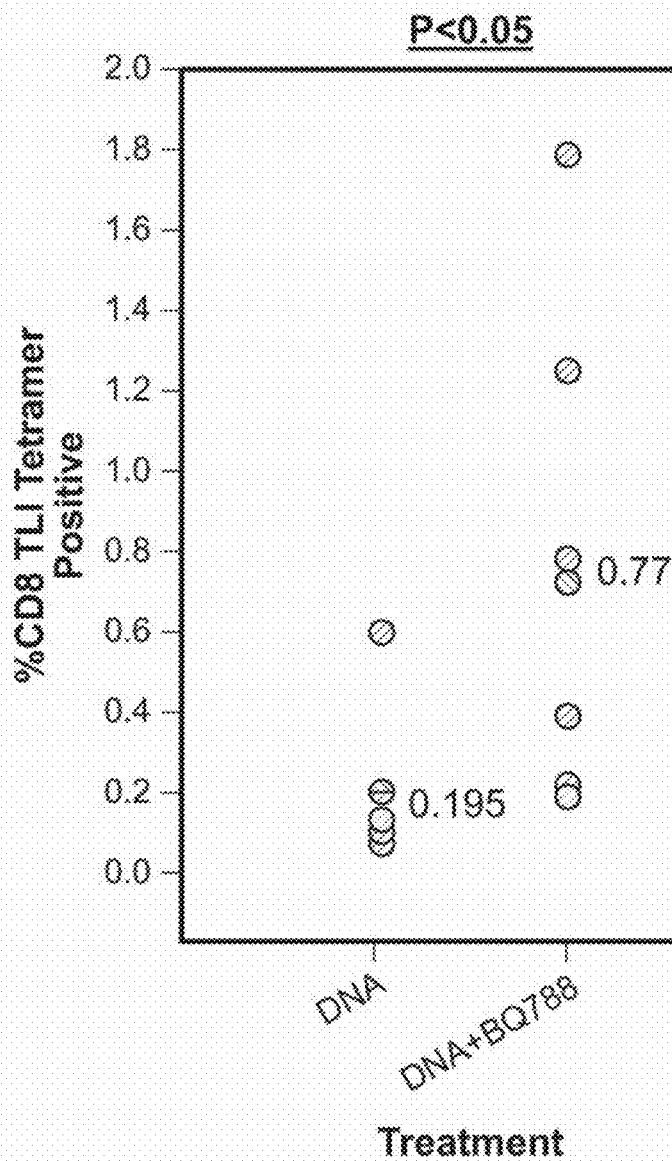
FIG. 8E. A graph showing flow cytometric quantification of total $CD8^+$tetramer+ cells in TC-1 tumors from a mouse treated with vaccine plus BQ-788 or vaccine alone. F. Shows ascites development in vaccinated animals treated with BQ-788 and animals treated with control peptide.

To confirm that ETRB plays a role in inhibiting T cell homing to human ovarian cancers, the ID8 syngeneic mouse model of ovarian cancer was utilized. This model responds modestly to potent dendritic cell (DC) vaccination. Strong expression of ETRB was detected in tumor endothelium in ID8 flank tumors by IHC (FIG. 7). Mice were vaccinated with a suboptimal preventive vaccine, containing UV-treated ID8 cells, which results in induction of systemic tumor-reactive interferon-gamma secreting T cells without significant delay in tumor growth Following vaccination, mice were inoculated with flank tumors, which were allowed to engraft for 2 or 5 weeks, and then mice were treated i.p. with the ETRB antagonist peptide, BQ-788, SKRGRRPGAKALSRVREDIVE (SEQ ID No: 90), every $2^{nd}$ day for 2 weeks or with control peptide that was a scrambled version of the above peptide. Additional controls included non-vaccinated animals treated with BQ-788 or control peptide. To confirm that the above vaccination scheme results in significant increase in the frequency of systemic tumor-reactive T cells, $CD3^+/CD8^+$ splenocytes from vaccinated animals treated with BQ-788 or control peptide, and from non-vaccinated mice, were labeled with CFSE and incubated with DC pulsed with UV-radiated ID8 for 6 days to assess proliferation. T cells from non-vaccinated animals showed minimal proliferation, while T cells from vaccinated animals exhibited robust proliferation, confirming the presence of anti-tumor T cells in these animals (FIG. 8C). Proliferation of lymphocytes from vaccinated mice treated with BQ-788 or control peptide was similar. Similarly, in CTL assays, $CD3^+/CD8^+$ splenocytes from vaccinated animals treated with BQ-788 or control peptide exhibited robust ID8 cell killing, while $CD3^+/CD8^+$ splenocytes from non-immunized mice exhibited no killing (FIG. 8D).

Treatment of vaccinated mice with BQ-788, starting at 2 or at 5 weeks, led to significant reduction in tumor growth (FIG. 6 B, FIG. 7). Tumor growth delay was not observed in non-vaccinated mice treated with BQ-788 or in vaccinated mice treated with control peptide. Tumors from vaccinated mice treated with BQ-788 exhibited areas with very strong infiltration by $CD8^+$ T cells. In contrast, non-vaccinated animals treated with BQ-788 as well as vaccinated animals treated with control peptide exhibited scarce intratumoral $CD8^+$ T cells (FIG. 8). Flow cytometry from mechanically dissected tumors confirmed the results observed with IHC: In non-vaccinated animals treated with BQ-788 as well as in vaccinated animals treated with control peptide, $CD3^+$ cells represented on average 4% of the cells (range 0.5 to 12%), while vaccinated animals treated with BQ-788, $CD3^+$ cells represented 15% of the cells (range 8 to 30%), containing both $CD4^+$ and $CD8^+$ cells (FIG. 8).

Figure 8F:
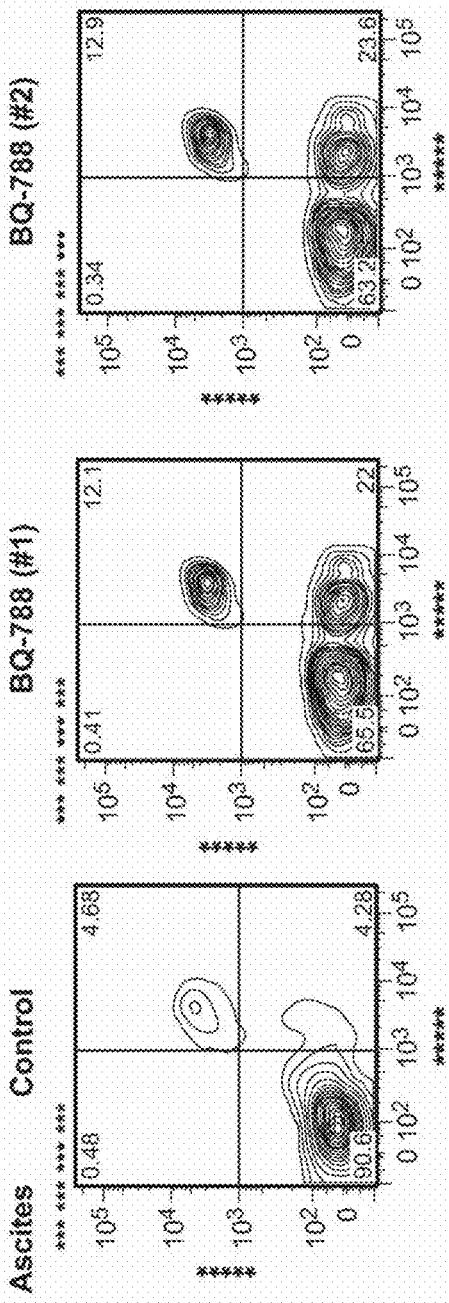
FIG. 8. ETRB inhibition leads to increased $CD8^+$ T-cell infiltration into tumors.

The impact of BQ-788 on survival in vaccinated animals was also tested in the orthotopic, intraperitoneal ID8 model of ovarian cancer. Following vaccination, mice were injected i.p. with ID8 cells. Two weeks later, animals received either BQ-788 or control peptide every $2^{nd}$ day for 2 weeks. Vaccinated animals treated with BQ-788 developed ascites later than vaccinated animals treated with control peptide and exhibited a significant prolongation of survival (FIG. 8F). Thus, systemic administration of an ETRB antagonist markedly enhances the ability of effector cells, previously induced through vaccination, to home to tumors and exert rejection.

EXAMPLE 6

ETRB Blockade Upregulates Endothelial ICAM-1

Figure 9A:
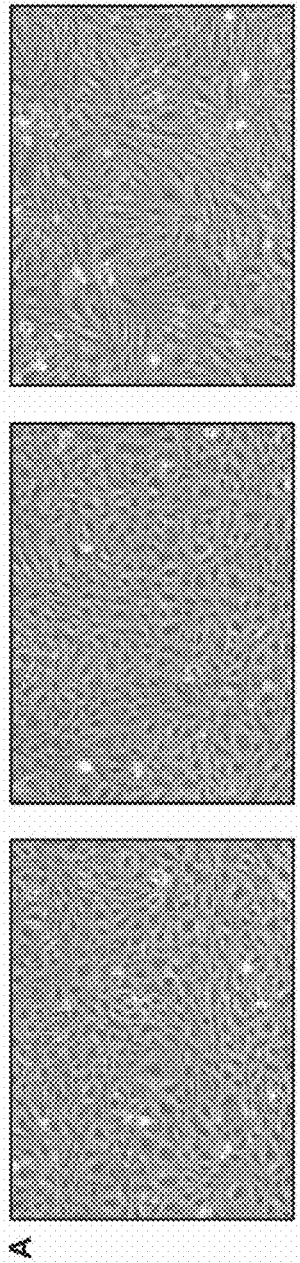
FIG. 9A. Morphologic changes observed in BQ788-treated HUVEC in the presence of Endothelin, as compared to Endothelin only or Endothelin plus BQ123 treated HUVEC.
Figure 9B:
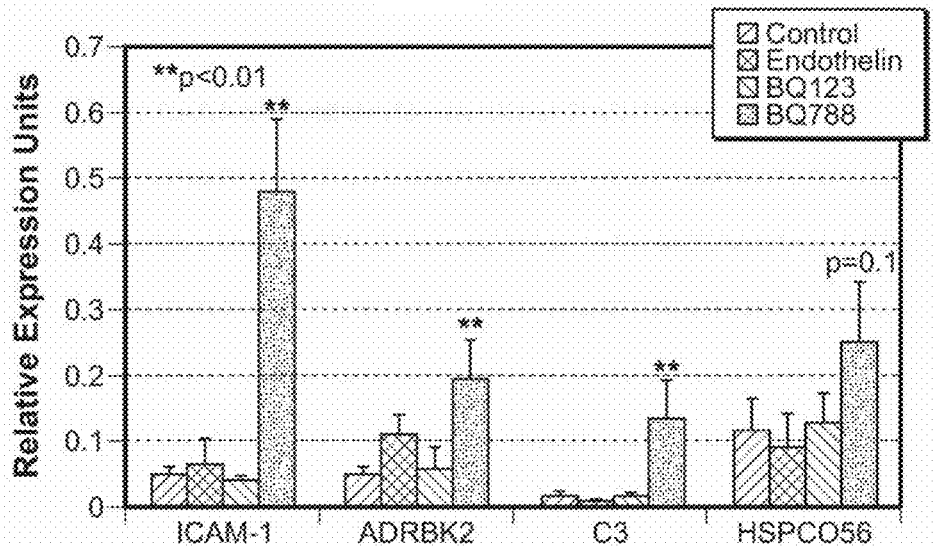
FIG. 9B. qRTPCR demonstrating increased expression of ICAM1 and decreased expression of VE-Cadherin in Endothelin+BQ788-treated HUVEC as compared to Endothelin alone, Endothelin+BQ788, or BQ788 alone treated HUVEC.
Figure 9C:
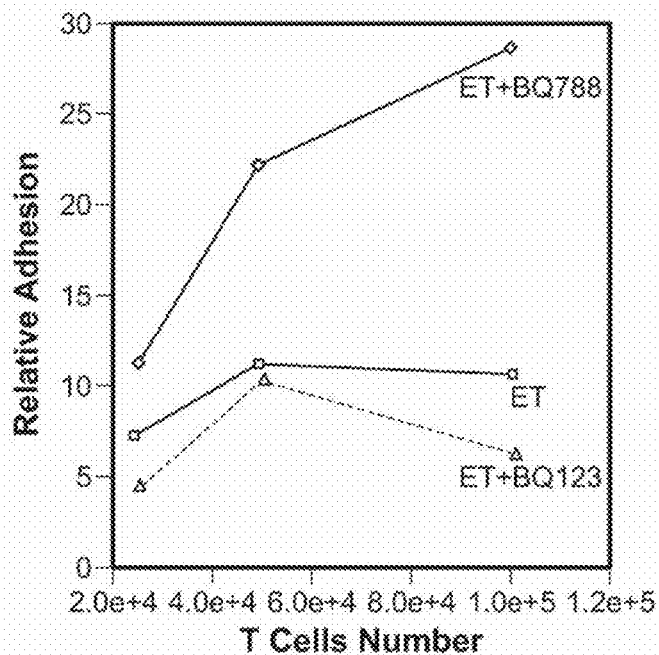
FIG. 9C. Demonstration of an increased ability of T cells to adhere to Endothelin+BQ788-treated HUVEC.

Next, the effect of BQ-788 on human and murine endothelial cells or T cells was tested in the presence or absence of ET-1 ligand. In addition, the effect of endothelin receptor A antagonist BQ123 was tested. Treatment of HUVEC with BQ-788 in the presence of Endothelin led to a distinct morphological change in the HUVEC cells (FIG. 9). In addition, qRT-PCR demonstrated over 7-fold increased expression of the ICAM-1 mRNA in HUVEC treated with Endothelin and BQ-788 compared to untreated HUVEC or HUVEC in the presence of Endothelin alone, or Endothelin plus the ETRA antagonist. Moreover, there was a decrease in the expression of VE-Cadherin mRNA in BQ788-treated cells (FIG. 9). No specific changes were detected in mRNA levels for ICAM-2, ICAM-3, E-selectin, JAM, CXCL-11, CCL-19, or CCL-21.

The ability of activated T cells to adhere to BQ-788-treated HUVEC was also tested. Human T cells activated with either PMA or CD3/CD28 cross-linking exhibited increased adherence to HUVEC treated with Endothelin in the presence of BQ-788, compared to HUVEC treated with Endothelin alone, or treated with Endothelin and ETRA antagonist, or untreated HUVEC (FIG. 9). T cell adherence to BQ788/Endothelin-treated HUVEC was 40% as effective as TNF-alpha activation of HUVEC. Thus, under the conditions utilized, BQ788 induces expression of ICAM-1 on endothelial cells and leads to increased T cell adhesion to tumor endothelium, playing a role in its increase of intratumoral T cells and enhancement of vaccine efficacy.

To further test the role of ETRB signaling in adhesion, the effects of NO antagonist L-NAME and NO donor DETANO were tested under the above experimental conditions. L-NAME restored T cell adhesion to HUVEC in the presence of TNF- and ET-1, while DETANO mimicked the effects of ET-1. Thus, ET-1, through ETRB, downregulates the ability of endothelium to respond to inflammatory signals present in the tumor microenvironment such as TNF-α, which is restored by blocking ETRB through BQ788. Further, an NO antagonist abrogated the effects of ET-1, while NO donor reproduced its effect, showing that NO plays a role in the inhibitory effect of ET-1. To further test whether ETRB signaling upregulates NO in endothelial cells, reactive oxidative species (ROS) were quantified in HUVEC. Exposure of HUVEC to rhET-1 upregulated ROS, while addition of BQ788 abrogated such response to ET-1. Suppression of ROS by BQ788 was as potent as bacterial LPS.

What is claimed is:

1. A method of enhancing an efficacy of a vaccine immunotherapy for a solid tumor expressing Endothelin B receptor (ETRB) in a subject, comprising the step of administering to said subject a therapeutically effective amount of a tumor cell-based vaccine that induces systemic tumor-reactive interferon-gamma secreting T cells; and administering to said vaccinated subject a therapeutically effective amount of an Endothelin B receptor (ETRB) inhibitor, and wherein said inhibitor is BQ788; Bosentan; tezosentan, or an antibody, thereby enhancing the efficacy of the vaccine immunotherapy for the solid tumor in said subject.

2. The method of claim 1, wherein said inhibitor is BQ788.

* * * * *

UNITED STATES PATENT AND TRADEMARK OFFICE
CERTIFICATE OF CORRECTION

PATENT NO. : 10,174,120 B2
APPLICATION NO. : 15/001241
DATED : January 8, 2019
INVENTOR(S) : Ronald J Buckanovich et al.

Page 1 of 1

It is certified that error appears in the above-identified patent and that said Letters Patent is hereby corrected as shown below:

In the Specification

Replace the paragraph in Column 1, Lines 18-22 with the following paragraph:
This invention was made with government support under grant numbers CA098951, CA083638, HD043459 and TW000671 awarded by the National Institutes of Health. The government has certain rights in the invention.

Signed and Sealed this
Sixteenth Day of July, 2019

Andrei Iancu
*Director of the United States Patent and Trademark Office*

```
                        SEQUENCE LISTING

<160> NUMBER OF SEQ ID NOS: 89

<210> SEQ ID NO 1
<211> LENGTH: 442
<212> TYPE: PRT
<213> ORGANISM: Homo sapiens

<400> SEQUENCE: 1

Met Gln Pro Pro Ser Leu Cys Gly Arg Ala Leu Val Ala Leu Val
1               5                   10                  15

Leu Ala Cys Gly Leu Ser Arg Ile Trp Gly Glu Arg Gly Phe Pro
                20                  25                  30

Pro Asp Arg Ala Thr Pro Leu Leu Gln Thr Ala Glu Ile Met Thr Pro
            35                  40                  45

Pro Thr Lys Thr Leu Trp Pro Lys Gly Ser Asn Ala Ser Leu Ala Arg
        50                  55                  60

Ser Leu Ala Pro Ala Glu Val Pro Lys Gly Asp Arg Thr Ala Gly Ser
65                  70                  75                  80

Pro Pro Arg Thr Ile Ser Pro Pro Cys Gln Gly Pro Ile Glu Ile
                85                  90                  95

Lys Glu Thr Phe Lys Tyr Ile Asn Thr Val Val Ser Cys Leu Val Phe
                100                 105                 110

Val Leu Gly Ile Ile Gly Asn Ser Thr Leu Leu Arg Ile Ile Tyr Lys
            115                 120                 125

Asn Lys Cys Met Arg Asn Gly Pro Asn Ile Leu Ile Ala Ser Leu Ala
        130                 135                 140

Leu Gly Asp Leu Leu His Ile Val Ile Asp Ile Pro Ile Asn Val Tyr
145                 150                 155                 160

Lys Leu Leu Ala Glu Asp Trp Pro Phe Gly Ala Glu Met Cys Lys Leu
                165                 170                 175

Val Pro Phe Ile Gln Lys Ala Ser Val Gly Ile Thr Val Leu Ser Leu
                180                 185                 190

Cys Ala Leu Ser Ile Asp Arg Tyr Arg Ala Val Ala Ser Trp Ser Arg
            195                 200                 205

Ile Lys Gly Ile Gly Val Pro Lys Trp Thr Ala Val Glu Ile Val Leu
        210                 215                 220

Ile Trp Val Val Ser Val Val Leu Ala Val Pro Glu Ala Ile Gly Phe
225                 230                 235                 240

Asp Ile Ile Thr Met Asp Tyr Lys Gly Ser Tyr Leu Arg Ile Cys Leu
                245                 250                 255

Leu His Pro Val Gln Lys Thr Ala Phe Met Gln Phe Tyr Lys Thr Ala
```

```
            260                 265                 270
Lys Asp Trp Trp Leu Phe Ser Phe Tyr Phe Cys Leu Pro Leu Ala Ile
            275                 280                 285

Thr Ala Phe Phe Tyr Thr Leu Met Thr Cys Glu Met Leu Arg Lys Lys
        290                 295                 300

Ser Gly Met Gln Ile Ala Leu Asn Asp His Leu Lys Gln Arg Arg Glu
305                 310                 315                 320

Val Ala Lys Thr Val Phe Cys Leu Val Leu Val Phe Ala Leu Cys Trp
                325                 330                 335

Leu Pro Leu His Leu Ser Arg Ile Leu Lys Leu Thr Leu Tyr Asn Gln
            340                 345                 350

Asn Asp Pro Asn Arg Cys Glu Leu Leu Ser Phe Leu Leu Val Leu Asp
        355                 360                 365

Tyr Ile Gly Ile Asn Met Ala Ser Leu Asn Ser Cys Ile Asn Pro Ile
370                 375                 380

Ala Leu Tyr Leu Val Ser Lys Arg Phe Lys Asn Cys Phe Lys Ser Cys
385                 390                 395                 400

Leu Cys Cys Trp Cys Gln Ser Phe Glu Glu Lys Gln Ser Leu Glu Glu
                405                 410                 415

Lys Gln Ser Cys Leu Lys Phe Lys Ala Asn Asp His Gly Tyr Asp Asn
                420                 425                 430

Phe Arg Ser Ser Asn Lys Tyr Ser Ser
            435                 440

<210> SEQ ID NO 2
<211> LENGTH: 212
<212> TYPE: PRT
<213> ORGANISM: Homo sapiens

<400> SEQUENCE: 2

Met Asp Tyr Leu Leu Met Ile Phe Ser Leu Leu Phe Val Ala Cys Gln
1               5                   10                  15

Gly Ala Pro Glu Thr Ala Val Leu Gly Ala Glu Leu Ser Ala Val Gly
            20                  25                  30

Glu Asn Gly Gly Glu Lys Pro Thr Pro Ser Pro Trp Arg Leu Arg
        35                  40                  45

Arg Ser Lys Arg Cys Ser Cys Ser Ser Leu Met Asp Lys Glu Cys Val
    50                  55                  60

Tyr Phe Cys His Leu Asp Ile Ile Trp Val Asn Thr Pro Glu His Val
65                  70                  75                  80

Val Pro Tyr Gly Leu Gly Ser Pro Arg Ser Lys Arg Ala Leu Glu Asn
                85                  90                  95

Leu Leu Pro Thr Lys Ala Thr Asp Arg Glu Asn Arg Cys Gln Cys Ala
            100                 105                 110

Ser Gln Lys Asp Lys Lys Cys Trp Asn Phe Cys Gln Ala Gly Lys Glu
        115                 120                 125

Leu Arg Ala Glu Asp Ile Met Glu Lys Asp Trp Asn Asn His Lys Lys
    130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu Glu His Leu Arg Gln
                165                 170                 175

Thr Arg Ser Glu Thr Met Arg Asn Ser Val Lys Ser Ser Phe His Asp
            180                 185                 190
```

Pro Lys Leu Lys Gly Asn Pro Ser Arg Glu Arg Tyr Val Thr His Asn
            195                 200                 205

Arg Ala His Trp
    210

<210> SEQ ID NO 3
<211> LENGTH: 571
<212> TYPE: DNA
<213> ORGANISM: Homo sapiens
<220> FEATURE:
<221> NAME/KEY: misc_feature
<222> LOCATION: (400)..(400)
<223> OTHER INFORMATION: n is a, c, g, or t
<220> FEATURE:
<221> NAME/KEY: misc_feature
<222> LOCATION: (520)..(520)
<223> OTHER INFORMATION: n is a, c, g, or t

<400> SEQUENCE: 3
tttgtcttta atgtctttgt ttagttattc tcttctcctg tctctcctgc acgctcctcc    60
ctttccactt ctttcttctc tcttcgggcc tccccgtggg aacctaatgt atacgaaaat   120
ctagtggtgc ctccagctgt attttcccat gaatgcttta ttgactttgc ttcaagcctt   180
tcaaatggca tctggtgctt acctgtgaga catcccacct gacctgccag ataaagacga   240
ttaaccctat tttgaaactg agataaacct ggcttggaaa agtttaccta ccccaaggtc   300
tcagcactaa gtaatttaac taggactcga acccaggcag cgactcctga ctgcttaaga   360
cggcatggta agaagcaggt ccagaagtcg agagacctgn gtgtgcaagt tcctagggga   420
tgccaagaac gagagaaggg ggagcaagtg tctctgtgaa gggagtgtaa agacacagaa   480
gtgaaccgga gccgcagagc cctgtgagag aaggcatgan aatgtgtcct tgtgtccatg   540
agccgaaaac atgacaagga ttaagccaca g                                   571

<210> SEQ ID NO 4
<211> LENGTH: 1594
<212> TYPE: DNA
<213> ORGANISM: Homo sapiens

<400> SEQUENCE: 4
cagacggcgg agagcagaga gggagcgcgc cttggctcgc tggccttggc ggcggctcct    60
caggagagct ggggcgccca cgagaggatc cctcacccgg gtctctcctc agggatgaca   120
tcatccgtcc acctccttgt cttcaaggac cacctcctct ccatgctgag ctgctgccaa   180
ggggcctgct gcccatctac acctcacgag ggcactagga gcacggtttc ctggatccca   240
ccaacataca aagcagccac tcactgaccc ccaggaccag gatggcaaag gatgaagagg   300
accggaactg accagccagc tgtccctctt acctaaagac ttaaaccaat gcccagtga   360 gggggcattg ggcattaagc cctgaccttt gctatgctca tactttgact ctatgagtac   420
tttcctataa gtctttgctt gtgttcacct gctagcaaac tggagtgttt ccctccccaa   480
gggggtgtca gtctttgtcg actgactctg tcatcaccct tatgatgtcc tgaatggaag   540 gatcccttg gaaattctca ggaggggac ctgggccaag gcttggcca gcatcctgct    600 gcaactccaa ggccctgggt gggcttctgg aatgagcatg ctactgaatc accaaaggca   660
cgccccacct ctctgaagat cttcctatcc ttttctgggg aatgggggtc gatgagagca   720
acctcctagg gttgttgtga gaattaaatg agataaaaga ggcctcaggc aggatctggc   780
atagaggagg tgatcagcaa atgtttgttg aaaaggtttg acaggtcagt cccttcccac   840
ccctcttgct tgtcttactt gtcttattta ttctccaaca gcactccagg cagcccttgt   900

-continued

```
ccacgggctc tccttgcatc agccaagctt cttgaaaggc ctgtctacac ttgctgtctt      960
ccttcctcac ctccaatttc ctcttcaacc cactgcttcc tgactcgctc tactccgtgg     1020
aagcacgctc acaaaggcac gtgggcgtgg cccggctggg tcggctgaag aactgcggat     1080
ggaagctgcg gaagagccct gatggggccc accatcccgg acccaagtct tcttcctggc     1140
gggcctctcg tctccttcct ggtttgggcg gaagccatca cctggatgcc tacgtgggaa     1200
gggacctcga atgtgggacc ccagcccctc tccagctcga atccctcca cagccacggg      1260 gacaccctgc acctattccc acgggacagg ctggacccag agactctgga cccggggcct    1320 cccccttgagt agagacccgc cctctgactg atggacgccg tgacctgggg tcagacccgt    1380
gggctggacc cctgcccacc ccgcaggaac cctgaggcct aggggagctg ttgagccttc     1440
agtgtctgca tgtgggaagt gggctccttc acctacctca cagggctgtt gtgaggggcg     1500
ctgtgatgcg gttccaaagc acagggcttg gcgcacccca ctgtgctctc aataaatgtg    1560
tttcctgtct taacaaaaaa aaaaaaaaaa aaaa                                 1594
```

<210> SEQ ID NO 5
<211> LENGTH: 68
<212> TYPE: PRT
<213> ORGANISM: Homo sapiens

<400> SEQUENCE: 5

```
Met Asp Gln Val Met Gln Phe Val Glu Pro Ser Arg Gln Phe Val Lys
1               5                   10                  15

Asp Ser Ile Arg Leu Val Lys Arg Cys Thr Lys Pro Asp Arg Lys Glu
            20                  25                  30

Phe Gln Lys Ile Ala Met Ala Thr Ala Ile Gly Phe Ala Ile Met Gly
        35                  40                  45

Phe Ile Gly Phe Phe Val Lys Leu Ile His Ile Pro Ile Asn Asn Ile
    50                  55                  60

Ile Val Gly Gly
65
```

<210> SEQ ID NO 6
<211> LENGTH: 799
<212> TYPE: DNA
<213> ORGANISM: Homo sapiens
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t

<400> SEQUENCE: 6

```
ctcagctgtt tttaaatgaa tgtgtgtgag gaacagatgg gaaagttggg agatctgtct    60
acagagaagc aaagttgtgg ttctcttgct aacttcaagg tgaggacat tgggcaccct    120
aagtttggga acttggttga taaatacgta tatggtccat tccataaatc agtggtgagt   180
gactggcctg ggttctagac ctctgggaac cagcacctga gtcacagctg tctaggcctc   240
ggtgctggcc tgggttctag atctctggga accagtgcct gagtcacagc tgtcagtgca   300
gccatttgcc cagggctgct cccgaggggg atgatgggaa attcagcagt gtagactcac   360
tttaaacaag ctccggtgat cctgaaatgc tgaagatcgt gtaggtgggt tgtggggtca   420
gcagagctgc cattctgccc acgtctggaa acaacacac ggtgagtcac cgttggccat    480
gagatctccc cacttaaagg tgctgtgagc ttgtctctaa gatatatacc tcttcctttt   540
gtcttttgct gtaagtttga ccttttgcag atctgatgaa aatacaacct cttattgtat   600
agtttgcctg attataagcc atagtaaatc gagctgttcg cattttttgca ggccttgcat   660
tttcnactgg gaggttcatc aaaccttcca cttagcaata gncctgaact caggcagnat   720
gcncccataa attagccttc caaagaaaaa tgcacgctca gaanaattn tgaaggggca    780
gaaccttatg ccgacaagg                                                799
```

```
<210> SEQ ID NO 7
<211> LENGTH: 456
<212> TYPE: PRT
<213> ORGANISM: Homo sapiens

<400> SEQUENCE: 7

Met Gly Asn Ser Arg Ser Arg Val Gly Arg Ser Phe Cys Ser Gln Phe
1               5                   10                  15
Leu Pro Glu Glu Gln Ala Glu Ile Asp Gln Leu Phe Asp Ala Leu Ser
            20                  25                  30
Ser Asp Lys Asn Ser Pro Asn Val Ser Lys Ser Phe Ser Leu Lys
        35                  40                  45
Ala Leu Gln Asn His Val Gly Glu Ala Leu Pro Pro Glu Met Val Thr
    50                  55                  60
Arg Leu Tyr Asp Gly Met Arg Arg Val Asp Leu Thr Gly Lys Ala Lys
65                  70                  75                  80
Gly Pro Ser Glu Asn Val Ser Gln Glu Gln Phe Thr Ala Ser Met Ser
                85                  90                  95
His Leu Leu Lys Gly Asn Ser Glu Glu Lys Ser Leu Met Ile Met Lys
            100                 105                 110
Met Ile Ser Ala Thr Glu Gly Pro Val Lys Ala Arg Glu Val Gln Lys
        115                 120                 125
Phe Thr Glu Asp Leu Val Gly Ser Val Val His Val Leu Ser His Arg
    130                 135                 140
Gln Glu Leu Arg Gly Trp Thr Gly Lys Glu Ala Pro Gly Pro Asn Pro
145                 150                 155                 160
Arg Val Gln Val Leu Ala Ala Gln Leu Leu Ser Glu Met Lys Leu Gln
                165                 170                 175
Asp Gly Lys Arg Leu Leu Gly Pro Gln Trp Leu Asp Tyr Asp Cys Asp
            180                 185                 190
Arg Ala Val Ile Glu Asp Trp Val Phe Arg Val Pro His Val Ala Ile
        195                 200                 205
Phe Leu Ser Val Val Ile Cys Lys Gly Phe Leu Val Leu Cys Ser Ser
    210                 215                 220
```

-continued

Leu Asp Leu Thr Thr Leu Val Pro Glu Arg Gln Val Asp Gln Gly Arg
225                 230                 235                 240

Gly Phe Glu Ser Ile Leu Asp Val Leu Ser Val Met Tyr Ile Asn Ala
            245                 250                 255

Gln Leu Pro Arg Glu Gln Arg His Arg Trp Arg Leu Leu Phe Ser Ser
        260                 265                 270

Glu Leu His Gly His Ser Phe Ser Gln Leu Cys Gly His Ile Thr His
    275                 280                 285

Arg Gly Pro Cys Val Ala Val Leu Glu Asp His Asp Lys His Val Phe
290                 295                 300

Gly Gly Phe Ala Ser Cys Ser Trp Glu Val Lys Pro Gln Phe Gln Gly
305                 310                 315                 320

Asp Asn Arg Cys Phe Leu Phe Ser Ile Cys Pro Ser Met Ala Val Tyr
            325                 330                 335

Thr His Thr Gly Tyr Asn Asp His Tyr Met Tyr Leu Asn His Gly Gln
        340                 345                 350

Gln Thr Ile Pro Asn Gly Leu Gly Met Gly Gln His Asn Tyr Phe
    355                 360                 365

Gly Leu Trp Val Asp Val Asp Phe Gly Lys Gly His Ser Arg Ala Lys
370                 375                 380

Pro Thr Cys Thr Thr Tyr Asn Ser Pro Gln Leu Ser Ala Gln Glu Asn
385                 390                 395                 400

Phe Gln Phe Asp Lys Met Glu Val Trp Ala Val Gly Asp Pro Ser Glu
            405                 410                 415

Glu Gln Leu Ala Lys Gly Asn Lys Ser Ile Leu Asp Ala Asp Pro Glu
        420                 425                 430

Ala Gln Ala Leu Leu Glu Ile Ser Gly His Ser Arg His Ser Glu Gly
    435                 440                 445

Leu Arg Glu Val Pro Asp Asp Glu
450                 455

<210> SEQ ID NO 8
<211> LENGTH: 396
<212> TYPE: PRT
<213> ORGANISM: Homo sapiens

<400> SEQUENCE: 8

Met Thr Thr Leu Val Leu Asp Asn Gly Ala Tyr Asn Ala Lys Ile Gly
1               5                   10                  15

Tyr Ser His Glu Asn Val Ser Val Ile Pro Asn Cys Gln Phe Arg Ser
            20                  25                  30

Lys Thr Ala Arg Leu Lys Thr Phe Thr Ala Asn Gln Ile Asp Glu Ile
        35                  40                  45

Lys Asp Pro Ser Gly Leu Phe Tyr Ile Leu Pro Phe Gln Lys Gly Tyr
    50                  55                  60

Leu Val Asn Trp Asp Val Gln Arg Gln Val Trp Asp Tyr Leu Phe Gly
65                  70                  75                  80

Lys Glu Met Tyr Gln Val Asp Phe Leu Asp Thr Asn Ile Ile Thr
            85                  90                  95

Glu Pro Tyr Phe Asn Phe Thr Ser Ile Gln Glu Ser Met Asn Glu Ile
        100                 105                 110

Leu Phe Glu Glu Tyr Gln Phe Gln Ala Val Leu Arg Val Asn Ala Gly
    115                 120                 125

Ala Leu Ser Ala His Arg Tyr Phe Arg Asp Asn Pro Ser Glu Leu Cys
130                 135                 140

```
Cys Ile Ile Val Asp Ser Gly Tyr Ser Phe Thr His Ile Val Pro Tyr
145                 150                 155                 160

Cys Arg Ser Lys Lys Lys Glu Ala Ile Ile Arg Ile Asn Val Gly
            165                 170                 175

Gly Lys Leu Leu Thr Asn His Leu Lys Glu Ile Ile Ser Tyr Arg Gln
            180                 185                 190

Leu His Val Met Asp Glu Thr His Val Ile Asn Gln Val Lys Glu Asp
            195                 200                 205

Val Cys Tyr Val Ser Gln Asp Phe Tyr Arg Asp Met Asp Ile Ala Lys
            210                 215                 220

Leu Lys Gly Glu Glu Asn Thr Val Met Ile Asp Tyr Val Leu Pro Asp
225                 230                 235                 240

Phe Ser Thr Ile Lys Lys Gly Phe Cys Lys Pro Arg Glu Glu Met Val
                245                 250                 255

Leu Ser Gly Lys Tyr Lys Ser Gly Glu Gln Ile Leu Arg Leu Ala Asn
                260                 265                 270

Glu Arg Phe Ala Val Pro Glu Ile Leu Phe Asn Pro Ser Asp Ile Gly
            275                 280                 285

Ile Gln Glu Met Gly Ile Pro Glu Ala Ile Val Tyr Ser Ile Gln Asn
            290                 295                 300

Leu Pro Glu Glu Met Gln Pro His Phe Phe Lys Asn Ile Val Leu Thr
305                 310                 315                 320

Gly Gly Asn Ser Leu Phe Pro Gly Phe Arg Asp Arg Val Tyr Ser Glu
                325                 330                 335

Val Arg Cys Leu Thr Pro Thr Asp Tyr Asp Val Ser Val Val Leu Pro
                340                 345                 350

Glu Asn Pro Ile Thr Tyr Ala Trp Glu Gly Gly Lys Leu Ile Ser Glu
            355                 360                 365

Asn Asp Asp Phe Glu Asp Met Val Val Thr Arg Glu Asp Tyr Glu Glu
370                 375                 380

Asn Gly His Ser Val Cys Glu Glu Lys Phe Asp Ile
385                 390                 395

<210> SEQ ID NO 9
<211> LENGTH: 2106
<212> TYPE: DNA
<213> ORGANISM: Homo sapiens

<400> SEQUENCE: 9
tgatgattga agtatgttta ttgtaagggc agaaatgtgt tggcatttgg ataaaaaact    60
gctaacatta tagaacttat tacctaacaa aatttcacac cacaaaaaat attttaatgg   120
caaattcaag gtgttttatt gcttacaaat cagcatcttt gactctttga acatcaattt   180
gtgtttacat tgaaatgaca aaagacaaa ctaagaagaa atacagcatg caagttggaa    240
ttcagagtta aaaccatgat gttgccgctc agccagctat gtgactgttg accctttcaa   300
gaacacacat ggatttaaaa gttggatgac atccattgtt ggggccttgg gggatatggt   360
aaagcatgaa aactaaacag ccaggagcct gtgaaatctg ctactgtatt ttccaggact   420
tcattccact ccttggctaa aaaaatcttg gaagtttcac agattatgat gtggacctgt   480
cacctgtaaa ttgtctcaat ctactcagac aagacactaa actgtctttg atactatag    540 atgtcagtgc ttatagcagc tggaatttgg ctagtgacaa tgtttaaaga tgtaatacta   600
gttagtatct attgaagctt aaactttgct ggtcaggttg tagctattgt aaaagtattt   660
```

-continued

```
attgaagaag ctcacagtcc ttcagttgta cagactgaaa aactttcatg aaagatccaa    720
catactaatg taaattatat ttattacaat gtatgatatt aatgtgtcaa actggtgtat    780
tttacaaaat atataatgca tacataaata agagttgtat attacagtgc ttttcaaata    840
tcagtgtctt ggaatattta agtcttcaca ttttttggtc taaaatatga aaatgtttca    900
tgatacaagt gattaatttt ccctagtagt gcttttgcat gtttgccttt ttatttaagt    960
ttttttctat atagacacaa tttggtgtca gactatcata agatcgatag tgaatataaa   1020
atatcttagc caaatggggt ctgtattgtc tacatttat atattaaata aaagttttg    1080 ttgtcttttc aggaggttta gagtattgtc actaaatatg atcaaagctt ccctttccaa   1140
atgcaaaagt cttgtcctac atttaaagtt gatctgtcat gttttagcag tcaagtggga   1200
tgggcattat ataacaacg ttacaatgta aggaaaatct taaggagat ggggagagaa    1260 aaaggcagct ggtataatcg ttactgctg cttagttcta cttaattttt tgtgttgctt    1320
cttcttaagg tgagatagca taatcttaac tgttttgaga tggaattta aagtaacaca    1380 ctaccagcga gttcaacact gctattgatt ttaatctgtt ttttttttgt ttagttgata   1440
acttaaattc caagtttcat agtgataatt gtatattatt tggctgctga attctgttag   1500 agtttttat tctgttgtac attgtattat acacataatc acaaattaat atgaaggtga    1560
atatatgtta catatcaaaa tttgtgaatt tgaattatag tatgttttag tgctattgca   1620
aaaaatgttt atttttatat tatctgtgat tttaatatag atgattgaac tagatttctt   1680
tttgagtgat agtgccattg aatgagcagt atggaaacag tgttacttga tattttgagc   1740
tttctcaggt ttatctaaat cagtggtagc ttaacaaaac ccagactaat tgtgtgtaat   1800
tgtattttta ataaaaggaa agtacatttc ctataatagc atagtactgt ttgcatgtaa   1860
gagtatgcaa aaccttgtgt gtgtgtgtgt gtgtgtgtgt gtgtgtgtgt cttagtgtgt   1920
gtaaggcatg gcagccaact ttgtatctgc tatttttagt acgagcagag cttcataatt   1980
gtggtcacta gaactgtact taccatggac agttaaaact gaaaaagact caataaaact   2040
atgaaacatg gaaaaaaaaa aaaaaaaaa aaaaaaaaa aaaaaaaaa aaaaaaaaa       2100 aaaaaa                                                              2106
```

<210> SEQ ID NO 10
<211> LENGTH: 912
<212> TYPE: PRT
<213> ORGANISM: Homo sapiens

<400> SEQUENCE: 10

Arg Met Asp Ser Arg Pro Arg Ala Gly Cys Cys Glu Trp Leu Arg Cys
1               5                   10                  15

Cys Gly Gly Gly Glu Ala Arg Pro Arg Thr Val Trp Leu Gly His Pro
            20                  25                  30

Glu Lys Arg Asp Gln Arg Tyr Pro Arg Asn Val Ile Asn Asn Gln Lys
        35                  40                  45

Tyr Asn Phe Phe Thr Phe Leu Pro Gly Val Leu Phe Asn Gln Phe Lys
    50                  55                  60

Tyr Phe Phe Asn Leu Tyr Phe Leu Leu Ala Cys Ser Gln Phe Val
65                  70                  75                  80

Pro Glu Met Arg Leu Gly Ala Leu Tyr Thr Tyr Trp Val Pro Leu Gly
                85                  90                  95

Phe Val Leu Ala Val Thr Val Ile Arg Glu Ala Val Glu Glu Ile Arg
            100                 105                 110

-continued

```
Cys Tyr Val Arg Asp Lys Glu Val Asn Ser Gln Val Tyr Ser Arg Leu
        115                 120                 125

Thr Ala Arg Gly Thr Val Val Gly Val Val Leu Tyr Thr Gly Arg Glu
        130                 135                 140

Leu Arg Ser Val Met Asn Thr Ser Asn Pro Arg Ser Lys Ile Gly Leu
145                 150                 155                 160

Phe Asp Leu Glu Val Asn Cys Leu Thr Lys Ile Leu Phe Gly Ala Leu
                165                 170                 175

Val Val Val Ser Leu Val Met Val Ala Leu Gln His Phe Ala Gly Arg
            180                 185                 190

Trp Tyr Leu Gln Ile Ile Arg Phe Leu Leu Leu Phe Ser Asn Ile Ile
        195                 200                 205

Pro Ile Ser Leu Arg Val Asn Leu Asp Met Gly Lys Ile Val Tyr Ser
    210                 215                 220

Trp Val Ile Arg Arg Asp Ser Lys Ile Pro Gly Thr Val Val Arg Ser
225                 230                 235                 240

Ser Thr Ile Pro Glu Gln Leu Gly Arg Ile Ser Tyr Leu Leu Thr Asp
                245                 250                 255

Lys Thr Gly Thr Leu Thr Gln Asn Glu Met Ile Phe Lys Arg Leu His
            260                 265                 270

Leu Gly Thr Val Ala Tyr Gly Leu Asp Ser Met Asp Glu Val Gln Ser
        275                 280                 285

His Ile Phe Ser Ile Tyr Thr Gln Gln Ser Gln Asp Pro Pro Ala Gln
    290                 295                 300

Lys Gly Pro Thr Leu Thr Thr Lys Val Arg Arg Thr Met Ser Ser Arg
305                 310                 315                 320

Val His Glu Ala Val Lys Ala Ile Ala Leu Cys His Asn Val Thr Pro
                325                 330                 335

Val Tyr Glu Ser Asn Gly Val Thr Asp Gln Ala Glu Ala Glu Lys Gln
            340                 345                 350

Tyr Glu Asp Ser Cys Arg Val Tyr Gln Ala Ser Ser Pro Asp Glu Val
        355                 360                 365

Ala Leu Val Gln Trp Thr Glu Ser Val Gly Leu Thr Leu Val Gly Arg
    370                 375                 380

Asp Gln Ser Ser Met Gln Leu Arg Thr Pro Gly Asp Gln Ile Leu Asn
385                 390                 395                 400

Phe Thr Ile Leu Gln Ile Phe Pro Phe Thr Tyr Glu Ser Lys Arg Met
                405                 410                 415

Gly Ile Ile Val Arg Asp Glu Ser Thr Gly Glu Ile Thr Phe Tyr Met
            420                 425                 430

Lys Gly Ala Asp Val Val Met Ala Gly Ile Val Gln Tyr Asn Asp Trp
        435                 440                 445

Leu Glu Glu Glu Cys Gly Asn Met Ala Arg Glu Gly Leu Arg Val Leu
    450                 455                 460

Val Val Ala Lys Lys Ser Leu Ala Glu Glu Gln Tyr Gln Asp Phe Glu
465                 470                 475                 480

Ala Arg Tyr Val Gln Ala Lys Leu Ser Val His Asp Arg Ser Leu Lys
                485                 490                 495

Val Ala Thr Val Ile Glu Ser Leu Glu Met Glu Met Glu Leu Leu Cys
            500                 505                 510

Leu Thr Gly Val Glu Asp Gln Leu Gln Ala Asp Val Arg Pro Thr Leu
        515                 520                 525

Glu Thr Leu Arg Asn Ala Gly Ile Lys Val Trp Met Leu Thr Gly Asp
```

```
              530                 535                 540
Lys Leu Glu Thr Ala Thr Cys Thr Ala Lys Asn Ala His Leu Val Thr
545                 550                 555                 560

Arg Asn Gln Asp Ile His Val Phe Arg Leu Val Thr Asn Arg Gly Glu
                565                 570                 575

Ala His Leu Glu Leu Asn Ala Phe Arg Arg Lys His Asp Cys Ala Leu
                580                 585                 590

Val Ile Ser Gly Asp Ser Leu Glu Val Cys Leu Lys Tyr Tyr Glu Tyr
                595                 600                 605

Glu Phe Met Glu Leu Ala Cys Gln Cys Pro Ala Val Val Cys Cys Arg
            610                 615                 620

Cys Ala Pro Thr Gln Lys Ala Gln Ile Val Arg Leu Leu Gln Glu Arg
625                 630                 635                 640

Thr Gly Lys Leu Thr Cys Ala Val Gly Asp Gly Gly Asn Asp Val Ser
                645                 650                 655

Met Ile Gln Glu Ser Asp Cys Gly Val Gly Val Glu Gly Lys Glu Gly
                660                 665                 670

Lys Gln Ala Ser Leu Ala Ala Asp Phe Ser Ile Thr Gln Phe Lys His
                675                 680                 685

Leu Gly Arg Leu Leu Met Val His Gly Arg Asn Ser Tyr Lys Arg Ser
690                 695                 700

Ala Ala Leu Ser Gln Phe Val Ile His Arg Ser Leu Cys Ile Ser Thr
705                 710                 715                 720

Met Gln Ala Val Phe Ser Ser Val Phe Tyr Phe Ala Ser Val Pro Leu
                725                 730                 735

Tyr Gln Gly Phe Leu Ile Ile Gly Tyr Ser Thr Ile Tyr Thr Met Phe
                740                 745                 750

Pro Val Phe Ser Leu Val Leu Asp Lys Asp Val Lys Ser Glu Val Ala
                755                 760                 765

Met Leu Tyr Pro Glu Leu Tyr Lys Asp Leu Leu Lys Gly Arg Pro Leu
770                 775                 780

Ser Tyr Lys Thr Phe Leu Ile Trp Val Leu Ile Ser Ile Tyr Gln Gly
785                 790                 795                 800

Ser Thr Ile Met Tyr Gly Ala Leu Leu Phe Glu Ser Glu Phe Val
                805                 810                 815

His Ile Val Ala Ile Ser Phe Thr Ser Leu Ile Leu Thr Glu Leu Leu
                820                 825                 830

Met Val Ala Leu Thr Ile Gln Thr Trp His Trp Leu Met Thr Val Ala
                835                 840                 845

Glu Leu Leu Ser Leu Ala Cys Tyr Ile Ala Ser Leu Val Phe Leu His
850                 855                 860

Glu Phe Ile Asp Val Tyr Phe Ile Ala Thr Leu Ser Phe Leu Trp Lys
865                 870                 875                 880

Val Ser Val Ile Thr Leu Val Ser Cys Leu Pro Leu Tyr Val Leu Lys
                885                 890                 895

Tyr Leu Arg Arg Arg Phe Ser Pro Pro Ser Tyr Ser Lys Leu Thr Ser
                900                 905                 910

<210> SEQ ID NO 11
<211> LENGTH: 390
<212> TYPE: DNA
<213> ORGANISM: Homo sapiens

<400> SEQUENCE: 11
```

```
ggcgcagtct gttaatatag ctgggccatg tcagtgactg ttgtgtttgt ggggtcaggt    60 gggggggcatg gtatttgcaa aaaaaacaaa ttatggctaa tttattattt tgttgcagtg   120
gggttaactg taaactcatg taagagtctg tgatttcctc attggttgat ctctctctct   180
gtaatcctca ttgcaaattt tcaccaggac agcgttttt gattagaggg gagctctggc    240
acagtatact tccagatgat ttaaattctc gatgctgtga tgacacacat atgatctttc   300
gtgtttctga cgactctac tttcattgtt tgccagcgtg gctcgttgct gttgcccaat    360
aaagcttgtg tacgttctgc aaaaaaaaaa                                    390

<210> SEQ ID NO 12
<211> LENGTH: 532
<212> TYPE: DNA
<213> ORGANISM: Homo sapiens
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (478)..(478)
<223> OTHER INFORMATION: n is a, c, g, or t

<400> SEQUENCE: 12 tttttttct tcttgttttt gtgttataat tttatcttgc ttgtccctct tctctaattt    60
taatctcagt attcttttca tatctagttg gattcttcag ggcttctttt tctgacttct   120
attcccagtc tgcatgccta acttgagtga tctttcattt ccttttcttc aactttttac   180
cttctctact tttccattct cagttctcac catcccccac atgaactcta gggctctagg   240
tcataggttg ttctctaata cttcctgttc cttagggact gcatgtcttt gttcatggtt   300
ctttctttca ttgggggatt gccccctttc anctttgggg gcttccngga taaataggc    360 ttaaaaaatc acccttaact gagggggggg ccagggatac ctcanctggc tggctggctt   420
ttggtgggct cttgtggagg ggggctctgg gaatcaaccct acccataatt cttttggnaa   480 cgggggggc ttctcttcca ggaggggca ggtggtgggc tcaaggggg gg              532

<210> SEQ ID NO 13
<211> LENGTH: 844
<212> TYPE: DNA
<213> ORGANISM: Homo sapiens

<400> SEQUENCE: 13
atcactcacc ttgtctgcat ccctgggcct gtgaatgatg acagcacctg acattctgca    60
ccagctacct ctgcctccat ggcagagaaa aggccataag aacagtggaa gaggagcatg   120
gactcagact tcaaggaaga agccatttcc ccaggtcctt ccttctgcat ctcaccaccc   180
ctagttacaa ataactccat tgaacagcat ctattcagaa actatgccga ataaaaagat   240
ggtggaaggg ctcatgtggt tagcaactat gaaacagaaa taggacactc agttacaaac   300
attatctcct ttagttttc agaaaatgca tccctgattt cattcatttc agcttgaaa    360 gccagccata ttactctagt ccctaccaaa ctgctctaga aggtcatttc catttgttgt   420
gatatttaga cgcgcagact tcaggaagtt caccttttaac ttcagcattc cagatgaagt   480
```

```
ttcctgactc agtgcttttg cataaggaac tagaaaaaaa aagtaggaaa attggagatg    540
ctaaatcctc ccccatccca atgacttaaa atatgcatgt cacctttcagg ttttataatt   600 tggactgttt gtttatgtat gtacagatta aattattggt accttttgagg aacataaatg   660 cttggttcta tgtatctgct catccacgga attcactttt caggtaatga tagaatgtgt   720
taaaaccaga aaaaaaaaaa aaaatggtgt gggggggcgga aagtttaaag tggggggggcg  780 gaaagaagga agcagacggg ggagtgttca caaggggggg ggtgaacagg ggtgtcgagc    840
aacc                                                                  844
```

<210> SEQ ID NO 14
<211> LENGTH: 1441
<212> TYPE: PRT
<213> ORGANISM: Homo sapiens

<400> SEQUENCE: 14

```
Met Ser Gly Leu Gly Asp Ser Ser Asp Pro Ala Asn Pro Asp Ser
1               5                   10                  15

His Lys Arg Lys Gly Ser Pro Cys Asp Thr Leu Ala Ser Ser Thr Glu
                20                  25                  30

Lys Arg Arg Glu Gln Glu Asn Lys Tyr Leu Glu Glu Leu Ala Glu
        35                  40                  45

Leu Leu Ser Ala Asn Ile Ser Asp Ile Asp Ser Leu Ser Val Lys Pro
50                  55                  60

Asp Lys Cys Lys Ile Leu Lys Lys Thr Val Asp Gln Ile Gln Leu Met
65                  70                  75                  80

Lys Arg Met Glu Gln Glu Lys Ser Thr Thr Asp Asp Val Gln Lys
                85                  90                  95

Ser Asp Ile Ser Ser Ser Gln Gly Val Ile Glu Lys Glu Ser Leu
            100                 105                 110

Gly Pro Leu Leu Leu Glu Ala Leu Asp Gly Phe Phe Phe Val Val Asn
        115                 120                 125

Cys Glu Gly Arg Ile Val Phe Val Ser Glu Asn Val Thr Ser Tyr Leu
    130                 135                 140

Gly Tyr Asn Gln Glu Glu Leu Met Asn Thr Ser Val Tyr Ser Ile Leu
145                 150                 155                 160

His Val Gly Asp His Ala Glu Phe Val Lys Asn Leu Leu Pro Lys Ser
                165                 170                 175

Leu Val Asn Gly Val Pro Trp Pro Gln Glu Ala Thr Arg Arg Asn Ser
            180                 185                 190

His Thr Phe Asn Cys Arg Met Leu Ile His Pro Pro Asp Glu Pro Gly
        195                 200                 205

Thr Glu Asn Gln Glu Ala Cys Gln Arg Tyr Glu Val Met Gln Cys Phe
    210                 215                 220

Thr Val Ser Gln Pro Lys Ser Ile Gln Glu Asp Gly Glu Asp Phe Gln
225                 230                 235                 240

Ser Cys Leu Ile Cys Ile Ala Arg Arg Leu Pro Arg Pro Ala Ile
                245                 250                 255

Thr Gly Val Glu Ser Phe Met Thr Lys Gln Asp Thr Gly Lys Ile
            260                 265                 270

Ile Ser Ile Asp Thr Ser Ser Leu Arg Ala Ala Gly Arg Thr Gly Trp
        275                 280                 285

Glu Asp Leu Val Arg Lys Cys Ile Tyr Ala Phe Phe Gln Pro Gln Gly
    290                 295                 300
```

```
Arg Glu Pro Ser Tyr Ala Arg Gln Leu Phe Gln Val Met Thr Arg
305                 310                 315                 320

Gly Thr Ala Ser Ser Pro Ser Tyr Arg Phe Ile Leu Asn Asp Gly Thr
            325                 330                 335

Met Leu Ser Ala His Thr Lys Cys Lys Leu Cys Tyr Pro Gln Ser Pro
                340                 345                 350

Asp Met Gln Pro Phe Ile Met Gly Ile His Ile Ile Asp Arg Glu His
            355                 360                 365

Ser Gly Leu Ser Pro Gln Asp Asp Thr Asn Ser Gly Met Ser Ile Pro
370                 375                 380

Arg Val Asn Pro Ser Val Asn Pro Ser Ile Ser Pro Ala His Gly Val
385                 390                 395                 400

Ala Arg Ser Ser Thr Leu Pro Pro Ser Asn Ser Asn Met Val Ser Thr
                405                 410                 415

Arg Ile Asn Arg Gln Gln Ser Ser Asp Leu His Ser Ser His Ser
            420                 425                 430

Asn Ser Ser Asn Ser Gln Gly Ser Phe Gly Cys Ser Pro Gly Ser Gln
            435                 440                 445

Ile Val Ala Asn Val Ala Leu Asn Gln Gly Gln Ala Ser Ser Gln Ser
450                 455                 460

Ser Asn Pro Ser Leu Asn Leu Asn Asn Ser Pro Met Glu Gly Thr Gly
465                 470                 475                 480

Ile Ser Leu Ala Gln Phe Met Ser Pro Arg Arg Gln Val Thr Ser Gly
            485                 490                 495

Leu Ala Thr Arg Pro Arg Met Pro Asn Asn Ser Phe Pro Pro Asn Ile
            500                 505                 510

Ser Thr Leu Ser Ser Pro Val Gly Met Thr Ser Ser Ala Cys Asn Asn
            515                 520                 525

Asn Asn Arg Ser Tyr Ser Asn Ile Pro Val Thr Ser Leu Gln Gly Met
            530                 535                 540

Asn Glu Gly Pro Asn Asn Ser Val Gly Phe Ser Ala Ser Ser Pro Val
545                 550                 555                 560

Leu Arg Gln Met Ser Ser Gln Asn Ser Pro Ser Arg Leu Asn Ile Gln
                565                 570                 575

Pro Ala Lys Ala Glu Ser Lys Asp Asn Lys Glu Ile Ala Ser Ile Leu
            580                 585                 590

Asn Glu Met Ile Gln Ser Asp Asn Ser Ser Asp Gly Lys Pro Leu
            595                 600                 605

Asp Ser Gly Leu Leu His Asn Asn Asp Arg Leu Ser Asp Gly Asp Ser
            610                 615                 620

Lys Tyr Ser Gln Thr Ser His Lys Leu Val Gln Leu Leu Thr Thr Thr
625                 630                 635                 640

Ala Glu Gln Gln Leu Arg His Ala Asp Ile Asp Thr Ser Cys Lys Asp
                645                 650                 655

Val Leu Ser Cys Thr Gly Thr Ser Asn Ser Ala Ser Ala Asn Ser Ser
            660                 665                 670

Gly Gly Ser Cys Pro Ser Ser His Ser Ser Leu Thr Glu Arg His Lys
            675                 680                 685

Ile Leu His Arg Leu Leu Gln Glu Gly Ser Pro Ser Asp Ile Thr Thr
            690                 695                 700

Leu Ser Val Glu Pro Asp Lys Lys Asp Ser Ala Ser Thr Ser Val Ser
705                 710                 715                 720
```

```
Val Thr Gly Gln Val Gln Gly Asn Ser Ser Ile Lys Leu Glu Leu Asp
                725                 730                 735

Ala Ser Lys Lys Lys Glu Ser Lys Asp His Gln Leu Leu Arg Tyr Leu
            740                 745                 750

Leu Asp Lys Asp Glu Lys Asp Leu Arg Ser Thr Pro Asn Leu Ser Leu
            755                 760                 765

Asp Asp Val Lys Val Lys Val Glu Lys Lys Glu Gln Met Asp Pro Cys
770                 775                 780

Asn Thr Asn Pro Thr Pro Met Thr Lys Pro Thr Pro Glu Glu Ile Lys
785                 790                 795                 800

Leu Glu Ala Gln Ser Gln Phe Thr Ala Asp Leu Asp Gln Phe Asp Gln
                805                 810                 815

Leu Leu Pro Thr Leu Glu Lys Ala Ala Gln Leu Pro Gly Leu Cys Glu
            820                 825                 830

Thr Asp Arg Met Asp Gly Ala Val Thr Ser Val Thr Ile Lys Ser Glu
            835                 840                 845

Ile Leu Pro Ala Ser Leu Gln Ser Ala Thr Ala Arg Pro Thr Ser Arg
    850                 855                 860

Leu Asn Arg Leu Pro Glu Leu Glu Leu Glu Ala Ile Asp Asn Gln Phe
865                 870                 875                 880

Gly Gln Pro Gly Thr Gly Asp Gln Ile Pro Trp Thr Asn Asn Thr Val
                885                 890                 895

Thr Ala Ile Asn Gln Ser Lys Ser Glu Asp Gln Cys Ile Ser Ser Gln
                900                 905                 910

Leu Asp Glu Leu Leu Cys Pro Pro Thr Thr Val Glu Gly Arg Asn Asp
            915                 920                 925

Glu Lys Ala Leu Leu Glu Gln Leu Val Ser Phe Leu Ser Gly Lys Asp
930                 935                 940

Glu Thr Glu Leu Ala Glu Leu Asp Arg Ala Leu Gly Ile Asp Lys Leu
945                 950                 955                 960

Val Gln Gly Gly Gly Leu Asp Val Leu Ser Arg Phe Pro Pro Gln
                965                 970                 975

Gln Ala Thr Pro Pro Leu Ile Met Glu Glu Arg Pro Asn Leu Tyr Ser
            980                 985                 990

Gln Pro Tyr Ser Ser Pro Ser Pro Thr Ala Asn Leu Pro Ser Pro Phe
            995                 1000                1005

Gln Gly Met Val Arg Gln Lys Pro Ser Leu Gly Thr Met Pro Val
    1010                1015                1020

Gln Val Thr Pro Pro Arg Gly Ala Phe Ser Pro Gly Met Gly Met
    1025                1030                1035

Gln Pro Arg Gln Thr Leu Asn Arg Pro Pro Ala Ala Pro Asn Gln
    1040                1045                1050

Leu Arg Leu Gln Leu Gln Gln Arg Leu Gln Gly Gln Gln Gln Leu
    1055                1060                1065

Ile His Gln Asn Arg Gln Ala Ile Leu Asn Gln Phe Ala Ala Thr
    1070                1075                1080

Ala Pro Val Gly Ile Asn Met Arg Ser Gly Met Gln Gln Gln Ile
    1085                1090                1095

Thr Pro Gln Pro Pro Leu Asn Ala Gln Met Leu Ala Gln Arg Gln
    1100                1105                1110

Arg Glu Leu Tyr Ser Gln Gln His Arg Gln Arg Gln Leu Ile Gln
    1115                1120                1125

Gln Gln Arg Ala Met Leu Met Arg Gln Gln Ser Phe Gly Asn Asn
```

-continued

```
                1130                1135                1140
Leu Pro Pro Ser Ser Gly Leu Pro Val Gln Met Gly Asn Pro Arg
    1145                1150                1155
Leu Pro Gln Gly Ala Pro Gln Gln Phe Pro Tyr Pro Pro Asn Tyr
    1160                1165                1170
Gly Thr Asn Pro Gly Thr Pro Pro Ala Ser Thr Ser Pro Phe Ser
    1175                1180                1185
Gln Leu Ala Ala Asn Pro Glu Ala Ser Leu Ala Asn Arg Asn Ser
    1190                1195                1200
Met Val Ser Arg Gly Met Thr Gly Asn Ile Gly Gln Phe Gly
    1205                1210                1215
Thr Gly Ile Asn Pro Gln Met Gln Gln Asn Val Phe Gln Tyr Pro
    1220                1225                1230
Gly Ala Gly Met Val Pro Gln Gly Glu Ala Asn Phe Ala Pro Ser
    1235                1240                1245
Leu Ser Pro Gly Ser Ser Met Val Pro Met Pro Ile Pro Pro Pro
    1250                1255                1260
Gln Ser Ser Leu Leu Gln Gln Thr Pro Pro Ala Ser Gly Tyr Gln
    1265                1270                1275
Ser Pro Asp Met Lys Ala Trp Gln Gln Gly Ala Ile Gly Asn Asn
    1280                1285                1290
Asn Val Phe Ser Gln Ala Val Gln Asn Gln Pro Thr Pro Ala Gln
    1295                1300                1305
Pro Gly Val Tyr Asn Asn Met Ser Ile Thr Val Ser Met Ala Gly
    1310                1315                1320
Gly Asn Thr Asn Val Gln Asn Met Asn Pro Met Met Ala Gln Met
    1325                1330                1335
Gln Met Ser Ser Leu Gln Met Pro Gly Met Asn Thr Val Cys Pro
    1340                1345                1350
Glu Gln Ile Asn Asp Pro Ala Leu Arg His Thr Gly Leu Tyr Cys
    1355                1360                1365
Asn Gln Leu Ser Ser Thr Asp Leu Leu Lys Thr Glu Ala Asp Gly
    1370                1375                1380
Thr Gln Gln Val Gln Gln Val Gln Val Phe Ala Asp Val Gln Cys
    1385                1390                1395
Thr Val Asn Leu Val Gly Gly Asp Pro Tyr Leu Asn Gln Pro Gly
    1400                1405                1410
Pro Leu Gly Thr Gln Lys Pro Thr Ser Gly Pro Gln Thr Pro Gln
    1415                1420                1425
Ala Gln Gln Lys Ser Leu Leu Gln Gln Leu Leu Thr Glu
    1430                1435                1440
```

<210> SEQ ID NO 15
<211> LENGTH: 92
<212> TYPE: PRT
<213> ORGANISM: Homo sapiens

<400> SEQUENCE: 15

```
Met Gln Arg Arg Gly Gln Pro Leu Glu Asn His Val Ala Leu Ile His
1               5                  10                  15

Trp Gln Ser Ala Gly Ile Pro Ala Ser Lys Val His Asn Tyr Cys Asn
            20                  25                  30

Met Lys Lys Ser Arg Leu Gly Arg Ser Arg Ala Val Arg Ile Ser Gln
        35                  40                  45
```

```
Pro Leu Leu Ser Pro Arg Arg Cys Pro Leu His Leu Thr Glu Arg Gly
        50                  55                  60

Ala Gly Leu Leu Gln Pro Gln Pro Gln Gly Pro Val Arg Thr Pro Gly
 65                  70                  75                  80

Pro Pro Ser Gly Ser His Pro Ala Ala Ala Asp Asn
                85                  90

<210> SEQ ID NO 16
<211> LENGTH: 427
<212> TYPE: DNA
<213> ORGANISM: Homo sapiens
<220> FEATURE:
<221> NAME/KEY: misc_feature
<222> LOCATION: (413)..(413)
<223> OTHER INFORMATION: n is a, c, g, or t

<400> SEQUENCE: 16
tactttatca agcatacaga ggtcctaaac aaatgcttta ttaattttt ttttaaatt      60 taacattact cacctacaaa catatccaat gcaatgggat ataaaggttt tagtaatata    120
atcccagcag agttttatg attgtctcat ggaaaaatta aattgtggaa atacggttct    180
gatttgtggt tcgagtcagt tcaaggcaaa ttcctggtga ctgctaagta cttttccaga    240
tcaaacatta ggcccaatta attaacattt ctaaatttac agtcacatga gtatttatga    300
gcttcaaaaa agtgcgctca cttttacttt ccctgttaaa gaacataaac gcatatgcca    360
ctgattccta aggaagatct ctttgccagg gtcttgggaa gatttttgtt canacagtac    420
taccccc                                                              427

<210> SEQ ID NO 17
<211> LENGTH: 553
<212> TYPE: DNA
<213> ORGANISM: Homo sapiens

<400> SEQUENCE: 17
tgagttagca ttttggagtc tttagtttga agatgctttt gccctaccat gtctgtgaat     60
gtctacatta gtctactttg ttagtaaaat ttataaaaat aggagtgcag cagctctta     120 taataaatgt cgcattcagt gtctcatact ggctgtgcct taagtaccaa atttataaac    180
gtaacaattt aaaaaatatt aataaaacgt caatatcaca ttttaaaaaa gaaaaaatat    240
atatccacac tacaatatgt tttaatgcca tctattgagt tgtacttcta cagttgctgt    300
tgccgaccta ttaccaatat ttaaaaaaaa gttaaattaa aaaatatcct tcatcataag    360
tatctttccc caaccgagga ccatatatta taacagccaa atgttaaaca tgtgcaaaga    420
ggaaactgtc agttttttccc accagtcaca gtgcagtgat gtttatactt tttattttta    480
aaattctgtt tacatctaca ataaattaaa aaaaattctt ccatagcctc tctggtgata    540
cttgcagcac tga                                                       553

<210> SEQ ID NO 18
<211> LENGTH: 151
<212> TYPE: PRT
<213> ORGANISM: Homo sapiens

<400> SEQUENCE: 18

Met Val Thr Arg Thr Lys Lys Ile Phe Val Gly Gly Leu Ser Ala Asn
  1               5                  10                  15

Thr Val Val Glu Asp Val Lys Gln Tyr Phe Glu Gln Phe Gly Lys Val
                 20                  25                  30
```

```
Glu Asp Ala Met Leu Met Phe Asp Lys Thr Thr Asn Arg His Arg Gly
             35                  40                  45

Phe Gly Phe Val Thr Phe Glu Asn Glu Asp Val Val Glu Lys Val Cys
 50                  55                  60

Glu Ile His Phe His Glu Ile Asn Asn Lys Met Val Glu Cys Lys Lys
 65                  70                  75                  80

Ala Gln Pro Lys Glu Val Met Phe Pro Pro Thr Arg Gly Arg Ala
                 85                  90                  95

Arg Gly Leu Pro Tyr Thr Met Asp Ala Phe Met Leu Gly Met Gly Met
            100                 105                 110

Leu Gly Tyr Pro Asn Phe Val Ala Thr Tyr Gly Arg Gly Tyr Pro Gly
            115                 120                 125

Phe Ala Pro Ser Tyr Gly Tyr Gln Phe Pro Asp Tyr Leu Pro Val Ser
130                 135                 140

Gln Asp Ile Ile Phe Ile Asn
145                 150

<210> SEQ ID NO 19
<211> LENGTH: 442
<212> TYPE: PRT
<213> ORGANISM: Homo sapiens

<400> SEQUENCE: 19

Met Gln Pro Pro Pro Ser Leu Cys Gly Arg Ala Leu Val Ala Leu Val
  1               5                  10                  15

Leu Ala Cys Gly Leu Ser Arg Ile Trp Gly Glu Glu Arg Gly Phe Pro
             20                  25                  30

Pro Asp Arg Ala Thr Pro Leu Leu Gln Thr Ala Glu Ile Met Thr Pro
         35                  40                  45

Pro Thr Lys Thr Leu Trp Pro Lys Gly Ser Asn Ala Ser Leu Ala Arg
 50                  55                  60

Ser Leu Ala Pro Ala Glu Val Pro Lys Gly Asp Arg Thr Ala Gly Ser
 65                  70                  75                  80

Pro Pro Arg Thr Ile Ser Pro Pro Cys Gln Gly Pro Ile Glu Ile
                 85                  90                  95

Lys Glu Thr Phe Lys Tyr Ile Asn Thr Val Val Ser Cys Leu Val Phe
            100                 105                 110

Val Leu Gly Ile Ile Gly Asn Ser Thr Leu Leu Arg Ile Ile Tyr Lys
            115                 120                 125

Asn Lys Cys Met Arg Asn Gly Pro Asn Ile Leu Ile Ala Ser Leu Ala
130                 135                 140

Leu Gly Asp Leu Leu His Ile Val Ile Asp Ile Pro Ile Asn Val Tyr
145                 150                 155                 160

Lys Leu Leu Ala Glu Asp Trp Pro Phe Gly Ala Glu Met Cys Lys Leu
                165                 170                 175

Val Pro Phe Ile Gln Lys Ala Ser Val Gly Ile Thr Val Leu Ser Leu
            180                 185                 190

Cys Ala Leu Ser Ile Asp Arg Tyr Arg Ala Val Ala Ser Trp Ser Arg
            195                 200                 205

Ile Lys Gly Ile Gly Val Pro Lys Trp Thr Ala Val Glu Ile Val Leu
210                 215                 220

Ile Trp Val Val Ser Val Val Leu Ala Val Pro Glu Ala Ile Gly Phe
225                 230                 235                 240

Asp Ile Ile Thr Met Asp Tyr Lys Gly Ser Tyr Leu Arg Ile Cys Leu
                245                 250                 255
```

```
Leu His Pro Val Gln Lys Thr Ala Phe Met Gln Phe Tyr Lys Thr Ala
        260                 265                 270

Lys Asp Trp Trp Leu Phe Ser Phe Tyr Phe Cys Leu Pro Leu Ala Ile
            275                 280                 285

Thr Ala Phe Phe Tyr Thr Leu Met Thr Cys Glu Met Leu Arg Lys Lys
        290                 295                 300

Ser Gly Met Gln Ile Ala Leu Asn Asp His Leu Lys Gln Arg Arg Glu
305                 310                 315                 320

Val Ala Lys Thr Val Phe Cys Leu Val Leu Val Phe Ala Leu Cys Trp
                325                 330                 335

Leu Pro Leu His Leu Ser Arg Ile Leu Lys Leu Thr Leu Tyr Asn Gln
            340                 345                 350

Asn Asp Pro Asn Arg Cys Glu Leu Leu Ser Phe Leu Leu Val Leu Asp
        355                 360                 365

Tyr Ile Gly Ile Asn Met Ala Ser Leu Asn Ser Cys Ile Asn Pro Ile
    370                 375                 380

Ala Leu Tyr Leu Val Ser Lys Arg Phe Lys Asn Cys Phe Lys Ser Cys
385                 390                 395                 400

Leu Cys Cys Trp Cys Gln Ser Phe Glu Glu Lys Gln Ser Leu Glu Glu
                405                 410                 415

Lys Gln Ser Cys Leu Lys Phe Lys Ala Asn Asp His Gly Tyr Asp Asn
            420                 425                 430

Phe Arg Ser Ser Asn Lys Tyr Ser Ser Ser
            435                 440

<210> SEQ ID NO 20
<211> LENGTH: 601
<212> TYPE: DNA
<213> ORGANISM: Homo sapiens

<400> SEQUENCE: 20
caactgcaat aaaatcagtg cagttcagaa aactcgacct ttcagtatcc gagaaggcag      60
ctttgtaagc actttctgtt cgaggaactt tgttaagcag ctgagggaa tctgacccag      120 ctcctgtgtt gtctggtgta gacagggcac cagactggga gtcaagtggc ctgggtgctt     180
cttcactgcc accagcactt cctaataatg gcaaatttac attttgttac ggtgctcaca     240
gcttacaaaa cacatacatg tgcatcatca cagtttgttc acctgtaaga tgaaagggtt     300
ggattctttg ttttctgtgg tcttttccag ttctagtgcc ttgctagtct gatagtgtga     360 attattttt attacagctg cgctgctgc tgcatcaggg ccatcctttc tgcaagacac       420
aatgaccaca gcaaagagcg ggaaagataa ctttccacga catcgccaca ttgtttgacg     480
tcctttcatc aaatcactgt atgctattaa aagtcaccgt gtaactggag ttacattatt     540
cacagaggcc attaagactt ctcttattag acaatataac ttttgtgaca gaaataggct     600
g                                                                     601

<210> SEQ ID NO 21
<211> LENGTH: 614
<212> TYPE: PRT
<213> ORGANISM: Homo sapiens

<400> SEQUENCE: 21

Met Ser Gly Ile Lys Lys Gln Lys Thr Glu Asn Gln Gln Lys Ser Thr
1               5                   10                  15

Asn Val Val Tyr Gln Ala His His Val Ser Arg Asn Lys Arg Gly Gln
```

```
            20                  25                  30
Val Val Gly Thr Arg Gly Gly Phe Arg Gly Cys Thr Val Trp Leu Thr
             35                  40                  45
Gly Leu Ser Gly Ala Gly Lys Thr Thr Ile Ser Phe Ala Leu Glu Glu
             50                  55                  60
Tyr Leu Val Ser His Ala Ile Pro Cys Tyr Ser Leu Asp Gly Asp Asn
 65                  70                  75                  80
Val Arg His Gly Leu Asn Arg Asn Leu Gly Phe Ser Pro Gly Asp Arg
                     85                  90                  95
Glu Glu Asn Ile Arg Arg Ile Ala Glu Val Ala Lys Leu Phe Ala Asp
                100                 105                 110
Ala Gly Leu Val Cys Ile Thr Ser Phe Ile Ser Pro Phe Ala Lys Asp
                115                 120                 125
Arg Glu Asn Ala Arg Lys Ile His Glu Ser Ala Gly Leu Pro Phe Phe
                130                 135                 140
Glu Ile Phe Val Asp Ala Pro Leu Asn Ile Cys Glu Ser Arg Asp Val
145                 150                 155                 160
Lys Gly Leu Tyr Lys Arg Ala Arg Ala Gly Glu Ile Lys Gly Phe Thr
                165                 170                 175
Gly Ile Asp Ser Asp Tyr Glu Lys Pro Glu Thr Pro Glu Arg Val Leu
                180                 185                 190
Lys Thr Asn Leu Ser Thr Val Ser Asp Cys Val His Gln Val Val Glu
                195                 200                 205
Leu Leu Gln Glu Gln Asn Ile Val Pro Tyr Thr Ile Ile Lys Asp Ile
                210                 215                 220
His Glu Leu Phe Val Pro Glu Asn Lys Leu Asp His Val Arg Ala Glu
225                 230                 235                 240
Ala Glu Thr Leu Pro Ser Leu Ser Ile Thr Lys Leu Asp Leu Gln Trp
                245                 250                 255
Val Gln Val Leu Ser Glu Gly Trp Ala Thr Pro Leu Lys Gly Phe Met
                260                 265                 270
Arg Glu Lys Glu Tyr Leu Gln Val Met His Phe Asp Thr Leu Leu Asp
                275                 280                 285
Asp Gly Val Ile Asn Met Ser Ile Pro Ile Val Leu Pro Val Ser Ala
                290                 295                 300
Glu Asp Lys Thr Arg Leu Glu Gly Cys Ser Lys Phe Val Leu Ala His
305                 310                 315                 320
Gly Gly Arg Arg Val Ala Ile Leu Arg Asp Ala Glu Phe Tyr Glu His
                325                 330                 335
Arg Lys Glu Glu Arg Cys Ser Arg Val Trp Gly Thr Thr Cys Thr Lys
                340                 345                 350
His Pro His Ile Lys Met Val Met Glu Ser Gly Asp Trp Leu Val Gly
                355                 360                 365
Gly Asp Leu Gln Val Leu Glu Lys Ile Arg Trp Asn Asp Gly Leu Asp
                370                 375                 380
Gln Tyr Arg Leu Thr Pro Leu Glu Leu Lys Gln Lys Cys Lys Glu Met
385                 390                 395                 400
Asn Ala Asp Ala Val Phe Ala Phe Gln Leu Arg Asn Pro Val His Asn
                405                 410                 415
Gly His Ala Leu Leu Met Gln Asp Thr Cys Arg Arg Leu Leu Glu Arg
                420                 425                 430
Gly Tyr Lys His Pro Val Leu Leu Leu His Pro Leu Gly Gly Trp Thr
                435                 440                 445
```

```
Lys Asp Asp Asp Val Pro Leu Asp Trp Arg Met Lys Gln His Ala Ala
    450                 455                 460

Val Leu Glu Glu Gly Val Leu Asp Pro Lys Ser Thr Ile Val Ala Ile
465                 470                 475                 480

Phe Pro Ser Pro Met Leu Tyr Ala Gly Pro Thr Glu Val Gln Trp His
                485                 490                 495

Cys Arg Ser Arg Met Ile Ala Gly Ala Asn Phe Tyr Ile Val Gly Arg
                500                 505                 510

Asp Pro Ala Gly Met Pro His Pro Glu Thr Lys Lys Asp Leu Tyr Glu
            515                 520                 525

Pro Thr His Gly Gly Lys Val Leu Ser Met Ala Pro Gly Leu Thr Ser
    530                 535                 540

Val Glu Ile Ile Pro Phe Arg Val Ala Ala Tyr Asn Lys Ala Lys Lys
545                 550                 555                 560

Ala Met Asp Phe Tyr Asp Pro Ala Arg His Asn Glu Phe Asp Phe Ile
                565                 570                 575

Ser Gly Thr Arg Met Arg Lys Leu Ala Arg Glu Gly Glu Asn Pro Pro
                580                 585                 590

Asp Gly Phe Met Ala Pro Lys Ala Trp Lys Val Leu Thr Asp Tyr Tyr
                595                 600                 605

Arg Ser Leu Glu Lys Asn
            610

<210> SEQ ID NO 22
<211> LENGTH: 364
<212> TYPE: PRT
<213> ORGANISM: Homo sapiens

<400> SEQUENCE: 22

Met Pro Tyr Gln Tyr Pro Ala Leu Thr Pro Glu Gln Lys Lys Glu Leu
1               5                   10                  15

Ser Asp Ile Ala His Arg Ile Val Ala Pro Gly Lys Gly Ile Leu Ala
            20                  25                  30

Ala Asp Glu Ser Thr Gly Ser Ile Ala Lys Arg Leu Gln Ser Ile Gly
        35                  40                  45

Thr Glu Asn Thr Glu Glu Asn Arg Arg Phe Tyr Arg Gln Leu Leu Leu
    50                  55                  60

Thr Ala Asp Asp Arg Val Asn Pro Cys Ile Gly Gly Val Ile Leu Phe
65                  70                  75                  80

His Glu Thr Leu Tyr Gln Lys Ala Asp Asp Gly Arg Pro Phe Pro Gln
                85                  90                  95

Val Ile Lys Ser Lys Gly Gly Val Val Gly Ile Lys Val Asp Lys Gly
            100                 105                 110

Val Val Pro Leu Ala Gly Thr Asn Gly Glu Thr Thr Thr Gln Gly Leu
        115                 120                 125

Asp Gly Leu Ser Glu Arg Cys Ala Gln Tyr Lys Lys Asp Gly Ala Asp
    130                 135                 140

Phe Ala Lys Trp Arg Cys Val Leu Lys Ile Gly Glu His Thr Pro Ser
145                 150                 155                 160

Ala Leu Ala Ile Met Glu Asn Ala Asn Val Leu Ala Arg Tyr Ala Ser
                165                 170                 175

Ile Cys Gln Gln Asn Gly Ile Val Pro Ile Val Glu Pro Glu Ile Leu
            180                 185                 190

Pro Asp Gly Asp His Asp Leu Lys Arg Cys Gln Tyr Val Thr Glu Lys
```

-continued

```
                195                 200                 205
Val Leu Ala Ala Val Tyr Lys Ala Leu Ser Asp His His Ile Tyr Leu
    210                 215                 220
Glu Gly Thr Leu Leu Lys Pro Asn Met Val Thr Pro Gly His Ala Cys
225                 230                 235                 240
Thr Gln Lys Phe Ser His Glu Glu Ile Ala Met Ala Thr Val Thr Ala
                245                 250                 255
Leu Arg Arg Thr Val Pro Pro Ala Val Thr Gly Ile Thr Phe Leu Ser
            260                 265                 270
Gly Gly Gln Ser Glu Glu Glu Ala Ser Ile Asn Leu Asn Ala Ile Asn
        275                 280                 285
Lys Cys Pro Leu Leu Lys Pro Trp Ala Leu Thr Phe Ser Tyr Gly Arg
290                 295                 300
Ala Leu Gln Ala Ser Ala Leu Lys Ala Trp Gly Gly Lys Lys Glu Asn
305                 310                 315                 320
Leu Lys Ala Ala Gln Glu Glu Tyr Val Lys Arg Ala Leu Ala Asn Ser
                325                 330                 335
Leu Ala Cys Gln Gly Lys Tyr Thr Pro Ser Gly Gln Ala Gly Ala Ala
            340                 345                 350
Ala Ser Glu Ser Leu Phe Val Ser Asn His Ala Tyr
            355                 360
```

<210> SEQ ID NO 23
<211> LENGTH: 623
<212> TYPE: DNA
<213> ORGANISM: Homo sapiens
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t

<400> SEQUENCE: 23

```
tttcgcatgg attcccttta ttgaactgta ctagttactg cagtcagatt aagtcacatt      60
taaaagcaga ccatccagtt gcactgaaac cgattatatt cattacatag ttttaatcac     120
tgtccggtga actggcaaat ccaatcaaag cattagtctt taattaaaaa attaaaagga     180
aatattcaga caatagccaa gcaatcacat cacgatgcac aattacctag aattgcaatt     240
aaaaagtagt taaccgaagg gggtgggggg tggggggaa gaaanacaan aaanaaaaaa     300
aagaaccaaa gaaaaaaaat cacactaatt cttttttaaa aactatcaat attatacatg     360
aaggaacgaa ngacaatanc cttaaaaagc aggtttctct gactctanaa atgtggtctg     420
cggcggaaag tctaaaagca cactagctgt tgcaggacaa tagaaaatac tgagcatgga     480
```

-continued

```
atactttgaa tctctgccgt taatttcatt tccagctgct tatgatagca gcgcgtcatg    540
gccaaatcat tagagtttta cattctgggt tgctgatgac actgtgattg gatgtaatgt    600
tcaaatggcc cgtcccaccg cga                                            623
```

<210> SEQ ID NO 24
<211> LENGTH: 1284
<212> TYPE: PRT
<213> ORGANISM: Homo sapiens

<400> SEQUENCE: 24

```
Met His Lys Lys Arg Val Glu Glu Gly Glu Ala Ser Asp Phe Ser Leu
1               5                   10                  15

Ala Trp Asp Ser Ser Val Thr Ala Ala Gly Gly Leu Glu Gly Glu Pro
            20                  25                  30

Glu Cys Asp Gln Lys Thr Ser Arg Ala Leu Glu Asp Arg Asn Ser Val
        35                  40                  45

Thr Ser Gln Glu Glu Arg Asn Glu Asp Asp Glu Asp Met Glu Asp Glu
    50                  55                  60

Ser Ile Tyr Thr Cys Asp His Cys Gln Gln Asp Phe Glu Ser Leu Ala
65                  70                  75                  80

Asp Leu Thr Asp His Arg Ala His Arg Cys Pro Gly Asp Gly Asp Asp
                85                  90                  95

Asp Pro Gln Leu Ser Trp Val Ala Ser Ser Pro Ser Ser Lys Asp Val
            100                 105                 110

Ala Ser Pro Thr Gln Met Ile Gly Asp Gly Cys Asp Leu Gly Leu Gly
        115                 120                 125

Glu Glu Glu Gly Gly Thr Gly Leu Pro Tyr Pro Cys Gln Phe Cys Asp
    130                 135                 140

Lys Ser Phe Ile Arg Leu Ser Tyr Leu Lys Arg His Glu Gln Ile His
145                 150                 155                 160

Ser Asp Lys Leu Pro Phe Lys Cys Thr Tyr Cys Ser Arg Leu Phe Lys
                165                 170                 175

His Lys Arg Ser Arg Asp Arg His Ile Lys Leu His Thr Gly Asp Lys
            180                 185                 190

Lys Tyr His Cys His Glu Cys Glu Ala Ala Phe Ser Arg Ser Asp His
        195                 200                 205

Leu Lys Ile His Leu Lys Thr His Ser Ser Ser Lys Pro Phe Lys Cys
    210                 215                 220

Thr Val Cys Lys Arg Gly Phe Ser Ser Thr Ser Ser Leu Gln Ser His
225                 230                 235                 240

Met Gln Ala His Lys Lys Asn Lys Glu His Leu Ala Lys Ser Glu Lys
                245                 250                 255

Glu Ala Lys Lys Asp Asp Phe Met Cys Asp Tyr Cys Glu Asp Thr Phe
            260                 265                 270

Ser Gln Thr Glu Glu Leu Glu Lys His Val Leu Thr Arg His Pro Gln
        275                 280                 285

Leu Ser Glu Lys Ala Asp Leu Gln Cys Ile His Cys Pro Glu Val Phe
    290                 295                 300

Val Asp Glu Asn Thr Leu Leu Ala His Ile His Gln Ala His Ala Asn
305                 310                 315                 320

Gln Lys His Lys Cys Pro Met Cys Pro Glu Gln Phe Ser Ser Val Glu
                325                 330                 335

Gly Val Tyr Cys His Leu Asp Ser His Arg Gln Pro Asp Ser Ser Asn
```

-continued

```
              340                 345                 350
His Ser Val Ser Pro Asp Pro Val Leu Gly Ser Val Ala Ser Met Ser
            355                 360                 365

Ser Ala Thr Pro Asp Ser Ser Ala Ser Val Glu Arg Gly Ser Thr Pro
370                 375                 380

Asp Ser Thr Leu Lys Pro Leu Arg Gly Gln Lys Met Arg Asp Asp
385                 390                 395                 400

Gly Gln Gly Trp Thr Lys Val Val Tyr Ser Cys Pro Tyr Cys Ser Lys
                405                 410                 415

Arg Asp Phe Asn Ser Leu Ala Val Leu Glu Ile His Leu Lys Thr Ile
            420                 425                 430

His Ala Asp Lys Pro Gln Gln Ser His Thr Cys Gln Ile Cys Leu Asp
            435                 440                 445

Ser Met Pro Thr Leu Tyr Asn Leu Asn Glu His Val Arg Lys Leu His
        450                 455                 460

Lys Asn His Ala Tyr Pro Val Met Gln Phe Gly Asn Ile Ser Ala Phe
465                 470                 475                 480

His Cys Asn Tyr Cys Pro Glu Met Phe Ala Asp Ile Asn Ser Leu Gln
                485                 490                 495

Glu His Ile Arg Val Ser His Cys Gly Pro Asn Ala Asn Pro Ser Asp
            500                 505                 510

Gly Asn Asn Ala Phe Phe Cys Asn Gln Cys Ser Met Gly Phe Leu Thr
            515                 520                 525

Glu Ser Ser Leu Thr Glu His Ile Gln Gln Ala His Cys Ser Val Gly
        530                 535                 540

Ser Ala Lys Leu Glu Ser Pro Val Val Gln Pro Thr Gln Ser Phe Met
545                 550                 555                 560

Glu Val Tyr Ser Cys Pro Tyr Cys Thr Asn Ser Pro Ile Phe Gly Ser
                565                 570                 575

Ile Leu Lys Leu Thr Lys His Ile Lys Glu Asn His Lys Asn Ile Pro
            580                 585                 590

Leu Ala His Ser Lys Lys Ser Lys Ala Glu Gln Ser Pro Val Ser Ser
            595                 600                 605

Asp Val Glu Val Ser Ser Pro Lys Arg Gln Arg Leu Ser Ala Ser Ala
        610                 615                 620

Asn Ser Ile Ser Asn Gly Glu Tyr Pro Cys Asn Gln Cys Asp Leu Lys
625                 630                 635                 640

Phe Ser Asn Phe Glu Ser Phe Gln Thr His Leu Lys Leu His Leu Glu
                645                 650                 655

Leu Leu Leu Arg Lys Gln Ala Cys Pro Gln Cys Lys Glu Asp Phe Asp
            660                 665                 670

Ser Gln Glu Ser Leu Leu Gln His Leu Thr Val His Tyr Met Thr Thr
            675                 680                 685

Ser Thr His Tyr Val Cys Glu Ser Cys Asp Lys Gln Phe Ser Ser Val
        690                 695                 700

Asp Asp Leu Gln Lys His Leu Leu Asp Met His Thr Phe Val Leu Tyr
705                 710                 715                 720

His Cys Thr Leu Cys Gln Glu Val Phe Asp Ser Lys Val Ser Ile Gln
                725                 730                 735

Val His Leu Ala Val Lys His Ser Asn Glu Lys Lys Met Tyr Arg Cys
            740                 745                 750

Thr Ala Cys Asn Trp Asp Phe Arg Lys Glu Ala Asp Leu Gln Val His
            755                 760                 765
```

-continued

Val Lys His Ser His Leu Gly Asn Pro Ala Lys Ala His Lys Cys Ile
    770             775             780

Phe Cys Gly Glu Thr Phe Ser Thr Glu Val Glu Leu Gln Cys His Ile
785             790             795             800

Thr Thr His Ser Lys Lys Tyr Asn Cys Lys Phe Cys Ser Lys Ala Phe
                805             810             815

His Ala Ile Ile Leu Leu Glu Lys His Leu Arg Glu Lys His Cys Val
                820             825             830

Phe Asp Ala Ala Thr Glu Asn Gly Thr Ala Asn Gly Val Pro Pro Met
                835             840             845

Ala Thr Lys Lys Ala Glu Pro Ala Asp Leu Gln Gly Met Leu Leu Lys
        850             855             860

Asn Pro Glu Ala Pro Asn Ser His Glu Ala Ser Glu Asp Asp Val Asp
865             870             875             880

Ala Ser Glu Pro Met Tyr Gly Cys Asp Ile Cys Gly Ala Ala Tyr Thr
                885             890             895

Met Glu Val Leu Leu Gln Asn His Arg Leu Arg Asp His Asn Ile Arg
                900             905             910

Pro Gly Glu Asp Asp Gly Ser Arg Lys Lys Ala Glu Phe Ile Lys Gly
        915             920             925

Ser His Lys Cys Asn Val Cys Ser Arg Thr Phe Phe Ser Glu Asn Gly
930             935             940

Leu Arg Glu His Leu Gln Thr His Arg Gly Pro Ala Lys His Tyr Met
945             950             955             960

Cys Pro Ile Cys Gly Glu Arg Phe Pro Ser Leu Leu Thr Leu Thr Glu
                965             970             975

His Lys Val Thr His Ser Lys Ser Leu Asp Thr Gly Thr Cys Arg Ile
                980             985             990

Cys Lys Met Pro Leu Gln Ser Glu Glu Glu Phe Ile Glu His Cys Gln
        995             1000            1005

Met His Pro Asp Leu Arg Asn Ser Leu Thr Gly Phe Arg Cys Val
    1010            1015            1020

Val Cys Met Gln Thr Val Thr Ser Thr Leu Glu Leu Lys Ile His
    1025            1030            1035

Gly Thr Phe His Met Gln Lys Leu Ala Gly Ser Ser Ala Ala Ser
    1040            1045            1050

Ser Pro Asn Gly Gln Gly Leu Gln Lys Leu Tyr Lys Cys Ala Leu
    1055            1060            1065

Cys Leu Lys Glu Phe Arg Ser Lys Gln Asp Leu Val Lys Leu Asp
    1070            1075            1080

Val Asn Gly Leu Pro Tyr Gly Leu Cys Ala Gly Cys Met Ala Arg
    1085            1090            1095

Ser Ala Asn Gly Gln Val Gly Gly Leu Ala Pro Pro Glu Pro Ala
    1100            1105            1110

Asp Arg Pro Cys Ala Gly Leu Arg Cys Pro Glu Cys Ser Val Lys
    1115            1120            1125

Phe Glu Ser Ala Glu Asp Leu Glu Ser His Met Gln Val Asp His
    1130            1135            1140

Arg Asp Leu Thr Pro Glu Thr Ser Gly Pro Arg Lys Gly Thr Gln
    1145            1150            1155

Thr Ser Pro Val Pro Arg Lys Lys Thr Tyr Gln Cys Ile Lys Cys
    1160            1165            1170

```
Gln Met Thr Phe Glu Asn Glu Arg Glu Ile Gln Ile His Val Ala
    1175                1180                1185

Asn His Met Ile Glu Glu Gly Ile Asn His Glu Cys Lys Leu Cys
    1190                1195                1200

Asn Gln Met Phe Asp Ser Pro Ala Lys Leu Leu Cys His Leu Ile
    1205                1210                1215

Glu His Ser Phe Glu Gly Met Gly Gly Thr Phe Lys Cys Pro Val
    1220                1225                1230

Cys Phe Thr Val Phe Val Gln Ala Asn Lys Leu Gln Gln His Ile
    1235                1240                1245

Phe Ala Val His Gly Gln Glu Asp Lys Ile Tyr Asp Cys Ser Gln
    1250                1255                1260

Cys Pro Gln Lys Phe Phe Phe Gln Thr Glu Leu Gln Asn His Thr
    1265                1270                1275

Met Ser Gln His Ala Gln
    1280

<210> SEQ ID NO 25
<211> LENGTH: 915
<212> TYPE: PRT
<213> ORGANISM: Homo sapiens

<400> SEQUENCE: 25

Met Ala Arg Arg Ser Ser Phe Gln Ser Cys Gln Ile Ile Ser Leu Phe
1               5                   10                  15

Thr Phe Ala Val Gly Val Ser Ile Cys Leu Gly Phe Thr Ala His Arg
            20                  25                  30

Ile Lys Arg Ala Glu Gly Trp Glu Glu Gly Pro Pro Thr Val Leu Ser
        35                  40                  45

Asp Ser Pro Trp Thr Asn Ile Ser Gly Ser Cys Lys Gly Arg Cys Phe
    50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Gly Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
    130                 135                 140

Val Asp Asp Asp Cys Glu Glu Ile Lys Ala Ala Glu Cys Pro Ala Gly
145                 150                 155                 160

Phe Val Arg Pro Pro Leu Ile Ile Phe Ser Val Asp Gly Phe Arg Ala
                165                 170                 175

Ser Tyr Met Lys Lys Gly Ser Lys Val Met Pro Asn Ile Glu Lys Leu
            180                 185                 190

Arg Ser Cys Gly Thr His Ser Pro Tyr Met Arg Pro Val Tyr Pro Thr
        195                 200                 205

Lys Thr Phe Pro Asn Leu Tyr Thr Leu Ala Thr Gly Leu Tyr Pro Glu
    210                 215                 220

Ser His Gly Ile Val Gly Asn Ser Met Tyr Asp Pro Val Phe Asp Ala
225                 230                 235                 240

Thr Phe His Leu Arg Gly Arg Glu Lys Phe Asn His Arg Trp Trp Gly
                245                 250                 255
```

```
Gly Gln Pro Leu Trp Ile Thr Ala Thr Lys Gln Gly Val Lys Ala Gly
            260                 265                 270

Thr Phe Phe Trp Ser Val Val Ile Pro His Glu Arg Ile Leu Thr
        275                 280                 285

Ile Leu Arg Trp Leu Thr Leu Pro Asp His Glu Arg Pro Ser Val Tyr
        290                 295                 300

Ala Phe Tyr Ser Glu Gln Pro Asp Phe Ser Gly His Lys Tyr Gly Pro
305                 310                 315                 320

Phe Gly Pro Glu Glu Ser Ser Tyr Gly Ser Pro Phe Thr Pro Ala Lys
                325                 330                 335

Arg Pro Lys Arg Lys Val Ala Pro Lys Arg Gln Glu Arg Pro Val
            340                 345                 350

Ala Pro Pro Lys Lys Arg Arg Lys Ile His Arg Met Asp His Tyr
        355                 360                 365

Ala Ala Glu Thr Arg Gln Asp Lys Met Thr Asn Pro Leu Arg Glu Ile
        370                 375                 380

Asp Lys Ile Val Gly Gln Leu Met Asp Gly Leu Lys Gln Leu Lys Leu
385                 390                 395                 400

Arg Arg Cys Val Asn Val Ile Phe Val Gly Asp His Gly Met Glu Asp
                405                 410                 415

Val Thr Cys Asp Arg Thr Glu Phe Leu Ser Asn Tyr Leu Thr Asn Val
            420                 425                 430

Asp Asp Ile Thr Leu Val Pro Gly Thr Leu Gly Arg Ile Arg Ser Lys
            435                 440                 445

Phe Ser Asn Asn Ala Lys Tyr Asp Pro Lys Ala Ile Ile Ala Asn Leu
        450                 455                 460

Thr Cys Lys Lys Pro Asp Gln His Phe Lys Pro Tyr Leu Lys Gln His
465                 470                 475                 480

Leu Pro Lys Arg Leu His Tyr Ala Asn Asn Arg Arg Ile Glu Asp Ile
                485                 490                 495

His Leu Leu Val Glu Arg Arg Trp His Val Ala Arg Lys Pro Leu Asp
                500                 505                 510

Val Tyr Lys Lys Pro Ser Gly Lys Cys Phe Phe Gln Gly Asp His Gly
        515                 520                 525

Phe Asp Asn Lys Val Asn Ser Met Gln Thr Val Phe Val Gly Tyr Gly
        530                 535                 540

Pro Thr Phe Lys Tyr Lys Thr Lys Val Pro Pro Phe Glu Asn Ile Glu
545                 550                 555                 560

Leu Tyr Asn Val Met Cys Asp Leu Leu Gly Leu Lys Pro Ala Pro Asn
                565                 570                 575

Asn Gly Thr His Gly Ser Leu Asn His Leu Leu Arg Thr Asn Thr Phe
            580                 585                 590

Arg Pro Thr Met Pro Glu Glu Val Thr Arg Pro Asn Tyr Pro Gly Ile
        595                 600                 605

Met Tyr Leu Gln Ser Asp Phe Asp Leu Gly Cys Thr Cys Asp Asp Lys
        610                 615                 620

Val Glu Pro Lys Asn Lys Leu Asp Glu Leu Asn Lys Arg Leu His Thr
625                 630                 635                 640

Lys Gly Ser Thr Glu Glu Arg His Leu Leu Tyr Gly Arg Pro Ala Val
            645                 650                 655

Leu Tyr Arg Thr Arg Tyr Asp Ile Leu Tyr His Thr Asp Phe Glu Ser
            660                 665                 670
```

Gly Tyr Ser Glu Ile Phe Leu Met Leu Leu Trp Thr Ser Tyr Thr Val
            675                 680                 685

Ser Lys Gln Ala Glu Val Ser Ser Val Pro Asp His Leu Thr Ser Cys
690                 695                 700

Val Arg Pro Asp Val Arg Val Ser Pro Ser Phe Ser Gln Asn Cys Leu
705                 710                 715                 720

Ala Tyr Lys Asn Asp Lys Gln Met Ser Tyr Gly Phe Leu Phe Pro Pro
                725                 730                 735

Tyr Leu Ser Ser Ser Pro Glu Ala Lys Tyr Asp Ala Phe Leu Val Thr
            740                 745                 750

Asn Met Val Pro Met Tyr Pro Ala Phe Lys Arg Val Trp Asn Tyr Phe
            755                 760                 765

Gln Arg Val Leu Val Lys Lys Tyr Ala Ser Glu Arg Asn Gly Val Asn
770                 775                 780

Val Ile Ser Gly Pro Ile Phe Asp Tyr Asp Tyr Asp Gly Leu His Asp
785                 790                 795                 800

Thr Glu Asp Lys Ile Lys Gln Tyr Val Glu Gly Ser Ser Ile Pro Val
                805                 810                 815

Pro Thr His Tyr Tyr Ser Ile Ile Thr Ser Cys Leu Asp Phe Thr Gln
            820                 825                 830

Pro Ala Asp Lys Cys Asp Gly Pro Leu Ser Val Ser Ser Phe Ile Leu
            835                 840                 845

Pro His Arg Pro Asp Asn Glu Glu Ser Cys Asn Ser Ser Glu Asp Glu
            850                 855                 860

Ser Lys Trp Val Glu Glu Leu Met Lys Met His Thr Ala Arg Val Arg
865                 870                 875                 880

Asp Ile Glu His Leu Thr Ser Leu Asp Phe Phe Arg Lys Thr Ser Arg
                885                 890                 895

Ser Tyr Pro Glu Ile Leu Thr Leu Lys Thr Tyr Leu His Thr Tyr Glu
            900                 905                 910

Ser Glu Ile
    915

<210> SEQ ID NO 26
<211> LENGTH: 358
<212> TYPE: PRT
<213> ORGANISM: Homo sapiens

<400> SEQUENCE: 26

Met Pro Gly Cys Glu Leu Pro Val Gly Thr Cys Pro Asp Met Cys Pro
1               5                   10                  15

Ala Ala Glu Arg Ala Gln Arg Glu Arg Glu His Arg Leu His Arg Leu
                20                  25                  30

Glu Val Val Pro Gly Cys Arg Gln Asp Pro Pro Arg Ala Asp Pro Gln
            35                  40                  45

Arg Ala Val Lys Glu Tyr Ser Arg Pro Ala Ala Gly Lys Pro Arg Pro
        50                  55                  60

Pro Pro Ser Gln Leu Arg Pro Pro Ser Val Leu Leu Ala Thr Val Arg
65                  70                  75                  80

Tyr Leu Ala Gly Glu Val Ala Glu Ser Ala Asp Ile Ala Arg Ala Glu
                85                  90                  95

Val Ala Ser Phe Val Ala Asp Arg Leu Arg Ala Val Leu Leu Asp Leu
            100                 105                 110

Ala Leu Gln Gly Ala Gly Asp Ala Glu Ala Ala Val Val Leu Glu Ala
        115                 120                 125

Ala Leu Ala Thr Leu Leu Thr Val Val Ala Arg Leu Gly Pro Asp Ala
    130                 135                 140

Ala Arg Gly Pro Ala Asp Pro Val Leu Leu Gln Ala Gln Val Gln Glu
145                 150                 155                 160

Gly Phe Gly Ser Leu Arg Arg Cys Tyr Ala Arg Gly Ala Gly Pro His
                165                 170                 175

Pro Arg Gln Pro Ala Phe Gln Gly Leu Phe Leu Tyr Asn Leu Gly
            180                 185                 190

Ser Val Glu Ala Leu His Glu Val Leu Gln Leu Pro Ala Ala Leu Arg
        195                 200                 205

Ala Cys Pro Pro Leu Arg Lys Ala Leu Ala Val Asp Ala Ala Phe Arg
210                 215                 220

Glu Gly Asn Ala Ala Arg Leu Phe Arg Leu Leu Gln Thr Leu Pro Tyr
225                 230                 235                 240

Leu Pro Ser Cys Ala Val Gln Cys His Val Gly His Ala Arg Arg Glu
                245                 250                 255

Ala Leu Ala Arg Phe Ala Arg Ala Phe Ser Thr Pro Lys Gly Gln Thr
                260                 265                 270

Leu Pro Leu Gly Phe Met Val Asn Leu Ala Leu Asp Gly Leu Arg
        275                 280                 285

Glu Ala Arg Asp Leu Cys Gln Ala His Gly Leu Pro Leu Asp Gly Glu
290                 295                 300

Glu Arg Val Val Phe Leu Arg Gly Arg Tyr Val Glu Glu Gly Leu Pro
305                 310                 315                 320

Pro Ala Ser Thr Cys Lys Val Leu Val Glu Ser Lys Leu Arg Gly Arg
                325                 330                 335

Thr Leu Glu Glu Val Val Met Ala Glu Glu Asp Glu Gly Thr Asp
        340                 345                 350

Arg Pro Gly Ser Pro Ala
        355

<210> SEQ ID NO 27
<211> LENGTH: 918
<212> TYPE: PRT
<213> ORGANISM: Homo sapiens

<400> SEQUENCE: 27

Leu Pro Glu Met Pro Arg Gly Ser Arg Ala Arg Gly Ser Lys Arg Lys
1               5                   10                  15

Arg Ser Trp Asn Thr Glu Cys Pro Ser Phe Pro Gly Arg Pro Leu
            20                  25                  30

Gln Val Arg Arg Ala Gly Leu Arg Thr Ala Gly Ala Ala Ser Leu
        35                  40                  45

Ser Glu Ala Trp Leu Arg Cys Gly Glu Gly Phe Gln Asn Thr Ser Gly
    50                  55                  60

Asn Pro Ser Leu Thr Ala Glu Glu Lys Thr Ile Thr Glu Lys His Leu
65                  70                  75                  80

Glu Leu Cys Pro Arg Pro Lys Gln Glu Thr Thr Thr Ser Lys Ser Thr
                85                  90                  95

Ser Gly Leu Thr Asp Ile Thr Trp Ser Ser Gly Ser Asp Leu Ser
                100                 105                 110

Asp Glu Asp Lys Thr Leu Ser Gln Leu Gln Arg Asp Glu Leu Gln Phe
        115                 120                 125

Ile Asp Trp Glu Ile Asp Ser Asp Arg Ala Glu Ala Ser Asp Cys Asp

```
            130                 135                 140

Glu Phe Glu Asp Asp Glu Gly Ala Val Glu Ile Ser Asp Cys Ala Ser
145                 150                 155                 160

Cys Ala Ser Asn Gln Ser Leu Thr Ser Asp Glu Lys Leu Ser Glu Leu
                165                 170                 175

Pro Lys Pro Ser Ser Ile Glu Ile Leu Glu Tyr Ser Ser Asp Ser Glu
                180                 185                 190

Lys Glu Asp Asp Leu Glu Asn Val Leu Leu Ile Asp Ser Glu Ser Pro
                195                 200                 205

His Lys Tyr His Val Gln Phe Ala Ser Asp Ala Arg Gln Ile Met Glu
                210                 215                 220

Arg Leu Ile Asp Pro Arg Thr Lys Ser Thr Glu Thr Ile Leu His Thr
225                 230                 235                 240

Pro Gln Lys Pro Thr Ala Lys Phe Pro Arg Thr Pro Glu Asn Ser Ala
                245                 250                 255

Lys Lys Lys Leu Leu Arg Gly Gly Leu Ala Glu Arg Leu Asn Gly Leu
                260                 265                 270

Gln Asn Arg Glu Arg Ser Ala Ile Ser Leu Trp Arg His Gln Cys Ile
                275                 280                 285

Ser Tyr Gln Lys Thr Leu Ser Gly Arg Lys Ser Gly Val Leu Thr Val
                290                 295                 300

Lys Ile Leu Glu Leu His Glu Glu Cys Ala Met Gln Val Ala Met Cys
305                 310                 315                 320

Glu Gln Leu Leu Gly Ser Pro Ala Thr Ser Ser Ser Gln Ser Val Ala
                325                 330                 335

Pro Arg Pro Gly Ala Gly Leu Lys Val Leu Phe Thr Lys Glu Thr Ala
                340                 345                 350

Gly Tyr Leu Arg Gly Arg Pro Gln Asp Thr Val Arg Ile Phe Pro Pro
                355                 360                 365

Trp Gln Lys Leu Ile Ile Pro Ser Gly Ser Cys Pro Val Ile Leu Asn
                370                 375                 380

Thr Tyr Phe Cys Glu Lys Val Val Ala Lys Glu Asp Ser Glu Lys Thr
385                 390                 395                 400

Cys Glu Val Tyr Cys Pro Asp Ile Pro Leu Pro Arg Arg Ser Ile Ser
                405                 410                 415

Leu Ala Gln Met Phe Val Ile Lys Gly Leu Thr Asn Asn Ser Pro Glu
                420                 425                 430

Ile Gln Val Val Cys Ser Gly Val Ala Thr Thr Gly Thr Ala Trp Thr
                435                 440                 445

His Gly His Lys Glu Ala Lys Gln Arg Ile Pro Thr Ser Thr Pro Leu
                450                 455                 460

Arg Asp Ser Leu Leu Asp Val Val Glu Ser Gln Gly Ala Ala Ser Trp
465                 470                 475                 480

Pro Gly Ala Gly Val Arg Val Val Gln Arg Val Tyr Ser Leu Pro
                485                 490                 495

Ser Arg Asp Ser Thr Arg Gly Gln Gln Gly Ala Ser Ser Gly His Thr
                500                 505                 510

Asp Pro Ala Gly Thr Arg Ala Cys Leu Leu Val Gln Asp Ala Cys Gly
                515                 520                 525

Met Phe Gly Glu Val His Leu Glu Phe Thr Met Ser Lys Ala Arg Gln
                530                 535                 540

Leu Glu Gly Lys Ser Cys Ser Leu Val Gly Met Lys Val Leu Gln Lys
545                 550                 555                 560
```

Val Thr Arg Gly Arg Thr Ala Gly Ile Phe Ser Leu Ile Asp Thr Leu
            565                 570                 575

Trp Pro Pro Ala Ile Pro Leu Lys Thr Pro Gly Arg Asp Gln Pro Cys
            580                 585                 590

Glu Glu Ile Lys Thr His Leu Pro Pro Ala Leu Cys Tyr Ile Leu
            595                 600                 605

Thr Ala His Pro Asn Leu Gly Gln Ile Asp Ile Asp Glu Asp Pro
        610                 615                 620

Ile Tyr Lys Leu Tyr Gln Pro Pro Val Thr Arg Cys Leu Arg Asp Ile
625                 630                 635                 640

Leu Gln Met Asn Asp Leu Gly Thr Arg Cys Ser Phe Tyr Ala Thr Val
            645                 650                 655

Ile Tyr Gln Lys Pro Gln Leu Lys Ser Leu Leu Leu Glu Gln Arg
            660                 665                 670

Glu Ile Trp Leu Leu Val Thr Asp Val Thr Leu Gln Thr Lys Glu Glu
            675                 680                 685

Arg Asp Pro Arg Leu Pro Lys Thr Leu Leu Val Tyr Val Ala Pro Leu
        690                 695                 700

Cys Val Leu Gly Ser Glu Val Leu Glu Ala Leu Ala Gly Ala Ala Pro
705                 710                 715                 720

His Ser Leu Phe Phe Lys Asp Ala Leu Arg Asp Gln Gly Arg Ile Val
            725                 730                 735

Cys Ala Glu Arg Thr Val Leu Leu Leu Gln Lys Pro Leu Leu Ser Val
            740                 745                 750

Val Ser Gly Ala Ser Ser Cys Glu Leu Pro Gly Pro Val Met Leu Asp
            755                 760                 765

Ser Leu Asp Ser Ala Thr Pro Val Asn Ser Ile Cys Ser Val Gln Gly
        770                 775                 780

Thr Val Val Gly Val Asp Glu Ser Thr Ala Phe Ser Trp Pro Val Cys
785                 790                 795                 800

Asp Met Cys Gly Asn Gly Arg Leu Glu Gln Arg Pro Glu Asp Arg Gly
            805                 810                 815

Ala Phe Ser Cys Gly Asp Cys Ser Arg Val Val Thr Ser Pro Val Leu
            820                 825                 830

Lys Arg His Leu Gln Val Phe Leu Asp Cys Arg Ser Arg Pro Gln Cys
            835                 840                 845

Arg Val Lys Val Lys Leu Leu Gln Arg Ser Ile Ser Ser Leu Leu Arg
850                 855                 860

Phe Ala Ala Gly Glu Asp Gly Ser Tyr Glu Val Lys Ser Val Leu Gly
865                 870                 875                 880

Lys Glu Val Gly Leu Leu Asn Cys Phe Val Gln Ser Val Thr Ala His
            885                 890                 895

Pro Thr Ser Cys Ile Gly Leu Glu Glu Ile Glu Leu Leu Ser Ala Gly
            900                 905                 910

Gly Ala Ser Ala Glu His
        915

<210> SEQ ID NO 28
<211> LENGTH: 351
<212> TYPE: DNA
<213> ORGANISM: Homo sapiens
<220> FEATURE:
<221> NAME/KEY: misc_feature
<222> LOCATION: (341)..(341)
<223> OTHER INFORMATION: n is a, c, g, or t

<400> SEQUENCE: 28

```
ttttcggcc tcagtctgtt ctcagaacat actccatcac ctggttccca gaactcagat    60
tgcgcagtgg tctcgtcatc atcggccagg actcacagtg cccgcggcag aggcctccct   120
agacctccct cccgtccagc ctcacccgct gccactctc  ctcacgcccc tgctccaggt   180
cccctggccc catttcgctc gccacgtttt cataatcctc tcaggctccg ggcaagcggc   240
gccgcccgca atgggacctg atcatataag gaaaatactg cgggctcatc cgggggctgc   300
aatggtaacc cgaaagcgcc ctagcctact acaatcaccg naccccaact g            351
```

<210> SEQ ID NO 29
<211> LENGTH: 534
<212> TYPE: DNA
<213> ORGANISM: Homo sapiens
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t

<400> SEQUENCE: 29

```
tctgagggca tattgataaa tctttattga caaaatattg acattgacat acttcttgga    60
agtatatagt gtgttagaat tctaacaaat taacacaaaa cacaaaaata tttacattct   120
ggtatagaag acattaagga agcatttgtc actctcttta gtaagtctat gatcttggaa   180
tagaaactca gtgcttgaaa acttgccgcc gtgcgcttgc cacacttaac atcatccccg   240
ctaactacag tccttcaggt tttgcaatag atagatttaa agtttggaat aggcattgca   300
gtgaatggtt gaactcggcc aatttctcca accactgaaa ggagaagttt gcatcagggt   360
tttaagcctc aggatgttag gaaagggaat gtccaagaaa tataattaaa tttaggggtt   420
ttttccagt acaagtcctg attctttttt ttttggggg gaacacccca cncaggcccn    480
cccgtcgtct gctccccgtt tttttgtaga ggacactatc gctgagctcg tgcc          534
```

<210> SEQ ID NO 30
<211> LENGTH: 252
<212> TYPE: PRT
<213> ORGANISM: Homo sapiens

<400> SEQUENCE: 30

```
Met Phe Gln Pro Ala Pro Lys Arg Cys Phe Thr Ile Glu Ser Leu Val
1               5                   10                  15

Ala Lys Asp Ser Pro Leu Pro Ala Ser Arg Ser Glu Asp Pro Ile Arg
            20                  25                  30

Pro Ala Ala Leu Ser Tyr Ala Asn Ser Ser Pro Ile Asn Pro Phe Leu
        35                  40                  45

Asn Gly Phe His Ser Ala Ala Ala Ala Ala Gly Arg Gly Val Tyr
    50                  55                  60

Ser Asn Pro Asp Leu Val Phe Ala Glu Ala Val Ser His Pro Asn
65                  70                  75                  80

Pro Ala Val Pro Val His Pro Val Pro Pro His Ala Leu Ala Ala
            85                  90                  95

His Pro Leu Pro Ser Ser His Ser Pro His Pro Leu Phe Ala Ser Gln
            100                 105                 110

Gln Arg Asp Pro Ser Thr Phe Tyr Pro Trp Leu Ile His Arg Tyr Arg
```

```
              115                 120                 125
Tyr Leu Gly His Arg Phe Gln Gly Asn Asp Thr Ser Pro Glu Ser Phe
        130                 135                 140

Leu Leu His Asn Ala Leu Ala Arg Lys Pro Lys Arg Ile Arg Thr Ala
145                 150                 155                 160

Phe Ser Pro Ser Gln Leu Leu Arg Leu Glu His Ala Phe Glu Lys Asn
                165                 170                 175

His Tyr Val Val Gly Ala Glu Arg Lys Gln Leu Ala His Ser Leu Ser
            180                 185                 190

Leu Thr Glu Thr Gln Val Lys Val Trp Phe Gln Asn Arg Arg Thr Lys
        195                 200                 205

Phe Lys Arg Gln Lys Leu Glu Glu Glu Gly Ser Asp Ser Gln Gln Lys
    210                 215                 220

Lys Lys Gly Thr His His Ile Asn Arg Trp Arg Ile Ala Thr Lys Gln
225                 230                 235                 240

Ala Ser Pro Glu Glu Ile Asp Val Thr Ser Asp Asp
                245                 250
```

<210> SEQ ID NO 31
<211> LENGTH: 447
<212> TYPE: DNA
<213> ORGANISM: Homo sapiens

<400> SEQUENCE: 31

```
ttttttttca gcttgtacac agatgcttta ttttggatgt taatatgtca acattgtatg      60
caagattctc ttacaatgaa gttttccata tatcacaaaa ctcaatttag tcagggtaat     120
tgctgtatta atgtgaaaac cttacaataa aatgcagtat tatgtatgtg tagtcagttt     180
ccatgcaagt atggctgcta catgttatgt ctggcatttg tataacatac tgaaagaaac     240
tcagaggaac aaaacagttt aaaggtgact taagatgcct gacatgttta agataaaaaa     300
tcttgcaaaa agcaacaaag cagttaactg aaggattcaa ccagtaccaa cccaaatatg     360
tattatgtcc aataagccca gacttatcca caatatatta ccatttagga taatttaatg     420
ctcaagaaaa aatatgcttt aaaaaat                                         447
```

<210> SEQ ID NO 32
<211> LENGTH: 355
<212> TYPE: PRT
<213> ORGANISM: Homo sapiens

<400> SEQUENCE: 32

```
Ile Gln His Asn Glu Gly Ala Met Glu Cys Gln Phe Asn Val Ser Leu
1               5                   10                  15

Val Leu Glu Gly Lys Lys Asn Thr Cys Asn Gly Gly Asn Ser Glu Ala
            20                  25                  30

Val Pro Leu Thr Ser Pro Asn Ile Ala Lys Phe Ser Thr Pro Pro Ala
        35                  40                  45

Ile Leu Arg Lys Lys Arg Lys Met Arg Val Gly His Ser Pro Gly Ser
    50                  55                  60

Glu Leu Arg Asp Gly Ser Leu Asn Asp Gly Asn Met Ala Leu Lys
65                  70                  75                  80

His Thr Pro Leu Lys Thr Leu Pro Phe Ser Pro Ser Gln Phe Phe Asn
                85                  90                  95

Thr Cys Pro Gly Asn Glu Gln Leu Asn Ile Glu Asn Pro Ser Phe Thr
            100                 105                 110
```

Ser Thr Pro Ile Cys Gly Gln Lys Ala Leu Ile Thr Thr Pro Leu His
            115                 120                 125

Lys Glu Thr Thr Pro Lys Asp Gln Lys Glu Asn Val Gly Phe Arg Thr
130                 135                 140

Pro Thr Ile Arg Arg Ser Ile Leu Gly Thr Thr Pro Arg Thr Pro Thr
145                 150                 155                 160

Pro Phe Lys Asn Ala Leu Ala Ala Gln Glu Lys Lys Tyr Gly Pro Leu
                165                 170                 175

Lys Ile Val Ser Gln Pro Leu Ala Phe Leu Glu Glu Asp Ile Arg Glu
                180                 185                 190

Val Leu Lys Glu Glu Thr Gly Thr Asp Leu Phe Leu Lys Glu Glu Asp
            195                 200                 205

Glu Pro Ala Tyr Lys Ser Cys Lys Gln Glu Asn Thr Ala Ser Gly Lys
            210                 215                 220

Lys Val Arg Lys Ser Leu Val Leu Asp Asn Trp Glu Lys Glu Glu Ser
225                 230                 235                 240

Gly Thr Gln Leu Leu Thr Glu Asp Ile Ser Asp Met Gln Ser Glu Asn
                245                 250                 255

Arg Phe Thr Thr Ser Leu Leu Met Ile Pro Leu Leu Glu Ile His Asp
                260                 265                 270

Asn Arg Cys Asn Leu Ile Pro Glu Lys Gln Asp Ile Asn Ser Thr Asn
            275                 280                 285

Lys Thr Tyr Thr Leu Thr Lys Lys Pro Asn Pro Asn Thr Ser Lys
            290                 295                 300

Val Val Lys Leu Glu Lys Asn Leu Gln Ser Asn Cys Glu Trp Glu Thr
305                 310                 315                 320

Val Val Tyr Gly Lys Thr Glu Asp Gln Leu Ile Met Thr Glu Gln Ala
                325                 330                 335

Arg Arg Tyr Leu Ser Thr Tyr Thr Ala Thr Ser Ser Thr Ser Arg Ala
                340                 345                 350

Leu Ile Leu
        355

<210> SEQ ID NO 33
<211> LENGTH: 214
<212> TYPE: PRT
<213> ORGANISM: Homo sapiens

<400> SEQUENCE: 33

Ser Thr Pro Thr Lys Arg Glu Ile Met Leu Thr Pro Val Thr Val Ala
1               5                   10                  15

Tyr Ser Pro Lys Arg Ser Pro Lys Glu Asn Leu Ser Pro Gly Phe Ser
                20                  25                  30

His Leu Leu Ser Lys Asn Glu Ser Pro Ile Arg Phe Asp Ile Leu
            35                  40                  45

Leu Asp Asp Leu Asp Thr Val Pro Val Ser Thr Leu Gln Arg Thr Asn
        50                  55                  60

Pro Arg Lys Gln Leu Gln Phe Leu Pro Leu Asp Asp Ser Glu Glu Lys
65                  70                  75                  80

Thr Tyr Ser Glu Lys Ala Thr Asp Asn His Val Asn His Ser Ser Cys
                85                  90                  95

Pro Glu Pro Val Pro Asn Gly Val Lys Lys Val Ser Val Arg Thr Ala
            100                 105                 110

Trp Glu Lys Asn Lys Ser Val Ser Tyr Glu Gln Cys Lys Pro Val Ser
            115                 120                 125

Val Thr Pro Gln Gly Asn Asp Phe Glu Tyr Thr Ala Lys Ile Arg Thr
    130                 135                 140

Leu Ala Glu Thr Glu Arg Phe Phe Asp Glu Leu Thr Lys Glu Lys Asp
145                 150                 155                 160

Gln Ile Glu Ala Ala Leu Ser Arg Met Pro Ser Pro Gly Gly Arg Ile
                165                 170                 175

Thr Leu Gln Thr Arg Leu Asn Gln Thr Pro Gln Ile Cys Glu Glu Ser
            180                 185                 190

Ser His Lys Cys Ala Phe Ala Gly His Tyr Val Pro Cys His Leu Tyr
        195                 200                 205

Asp Tyr Arg Phe Gln Gly
        210

<210> SEQ ID NO 34
<211> LENGTH: 468
<212> TYPE: DNA
<213> ORGANISM: Homo sapiens

<400> SEQUENCE: 34
tggtatttct tgtagagatg gggtttcacc acagttgcca aattggtctt gaactactag      60
gctcaagaga ttcacccact tcagcctccc gaagtgctgg gattacagat gtgagccact    120
gcacccagcc tggattttgg ctcttaaaca ttaatacaca catatgaaaa ggacacagga    180
accagccagc aggagtttcc actggccata tctgaaatca agtgagcagc agaaaacccc    240
atgactgtga ctacaacaca atgaatagtc agttggcaca cagtgattca caaaggaagg    300
atggagggaa agaagcagag gagtgaaagg aaaacactga tttccacaac tataggtgac    360
tatcttcctt tcaaatggat aaaggacaga atgaaacatt gacgctgctt ttttagaaga    420
atctatgatg ttctcttatt gatgataaga agtttcttta cagaatgc                468

<210> SEQ ID NO 35
<211> LENGTH: 442
<212> TYPE: PRT
<213> ORGANISM: Homo sapiens

<400> SEQUENCE: 35

Met Gln Pro Pro Pro Ser Leu Cys Gly Arg Ala Leu Val Ala Leu Val
1               5                   10                  15

Leu Ala Cys Gly Leu Ser Arg Ile Trp Gly Glu Glu Arg Gly Phe Pro
            20                  25                  30

Pro Asp Arg Ala Thr Pro Leu Leu Gln Thr Ala Glu Ile Met Thr Pro
        35                  40                  45

Pro Thr Lys Thr Leu Trp Pro Lys Gly Ser Asn Ala Ser Leu Ala Arg
    50                  55                  60

Ser Leu Ala Pro Ala Glu Val Pro Lys Gly Asp Arg Thr Ala Gly Ser
65                  70                  75                  80

Pro Pro Arg Thr Ile Ser Pro Pro Cys Gln Gly Pro Ile Glu Ile
                85                  90                  95

Lys Glu Thr Phe Lys Tyr Ile Asn Thr Val Val Ser Cys Leu Val Phe
                100                 105                 110

Val Leu Gly Ile Ile Gly Asn Ser Thr Leu Leu Arg Ile Ile Tyr Lys
            115                 120                 125

Asn Lys Cys Met Arg Asn Gly Pro Asn Ile Leu Ile Ala Ser Leu Ala
        130                 135                 140

Leu Gly Asp Leu Leu His Ile Val Ile Asp Ile Pro Ile Asn Val Tyr

```
                145                 150                 155                 160
Lys Leu Leu Ala Glu Asp Trp Pro Phe Gly Ala Glu Met Cys Lys Leu
                165                 170                 175

Val Pro Phe Ile Gln Lys Ala Ser Val Gly Ile Thr Val Leu Ser Leu
                180                 185                 190

Cys Ala Leu Ser Ile Asp Arg Tyr Arg Ala Val Ala Ser Trp Ser Arg
                195                 200                 205

Ile Lys Gly Ile Gly Val Pro Lys Trp Thr Ala Val Glu Ile Val Leu
210                 215                 220

Ile Trp Val Val Ser Val Val Leu Ala Val Pro Glu Ala Ile Gly Phe
225                 230                 235                 240

Asp Ile Ile Thr Met Asp Tyr Lys Gly Ser Tyr Leu Arg Ile Cys Leu
                245                 250                 255

Leu His Pro Val Gln Lys Thr Ala Phe Met Gln Phe Tyr Lys Thr Ala
                260                 265                 270

Lys Asp Trp Trp Leu Phe Ser Phe Tyr Phe Cys Leu Pro Leu Ala Ile
                275                 280                 285

Thr Ala Phe Phe Tyr Thr Leu Met Thr Cys Glu Met Leu Arg Lys Lys
                290                 295                 300

Ser Gly Met Gln Ile Ala Leu Asn Asp His Leu Lys Gln Arg Arg Glu
305                 310                 315                 320

Val Ala Lys Thr Val Phe Cys Leu Val Leu Val Phe Ala Leu Cys Trp
                325                 330                 335

Leu Pro Leu His Leu Ser Arg Ile Leu Lys Leu Thr Leu Tyr Asn Gln
                340                 345                 350

Asn Asp Pro Asn Arg Cys Glu Leu Leu Ser Phe Leu Leu Val Leu Asp
                355                 360                 365

Tyr Ile Gly Ile Asn Met Ala Ser Leu Asn Ser Cys Ile Asn Pro Ile
370                 375                 380

Ala Leu Tyr Leu Val Ser Lys Arg Phe Lys Asn Cys Phe Lys Ser Cys
385                 390                 395                 400

Leu Cys Cys Trp Cys Gln Ser Phe Glu Glu Lys Gln Ser Leu Glu Glu
                405                 410                 415

Lys Gln Ser Cys Leu Lys Phe Lys Ala Asn Asp His Gly Tyr Asp Asn
                420                 425                 430

Phe Arg Ser Ser Asn Lys Tyr Ser Ser Ser
                435                 440

<210> SEQ ID NO 36
<211> LENGTH: 461
<212> TYPE: DNA
<213> ORGANISM: Homo sapiens
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t

<400> SEQUENCE: 36
catttgaagt gtttgttcac tgttctcgga gcacctgacg aagagtttcc acttttaata      60
cagttgaacc gaaagaaaat attattgtag taaatttcct ttaaaaaagc aatattgatg     120
```

```
ttcccgtatt tttggaataa aaaagcaccc ttttttttt  aaattattat actttaagtt     180
ttagggtaca tgtgcacaat gtgcagggtt acatatgtat acatgtgaca tgctggtgcg     240
ctgcacccac ctaactcgtc attgaacaat gaaaagcacc ctattttaa  aatgcattat     300 gtaaatagnc tcattccaaa gctgaccata aggcantacc natagtaact tggaaagggg     360
gagaggagga aggcccctg  aggttaccgg ttcccaaggc atttaaaggt tggacttccc     420
gctgggccga ggtacatttt ccccaaggct ttttccctct c                         461

<210> SEQ ID NO 37
<211> LENGTH: 558
<212> TYPE: DNA
<213> ORGANISM: Homo sapiens

<400> SEQUENCE: 37
cccgctccac tcccccaag  cggggggggg ggaggatgac gtcgtggatc cgcggggaac      60
cctcctaaag gaatagctgc ggccgcagaa ttttttttt  tttttctttt ttggagatgg     120
gtctcactct gttgcccagg atggagtgca gtggctcaat cttgggtcac cgcaacctct     180
gcctcttggg ttcaggcaat tctcctgcct cagcctccca ggtagttgga actacaggct     240
gtatcaattt aaatgaacat tattcaaagt gtgcaaggta cgctgtcaaa aactgttacc     300
tcttttaggg tacttggctt tttgaatcaa aacgttttc  acactgtgac agctaaacaa     360
tgacacagaa ttcattcaga tgttgaaaca ctgaacgact acaatggcaa tctagaatat     420
tctgattacg attttctggt taaaacacct cattgtaccc ttgactaact ttacattagg     480
aaaagcttta cattataact tacaattata aaaatgtccc tttcatatac attggagttt     540
aatgcagctt acaataaa                                                   558

<210> SEQ ID NO 38
<211> LENGTH: 524
<212> TYPE: DNA
<213> ORGANISM: Homo sapiens

<400> SEQUENCE: 38
ttttttactt tcatggaaac tacatgtcct tttagtaaaa gtctgtcaaa gaaatttaca      60
aaaacaaaat agacaacaaa caaaacaact tcaagtcata aactctaaat ttaaattgcc     120
ttgttttcct tccaactgct cgggcccttt ccccaccatg tttccgggca ctgcgcaggc     180
tgagctcaag ggaaatttct ttgaacgatg gcttttctc  tagccttgtt tctgtccagc     240
gtcattacag acctggctga atcacagtg  gatttcagag aaagccagaa ttaaacacga     300
taaaaattta aaaataact  acttcataaa tatttattat ttacattagg ggcaatcttt     360
tagtctgaag agtttttata caagttgatg aaatgtacaa gcagtgagaa gagactccag     420
cagtttaaag aagggcaaaa ttagaatgca acgaagatat aaaatacatt aaacaaaaat     480
aatttgcaca aaagcaaaca ggacatgata gaaacctttt tctt                      524

<210> SEQ ID NO 39
<211> LENGTH: 681
<212> TYPE: PRT
<213> ORGANISM: Homo sapiens

<400> SEQUENCE: 39

Thr Arg Pro Val Gln Leu Ser Ala Cys His Leu Leu Thr Asp Val Leu
1               5                   10                  15

Gln Arg Tyr Leu Gln Gln Leu Gly Arg Gly Cys His Arg Tyr Ser Glu
```

```
                    20                  25                  30
Leu Tyr Gly Arg Thr Asp Pro Ile Leu Asp Asp Val Gly Glu Ala Phe
                35                  40                  45
Gln Leu Met Gly Val Ser Leu His Glu Leu Glu Asp Tyr Ile His Asn
            50                  55                  60
Ile Glu Pro Val Thr Phe Pro His Gln Ile Pro Ser Phe Pro Val Ser
 65                  70                  75                  80
Lys Asn Asn Val Leu Gln Phe Pro Gln Pro Gly Ser Lys Asp Ala Glu
                85                  90                  95
Glu Arg Lys Glu Tyr Ile Pro Asp Tyr Leu Pro Pro Ile Val Ser Ser
            100                 105                 110
Gln Glu Glu Glu Glu Glu Gln Val Pro Thr Asp Gly Gly Thr Ser
            115                 120                 125
Ala Glu Ala Met Gln Val Pro Leu Glu Glu Asp Asp Glu Leu Glu Glu
            130                 135                 140
Glu Glu Ile Ile Asn Asp Glu Asn Phe Leu Gly Lys Arg Pro Leu Asp
145                 150                 155                 160
Ser Pro Glu Ala Glu Glu Leu Pro Ala Met Lys Arg Pro Arg Leu Leu
                165                 170                 175
Ser Thr Lys Gly Asp Thr Leu Asp Val Val Leu Leu Glu Ala Arg Glu
            180                 185                 190
Pro Leu Ser Ser Ile Asn Thr Gln Lys Ile Pro Pro Met Leu Ser Pro
            195                 200                 205
Val His Val Gln Asp Ser Thr Asp Leu Ala Pro Pro Ser Pro Glu Pro
        210                 215                 220
Pro Met Leu Ala Pro Val Ala Lys Ser Gln Met Pro Thr Ala Lys Pro
225                 230                 235                 240
Leu Glu Thr Lys Ser Phe Thr Pro Lys Thr Lys Thr Lys Thr Ser Ser
                245                 250                 255
Pro Gly Gln Lys Thr Lys Ser Pro Lys Thr Ala Gln Ser Pro Ala Met
                260                 265                 270
Val Gly Ser Pro Ile Arg Ser Pro Lys Thr Val Ser Lys Glu Lys Lys
            275                 280                 285
Ser Pro Gly Arg Ser Lys Ser Pro Leu Ser Pro Lys Ser Pro Lys Val
            290                 295                 300
Thr Thr His Ile Pro Gln Thr Pro Val Arg Pro Glu Thr Pro Asn Arg
305                 310                 315                 320
Thr Pro Ser Ala Thr Leu Ser Glu Lys Ile Ser Lys Glu Thr Ile Gln
                325                 330                 335
Val Lys Gln Ile Gln Thr Pro Pro Asp Ala Gly Lys Leu Asn Ser Glu
            340                 345                 350
Asn Gln Pro Lys Lys Ala Val Val Ala Asp Lys Thr Ile Glu Ala Ser
            355                 360                 365
Ile Asp Ala Val Ile Ala Arg Ala Cys Ala Glu Arg Glu Pro Asp Pro
        370                 375                 380
Phe Glu Phe Ser Ser Gly Ser Glu Ser Glu Gly Asp Ile Phe Thr Ser
385                 390                 395                 400
Pro Lys Arg Ile Ser Gly Pro Glu Cys Thr Thr Pro Lys Ala Ser Thr
            405                 410                 415
Ser Ala Asn Asn Phe Thr Lys Ser Gly Ser Thr Pro Leu Pro Leu Ser
            420                 425                 430
Gly Gly Thr Ser Ser Ser Asp Asn Ser Trp Thr Met Asp Ala Ser Ile
            435                 440                 445
```

Asp Glu Val Val Arg Lys Ala Lys Leu Gly Thr Pro Ser Asn Met Pro
    450                 455                 460

Pro Asn Phe Pro Tyr Ile Ser Ser Pro Ser Val Ser Pro Pro Thr Pro
465                 470                 475                 480

Glu Pro Leu His Lys Val Tyr Glu Glu Lys Thr Lys Leu Pro Ser Ser
                485                 490                 495

Val Glu Val Lys Lys Leu Lys Lys Glu Leu Lys Thr Lys Met Lys
            500                 505                 510

Lys Lys Glu Lys Gln Arg Asp Arg Glu Arg Glu Lys Asp Lys Asn Lys
        515                 520                 525

Asp Lys Ser Lys Glu Lys Asp Lys Val Lys Glu Lys Glu Lys Asp Lys
    530                 535                 540

Glu Thr Gly Arg Glu Thr Lys Tyr Pro Trp Lys Glu Phe Leu Lys Glu
545                 550                 555                 560

Glu Glu Ala Asp Pro Tyr Lys Phe Lys Ile Lys Glu Phe Glu Asp Val
                565                 570                 575

Asp Pro Lys Val Lys Leu Lys Asp Gly Leu Val Arg Lys Glu Lys Glu
            580                 585                 590

Lys His Lys Asp Lys Lys Asp Arg Glu Lys Gly Lys Lys Asp Lys
        595                 600                 605

Asp Lys Arg Glu Lys Glu Lys Val Lys Asp Lys Gly Arg Glu Asp Lys
    610                 615                 620

Met Lys Ala Pro Ala Pro Leu Val Leu Pro Lys Glu Leu Ala
625                 630                 635                 640

Leu Pro Leu Phe Ser Pro Ala Thr Ala Ser Arg Val Pro Ala Met Leu
                645                 650                 655

Pro Ser Leu Leu Pro Val Leu Pro Glu Lys Leu Phe Glu Glu Lys Glu
            660                 665                 670

Lys Ala Lys Glu Lys Lys Lys Lys
        675                 680

<210> SEQ ID NO 40
<211> LENGTH: 796
<212> TYPE: DNA
<213> ORGANISM: Homo sapiens

<400> SEQUENCE: 40
ccacgcgtcg ggtaccccca ttcacaggtt cccaggtccc ctggcttggc tgatttcaaa     60
atatagagcc ctttcttgcc agtacatcca agtttaaaat tatcagcgaa atggtccatg    120
tttttccaat tacctgctga cacggttcta agctaagtga aggggaagat ctgagagcgt    180
gctgttgtgg ctgtgatgca tattcgtgat gtaacaggtc ctggggcctc actttacccc    240
attgtaaaat ggggctaatg tcacctgcct cttacctacc tcagagggat tggtgaagca    300
aactgttaat cttcgaaaac gaccatttca cttcttggat atcaagtgct aacccagtat    360
gttcttcttt tttatgtaag ggacagcttg gagaaaggac tgctctgtgg agcagagtcc    420
tttctgctgg tgaggacagc atttctgagc agggcttgtt ctctatgtgc attaggactt    480
ttatcatgcc cttgttctgt gtgtagttac ttgacgcat caaatgccgc ctcttcctaa     540
tgtccttcaa gttttcatga actagcaacc caccct tcac accatggttc tggagcgcct    600
gatttgctgt gactcccaga accagccact gttttctgca ccctgtaaac aggccattaa    660
agctccccag tgttcagctc cttaactccc ttgttttccc tgtgctatgt gtcacctggg    720
cctacagaca ggggcaaagc ttatgggtgt gtgtccattg agatgaaatg gttataggaa    780
gggaacataa ggcaac                                                796

<210> SEQ ID NO 41
<211> LENGTH: 532
<212> TYPE: PRT
<213> ORGANISM: Homo sapiens

<400> SEQUENCE: 41

```
Met Glu Lys Ser Asn Glu Thr Asn Gly Tyr Leu Asp Ser Ala Gln Ala
1               5                   10                  15

Gly Pro Ala Ala Gly Pro Gly Ala Pro Gly Thr Ala Ala Gly Arg Ala
            20                  25                  30

Arg Arg Cys Ala Gly Phe Leu Arg Arg Gln Ala Leu Val Leu Leu Thr
        35                  40                  45

Val Ser Gly Val Leu Ala Gly Ala Gly Leu Gly Ala Ala Leu Arg Gly
    50                  55                  60

Leu Ser Leu Ser Arg Thr Gln Val Thr Tyr Leu Ala Phe Pro Gly Glu
65                  70                  75                  80

Met Leu Leu Arg Met Leu Arg Met Ile Ile Leu Pro Leu Val Val Cys
                85                  90                  95

Ser Leu Val Ser Gly Ala Ala Ser Leu Asp Ala Ser Cys Leu Gly Arg
            100                 105                 110

Leu Gly Gly Ile Ala Val Ala Tyr Phe Gly Leu Thr Thr Leu Ser Ala
        115                 120                 125

Ser Ala Leu Ala Val Ala Leu Ala Phe Ile Ile Lys Pro Gly Ser Gly
    130                 135                 140

Ala Gln Thr Leu Gln Ser Ser Asp Leu Gly Leu Glu Asp Ser Gly Pro
145                 150                 155                 160

Pro Pro Val Pro Lys Glu Thr Val Asp Ser Phe Leu Asp Leu Ala Arg
                165                 170                 175

Asn Leu Phe Pro Ser Asn Leu Val Val Ala Ala Phe Arg Thr Tyr Ala
            180                 185                 190

Thr Asp Tyr Lys Val Val Thr Gln Asn Ser Ser Ser Gly Asn Val Thr
        195                 200                 205

His Glu Lys Ile Pro Ile Gly Thr Glu Ile Glu Gly Met Asn Ile Leu
    210                 215                 220

Gly Leu Val Leu Phe Ala Leu Val Leu Gly Val Ala Leu Lys Lys Leu
225                 230                 235                 240

Gly Ser Glu Gly Glu Asp Leu Ile Arg Phe Phe Asn Ser Leu Asn Glu
                245                 250                 255

Ala Thr Met Val Leu Val Ser Trp Ile Met Trp Tyr Val Pro Val Gly
            260                 265                 270

Ile Met Phe Leu Val Gly Ser Lys Ile Val Glu Met Lys Asp Ile Ile
        275                 280                 285

Val Leu Val Thr Ser Leu Gly Lys Tyr Ile Phe Ala Ser Ile Leu Gly
    290                 295                 300

His Val Ile His Gly Gly Ile Val Leu Pro Leu Ile Tyr Phe Val Phe
305                 310                 315                 320

Thr Arg Lys Asn Pro Phe Arg Phe Leu Leu Gly Leu Leu Ala Pro Phe
                325                 330                 335

Ala Thr Ala Phe Ala Thr Cys Ser Ser Ser Ala Thr Leu Pro Ser Met
            340                 345                 350

Met Lys Cys Ile Glu Glu Asn Asn Gly Val Asp Lys Arg Ile Ser Arg
        355                 360                 365
```

```
Phe Ile Leu Pro Ile Gly Ala Thr Val Asn Met Asp Gly Ala Ala Ile
    370                 375                 380

Phe Gln Cys Val Ala Ala Val Phe Ile Ala Gln Leu Asn Asn Val Glu
385                 390                 395                 400

Leu Asn Ala Gly Gln Ile Phe Thr Ile Leu Val Thr Thr Ala Ser
                405                 410                 415

Ser Val Gly Ala Ala Gly Val Pro Ala Gly Gly Val Leu Thr Ile Ala
            420                 425                 430

Ile Ile Leu Glu Ala Ile Gly Leu Pro Thr His Asp Leu Pro Leu Ile
        435                 440                 445

Leu Ala Val Asp Trp Ile Val Asp Arg Thr Thr Thr Val Val Asn Val
    450                 455                 460

Glu Gly Asp Ala Leu Gly Ala Gly Ile Leu His His Leu Asn Gln Lys
465                 470                 475                 480

Ala Thr Lys Lys Gly Glu Gln Glu Leu Ala Glu Val Lys Val Glu Ala
                485                 490                 495

Ile Pro Asn Cys Lys Ser Glu Glu Thr Ser Pro Leu Val Thr His
            500                 505                 510

Gln Asn Pro Ala Gly Pro Val Ala Ser Ala Pro Glu Leu Glu Ser Lys
        515                 520                 525

Glu Ser Val Leu
    530

<210> SEQ ID NO 42
<211> LENGTH: 538
<212> TYPE: DNA
<213> ORGANISM: Homo sapiens

<400> SEQUENCE: 42
gtgctgataa cagcggaatc ccccgtctac ctctctcctt ggtcctggaa cagcgctact     60
gatcaccaag tagccacaaa atataataaa ccctcagcac ttgctcagta gtttgtgaaa    120
gtctcaagta aaagagacac aatacaaaaa aattctttt cggtgaagaa ctccaaaaat    180
aaaattctct agaggcaaaa aaaaaaaaaa ataaaagaaa agaaaaaagg tgtggtcggg    240
ggcccacggg gccccaggga agatgtttt caaacaccat gcccgcgggg gcgcgcggcg    300
ggcccccagc aattggttga cggggacaac cgtggctacc agaggtggt ccgccagaag    360 ggaagatccg cgggctcgag cgaacacggg gcggggtttc ttccccaatt aagaagaagg    420
cccggcgcgg ggaaccgcgg aggctttcgt gaaacaaaat tgcagatggg gctgcgaggg    480
cacatgacgg ggatccactc cggcggggct ccccagcagg agcgaataga attaggcc    538

<210> SEQ ID NO 43
<211> LENGTH: 277
<212> TYPE: PRT
<213> ORGANISM: Homo sapiens

<400> SEQUENCE: 43

Met Pro Ala Asp Ile Met Glu Lys Asn Ser Ser Pro Val Ala Ala
1               5                   10                  15

Ser Val Asn Thr Thr Pro Asp Lys Pro Lys Thr Ala Ser Glu His Arg
            20                  25                  30

Lys Ser Ser Lys Pro Ile Met Glu Lys Arg Arg Arg Ala Arg Ile Asn
        35                  40                  45

Glu Ser Leu Ser Gln Leu Lys Thr Leu Ile Leu Asp Ala Leu Lys Lys
50                  55                  60
```

```
Asp Ser Ser Arg His Ser Lys Leu Glu Lys Ala Asp Ile Leu Glu Met
 65                  70                  75                  80

Thr Val Lys His Leu Arg Asn Leu Gln Arg Ala Gln Met Thr Ala Ala
                 85                  90                  95

Leu Ser Thr Asp Pro Ser Val Leu Gly Lys Tyr Arg Ala Gly Phe Ser
                100                 105                 110

Glu Cys Met Asn Glu Val Thr Arg Phe Leu Ser Thr Cys Glu Gly Val
                115                 120                 125

Asn Thr Glu Val Arg Thr Arg Leu Leu Gly His Leu Ala Asn Cys Met
130                 135                 140

Thr Gln Ile Asn Ala Met Thr Tyr Pro Gly Gln Pro His Pro Ala Leu
145                 150                 155                 160

Gln Ala Pro Pro Pro Pro Pro Gly Pro Gly Gly Pro Gln His Ala
                165                 170                 175

Pro Phe Ala Pro Pro Pro Leu Val Pro Ile Pro Gly Gly Ala Ala
                180                 185                 190

Pro Pro Pro Gly Gly Ala Pro Cys Lys Leu Gly Ser Gln Ala Gly Glu
            195                 200                 205

Ala Ala Lys Val Phe Gly Gly Phe Gln Val Val Pro Ala Pro Asp Gly
210                 215                 220

Gln Phe Ala Phe Leu Ile Pro Asn Gly Ala Phe Ala His Ser Gly Pro
225                 230                 235                 240

Val Ile Pro Val Tyr Thr Ser Asn Ser Gly Thr Ser Val Gly Pro Asn
                245                 250                 255

Ala Val Ser Pro Ser Ser Gly Pro Ser Leu Thr Ala Asp Ser Met Trp
                260                 265                 270

Arg Pro Trp Arg Asn
            275

<210> SEQ ID NO 44
<211> LENGTH: 382
<212> TYPE: PRT
<213> ORGANISM: Homo sapiens

<400> SEQUENCE: 44

Met Thr Ala Thr Glu Ala Leu Leu Arg Val Leu Leu Leu Leu Leu Ala
 1               5                  10                  15

Phe Gly His Ser Thr Tyr Gly Ala Glu Cys Phe Pro Ala Cys Asn Pro
                20                  25                  30

Gln Asn Gly Phe Cys Glu Asp Asp Asn Val Cys Arg Cys Gln Pro Gly
                35                  40                  45

Trp Gln Gly Pro Leu Cys Asp Gln Cys Val Thr Ser Pro Gly Cys Leu
            50                  55                  60

His Gly Leu Cys Gly Glu Pro Gly Gln Cys Ile Cys Thr Asp Gly Trp
 65                  70                  75                  80

Asp Gly Glu Leu Cys Asp Arg Asp Val Arg Ala Cys Ser Ser Ala Pro
                 85                  90                  95

Cys Ala Asn Asn Gly Thr Cys Val Ser Leu Asp Gly Gly Leu Tyr Glu
                100                 105                 110

Cys Ser Cys Ala Pro Gly Tyr Ser Gly Lys Asp Cys Gln Lys Lys Asp
                115                 120                 125

Gly Pro Cys Val Ile Asn Gly Ser Pro Cys Gln His Gly Gly Thr Cys
            130                 135                 140

Val Asp Asp Glu Gly Arg Ala Ser His Ala Ser Cys Leu Cys Pro Pro
```

```
            145                 150                 155                 160
Gly Phe Ser Gly Asn Phe Cys Glu Ile Val Ala Asn Ser Cys Thr Pro
                165                 170                 175

Asn Pro Cys Glu Asn Asp Gly Val Cys Thr Asp Ile Gly Gly Asp Phe
            180                 185                 190

Arg Cys Arg Cys Pro Ala Gly Phe Ile Asp Lys Thr Cys Ser Arg Pro
        195                 200                 205

Val Thr Asn Cys Ala Ser Ser Pro Cys Gln Asn Gly Gly Thr Cys Leu
    210                 215                 220

Gln His Thr Gln Val Ser Tyr Glu Cys Leu Cys Lys Pro Glu Phe Thr
225                 230                 235                 240

Gly Leu Thr Cys Val Lys Lys Arg Ala Leu Ser Pro Gln Gln Val Thr
                245                 250                 255

Arg Leu Pro Ser Gly Tyr Gly Leu Ala Tyr Arg Leu Thr Pro Gly Val
            260                 265                 270

His Glu Leu Pro Val Gln Gln Pro Glu His Arg Ile Leu Lys Val Ser
        275                 280                 285

Met Lys Glu Leu Asn Lys Lys Thr Pro Leu Leu Thr Glu Gly Gln Ala
    290                 295                 300

Ile Cys Phe Thr Ile Leu Gly Val Leu Thr Ser Leu Val Val Leu Gly
305                 310                 315                 320

Thr Val Gly Ile Val Phe Leu Asn Lys Cys Glu Thr Trp Val Ser Asn
                325                 330                 335

Leu Arg Tyr Asn His Met Leu Arg Lys Lys Asn Leu Leu Leu Gln Tyr
            340                 345                 350

Asn Ser Gly Glu Asp Leu Ala Val Asn Ile Ile Phe Pro Glu Lys Ile
        355                 360                 365

Asp Met Thr Thr Phe Ser Lys Glu Ala Gly Asp Glu Glu Ile
    370                 375                 380

<210> SEQ ID NO 45
<211> LENGTH: 318
<212> TYPE: PRT
<213> ORGANISM: Homo sapiens

<400> SEQUENCE: 45

Met Ala Ala Ala Ala Ala Ala Ala Glu Gln Gln Ser Ser Asn Gly
1               5                   10                  15

Pro Val Lys Lys Ser Met Arg Glu Lys Ala Val Glu Arg Arg Ser Val
            20                  25                  30

Asn Lys Glu His Asn Ser Asn Phe Lys Ala Gly Tyr Ile Pro Ile Asp
        35                  40                  45

Glu Asp Arg Leu His Lys Thr Gly Leu Arg Gly Arg Lys Gly Asn Leu
    50                  55                  60

Ala Ile Cys Val Ile Ile Leu Phe Ile Leu Ala Val Ile Asn Leu
65                  70                  75                  80

Ile Ile Thr Leu Val Ile Trp Ala Val Ile Arg Ile Gly Pro Asn Gly
                85                  90                  95

Cys Asp Ser Met Glu Phe His Glu Ser Gly Leu Leu Arg Phe Lys Gln
            100                 105                 110

Val Ser Asp Met Gly Val Ile His Pro Leu Tyr Lys Ser Thr Val Gly
        115                 120                 125

Gly Arg Arg Asn Glu Asn Leu Val Ile Thr Gly Asn Asn Gln Pro Ile
    130                 135                 140
```

```
Val Phe Gln Gln Gly Thr Thr Lys Leu Ser Val Glu Asn Asn Lys Thr
145                 150                 155                 160

Ser Ile Thr Ser Asp Ile Gly Met Gln Phe Phe Asp Pro Arg Thr Gln
            165                 170                 175

Asn Ile Leu Phe Ser Thr Asp Tyr Glu Thr His Glu Phe His Leu Pro
        180                 185                 190

Ser Gly Val Lys Ser Leu Asn Val Gln Lys Ala Ser Thr Glu Arg Ile
    195                 200                 205

Thr Ser Asn Ala Thr Ser Asp Leu Asn Ile Lys Val Asp Gly Arg Ala
210                 215                 220

Ile Val Arg Gly Asn Glu Gly Val Phe Ile Met Gly Lys Thr Ile Glu
225                 230                 235                 240

Phe His Met Gly Gly Asn Met Glu Leu Lys Ala Glu Asn Ser Ile Ile
                245                 250                 255

Leu Asn Gly Ser Val Met Val Ser Thr Thr Arg Leu Pro Ser Ser Ser
            260                 265                 270

Ser Gly Asp Gln Leu Gly Ser Gly Asp Trp Val Arg Tyr Lys Leu Cys
        275                 280                 285

Met Cys Ala Asp Gly Thr Leu Phe Lys Val Gln Val Thr Ser Gln Asn
    290                 295                 300

Met Gly Cys Gln Ile Ser Asp Asn Pro Cys Gly Asn Thr His
305                 310                 315

<210> SEQ ID NO 46
<211> LENGTH: 1663
<212> TYPE: PRT
<213> ORGANISM: Homo sapiens

<400> SEQUENCE: 46

Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
            20                  25                  30

Ile Leu Arg Leu Glu Ser Glu Glu Thr Met Val Leu Glu Ala His Asp
        35                  40                  45

Ala Gln Gly Asp Val Pro Val Thr Val Thr Val His Asp Phe Pro Gly
    50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205
```

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Gln Arg Ile Ser Leu Pro Glu Ser Leu
        275                 280                 285

Lys Arg Ile Pro Ile Glu Asp Gly Ser Gly Val Val Leu Ser Arg
290                 295                 300

Lys Val Leu Leu Asp Gly Val Gln Asn Pro Arg Ala Glu Asp Leu Val
305                 310                 315                 320

Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro
            340                 345                 350

Tyr Gln Ile His Phe Thr Lys Thr Pro Lys Tyr Phe Lys Pro Gly Met
        355                 360                 365

Pro Phe Asp Leu Met Val Phe Val Thr Asn Pro Asp Gly Ser Pro Ala
370                 375                 380

Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
                405                 410                 415

Gln Lys Pro Leu Ser Ile Thr Val Arg Thr Lys Lys Gln Glu Leu Ser
            420                 425                 430

Glu Ala Glu Gln Ala Thr Arg Thr Met Gln Ala Leu Pro Tyr Ser Thr
        435                 440                 445

Val Gly Asn Ser Asn Asn Tyr Leu His Leu Ser Val Leu Arg Thr Glu
450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
                485                 490                 495

Lys Gly Arg Leu Leu Lys Ala Gly Arg Gln Val Arg Glu Pro Gly Gln
            500                 505                 510

Asp Leu Val Val Leu Pro Leu Ser Ile Thr Thr Asp Phe Ile Pro Ser
        515                 520                 525

Phe Arg Leu Val Ala Tyr Tyr Thr Leu Ile Gly Ala Ser Gly Gln Arg
530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
            580                 585                 590

Val Val Leu Val Ala Val Asp Lys Gly Val Phe Val Leu Asn Lys Lys
        595                 600                 605

Asn Lys Leu Thr Gln Ser Lys Ile Trp Asp Val Val Glu Lys Ala Asp
610                 615                 620

```
Ile Gly Cys Thr Pro Gly Ser Gly Lys Asp Tyr Ala Gly Val Phe Ser
625                 630                 635                 640

Asp Ala Gly Leu Thr Phe Thr Ser Ser Gly Gln Gln Thr Ala Gln
                645                 650                 655

Arg Ala Glu Leu Gln Cys Pro Gln Pro Ala Arg Arg Arg Ser
            660                 665                 670

Val Gln Leu Thr Glu Lys Arg Met Asp Lys Val Gly Lys Tyr Pro Lys
            675                 680                 685

Glu Leu Arg Lys Cys Cys Glu Asp Gly Met Arg Glu Asn Pro Met Arg
            690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
                740                 745                 750

Glu Asp Ile Ile Ala Glu Glu Asn Ile Val Ser Arg Ser Glu Phe Pro
                755                 760                 765

Glu Ser Trp Leu Trp Asn Val Glu Asp Leu Lys Glu Pro Pro Lys Asn
770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
                805                 810                 815

Val Ala Asp Pro Phe Glu Val Thr Val Met Gln Asp Phe Phe Ile Asp
                820                 825                 830

Leu Arg Leu Pro Tyr Ser Val Val Arg Asn Glu Gln Val Glu Ile Arg
                835                 840                 845

Ala Val Leu Tyr Asn Tyr Arg Gln Asn Gln Glu Leu Lys Val Arg Val
                850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
                900                 905                 910

Lys Ala Ala Val Tyr His His Phe Ile Ser Asp Gly Val Arg Lys Ser
                915                 920                 925

Leu Lys Val Val Pro Glu Gly Ile Arg Met Asn Lys Thr Val Ala Val
            930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Asp Thr Glu Ser
                965                 970                 975

Glu Thr Arg Ile Leu Leu Gln Gly Thr Pro Val Ala Gln Met Thr Glu
                980                 985                 990

Asp Ala Val Asp Ala Glu Arg Leu  Lys His Leu Ile Val  Thr Pro Ser
                995                 1000                1005

Gly Cys  Gly Glu Gln Asn Met  Ile Gly Met Thr Pro  Thr Val Ile
        1010                 1015                 1020

Ala Val  His Tyr Leu Asp Glu  Thr Glu Gln Trp Glu  Lys Phe Gly
        1025                 1030                 1035

Leu Glu  Lys Arg Gln Gly Ala  Leu Glu Leu Ile Lys  Lys Gly Tyr
```

|  |  | 1040 |  |  |  | 1045 |  |  |  | 1050 |  |
| --- | --- | --- | --- | --- | --- | --- | --- | --- | --- | --- | --- |
| Thr | Gln | Gln | Leu | Ala | Phe | Arg | Gln | Pro | Ser | Ser | Ala | Phe | Ala | Ala |
|  |  | 1055 |  |  |  | 1060 |  |  |  | 1065 |  |

Phe Val Lys Arg Ala Pro Ser Thr Trp Leu Thr Ala Tyr Val Val
  1070                1075              1080

Lys Val Phe Ser Leu Ala Val Asn Leu Ile Ala Ile Asp Ser Gln
  1085                1090              1095

Val Leu Cys Gly Ala Val Lys Trp Leu Ile Leu Glu Lys Gln Lys
  1100                1105              1110

Pro Asp Gly Val Phe Gln Glu Asp Ala Pro Val Ile His Gln Glu
  1115                1120              1125

Met Ile Gly Gly Leu Arg Asn Asn Asn Glu Lys Asp Met Ala Leu
  1130                1135              1140

Thr Ala Phe Val Leu Ile Ser Leu Gln Glu Ala Lys Asp Ile Cys
  1145                1150              1155

Glu Glu Gln Val Asn Ser Leu Pro Gly Ser Ile Thr Lys Ala Gly
  1160                1165              1170

Asp Phe Leu Glu Ala Asn Tyr Met Asn Leu Gln Arg Ser Tyr Thr
  1175                1180              1185

Val Ala Ile Ala Gly Tyr Ala Leu Ala Gln Met Gly Arg Leu Lys
  1190                1195              1200

Gly Pro Leu Leu Asn Lys Phe Leu Thr Thr Ala Lys Asp Lys Asn
  1205                1210              1215

Arg Trp Glu Asp Pro Gly Lys Gln Leu Tyr Asn Val Glu Ala Thr
  1220                1225              1230

Ser Tyr Ala Leu Leu Ala Leu Leu Gln Leu Lys Asp Phe Asp Phe
  1235                1240              1245

Val Pro Pro Val Val Arg Trp Leu Asn Glu Gln Arg Tyr Tyr Gly
  1250                1255              1260

Gly Gly Tyr Gly Ser Thr Gln Ala Thr Phe Met Val Phe Gln Ala
  1265                1270              1275

Leu Ala Gln Tyr Gln Lys Asp Ala Pro Asp His Gln Glu Leu Asn
  1280                1285              1290

Leu Asp Val Ser Leu Gln Leu Pro Ser Arg Ser Ser Lys Ile Thr
  1295                1300              1305

His Arg Ile His Trp Glu Ser Ala Ser Leu Leu Arg Ser Glu Glu
  1310                1315              1320

Thr Lys Glu Asn Glu Gly Phe Thr Val Thr Ala Glu Gly Lys Gly
  1325                1330              1335

Gln Gly Thr Leu Ser Val Val Thr Met Tyr His Ala Lys Ala Lys
  1340                1345              1350

Asp Gln Leu Thr Cys Asn Lys Phe Asp Leu Lys Val Thr Ile Lys
  1355                1360              1365

Pro Ala Pro Glu Thr Glu Lys Arg Pro Gln Asp Ala Lys Asn Thr
  1370                1375              1380

Met Ile Leu Glu Ile Cys Thr Arg Tyr Arg Gly Asp Gln Asp Ala
  1385                1390              1395

Thr Met Ser Ile Leu Asp Ile Ser Met Met Thr Gly Phe Ala Pro
  1400                1405              1410

Asp Thr Asp Asp Leu Lys Gln Leu Ala Asn Gly Val Asp Arg Tyr
  1415                1420              1425

Ile Ser Lys Tyr Glu Leu Asp Lys Ala Phe Ser Asp Arg Asn Thr
  1430                1435              1440

```
Leu Ile Ile Tyr Leu Asp Lys Val Ser His Ser Glu Asp Asp Cys
    1445            1450                1455

Leu Ala Phe Lys Val His Gln Tyr Phe Asn Val Glu Leu Ile Gln
    1460            1465                1470

Pro Gly Ala Val Lys Val Tyr Ala Tyr Tyr Asn Leu Glu Glu Ser
    1475            1480                1485

Cys Thr Arg Phe Tyr His Pro Glu Lys Glu Asp Gly Lys Leu Asn
    1490            1495                1500

Lys Leu Cys Arg Asp Glu Leu Cys Arg Cys Ala Glu Glu Asn Cys
    1505            1510                1515

Phe Ile Gln Lys Ser Asp Asp Lys Val Thr Leu Glu Glu Arg Leu
    1520            1525                1530

Asp Lys Ala Cys Glu Pro Gly Val Asp Tyr Val Tyr Lys Thr Arg
    1535            1540                1545

Leu Val Lys Val Gln Leu Ser Asn Asp Phe Asp Glu Tyr Ile Met
    1550            1555                1560

Ala Ile Glu Gln Thr Ile Lys Ser Gly Ser Asp Glu Val Gln Val
    1565            1570                1575

Gly Gln Gln Arg Thr Phe Ile Ser Pro Ile Lys Cys Arg Glu Ala
    1580            1585                1590

Leu Lys Leu Glu Glu Lys Lys His Tyr Leu Met Trp Gly Leu Ser
    1595            1600                1605

Ser Asp Phe Trp Gly Glu Lys Pro Asn Leu Ser Tyr Ile Ile Gly
    1610            1615                1620

Lys Asp Thr Trp Val Glu His Trp Pro Glu Glu Asp Glu Cys Gln
    1625            1630                1635

Asp Glu Glu Asn Gln Lys Gln Cys Gln Asp Leu Gly Ala Phe Thr
    1640            1645                1650

Glu Ser Met Val Val Phe Gly Cys Pro Asn
    1655            1660
```

<210> SEQ ID NO 47
<211> LENGTH: 444
<212> TYPE: DNA
<213> ORGANISM: Homo sapiens

<400> SEQUENCE: 47

```
ccgcctacta ctactaaatt cgcggccgcg tcgacaatat ggcgaggaaa actgaaaaag    60
gtggaaaatt tagaaatgtc cactctagga cgtggaatat ggcaagaaaa ctgaaaatca   120
tggaaaatga gaaacatcca cttgacgact tgaaaaatga cgaaatcact aaaaaacgtg   180
aaaaatgaga aatgcccact gaaggacctg gaatatggcg agaaaactga aaatcacgga   240
aaatgagaaa tacacacttt aggacgtgaa atatggcgag aaaaactgaa aaggtggaa   300
aatttagaaa tgtccactgt aggacgtgga atatggcaag aaaactgaaa atcatggaaa   360
atgagaaaca aatgtcagct ttctttgtgt gctcctgacg cacagtgagt ccccactgga   420
aaagatgcag ccagcgagct gaag                                          444
```

<210> SEQ ID NO 48
<211> LENGTH: 617
<212> TYPE: DNA
<213> ORGANISM: Homo sapiens
<220> FEATURE:
<221> NAME/KEY: misc_feature
<222> LOCATION: (603)..(603)
<223> OTHER INFORMATION: n is a, c, g, or t

<400> SEQUENCE: 48

```
tcattagaaa gtcttatttta tttattacaa aagcaaagct tcattcacaa tatgaactgc    60
atactagata tagttatttc tgcattaaac tgctttccgg aatccctaaa caatatagtg   120
tattgtacaa ccataataca agttatgttt tgcatacaaa atatgttctt tacatcaaag   180
cacatgttaa caaaaacaag ttctagaaag catataccct ctaagactaa tgaaaacgtc   240
tttagcaggg aattaaaaaa aaattaacat tcatttgata aatattttgt agaacttgaa   300
atgaggattt tatctctgag tattttttgt agtattcccc ttgtccagtt tttgcagaag   360
aatggcaaac acttatttct aaaatgaaat agccctggaa acacccagtg gaattttttc   420
aaagtaaatg tctagcctta acttgaagtt caagaagttg tagctacata ctacattagt   480
aaaatctgaa ataaaattat tcccagttaa tctcttcaca gtttcttaaa aaaatattag   540
tggagataaa ttatctacca actttaaaaa tctaaactta tgttcactga acaaaaataa   600
atntagtttc agaacat                                                  617
```

<210> SEQ ID NO 49
<211> LENGTH: 1707
<212> TYPE: DNA
<213> ORGANISM: Homo sapiens

<400> SEQUENCE: 49

```
tttatattgt gtaataactc acgtactctg aagagagctt ggtcaaacaa taaaatacat    60
tgttactaac ttggtttctt ttctgtgtac tttgcaaaaa ttctattttt aattttgttc   120
atatgttgaa tgtgcccta attggcatct aaagagaat agtaagcatc tattaaccaa    180
aaaagaactc taatagtaaa ggaaagggaa atattggtgg tatgtaccca caaaaccccc   240
aagtgccaag ttaatggaat ctctgctttc cctttcagat gctagaaagc cactgtaatg   300
agttcttgca gttagcatc cagtctaagc tactgcattg tttaaagggc agcatcaagg   360
acactttctc caaactggaa ctctcttctt tgtcaaatct tgtactttaa aattctacaa   420
ttctgttaca ttgttgttta aatcacagac tgctcagatc cattttactg cagtagtttc   480
caagtgtgta acttggcttt agtatttatc agttgccaga aagaaacagg ttgtcatttg   540
gaagttttg tggttatttt ttcccatttt tattcttcag ataaaagcag taccccaaaa   600
tagaaaatga aaattttcat gaaacaaaga gaactcccctt gttaaaaccca gcttattaac   660
tctgtattct gtcaaatgca ttttttcta caactgacc atggatgttg tgaaggtgca    720
ttttaattta aacatggaaa agatttttt cataattaca tactagaatg taaaattata   780
attttgccat gacttaaaga gcacagttga tatcccaaag gttttgatgc taagaagcta   840
cagttattct aaatgcacta aaatgtttga ggcaaatcta ccttagaggc ttttttggta   900
tggtatttt taaaatattt agattttatt taaatttcct gtgagttatt ctgtatttga   960
aaagatgttc gtgtcttccc ctctgtattg aatgtttcac tcatttttatt tttaatcaaa  1020
tattttatag aaatgagttg ttgggaagag tttaacatgc actatttata gtactttgcc  1080
gttaacaggc aatgttctga aactaaattt attttttgttc agtgaacata agtttagatt  1140
tttaaagttg gtagataatt tatctccact aatatttttt taagaaactg tgaagagatt  1200
aactgggaat aattttattt cagatttttac taatgtagta tgtagctaca acttcttgaa  1260
cttcaagtta aggctagaca tttactttga aaaaattcca ctgggtgttt ccagggctat  1320
ttcatttttag aaataagtgt ttgccattct tctgcaaaaa ctggacaagg ggaatactac  1380
```

| | |
|---|---|
| aaaaaatact cagagataaa atcctcattt caagttctac aaaatattta tcaaatgaat | 1440 |
| gttaattttt ttttaattcc ctgctaaaga cgttttcatt agtcttagag ggtatatgct | 1500 |
| ttctagaact tgtttttgtt aacatgtgct ttgatgtaaa gaacatattt tgtatgcaaa | 1560 |
| acataacttg cattatggtt gtacaataca ctatattgtt tagggattcc ggaaagcagt | 1620 |
| ttaatgcaga ataactata tctagtatgc agttcatatt gtgaatgaag ctttgctttt | 1680 |
| gtaataaata aataagactt tctaatg | 1707 |

<210> SEQ ID NO 50
<211> LENGTH: 473
<212> TYPE: DNA
<213> ORGANISM: Homo sapiens

<400> SEQUENCE: 50

| | |
|---|---|
| ttaaacatca tacattttta ttaagagaga aaataaaaag caaagaatcc acttgaagct | 60 |
| ctctagggag catcccgtca ccgccatgtg caagaaatct ggtcttcacc cgcatttttag | 120 |
| ctgtgttgcc cagcatgatg tcccgtccag ggccacactg ggatgttcgt gggcccagg | 180 |
| catttctgcc ttcatgaact cctttctcta tcaatagaat atttaaagtt atattttatg | 240 |
| gctgttggat aaagacaaat aagttattgc tgtgtactaa aacattttct tcagcctaaa | 300 |
| ggttaatgtc ttccttctga tttttaaagac acagaacgac ttccatggac gcccagggca | 360 |
| ctgtgggcct ggcacggtgc cgactggcca gccccatagg gatcccgccc tggtcacggt | 420 |
| gtgggggggcc ctggagccag ggcagaaggc acacaggtct ggagggaagg gtg | 473 |

<210> SEQ ID NO 51
<211> LENGTH: 1488
<212> TYPE: DNA
<213> ORGANISM: Homo sapiens

<400> SEQUENCE: 51

| | |
|---|---|
| gctgaaaggg ccacgtttgt tttcattaca aataagacca ccgagtgggc tcctggcgtg | 60 |
| ggggcgggag cagccgcgcg cagtcttcag aggcagcccc ccaggctgtc tctggagggt | 120 |
| gtgtctctgc ttccctttcc ccgtgtttat tttcagacga agccaagtgg cccgggggga | 180 |
| ccctccggac tcccagcctt cagagaggag ggcagctcgg gctttcgccg cagtgcttcc | 240 |
| tgcccgtcac gtgtgtgctc ctagccgggg tcggggagc tggtatcttg gcccttctgg | 300 |
| gaggacgcgc acagcccgag gaggcagagc cccagacggg aatgggcttt tcagaggtgg | 360 |
| ggtgcgggcg aggggacgat gcattatttt taatatttga tttatttttc caactggact | 420 |
| tcttcccggg gctctttctg ggcccagctg cctttgtgat cccgcgcccc ggtcctcggc | 480 |
| ctctcacctc cagcgccggg gcgcccctg ctgtcggaag cggctgtgac cgggcagagg | 540 |
| tgctatctgg gactctgggt tctcagcccg gggacagcga accgaggggc agatgatcca | 600 |
| tcagaaaaga gccggcactg cccagccccg cgccctgcc cctgcctttt tccgggagcg | 660 |
| cgccgcgccg cacccgctac ggccgcttga ccccatcttt gagcccggcc caagctctg | 720 |
| ggaccgtcgt gcccctcatc aaggaagagc caaggacccc aaggagaagg tcaggagcgg | 780 |
| cggtgtggat gtcccttggc tgcaggcccc gccgcgcact cccttcagtc cttcccttct | 840 |
| ctagggacca ggtagcatca gtgcctggat ctcggccttg tgtgccctgc tccctgcccc | 900 |
| acctactaag aaccaagtct ggttcaccgg ctcccaagag ctggaaccca ttctcagcta | 960 |
| gctggggggcc caggccaccc cttccctcca gacctgtgtg ccttctgccc tggctccagg | 1020 |
| gccccccaca ccgtgaccag gcgggatccc ctatggggct ggccagtcgg caccgtgcca | 1080 |

| | | |
|---|---|---|
| ggcccacagt gccctgggcg tccatggaag tcgttctgtg tctttaaaat cagaaggaag | | 1140 |
| acattaacct ttaggctgaa gaaaatgttt tagtacacag caataactta tttgtcttta | | 1200 |
| tccaacagcc ataaaatata actttaaata ttctattgat agagaaagga gttcatgaag | | 1260 |
| gcagaaatgc ctggggccca cgaacatccc agtgtggccc tggacgggac atcatgctgg | | 1320 |
| gcaacacagc taaaatgcgg gtgaagacca gatttcttgc acatggcggt gacgggatgc | | 1380 |
| tccctagaga gcttcaagtg gattctttgc ttttattt ctctcttaat aaaaatgtat | | 1440 |
| gatgtttaca ttgtcagaga acaaacagaa aaaaaaaaa aaaaaaa | | 1488 |

<210> SEQ ID NO 52
<211> LENGTH: 233
<212> TYPE: PRT
<213> ORGANISM: Homo sapiens

<400> SEQUENCE: 52

Met Ala Trp Thr Val Leu Leu Leu Gly Leu Leu Ser His Cys Thr Gly
1               5                   10                  15

Ser Val Thr Ser Tyr Val Leu Thr Gln Pro Pro Ser Val Ser Val Ala
            20                  25                  30

Pro Gly Lys Ala Ala Arg Ile Thr Cys Gly Gly Ile Asn Ile Ala Ser
        35                  40                  45

Lys Ser Val His Trp Tyr Gln Gln Lys Pro Gly Gln Ala Pro Val Leu
    50                  55                  60

Val Val Tyr Gly Asp Ser Asp Arg Pro Ser Gly Ile Pro Glu Arg Phe
65                  70                  75                  80

Ser Gly Ser Asn Ser Gly Asn Thr Ala Thr Leu Asn Ile Ser Arg Val
                85                  90                  95

Glu Ala Gly Asp Glu Ala Ala Tyr Tyr Cys Gln Val Trp Asp Ser Ser
            100                 105                 110

Ser Asp His Val Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 53
<211> LENGTH: 693
<212> TYPE: PRT
<213> ORGANISM: Homo sapiens

<400> SEQUENCE: 53

Met Met Gln Ala Val Gly Gly Pro Ala Arg Pro Thr Gly Glu Tyr
1               5                   10                  15

-continued

```
Ile Cys Asn Gln Cys Gly Ala Lys Tyr Thr Ser Leu Asp Ser Phe Gln
            20                  25                  30

Thr His Leu Lys Thr His Leu Asp Thr Val Leu Pro Lys Leu Thr Cys
            35                  40                  45

Pro Gln Cys Asn Lys Glu Phe Pro Asn Gln Glu Ser Leu Leu Lys His
 50                  55                  60

Val Thr Ile His Phe Met Ile Thr Ser Thr Tyr Tyr Ile Cys Glu Ser
 65                  70                  75                  80

Cys Asp Lys Gln Phe Thr Ser Val Asp Asp Leu Gln Lys His Leu Leu
            85                  90                  95

Asp Met His Thr Phe Val Phe Phe Arg Cys Thr Leu Cys Gln Glu Val
            100                 105                 110

Phe Asp Ser Lys Val Ser Ile Gln Leu His Leu Ala Val Lys His Ser
            115                 120                 125

Asn Glu Lys Lys Val Tyr Arg Cys Thr Ser Cys Asn Trp Asp Phe Arg
 130                 135                 140

Asn Glu Thr Asp Leu Gln Leu His Val Lys His Asn His Leu Glu Asn
 145                 150                 155                 160

Gln Gly Lys Val His Lys Cys Ile Phe Cys Gly Glu Ser Phe Gly Thr
            165                 170                 175

Glu Val Glu Leu Gln Cys His Ile Thr Thr His Ser Lys Lys Tyr Asn
            180                 185                 190

Cys Lys Phe Cys Ser Lys Ala Phe His Ala Ile Ile Leu Leu Glu Lys
            195                 200                 205

His Leu Arg Glu Lys His Cys Val Phe Glu Thr Lys Thr Pro Asn Cys
 210                 215                 220

Gly Thr Asn Gly Ala Ser Glu Gln Val Gln Lys Glu Val Glu Leu
225                 230                 235                 240

Gln Thr Leu Leu Thr Asn Ser Gln Glu Ser His Asn Ser His Asp Gly
            245                 250                 255

Ser Glu Glu Asp Val Asp Thr Ser Glu Pro Met Tyr Gly Cys Asp Ile
            260                 265                 270

Cys Gly Ala Ala Tyr Thr Met Glu Thr Leu Leu Gln Asn His Gln Leu
            275                 280                 285

Arg Asp His Asn Ile Arg Pro Gly Glu Ser Ala Ile Val Lys Lys Lys
 290                 295                 300

Ala Glu Leu Ile Lys Gly Asn Tyr Lys Cys Asn Val Cys Ser Arg Thr
305                 310                 315                 320

Phe Phe Ser Glu Asn Gly Leu Arg Glu His Met Gln Thr His Leu Gly
            325                 330                 335

Pro Val Lys His Tyr Met Cys Pro Ile Cys Gly Glu Arg Phe Pro Ser
            340                 345                 350

Leu Leu Thr Leu Thr Glu His Lys Val Thr His Ser Lys Ser Leu Asp
            355                 360                 365

Thr Gly Asn Cys Arg Ile Cys Lys Met Pro Leu Gln Ser Glu Glu Glu
 370                 375                 380

Phe Leu Glu His Cys Gln Met His Pro Asp Leu Arg Asn Ser Leu Thr
385                 390                 395                 400

Gly Phe Arg Cys Val Val Cys Met Gln Thr Val Thr Ser Thr Leu Glu
            405                 410                 415

Leu Lys Ile His Gly Thr Phe His Met Gln Lys Thr Gly Asn Gly Ser
            420                 425                 430

Ala Val Gln Thr Thr Gly Arg Gly Gln His Val Gln Lys Leu Tyr Lys
```

|     |     |     |     |     | 435 |     |     |     |     | 440 |     |     |     |     | 445 |     |     |
| --- | --- | --- | --- | --- | --- | --- | --- | --- | --- | --- | --- | --- | --- | --- | --- | --- | --- |

Cys Ala Ser Cys Leu Lys Glu Phe Arg Ser Lys Gln Asp Leu Val Lys
        450                     455                     460

Leu Asp Ile Asn Gly Leu Pro Tyr Gly Leu Cys Ala Gly Cys Val Asn
465                     470                     475                     480

Leu Ser Lys Ser Ala Ser Pro Gly Ile Asn Val Pro Pro Gly Thr Asn
                        485                     490                     495

Arg Pro Gly Leu Gly Gln Asn Glu Asn Leu Ser Ala Ile Glu Gly Lys
            500                     505                     510

Gly Lys Val Gly Gly Leu Lys Thr Arg Cys Ser Ser Cys Asn Val Lys
    515                     520                     525

Phe Glu Ser Glu Ser Glu Leu Gln Asn His Ile Gln Thr Ile His Arg
530                     535                     540

Glu Leu Val Pro Asp Ser Asn Ser Thr Gln Leu Lys Thr Pro Gln Val
545                     550                     555                     560

Ser Pro Met Pro Arg Ile Ser Pro Ser Gln Ser Asp Glu Lys Lys Thr
                565                     570                     575

Tyr Gln Cys Ile Lys Cys Gln Met Val Phe Tyr Asn Glu Trp Asp Ile
            580                     585                     590

Gln Val His Val Ala Asn His Met Ile Asp Glu Gly Leu Asn His Glu
    595                     600                     605

Cys Lys Leu Cys Ser Gln Thr Phe Asp Ser Pro Ala Lys Leu Gln Cys
610                     615                     620

His Leu Ile Glu His Ser Phe Glu Gly Met Gly Gly Thr Phe Lys Cys
625                     630                     635                     640

Pro Val Cys Phe Thr Val Phe Val Gln Ala Asn Lys Leu Gln Gln His
                645                     650                     655

Ile Phe Ser Ala His Gly Gln Glu Asp Lys Ile Tyr Asp Cys Thr Gln
            660                     665                     670

Cys Pro Gln Lys Phe Phe Phe Gln Thr Glu Leu Gln Asn His Thr Met
    675                     680                     685

Thr Gln His Ser Ser
    690

<210> SEQ ID NO 54
<211> LENGTH: 1711
<212> TYPE: DNA
<213> ORGANISM: Homo sapiens

<400> SEQUENCE: 54
tttttttttt taaatctaag ctattcccat ctcccccatt ctatgctggg gtgatatacc     60
acaagaagtt acaggaacaa ctgctaaaag aattaaacat cttgggcctt tacacagctg    120
ttgctatatc atggctttgg tgcatggtcg gtcacagatg ctgtcaagag cttatgttt     180 agttatcctt tgcttcccc aaccccaca ttaaaggtct ccttcacctt ctctgtcctt      240
tttgctacct cccttcttcc tgctccaagc tcccacaaac cagccttaat aaaagaggaa    300
ggatcaaggc aacactccac atcagtcata tttcagggca gcttgatgtt tgtttgctaa    360
tagatggttg gtattatcta accaataggg tgactccaag ttttaaaaaa cagcaagact    420
aattcagaaa taatattatt tcttaatttt tttaaaaata gagatggggt ctcactttgt    480
tgcctaggct ggtcttgaat gcctaggctc aagcaatcct cccaccttgt cctcccaaag    540
tgctaggatt acaggcgtga gccattgcac ccgggctctc agaaatctta aaaaggatt    600 agtttcattt aaaaataaca aacacagttc cccaaatctg aaatttagtt attgaaactg    660

```
gaccatgttg tccatggaaa acatatctta ctttatacca gatttttaaaa ttaacactgg      720 tgtaagtgca gcctaaaatt cctctgagcc ccacttttac ataagaaaaa ttattgaata      780
tgataaaggt agcatttcca atcagtgaga aagataggt tattcaattt gtgttgggac       840
tggtggatat atatctagga aaaaaagta cagactctaa atattgaaag gtaaaactga       900
aaacataaaa atatttgaag aaatcactgg aaaattattc tacaaactgc atggggaatg      960
acagtctgtg ataatagtaa ccaagaacca tgaaagaata gattggtaac aattcagcta     1020
cataaaaatc cctaaatttc tctatggcag aaaccatgaa acagataaat ttaccaaact     1080
ggaaaaaatt ttcacaaatc atgtcacaaa gagctaattt tcttaaaata tataaaaag      1140 atctttcaaa gtgtcataca caaaacactg cttttcgaaa aacataagct cctacaaagc     1200
agtaagaaaa tgatgaacaa atagaaaaat gggcaaaggt gatgatttaa cagttcacag     1260
agaaatacaa atggcttcta aaatatataa aaagatgccc aacttcgttc ataatatgaa     1320
aaatgtaaat taagactaca ctaagataca attttcaca gatctgtttt ctaaaaataa     1380
aataagcttg agagagagcc tcttatctga attctgggac agcctgattt gcatgaggga     1440
aataggcatc ctcctgcact gctggtggga gggtaaaggt acagtctcag tggaggacag     1500
tttgctgtta cctctcagaa ttacaaatgc atgtgtttgt tttgatgtag caatttccca     1560
tctaggaatt tattcttgaa agacagtcat acaagatttt cacaccagca ttatttgtaa     1620
tagcaaaaag atgggaaatt acctaaatgc tcatatatag gggactgcta aattgtggaa     1680
ttccatgcaa ttctaaaaaa aaaaaaaaaa a                                    1711
```

<210> SEQ ID NO 55
<211> LENGTH: 476
<212> TYPE: DNA
<213> ORGANISM: Homo sapiens

<400> SEQUENCE: 55

```
aggcagtggt ggtggtggtg tggtggtgat taggtacagt gctttcaatg cagtcttgca       60
gacagaaaaa aaatctttct caaagcttac aaacatttcc cccctactat ttccacccctt     120 cctcaggcca catgaatttg tgtcacccag ataataaaga agcagcatgt atgctcttaa      180
ttaccagtca aatataaatc aatactaccc taaattaatg gctttctgca agtctacatt      240
aagctgaggt ctacatgttg gcaaatcagg gttttgactt ttttttttat ggaaagtttc      300
caaccagttc ctttccccct ctttattacc agttaatttc caggggtttg tttttgcctt      360
tttgttgttg tttttgtttt tgttgttgag atggactctc tccctgttgc ccagtggagt      420
gcagtggcac aatctcagct cattgcaacc tctgcctccc aggttcaagt gattca          476
```

<210> SEQ ID NO 56
<211> LENGTH: 538
<212> TYPE: PRT
<213> ORGANISM: Homo sapiens

<400> SEQUENCE: 56

```
Met Asp Asp Phe Glu Arg Arg Arg Glu Leu Arg Arg Gln Lys Arg Glu
1               5                   10                  15

Glu Met Arg Leu Glu Ala Glu Arg Ile Ala Tyr Gln Arg Asn Asp Asp
            20                  25                  30

Asp Glu Glu Glu Ala Ala Arg Glu Arg Arg Arg Ala Arg Gln Glu
        35                  40                  45

Arg Leu Arg Gln Lys Gln Glu Glu Glu Ser Leu Gly Gln Val Thr Asp
```

```
                 50                  55                  60
Gln Val Glu Val Asn Ala Gln Asn Ser Val Pro Asp Glu Ala Lys
 65                  70                  75                  80

Thr Thr Thr Thr Asn Thr Gln Val Glu Gly Asp Asp Glu Ala Ala Phe
                     85                  90                  95

Leu Glu Arg Leu Ala Arg Arg Glu Glu Arg Arg Gln Lys Arg Leu Gln
             100                 105                 110

Glu Ala Leu Glu Arg Gln Lys Glu Phe Asp Pro Thr Ile Thr Asp Ala
             115                 120                 125

Ser Leu Ser Leu Pro Ser Arg Arg Met Gln Asn Asp Thr Ala Glu Asn
             130                 135                 140

Glu Thr Thr Glu Lys Glu Glu Lys Ser Glu Ser Arg Gln Glu Arg Tyr
145                 150                 155                 160

Glu Ile Glu Glu Thr Glu Thr Val Thr Lys Ser Tyr Gln Lys Asn Asp
                     165                 170                 175

Trp Arg Asp Ala Glu Glu Asn Lys Lys Glu Asp Lys Glu Lys Glu Glu
                 180                 185                 190

Glu Glu Glu Glu Lys Pro Lys Arg Gly Ser Ile Gly Glu Asn Gln Ile
                 195                 200                 205

Lys Asp Glu Lys Ile Lys Lys Asp Lys Glu Pro Lys Glu Glu Val Lys
             210                 215                 220

Ser Phe Met Asp Arg Lys Lys Gly Phe Thr Glu Val Lys Ser Gln Asn
225                 230                 235                 240

Gly Glu Phe Met Thr His Lys Leu Lys His Thr Glu Asn Thr Phe Ser
                     245                 250                 255

Arg Pro Gly Gly Arg Ala Ser Val Asp Thr Lys Glu Ala Glu Gly Ala
                 260                 265                 270

Pro Gln Val Glu Ala Gly Lys Arg Leu Glu Glu Leu Arg Arg Arg Arg
                 275                 280                 285

Gly Glu Thr Glu Ser Glu Glu Phe Glu Lys Leu Lys Gln Lys Gln Gln
                 290                 295                 300

Glu Ala Ala Leu Glu Leu Glu Glu Leu Lys Lys Lys Arg Glu Glu Arg
305                 310                 315                 320

Arg Lys Val Leu Glu Glu Glu Gln Arg Arg Lys Gln Glu Glu Ala
                     325                 330                 335

Asp Arg Lys Leu Arg Glu Glu Glu Lys Arg Arg Leu Lys Glu Glu
                 340                 345                 350

Ile Glu Arg Arg Arg Ala Glu Ala Ala Glu Lys Arg Gln Lys Met Pro
                 355                 360                 365

Glu Asp Gly Leu Ser Asp Asp Lys Lys Pro Phe Lys Cys Phe Thr Pro
370                 375                 380

Lys Gly Ser Ser Leu Lys Ile Glu Glu Arg Ala Glu Phe Leu Asn Lys
385                 390                 395                 400

Ser Val Gln Lys Ser Ser Gly Val Lys Ser Thr His Gln Ala Ala Ile
                 405                 410                 415

Val Ser Lys Ile Asp Ser Arg Leu Glu Gln Tyr Thr Ser Ala Ile Glu
                 420                 425                 430

Gly Thr Lys Ser Ala Lys Pro Thr Lys Pro Ala Ala Ser Asp Leu Pro
                 435                 440                 445

Val Pro Ala Glu Gly Val Arg Asn Ile Lys Ser Met Trp Glu Lys Gly
             450                 455                 460

Asn Val Phe Ser Ser Pro Thr Ala Ala Gly Thr Pro Asn Lys Glu Thr
465                 470                 475                 480
```

```
Ala Gly Leu Lys Val Gly Val Ser Ser Arg Ile Asn Glu Trp Leu Thr
            485                 490                 495

Lys Thr Pro Asp Gly Asn Lys Ser Pro Ala Pro Lys Pro Ser Asp Leu
            500                 505                 510

Arg Pro Gly Asp Val Ser Ser Lys Arg Asn Leu Trp Glu Lys Gln Ser
            515                 520                 525

Val Asp Lys Val Thr Ser Pro Thr Lys Val
            530                 535

<210> SEQ ID NO 57
<211> LENGTH: 543
<212> TYPE: PRT
<213> ORGANISM: Homo sapiens

<400> SEQUENCE: 57

Met Gly Thr Ser Leu Ser Pro Asn Asp Pro Trp Pro Leu Asn Pro Leu
1               5                   10                  15

Ser Ile Gln Gln Thr Thr Leu Leu Leu Leu Ser Val Leu Ala Thr
            20                  25                  30

Val His Val Gly Gln Arg Leu Leu Arg Gln Arg Arg Gln Leu Arg
            35                  40                  45

Ser Ala Pro Pro Gly Pro Phe Ala Trp Pro Leu Ile Gly Asn Ala Ala
    50                  55                  60

Ala Val Gly Gln Ala Ala His Leu Ser Phe Ala Arg Leu Ala Arg Arg
65              70                  75                  80

Tyr Gly Asp Val Phe Gln Ile Arg Leu Gly Ser Cys Pro Ile Val Val
                85                  90                  95

Leu Asn Gly Glu Arg Ala Ile His Gln Ala Leu Val Gln Gln Gly Ser
            100                 105                 110

Ala Phe Ala Asp Arg Pro Ala Phe Ala Ser Phe Arg Val Val Ser Gly
            115                 120                 125

Gly Arg Ser Met Ala Phe Gly His Tyr Ser Glu His Trp Lys Val Gln
    130                 135                 140

Arg Arg Ala Ala His Ser Met Met Arg Asn Phe Phe Thr Arg Gln Pro
145                 150                 155                 160

Arg Ser Arg Gln Val Leu Glu Gly His Val Leu Ser Glu Ala Arg Glu
                165                 170                 175

Leu Val Ala Leu Leu Val Arg Gly Ser Ala Asp Gly Ala Phe Leu Asp
            180                 185                 190

Pro Arg Pro Leu Thr Val Val Ala Val Ala Asn Val Met Ser Ala Val
            195                 200                 205

Cys Phe Gly Cys Arg Tyr Ser His Asp Asp Pro Glu Phe Arg Glu Leu
    210                 215                 220

Leu Ser His Asn Glu Glu Phe Gly Arg Thr Val Gly Ala Gly Ser Leu
225                 230                 235                 240

Val Asp Val Met Pro Trp Leu Gln Tyr Phe Pro Asn Pro Val Arg Thr
                245                 250                 255

Val Phe Arg Glu Phe Glu Gln Leu Asn Arg Asn Phe Ser Asn Phe Ile
            260                 265                 270

Leu Asp Lys Phe Leu Arg His Cys Glu Ser Leu Arg Pro Gly Ala Ala
            275                 280                 285

Pro Arg Asp Met Met Asp Ala Phe Ile Leu Ser Ala Glu Lys Lys Ala
    290                 295                 300

Ala Gly Asp Ser His Gly Gly Ala Arg Leu Asp Leu Glu Asn Val
```

```
            305                 310                 315                 320
Pro Ala Thr Ile Thr Asp Ile Phe Gly Ala Ser Gln Asp Thr Leu Ser
                    325                 330                 335

Thr Ala Leu Gln Trp Leu Leu Leu Phe Thr Arg Tyr Pro Asp Val
                340                 345                 350

Gln Thr Arg Val Gln Ala Glu Leu Asp Gln Val Val Gly Arg Asp Arg
            355                 360                 365

Leu Pro Cys Met Gly Asp Gln Pro Asn Leu Pro Tyr Val Leu Ala Phe
        370                 375                 380

Leu Tyr Glu Ala Met Arg Phe Ser Ser Phe Val Pro Val Thr Ile Pro
385                 390                 395                 400

His Ala Thr Thr Ala Asn Thr Ser Val Leu Gly Tyr His Ile Pro Lys
                405                 410                 415

Asp Thr Val Val Phe Val Asn Gln Trp Ser Val Asn His Asp Pro Val
            420                 425                 430

Lys Trp Pro Asn Pro Glu Asn Phe Asp Pro Ala Arg Phe Leu Asp Lys
        435                 440                 445

Asp Gly Leu Ile Asn Lys Asp Leu Thr Ser Arg Val Met Ile Phe Ser
    450                 455                 460

Val Gly Lys Arg Arg Cys Ile Gly Glu Glu Leu Ser Lys Met Gln Leu
465                 470                 475                 480

Phe Leu Phe Ile Ser Ile Leu Ala His Gln Cys Asp Phe Arg Ala Asn
                485                 490                 495

Pro Asn Glu Pro Ala Lys Met Asn Phe Ser Tyr Gly Leu Thr Ile Lys
            500                 505                 510

Pro Lys Ser Phe Lys Val Asn Val Thr Leu Arg Glu Ser Met Glu Leu
        515                 520                 525

Leu Asp Ser Ala Val Gln Asn Leu Gln Ala Lys Glu Thr Cys Gln
    530                 535                 540

<210> SEQ ID NO 58
<211> LENGTH: 712
<212> TYPE: DNA
<213> ORGANISM: Homo sapiens

<400> SEQUENCE: 58
agaataaatt cttctggtga aagtggtgat gaatcagatg aattttttgca atctagaaaa       60 ggacagaaaa aaaatcagaa aaacaagcca ggtcctaaca tagaaagtgg gaatgaagat      120
gatgacgcct ccttcaaaat taagacagtg gcccaaaaga aggcagaaaa gaaggagcgc      180
gagagaaaaa agcgagatga agaaaaagcg aaactgcgga agctgaaaga aaagaagag      240 ttagaaacag gtaaaaagga tcagagtaaa caaaaggaat ctcaaggaa atttgaagaa      300 gaaactgtaa aatccaaagt gactgttgat actggagtaa ttcctgcctc tgaagagaaa      360
gcagagactc ccacagctgc agaagatgac aatgaaggag acaaacaaga cgaacgata      420 acgaagaaaa agaaaaggag acaaacagga cacgaacaca agaaagag aagaaaaaag      480 gacctagcaa agccactgtt aaagctatgc aagaagctct ggctaaagct taacagagga      540
cagaagacag acagaaagag agaagaggaa gaacgtcata aaaacggctt gaagaattag      600
aagccaagcg taagaagag gaacgatgga acaacgaaaa cagagaacag gcacacagca      660
aacacagaaa aagaaaaga aaagaccgct tgacagaaaa caaaaacaac ag             712

<210> SEQ ID NO 59
<211> LENGTH: 1220
```

```
<212> TYPE: PRT
<213> ORGANISM: Homo sapiens

<400> SEQUENCE: 59

Met Gly Lys Lys Gln Lys Asn Lys Ser Glu Asp Ser Thr Lys Asp Asp
1               5                   10                  15

Ile Asp Leu Asp Ala Leu Ala Ala Glu Ile Glu Gly Ala Gly Ala Ala
            20                  25                  30

Lys Glu Gln Glu Pro Gln Lys Ser Lys Gly Lys Lys Lys Glu Lys
        35                  40                  45

Lys Lys Gln Asp Phe Asp Glu Asp Ile Leu Lys Glu Leu Glu Glu
    50                  55                  60

Leu Ser Leu Glu Ala Gln Gly Ile Lys Ala Asp Arg Glu Thr Val Ala
65              70                  75                  80

Val Lys Pro Thr Glu Asn Asn Glu Glu Phe Thr Ser Lys Asp Lys
            85                  90                  95

Lys Lys Lys Gly Gln Lys Gly Lys Lys Gln Ser Phe Asp Asp Asn Asp
            100                 105                 110

Ser Glu Glu Leu Glu Asp Lys Asp Ser Lys Ser Lys Lys Thr Ala Lys
            115                 120                 125

Pro Lys Val Glu Met Tyr Ser Gly Ser Asp Asp Asp Asp Phe Asn
            130                 135                 140

Lys Leu Pro Lys Ala Lys Gly Lys Ala Gln Lys Ser Asn Lys Lys
145             150                 155                 160

Trp Asp Gly Ser Glu Glu Asp Glu Asp Asn Ser Lys Lys Ile Lys Glu
            165                 170                 175

Arg Ser Arg Ile Asn Ser Ser Gly Glu Ser Gly Asp Glu Ser Asp Glu
            180                 185                 190

Phe Leu Gln Ser Arg Lys Gly Gln Lys Lys Asn Gln Lys Asn Lys Pro
            195                 200                 205

Gly Pro Asn Ile Glu Ser Gly Asn Glu Asp Asp Asp Ala Ser Phe Lys
            210                 215                 220

Ile Lys Thr Val Ala Gln Lys Ala Glu Lys Glu Arg Glu Arg
225             230                 235                 240

Lys Lys Arg Asp Glu Glu Lys Ala Lys Leu Arg Lys Leu Lys Glu Lys
            245                 250                 255

Glu Glu Leu Glu Thr Gly Lys Lys Asp Gln Ser Lys Gln Lys Glu Ser
            260                 265                 270

Gln Arg Lys Phe Glu Glu Glu Thr Val Lys Ser Lys Val Thr Val Asp
            275                 280                 285

Thr Gly Val Ile Pro Ala Ser Glu Gly Lys Ala Glu Thr Pro Thr Ala
            290                 295                 300

Ala Glu Asp Asp Asn Gly Asp Lys Lys Lys Asp Lys Lys Lys
305             310                 315                 320

Lys Lys Gly Glu Lys Glu Glu Lys Glu Lys Lys Lys Gly Pro
            325                 330                 335

Ser Lys Ala Thr Val Lys Ala Met Gln Glu Ala Leu Ala Lys Leu Lys
            340                 345                 350

Glu Glu Glu Glu Arg Gln Lys Arg Glu Glu Glu Arg Ile Lys Arg
            355                 360                 365

Leu Glu Glu Leu Glu Ala Lys Arg Lys Glu Glu Arg Leu Glu Gln
            370                 375                 380

Glu Lys Arg Glu Arg Lys Lys Gln Lys Glu Lys Glu Arg Lys Glu Arg
385             390                 395                 400
```

```
Leu Lys Lys Glu Gly Lys Leu Leu Thr Lys Ser Gln Arg Glu Ala Arg
            405                 410                 415

Ala Arg Ala Glu Ala Thr Leu Lys Leu Leu Gln Ala Gln Gly Val Glu
            420                 425                 430

Val Pro Ser Lys Asp Ser Leu Pro Lys Lys Arg Pro Ile Tyr Glu Asp
            435                 440                 445

Lys Lys Arg Lys Lys Ile Pro Gln Gln Leu Glu Ser Lys Glu Val Ser
            450                 455                 460

Glu Ser Met Glu Leu Cys Ala Ala Val Glu Val Met Glu Gln Gly Val
465                 470                 475                 480

Pro Glu Lys Glu Glu Thr Pro Pro Val Pro Glu Glu Glu Glu Glu Glu
            485                 490                 495

Asp Thr Glu Asp Ala Gly Leu Asp Asp Trp Glu Ala Met Ala Ser Asp
            500                 505                 510

Glu Glu Thr Glu Lys Val Glu Gly Asn Thr Val His Ile Glu Val Lys
            515                 520                 525

Glu Asn Pro Glu Glu Glu Glu Glu Glu Glu Glu Glu Glu Glu Glu Asp
            530                 535                 540

Glu Glu Ser Glu Glu Glu Glu Glu Glu Gly Glu Ser Glu Gly Ser
545                 550                 555                 560

Glu Gly Asp Glu Glu Asp Glu Lys Val Ser Asp Glu Lys Asp Ser Gly
            565                 570                 575

Lys Thr Leu Asp Lys Lys Pro Ser Lys Glu Met Ser Ser Asp Ser Glu
            580                 585                 590

Tyr Asp Ser Asp Asp Asp Arg Thr Lys Glu Glu Arg Ala Tyr Asp Lys
            595                 600                 605

Ala Lys Arg Arg Ile Glu Lys Arg Arg Leu Glu His Ser Lys Asn Val
            610                 615                 620

Asn Thr Glu Lys Leu Arg Ala Pro Ile Ile Cys Val Leu Gly His Val
625                 630                 635                 640

Asp Thr Gly Lys Thr Lys Ile Leu Asp Lys Leu Arg His Thr His Val
            645                 650                 655

Gln Asp Gly Glu Ala Gly Gly Ile Thr Gln Gln Ile Gly Ala Thr Asn
            660                 665                 670

Val Pro Leu Glu Ala Ile Asn Glu Gln Thr Lys Met Ile Lys Asn Phe
            675                 680                 685

Asp Arg Glu Asn Val Arg Ile Pro Gly Met Leu Ile Ile Asp Thr Pro
            690                 695                 700

Gly His Glu Ser Phe Ser Asn Leu Arg Asn Arg Gly Ser Ser Leu Cys
705                 710                 715                 720

Asp Ile Ala Ile Leu Val Val Asp Ile Met His Gly Leu Glu Pro Gln
            725                 730                 735

Thr Ile Glu Ser Ile Asn Leu Leu Lys Ser Lys Lys Cys Pro Phe Ile
            740                 745                 750

Val Ala Leu Asn Lys Ile Asp Arg Leu Tyr Asp Trp Lys Lys Ser Pro
            755                 760                 765

Asp Ser Asp Val Ala Ala Thr Leu Lys Lys Gln Lys Lys Asn Thr Lys
            770                 775                 780

Asp Glu Phe Glu Glu Arg Ala Lys Ala Ile Ile Val Glu Phe Ala Gln
785                 790                 795                 800

Gln Gly Leu Asn Ala Ala Leu Phe Tyr Glu Asn Lys Asp Pro Arg Thr
            805                 810                 815
```

```
Phe Val Ser Leu Val Pro Thr Ser Ala His Thr Gly Asp Gly Met Gly
                820                 825                 830

Ser Leu Ile Tyr Leu Leu Val Glu Leu Thr Gln Thr Met Leu Ser Lys
            835                 840                 845

Arg Leu Ala His Cys Glu Glu Leu Arg Ala Gln Val Met Glu Val Lys
        850                 855                 860

Ala Leu Pro Gly Met Gly Thr Thr Ile Asp Val Ile Leu Ile Asn Gly
865                 870                 875                 880

Arg Leu Lys Glu Gly Asp Thr Ile Ile Val Pro Gly Val Glu Gly Pro
                885                 890                 895

Ile Val Thr Gln Ile Arg Gly Leu Leu Leu Pro Pro Pro Met Lys Glu
            900                 905                 910

Leu Arg Val Lys Asn Gln Tyr Glu Lys His Lys Glu Val Glu Ala Ala
        915                 920                 925

Gln Gly Val Lys Ile Leu Gly Lys Asp Leu Glu Lys Thr Leu Ala Gly
            930                 935                 940

Leu Pro Leu Leu Val Ala Tyr Lys Glu Asp Glu Ile Pro Val Leu Lys
945                 950                 955                 960

Asp Glu Leu Ile His Glu Leu Lys Gln Thr Leu Asn Ala Ile Lys Leu
                965                 970                 975

Glu Glu Lys Gly Val Tyr Val Gln Ala Ser Thr Leu Gly Ser Leu Glu
            980                 985                 990

Ala Leu Leu Glu Phe Leu Lys Thr Ser Glu Val Pro Tyr Ala Gly Ile
        995                 1000                1005

Asn Ile Gly Pro Val His Lys Lys Asp Val Met Lys Ala Ser Val
    1010                1015                1020

Met Leu Glu His Asp Pro Gln Tyr Ala Val Asn Leu Ala Phe Asp
    1025                1030                1035

Val Arg Ile Glu Arg Asp Ala Gln Glu Met Ala Asp Ser Leu Gly
    1040                1045                1050

Val Arg Ile Phe Ser Ala Glu Ile Ile Tyr His Leu Phe Asp Ala
    1055                1060                1065

Phe Thr Lys Tyr Arg Gln Asp Tyr Lys Lys Gln Lys Gln Glu Glu
    1070                1075                1080

Phe Lys His Ile Ala Val Phe Pro Cys Lys Ile Lys Ile Leu Pro
    1085                1090                1095

Gln Tyr Ile Phe Asn Ser Arg Asp Pro Ile Val Met Gly Val Thr
    1100                1105                1110

Val Glu Ala Gly Gln Val Lys Gln Gly Thr Pro Met Cys Val Pro
    1115                1120                1125

Ser Lys Asn Phe Val Asp Ile Gly Ile Val Thr Ser Ile Glu Ile
    1130                1135                1140

Asn His Lys Gln Val Asp Val Ala Lys Lys Gly Gln Glu Val Cys
    1145                1150                1155

Val Lys Ile Glu Pro Ile Pro Gly Glu Ser Pro Lys Met Phe Gly
    1160                1165                1170

Arg His Phe Glu Ala Thr Asp Ile Leu Val Ser Lys Ile Ser Arg
    1175                1180                1185

Gln Ser Ile Asp Ala Leu Lys Asp Trp Phe Arg Asp Glu Met Gln
    1190                1195                1200

Lys Ser Asp Trp Gln Leu Ile Val Glu Leu Lys Lys Val Phe Glu
    1205                1210                1215

Ile Ile
```

<210> SEQ ID NO 60
<211> LENGTH: 355
<212> TYPE: DNA
<213> ORGANISM: Homo sapiens

<400> SEQUENCE: 60
aaagacagga tctttaccat gcctagcctt agtttcccca ttatatcacc agagagacac    60
taacaaaggt cctcccctct ccctttthccc atttcccatg tccctcacaa gatgacagtt   120
gtagcgtaga taagaccaac gtctagataa aaggttgctc tgacattttt aattaataat   180
gattttcggc caagcatggt gtctcatgcc tgtaatccca actctttggg tgggctgaag   240
caggaggatc acttgagcat ggtagggtga ggctgcagtg agctgtgatc atgtcactgc   300
attccagcca gggtgacaga gtgagatcct gttctctcaa aaaaaaagt aattt         355

<210> SEQ ID NO 61
<211> LENGTH: 565
<212> TYPE: DNA
<213> ORGANISM: Homo sapiens

<400> SEQUENCE: 61
aggtgagtcc agtacacagc caaggttgaa gatcactgac ctagactaaa atgagaggat    60
tcagaagtct gacctagaa catgagagag tggaaaacct caggatgttt cagccaaaca   120
agaagagaag aaaatattgt tgaaattaac aatgatcagg gaaatatca tctattaaga   180 acagggaacc acatttagc tgtagattag gaatggtaat ttttatctgg tgttttagtt    240
ttcaaaacat ttacatattg atctactcct cgccctagac caaacctaat tccattctta   300
ctgatatgca caatcactct ctgtcctcat tgtcacctct agcccctaaa ttcctccctt    360
tctcagtcta cctactcttt gtgactccct catatctttt ccccctggca tggatgtcct    420
gctcagacac tccacttaga agacagtttc ccttttcac tgtcctccca ccattcatta   480
ctcctcctcc agataccaac tgctgatgtt gctctagaaa aaccaccaaa catgactgtt   540
ctttccgtgt aagctatccc acctc                                         565

<210> SEQ ID NO 62
<211> LENGTH: 659
<212> TYPE: PRT
<213> ORGANISM: Homo sapiens

<400> SEQUENCE: 62

Met Glu Val Thr Ala Ser Ser Arg His Tyr Val Asp Arg Leu Phe Asp
1               5                   10                  15

Pro Asp Pro Gln Lys Val Leu Gln Gly Val Ile Asp Met Lys Asn Ala
            20                  25                  30

Val Ile Gly Asn Asn Lys Gln Lys Ala Asn Leu Ile Val Leu Gly Ala
        35                  40                  45

Val Pro Arg Leu Leu Tyr Leu Leu Gln Gln Glu Thr Ser Ser Thr Glu
    50                  55                  60

Leu Lys Thr Glu Cys Ala Val Val Leu Gly Ser Leu Ala Met Gly Thr
65                  70                  75                  80

Glu Asn Asn Val Lys Ser Leu Leu Asp Cys His Ile Ile Pro Ala Leu
                85                  90                  95

Leu Gln Gly Leu Leu Ser Pro Asp Leu Lys Phe Ile Glu Ala Cys Leu
            100                 105                 110

```
Arg Cys Leu Arg Thr Ile Phe Thr Ser Pro Val Thr Pro Glu Glu Leu
            115                 120                 125

Leu Tyr Thr Asp Ala Thr Val Ile Pro His Leu Met Ala Leu Leu Ser
        130                 135                 140

Arg Ser Arg Tyr Thr Gln Glu Tyr Ile Cys Gln Ile Phe Ser His Cys
145                 150                 155                 160

Cys Lys Gly Pro Asp His Gln Thr Ile Leu Phe Asn His Gly Ala Val
                165                 170                 175

Gln Asn Ile Ala His Leu Leu Thr Ser Leu Ser Tyr Lys Val Arg Met
            180                 185                 190

Gln Ala Leu Lys Cys Phe Ser Val Leu Ala Phe Glu Asn Pro Gln Val
        195                 200                 205

Ser Met Thr Leu Val Asn Val Leu Ala Asp Gly Glu Leu Leu Pro Gln
210                 215                 220

Ile Phe Val Lys Met Leu Gln Arg Asp Lys Pro Ile Glu Met Gln Leu
225                 230                 235                 240

Thr Ser Ala Lys Cys Leu Thr Tyr Met Cys Arg Ala Gly Ala Ile Arg
                245                 250                 255

Thr Asp Asp Asn Cys Ile Val Leu Lys Thr Leu Pro Cys Leu Val Arg
            260                 265                 270

Met Cys Ser Lys Glu Arg Leu Leu Glu Glu Arg Val Glu Gly Ala Glu
        275                 280                 285

Thr Leu Ala Tyr Leu Ile Glu Pro Asp Val Glu Leu Gln Arg Ile Ala
290                 295                 300

Ser Ile Thr Asp His Leu Ile Ala Met Leu Ala Asp Tyr Phe Lys Tyr
305                 310                 315                 320

Pro Ser Ser Val Ser Ala Ile Thr Asp Ile Lys Arg Leu Asp His Asp
                325                 330                 335

Leu Lys His Ala His Glu Leu Arg Gln Ala Ala Phe Lys Leu Tyr Ala
            340                 345                 350

Ser Leu Gly Ala Asn Asp Glu Asp Ile Arg Lys Lys Ile Ile Glu Thr
        355                 360                 365

Glu Asn Met Met Asp Arg Ile Val Thr Gly Leu Ser Glu Ser Ser Val
370                 375                 380

Lys Val Arg Leu Ala Ala Val Arg Cys Leu His Ser Leu Ser Arg Ser
385                 390                 395                 400

Val Gln Gln Leu Arg Thr Ser Phe Gln Asp His Ala Val Trp Lys Pro
                405                 410                 415

Leu Met Lys Val Leu Gln Asn Ala Pro Asp Glu Ile Leu Val Val Ala
            420                 425                 430

Ser Ser Met Leu Cys Asn Leu Leu Glu Phe Ser Pro Ser Lys Glu
        435                 440                 445

Pro Ile Leu Glu Ser Gly Ala Val Glu Leu Leu Cys Gly Leu Thr Gln
450                 455                 460

Ser Glu Asn Pro Ala Leu Arg Val Asn Gly Ile Trp Ala Leu Met Asn
465                 470                 475                 480

Met Ala Phe Gln Ala Glu Gln Lys Ile Lys Ala Asp Ile Leu Arg Ser
                485                 490                 495

Leu Ser Thr Glu Gln Leu Phe Arg Leu Leu Ser Asp Ser Asp Leu Asn
            500                 505                 510

Val Leu Met Lys Thr Leu Gly Leu Leu Arg Asn Leu Leu Ser Thr Arg
        515                 520                 525

Pro His Ile Asp Lys Ile Met Ser Thr His Gly Lys Gln Ile Met Gln
```

```
                530             535             540
Ala Val Thr Leu Ile Leu Glu Gly Glu His Asn Ile Glu Val Lys Glu
545                 550                 555                 560

Gln Thr Leu Cys Ile Leu Ala Asn Ile Ala Asp Gly Thr Thr Ala Lys
                565                 570                 575

Asp Leu Ile Met Thr Asn Asp Asp Ile Leu Gln Lys Ile Lys Tyr Tyr
                580                 585                 590

Met Gly His Ser His Val Lys Leu Gln Leu Ala Ala Met Phe Cys Ile
                595                 600                 605

Ser Asn Leu Ile Trp Asn Glu Glu Gly Ser Gln Glu Arg Gln Asp
            610                 615                 620

Lys Leu Arg Asp Met Gly Ile Val Asp Ile Leu His Lys Leu Ser Gln
625                 630                 635                 640

Ser Pro Asp Ser Asn Leu Cys Asp Lys Ala Lys Met Ala Leu Gln Gln
                645                 650                 655

Tyr Leu Ala

<210> SEQ ID NO 63
<211> LENGTH: 443
<212> TYPE: DNA
<213> ORGANISM: Homo sapiens

<400> SEQUENCE: 63
tttttggatg aaaaaggact tacatacccc tgatttatta aaattcattg ttctttata       60 tacatttctc tttaaaattc tgaaatgaac atttgtttat gcagtatgac atgaatgatt     120
taataactta tatgacaagc ttaataaggc tgacattcaa tgaacagaaa agtaatttac     180
cttttagtaa tcagaaaaat ttccaatcca tttttatctt attttaagt gtctgttatt     240 aaagcttgtg attttatta atgtgaataa gccaaagggt gattgttttt gacacacggc     300
attgtgccat agtaaaatgg gtagtatcct tctcagttaa cctttaatac tctgtacaca     360
ctattctgaa atactgtggt gaagtaaggc ctggcgtctt cgagcaggac gctacataag    420
ggagggttag ctgcattgga agg                                            443

<210> SEQ ID NO 64
<211> LENGTH: 4034
<212> TYPE: DNA
<213> ORGANISM: Homo sapiens

<400> SEQUENCE: 64
cggggacaag tccgttgagg ctgccaggcg agtcaggtct ctctggacct cgcctgactc       60
ggctgggctg tgcctgaaat tgacccagct ccaccatact ccttgattat gagaaaacaa     120
ggagtaagct caaagcggct gcaatcttcc ggccgcagcc agtctaaggg gcggcgcggg     180
gcctccctcg cccgggagcc ggaggtagag gaggaggtgg aaaagtcggt cctaggcggc     240
gggaaactgc caaggggcgc ctggaggtcc tccccgggga ggatccaaag tctgaaagag     300
cgaaaaggct tggagctaga ggtggtggcc aagacctttc ttctcggccc cttccagttc     360
gtccgtaatt ccctggcgca gctccgggaa aaggtgcagg aactgcaggc gcggcggttc     420
tccagcagaa ccactctcgg catcgctgtc tttgtggcaa ttttacattg gttacattta     480
gtaacacttt ttgaaaatga tcgtcatttc tctcacctct catctttgga acgggagatg     540
acttttcgca ctgaaatggg acttattat tcatacttca agaccattat tgaagcacct       600
tcgtttttgg aaggactgtg gatgattatg aatgacaggc ttactgaata tcctcttata     660
```

```
attaatgcaa taaaacgctt ccatctttat ccagaggtaa tcatagcctc ctggtattgc   720
acattcatgg gaataatgaa tttatttgga ctagaaacta agacctgctg gaatgtcacc   780
agaatagaac ctcttaatga agttcaaagc tgtgaaggat tgggagatcc tgcttgcttt   840
tatgttggtg taatctttat tttaaatgga ctaatgatgg gattgttctt catgtatgga   900
gcatacctga gtgggactca actgggaggt cttattacag tactgtgctt cttttcaac    960 catgagagg ccacccgtgt gatgtggaca ccacctctcc gtgaaagttt ttcctatcct   1020
ttccttgtac ttcagatgtg tattttaact ttgattctca ggacctcaag caatgataga  1080 aggccccttca ttgcactctg tctttccaat gttgctttta tgcttccctg caatttgct   1140 cagtttatac tttttacaca gatagcatca ttatttccca tgtatgttgt gggatacatt  1200
gaaccaagca aatttcagaa gatcatttat atgaacatga tttcagttac ccttagtttc  1260
attttgatgt ttggaaattc aatgtactta tcttcttatt attcttcatc tttgttaatg  1320
acgtgggcaa taattctaaa gagaaatgaa attcaaaaac tgggagtatc taaactcaac  1380
ttttggctaa ttcaaggtag tgcctggtgg tgtggaacaa tcattttgaa atttctgaca  1440
tctaaaatct taggcgtttc agaccacatt cgcctgagtg atcttatagc agccagaatc  1500
ttaaggtata cagattttga tactttaata tacctgtg ctcccgaatt tgacttcatg     1560
gaaaaagcga ctccgctgag atacacaaag acattattgc ttccagttgt tatggtgatt  1620
acatgtttta tctttaaaaa gactgttcgt gatatttcat atgttttagc tacaaacatt  1680
tatctaagaa aacagctcct tgaacacagt gagctggctt ttcacacatt gcagttgtta  1740
gtgtttactg cccttgccat tttaattatg aggctaaaga tgttttttgac accgcacatg  1800 tgtgttatgg cttccttgat atgctctcga cagctctttg gctggctttt tcgcagagtt  1860
cgttttgaga aggttatctt tggcatttta acagtgatgt caatacaagg ttatgcaaac  1920
ctccgtaatc aatggagcat aataggagaa tttaataatt tgcctcagga agaacttta   1980 cagtggatca aatacagtac cacatcagat gctgtctttg caggtgccat gcctacaatg  2040
gcaagcatca agctgtctac acttcatccc attgtgaatc atccacatta cgaagatgca  2100
gacttgaggg ctcggacaaa aatagtttat tctacatata gtcgaaaatc tgccaaagaa  2160
gtaagagata aattgttgga gttacatgtg aattattatg ttttagaaga ggcatggtgt  2220
gttgtgagaa ctaagcctgg ttgcagtatg cttgaaatct gggatgtgga agaccttcc   2280 aatgcagcta accctccctt atgtagcgtc ctgctcgaag acgccaggcc ttacttcacc  2340
acagtatttc agaatagtgt gtacagagta ttaaaggtta actgagaagg atactaccca  2400
ttttactatg gcacaatgcc gtgtgtcaaa acaatcacc ctttggctta ttcacattaa   2460
taaaaatcac aagctttaat aacagacact taaaaataag ataaaaatgg attggaaatt  2520
tttctgatta ctaaaaggta aattactttt ctgttcattg aatgtcggcc ttattaagct  2580
tgtcatataa gttattaaat cattcatgtc atactgcata aacaaatgtt catttcagaa  2640
ttttaaagag aaatgtatat aaaagaacaa tgaattttaa taaatcaggg gtatgtaagt  2700 ccttttttcat ccaactaggt gaattgcttc agattttctc tagtaccaga gggtacctcc  2760
tcaaactctt tgaaccactt aaggcagaag aatgcaagct ctgaaatgac atccttaaaa  2820
tgctgatact ggtcacagcc tctttacctc tgtgaggaaa ttgtaacagt gtgtctttta  2880
aggtgttttt attttaccag cccttaagaa agatctctaa taccttttaa tactttttt    2940 taataattc aagttgaagt gttttaaaa acactttgtt ttgtaatgtt ttgaatctct    3000
tgagatgtgt ttaccccact agatacatat ttgccactgg ttagttctcc atctaagctc  3060
```

```
aagaggttat tcatctctct ttagattcca gtggcttttc ttttaacatc caggtaaaac    3120
agaaactgct atggtataca accaagtttt ggggttaaac ataatcagaa aagaaaatcc    3180
agttaaattt atgaagtgag attttcagat cctagatctt gaataaagga aaggtctttt    3240
catcttgatg gccccaaagc ttgttggtca tggtctttat ttctggccac tatcttctta    3300
aataatatat tttaagccc tcatttattt ttggttttgg gtgaggaaag tcatgttttc    3360
taagtcctct cccctaataa aacctaccca acaatagtgc tttgaaaagt ggtagttatc    3420
ttgaagatac tcttgccaaa tgcaaagata acattctttt tgtctgcttt tataaatatg    3480
aaatatgcca gatctatagt attttaatgt gcatctactt taaatgagtc atcttggggt    3540
ttttataatt cccttatgtt cttgcccctc tacacttgaa ataacaaaat gccttaattt    3600
tatggattag ttctcttata gtagacaggc agctatatgc agcaaaacca ataaagttat    3660
ttttcaactt tcatagttgt aaaatatctt ataacagaat acaaacagc taagaaaaca    3720 tgccacattt tattttagca ttttcaaata atttgttttt ggtgtaagca caggataaaa    3780
aaggagagcg tcaaagaaaa gagacataac acctaacatt cataaaaatt aacaaagtat    3840 atttggatg atgttttac aggaaatatt ttaaataagt tggtagaact tttaaaatgg    3900
tactgtatta gctaataaaa tattcagtac aaatatatgt ttggatttat gcattaaaaa    3960
actaataaaa ttaaaaaaaa aaaaaaaaaa aaaaaaaaaa aaaaaaaaaa aaagaaaaa    4020 aaaaaaaaaa aaaa                                                     4034

<210> SEQ ID NO 65
<211> LENGTH: 418
<212> TYPE: DNA
<213> ORGANISM: Homo sapiens

<400> SEQUENCE: 65
ttttaggttg ttctgacaaa aactgaaaag cctggtggac aatttctaaa agagctgtta     60
acactgccaa aagcatttct aatttaacca tgaaattgta cccggctcta agtcctcact    120
acaaactcca catatcttta tatgaacatg aggataagat tacaccaaga tttaacttct    180
caagataaaa gattaactaa agaacaattc cgataccttg tactaagtac taggaacaca    240
acaaccataa gtgactatat gatacttatg ctcatgaaca ccctcaaaaa tcttttgttt    300
catcactcaa taacaaaata acttttgctg aaatcattaa aattagctca gtaaaaaaac    360
aaatgcacaa agaagtacaa ggatatttat tttatagcat tattagtagt aacaaaag     418

<210> SEQ ID NO 66
<211> LENGTH: 221
<212> TYPE: PRT
<213> ORGANISM: Homo sapiens

<400> SEQUENCE: 66

Met Ser Ala Glu Val Ile His Gln Val Glu Glu Ala Leu Asp Thr Asp
1               5                   10                  15

Glu Lys Glu Met Leu Leu Phe Leu Cys Arg Asp Val Ala Ile Asp Val
                20                  25                  30

Val Pro Pro Asn Val Arg Asp Leu Leu Asp Ile Leu Arg Glu Arg Gly
            35                  40                  45

Lys Leu Ser Val Gly Asp Leu Ala Glu Leu Leu Tyr Arg Val Arg Arg
        50                  55                  60

Phe Asp Leu Leu Lys Arg Ile Leu Lys Met Asp Arg Lys Ala Val Glu
65                  70                  75                  80
```

```
Thr His Leu Leu Arg Asn Pro His Leu Val Ser Asp Tyr Arg Val Leu
                85                  90                  95
Met Ala Glu Ile Gly Glu Asp Leu Asp Lys Ser Asp Val Ser Ser Leu
            100                 105                 110
Ile Phe Leu Met Lys Asp Tyr Met Gly Arg Gly Lys Ile Ser Lys Glu
        115                 120                 125
Lys Ser Phe Leu Asp Leu Val Val Glu Leu Glu Lys Leu Asn Leu Val
130                 135                 140
Ala Pro Asp Gln Leu Asp Leu Leu Glu Lys Cys Leu Lys Asn Ile His
145                 150                 155                 160
Arg Ile Asp Leu Lys Thr Lys Ile Gln Lys Tyr Lys Gln Ser Val Gln
                165                 170                 175
Gly Ala Gly Thr Ser Tyr Arg Asn Val Leu Gln Ala Ala Ile Gln Lys
            180                 185                 190
Ser Leu Lys Asp Pro Ser Asn Asn Phe Arg Met Ile Thr Pro Tyr Ala
        195                 200                 205
His Cys Pro Asp Leu Lys Ile Leu Gly Asn Cys Ser Met
210                 215                 220

<210> SEQ ID NO 67
<211> LENGTH: 493
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t

<400> SEQUENCE: 67
ncagtaaata agcaaataat gacaaattaa aatctatgaa tggagtttnc tgtncttaac      60
angaaaaact taaattaggc tccaaaagct gtgaaagcct gcctagtttg gcaaaagggg     120
```

```
cactaggatg gggaatcagg aaatctggaa gtcctagcat catacccctg ccactggaaa      180
agtcaacaac agttggcttt gagataaaga tatctcccta tnattcccct ttcnccttcc      240
atttaagaaa tgtgaagact gaaccaagtt ttatgcttta aggttcctta ttngtggtaa      300
aaagatcctg atgacaggta aggtacctag aagaaattaa agcagttaag caactaatca      360
tttacaaaan gaactttat ngaaaaggac aaattgactc cgtatgatga tgacaaatgc      420
tcatcaagca cctgactaaa ttacctagca ttatttcctt taagatatac ncatgtggcc      480
aggcgcagtg gct                                                         493
```

<210> SEQ ID NO 68
<211> LENGTH: 610
<212> TYPE: DNA
<213> ORGANISM: Homo sapiens
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (581)..(581)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (607)..(607)
<223> OTHER INFORMATION: n is a, c, g, or t
<400> SEQUENCE: 68

```
taggtgtgca tgtaataaca aaacacaata gatttccatt agaaccatcc tttaattcaa      60
taaattcttt ggatgaactc tgtaaataga ctactgacac atagcactca aaagtctta      120 tgaaccttaa aacacaaagt agtagactgg gtagacatag ggacaataca gctcatcatt     180
tcatttttga catgttggac ttcaccatgc aagtaaatta atgcatatat gatatttgt      240 tttgttttga gaaagggtct tactgtgtta cccaggctgg aatgcagtgg caatgatctt     300
ggctcacagc aaattctgtc tcctgggctc aagtgatcct cccacccag cctcccaagt      360 aggtgggact aagatgcata cctctatgct cagctaattt ttaaactttt ttttggtaga     420
gatgaggtct cactatantg ctcaggctgg tcctgaactc tcgaagtggt ggggattaca     480
atgtgagccc ccgtgccgaa ttcctnggcc tccgagggc aaaattcccn atagtgagtc      540
gaaggncttt ccggaatcca ggccaagctg gttcccgggg ngaaatggtt atccgntccc     600 nattccncac                                                            610
```

<210> SEQ ID NO 69

<211> LENGTH: 465
<212> TYPE: PRT
<213> ORGANISM: Homo sapiens

<400> SEQUENCE: 69

```
Met Ala Asn Asn Ser Pro Ala Leu Thr Gly Asn Ser Gln Pro Gln His
1               5                   10                  15

Gln Ala Ala Ala Ala Ala Gln Gln Gln Gln Cys Gly Gly Gly
            20                  25                  30

Gly Ala Thr Lys Pro Ala Val Ser Gly Lys Gln Gly Asn Val Leu Pro
            35                  40                  45

Leu Trp Gly Asn Glu Lys Thr Met Asn Leu Asn Pro Met Ile Leu Thr
    50                  55                  60

Asn Ile Leu Ser Ser Pro Tyr Phe Lys Val Gln Leu Tyr Glu Leu Lys
65                  70                  75                  80

Thr Tyr His Glu Val Val Asp Glu Ile Tyr Phe Lys Val Thr His Val
                85                  90                  95

Glu Pro Trp Glu Lys Gly Ser Arg Lys Thr Ala Gly Gln Thr Gly Met
            100                 105                 110

Cys Gly Gly Val Arg Gly Val Gly Thr Gly Gly Ile Val Ser Thr Ala
            115                 120                 125

Phe Cys Leu Leu Tyr Lys Leu Phe Thr Leu Lys Leu Thr Arg Lys Gln
130                 135                 140

Val Met Gly Leu Ile Thr His Thr Asp Ser Pro Tyr Ile Arg Ala Leu
145                 150                 155                 160

Gly Phe Met Tyr Ile Arg Tyr Thr Gln Pro Pro Thr Asp Leu Trp Asp
                165                 170                 175

Trp Phe Glu Ser Phe Leu Asp Asp Glu Glu Asp Leu Asp Val Lys Ala
            180                 185                 190

Gly Gly Gly Cys Val Met Thr Ile Gly Glu Met Leu Arg Ser Phe Leu
            195                 200                 205

Thr Lys Leu Glu Trp Phe Ser Thr Leu Phe Pro Arg Ile Pro Val Pro
210                 215                 220

Val Gln Lys Asn Ile Asp Gln Gln Ile Lys Thr Arg Pro Arg Lys Ile
225                 230                 235                 240

Lys Lys Asp Gly Lys Glu Gly Ala Glu Ile Asp Arg His Val Glu
                245                 250                 255

Arg Arg Arg Ser Arg Ser Pro Arg Ser Leu Ser Pro Arg Arg Ser
            260                 265                 270

Pro Arg Arg Ser Arg Ser Arg Ser His His Arg Glu Gly His Gly Ser
            275                 280                 285

Ser Ser Phe Asp Arg Glu Leu Glu Arg Glu Lys Glu Arg Gln Arg Leu
    290                 295                 300

Glu Arg Glu Ala Lys Glu Arg Glu Lys Glu Arg Arg Ser Arg Ser
305                 310                 315                 320

Ile Asp Arg Gly Leu Glu Arg Arg Ser Arg Ser Glu Arg His
                325                 330                 335

Arg Ser Arg Ser Arg Ser Arg Asp Arg Lys Gly Asp Arg Arg Asp Arg
            340                 345                 350

Asp Arg Glu Arg Glu Lys Glu Asn Glu Arg Gly Arg Arg Asp Arg
            355                 360                 365

Asp Tyr Asp Lys Glu Arg Gly Asn Glu Arg Glu Lys Glu Arg Glu Arg
    370                 375                 380

Ser Arg Glu Arg Ser Lys Glu Gln Arg Ser Arg Gly Glu Val Glu Glu
```

```
                385                 390                 395                 400
Lys Lys His Lys Glu Asp Lys Asp Arg Arg His Arg Asp Asp Lys
                    405                 410                 415

Arg Asp Ser Lys Lys Glu Lys Lys His Ser Arg Ser Arg Ser Arg Glu
                    420                 425                 430

Arg Lys His Arg Ser Arg Ser Arg Ser Arg Asn Ala Gly Lys Arg Ser
                    435                 440                 445

Arg Ser Arg Ser Lys Glu Lys Ser Ser Lys His Lys Lys Lys Lys
    450                 455                 460

Lys
465

<210> SEQ ID NO 70
<211> LENGTH: 297
<212> TYPE: PRT
<213> ORGANISM: Homo sapiens

<400> SEQUENCE: 70

Met Lys Pro Asn Leu Asp Gly Val Asp Leu Phe Asn Asn Gly Gly Ser
1               5                   10                  15

Gly Asn Gly Glu Thr Lys Thr Gly Leu Arg Leu Lys Ala Ile Asn Leu
            20                  25                  30

Pro Leu Glu Asn Glu Val Thr Glu Ile Ser Ala Leu Gln Val His Leu
        35                  40                  45

Asp Glu Phe Gln Lys Ile Leu Trp Lys Glu Arg Glu Met Arg Thr Ala
    50                  55                  60

Leu Glu Lys Glu Ile Glu Arg Leu Glu Ser Ala Leu Ser Leu Trp Lys
65                  70                  75                  80

Trp Lys Tyr Glu Glu Leu Lys Glu Ser Lys Pro Lys Asn Val Lys Glu
                85                  90                  95

Phe Asp Ile Leu Leu Gly Gln His Asn Asp Glu Met Gln Glu Leu Ser
            100                 105                 110

Gly Asn Ile Lys Glu Glu Ser Lys Ser Gln Asn Ser Lys Asp Arg Val
        115                 120                 125

Ile Cys Glu Leu Arg Ala Glu Leu Glu Arg Leu Gln Ala Glu Asn Thr
    130                 135                 140

Ser Glu Trp Asp Lys Arg Glu Ile Leu Glu Arg Glu Lys Gln Gly Leu
145                 150                 155                 160

Glu Arg Glu Asn Arg Arg Leu Lys Ile Gln Val Lys Glu Met Glu Glu
                165                 170                 175

Leu Leu Asp Lys Lys Asn Arg Leu Ser Ala Asn Ser Gln Ser Pro Asp
            180                 185                 190

Phe Lys Met Ser Gln Ile Asp Leu Gln Glu Lys Asn Gln Glu Leu Leu
        195                 200                 205

Asn Leu Gln His Ala Tyr Tyr Lys Leu Asn Arg Gln Tyr Gln Ala Asn
    210                 215                 220

Ile Ala Glu Leu Thr His Ala Asn Asn Arg Val Asp Gln Asn Glu Ala
225                 230                 235                 240

Glu Val Lys Lys Leu Arg Leu Arg Val Glu Glu Leu Lys Gln Gly Leu
                245                 250                 255

Asn Gln Lys Glu Asp Glu Leu Asp Asp Ser Leu Asn Gln Ile Arg Lys
            260                 265                 270

Leu Gln Arg Ser Leu Asp Glu Glu Lys Glu Arg Asn Glu Asn Leu Glu
        275                 280                 285
```

Thr Glu Leu Arg His Leu Gln Asn Trp
    290                 295

<210> SEQ ID NO 71
<211> LENGTH: 499
<212> TYPE: DNA
<213> ORGANISM: Homo sapiens

<400> SEQUENCE: 71

| | | | | | |
|---|---|---|---|---|---|
| cattctgtaa | gttttagctc | aaataccatc | tctaagaaat | ttgccactaa | acttcacgtt | 60 |
| atcatgtctg | tctttacata | acactatgtt | atcatttacc | atattatact | aaaattattt | 120 |
| ttcttatgtg | tgtgtctttc | cacttctata | agctccttga | gaactgcaac | catgacaagc | 180 |
| cctccttata | tctgggatag | tacttgacaa | ggattaaggt | ctgtcacttt | tgttcaact | 240 |
| gagccatact | cctccataga | tgagttttca | agtgaagtca | agagtttgta | gcatagttca | 300 |
| actggtaaac | atctgaattt | gtgctaatag | gataatgctc | atgattgata | ctgtttcaat | 360 |
| tatttctca | aagatcagca | acctaaataa | gaacaaactc | tagtttcatc | agcatgcatt | 420 |
| tcacattgac | aatctttctc | aaaaaataaa | tcttgcttca | ttaatgattc | tttacgtcca | 480 |
| taccaatatc | agtctttgc | | | | | 499 |

<210> SEQ ID NO 72
<211> LENGTH: 534
<212> TYPE: DNA
<213> ORGANISM: Homo sapiens

<400> SEQUENCE: 72

| | | | | | |
|---|---|---|---|---|---|
| tttttttttt | tttttttaag | aaaaaacatg | attttgatca | ttgtaccaca | tgcctttata | 60 |
| aacttttggt | gttatgatgc | aagatctaat | tattatcaaa | tgtagtgacg | cttgttccaa | 120 |
| attctaaaat | tgtttcaatt | atgccttggt | tagggtgac | aggaaggctc | tggtctttag | 180 |
| cttatggtac | atgcctttcg | tcgtctcatt | ttcgtctgga | gatcctgtat | ctcatttttc | 240 |
| attattctgc | tttcttttg | aaatccctct | tttagtagtt | gctcctgttc | ctaaaaaggg | 300 |
| acaaacgaag | gctgagtaaa | gtgtagcatc | aggcaaattg | aaacattcta | tctggttcc | 360 |
| acattaaatg | atttgttatt | taattttctc | tgagtcacgc | aagacgtaaa | tgtcatactt | 420 |
| tggcctatca | ttgaccaaag | cacagccatg | ttccttaccc | tattatgtat | atgacataac | 480 |
| accgaaataa | gcaaagtatc | ctcaaaatcc | cataaggtgt | atgaatcatg | gatt | 534 |

<210> SEQ ID NO 73
<211> LENGTH: 282
<212> TYPE: PRT
<213> ORGANISM: Homo sapiens

<400> SEQUENCE: 73

Asn Ile Tyr Tyr Leu Ala Leu Tyr Arg Asn Thr Tyr Ile Arg Gln Phe
1               5                   10                  15

Tyr Asn Phe Leu Asn Val Phe Leu Gly Thr Ser Gln Lys Asp Glu Thr
            20                  25                  30

Phe Asn Leu Pro Arg Leu Cys Ile Arg Lys Phe Phe Pro Lys Lys Lys
        35                  40                  45

Cys Phe Val Phe Asp Arg Pro Val His Arg Arg Lys Leu Ala Gln Leu
    50                  55                  60

Glu Lys Leu Gln Asp Glu Glu Leu Asp Pro Glu Phe Val Gln Gln Val
65                  70                  75                  80

Ala Asp Phe Cys Ser Tyr Ile Phe Ser Asn Ser Lys Thr Lys Thr Leu

```
                85                  90                  95
Ser Gly Gly Ile Gln Val Asn Gly Pro Arg Leu Glu Ser Leu Val Leu
            100                 105                 110
Thr Tyr Val Asn Ala Ile Ser Ser Gly Asp Leu Pro Cys Met Glu Asn
            115                 120                 125
Ala Val Leu Ala Leu Ala Gln Ile Glu Asn Ser Ala Ala Val Gln Lys
        130                 135                 140
Ala Ile Ala His Tyr Glu Gln Gln Met Gly Gln Lys Val Gln Leu Pro
145                 150                 155                 160
Thr Glu Ser Leu Gln Glu Leu Leu Asp Leu His Arg Asp Ser Glu Arg
                165                 170                 175
Glu Ala Ile Glu Val Phe Ile Arg Ser Ser Phe Lys Asp Val Asp His
            180                 185                 190
Leu Phe Gln Lys Glu Leu Ala Ala Gln Leu Glu Lys Lys Arg Asp His
            195                 200                 205
Phe Cys Lys Gln Asn Gln Glu Ala Ser Ser Asp Arg Cys Ser Ala Leu
        210                 215                 220
Leu Gln Val Ile Phe Ser Pro Leu Glu Glu Val Lys Ala Gly Ile
225                 230                 235                 240
Tyr Ser Lys Pro Gly Gly Tyr Arg Leu Phe Val Gln Lys Leu Gln Asp
                245                 250                 255
Leu Lys Lys Lys Tyr Tyr Glu Glu Pro Arg Lys Gly Ile Gln Val Thr
            260                 265                 270
Lys Ile Tyr Leu Ser Ile Met Glu Ser Cys
        275                 280

<210> SEQ ID NO 74
<211> LENGTH: 437
<212> TYPE: DNA
<213> ORGANISM: Homo sapiens

<400> SEQUENCE: 74
ttctattttg cagactttct tttttaaaag caaaataaat tgacatgact tgttcagggt    60
taactgtttg gcaggtggat gatctgtggc catccatgat gagatcacct ccctgccccg   120
ctggccccca gcctctagaa gtcagggctt ctgaggccca gaagctcagc gccacacctg   180
ttgaaggcca gtgatgtcag agttactctt ccttcctcca gcagcactga cagcagttta   240
ttgtacgcaa tttctagaac tcagatgttc tagaaggaag caaacatatt ctgagatcac   300
agactatgac tatgctctca gaatatgttc tagaacacct aagttgcaat tcttaaaatc   360
aacacagcgt aagactgctt taggaggaag tgatcaagct caaagcaacc taggcatgat   420
gtgccttgtt tgtttat                                                  437

<210> SEQ ID NO 75
<211> LENGTH: 614
<212> TYPE: DNA
<213> ORGANISM: Homo sapiens
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t
```

<220> FEATURE:
<221> NAME/KEY: misc_feature
<222> LOCATION: (585)..(585)
<223> OTHER INFORMATION: n is a, c, g, or t

<400> SEQUENCE: 75

| | |
|---|---|
| tagacaagaa attattttag tcctttagta cagtctgttt cctccttcac ccccagaaca | 60 |
| aaaatcgaac ttctggttgg acagcgtcag atgtcactga ggtgacccca gcctgtttgc | 120 |
| agttccaagt cttccgtgta ggcgtcactg ctactggaac tttgtagatg aggagcctgt | 180 |
| atgatgatgt cctgaacatt tctatccttt cctcacacag agggaagcta cagaatgaag | 240 |
| gggctggaaa acgttggtct ggttcctttt agagctgatt ccccattgga tactgcctgg | 300 |
| aggccttggg gatgaatgag aagttctgca gtttggatca gtagcagaag caggtaacac | 360 |
| atcagggaac cggtcagcct tttagggtct cagcttcctc atctggaaaa ttagaacana | 420 |
| atatctacct cacaatggtc acctgtggat ttaatgagaa atatgtgtaa gatgcttaga | 480 |
| acatttccag atatataaca gatgtgaaat aaatantta atnggtgtat cgagtggttc | 540 |
| taggattaac tttggggctt ggaacctgcc cataagtctg ggccngtaat atcccttaa | 600 |
| ctttgccaat gcag | 614 |

<210> SEQ ID NO 76
<211> LENGTH: 248
<212> TYPE: PRT
<213> ORGANISM: Homo sapiens

<400> SEQUENCE: 76

```
Met Ser Gly Gly Gly Val Ile Arg Gly Pro Ala Gly Asn Asn Asp Cys
1               5                   10                  15

Arg Ile Tyr Val Gly Asn Leu Pro Pro Asp Ile Arg Thr Lys Asp Ile
            20                  25                  30

Glu Asp Val Phe Tyr Lys Tyr Gly Ala Ile Arg Asp Ile Asp Leu Lys
        35                  40                  45

Asn Arg Arg Gly Gly Pro Pro Phe Ala Phe Val Glu Phe Glu Asp Pro
    50                  55                  60

Arg Asp Ala Glu Asp Ala Val Tyr Gly Arg Asp Gly Tyr Asp Tyr Asp
65                  70                  75                  80

Gly Tyr Arg Leu Arg Val Glu Phe Pro Arg Ser Gly Arg Gly Thr Gly
                85                  90                  95

Arg Gly Gly Gly Gly Gly Gly Gly Ala Pro Arg Gly Arg Tyr
            100                 105                 110

Gly Pro Pro Ser Arg Arg Ser Glu Asn Arg Val Val Val Ser Gly Leu
        115                 120                 125

Pro Pro Ser Gly Ser Trp Gln Asp Leu Lys Asp His Met Arg Glu Ala
    130                 135                 140

Gly Asp Val Cys Tyr Ala Asp Val Tyr Arg Asp Gly Thr Gly Val Val
145                 150                 155                 160

Glu Phe Val Arg Lys Glu Asp Met Thr Tyr Ala Val Arg Lys Leu Asp
                165                 170                 175

Asn Thr Lys Phe Arg Ser His Glu Gly Glu Thr Ala Tyr Ile Arg Val
            180                 185                 190

Lys Val Asp Gly Pro Arg Ser Pro Ser Tyr Gly Arg Ser Arg Ser Arg
        195                 200                 205

Ser Arg Ser Arg Ser Arg Ser Arg Ser Arg Ser Asn Ser Arg Ser Arg
    210                 215                 220
```

Ser Tyr Ser Pro Arg Arg Ser Arg Gly Ser Pro Arg Tyr Ser Pro Arg
225                 230                 235                 240

His Ser Arg Ser Arg Ser Arg Thr
                245

<210> SEQ ID NO 77
<211> LENGTH: 1067
<212> TYPE: PRT
<213> ORGANISM: Homo sapiens

<400> SEQUENCE: 77

Met Ala Ser Pro Thr Ser Thr Asn Pro Ala His Ala His Phe Glu Ser
1               5                   10                  15

Phe Leu Gln Ala Gln Leu Cys Gln Asp Val Leu Ser Ser Phe Gln Glu
                20                  25                  30

Leu Cys Gly Ala Leu Gly Leu Glu Pro Gly Gly Gly Leu Pro Gln Tyr
            35                  40                  45

His Lys Ile Lys Asp Gln Leu Asn Tyr Trp Ser Ala Lys Ser Leu Trp
50                  55                  60

Thr Lys Leu Asp Lys Arg Ala Gly Gln Pro Val Tyr Gln Gln Gly Arg
65                  70                  75                  80

Ala Cys Thr Ser Thr Lys Cys Leu Val Val Gly Ala Gly Pro Cys Gly
                85                  90                  95

Leu Arg Val Ala Val Glu Leu Ala Leu Leu Gly Ala Arg Val Val Leu
            100                 105                 110

Val Glu Lys Arg Thr Lys Phe Ser Arg His Asn Val Leu His Leu Trp
        115                 120                 125

Pro Phe Thr Ile His Asp Leu Arg Ala Leu Gly Ala Lys Lys Phe Tyr
130                 135                 140

Gly Arg Phe Cys Thr Gly Thr Leu Asp His Ile Ser Ile Arg Gln Leu
145                 150                 155                 160

Gln Leu Leu Leu Leu Lys Val Ala Leu Leu Gly Val Glu Ile His
                165                 170                 175

Trp Gly Val Thr Phe Thr Gly Leu Gln Pro Pro Arg Lys Gly Ser
            180                 185                 190

Gly Trp Arg Ala Gln Leu Gln Pro Asn Pro Ala Gln Leu Ala Asn
        195                 200                 205

Tyr Glu Phe Asp Val Leu Ile Ser Ala Ala Gly Gly Lys Phe Val Pro
    210                 215                 220

Glu Gly Phe Lys Val Arg Glu Met Arg Gly Lys Leu Ala Ile Gly Ile
225                 230                 235                 240

Thr Ala Asn Phe Val Asn Gly Arg Thr Val Glu Glu Thr Gln Val Pro
                245                 250                 255

Glu Ile Ser Gly Val Ala Arg Ile Tyr Asn Gln Ser Phe Phe Gln Ser
            260                 265                 270

Leu Leu Lys Ala Thr Gly Ile Asp Leu Glu Asn Ile Val Tyr Tyr Lys
        275                 280                 285

Asp Asp Thr His Tyr Phe Val Met Thr Ala Lys Lys Gln Cys Leu Leu
    290                 295                 300

Arg Leu Gly Val Leu Arg Gln Asp Trp Pro Asp Thr Asn Arg Leu Leu
305                 310                 315                 320

Gly Ser Ala Asn Val Val Pro Glu Ala Leu Gln Arg Phe Thr Arg Ala
                325                 330                 335

Ala Ala Asp Phe Ala Thr His Gly Lys Leu Gly Lys Leu Glu Phe Ala
            340                 345                 350

```
Gln Asp Ala His Gly Gln Pro Asp Val Ser Ala Phe Asp Phe Thr Ser
            355                 360                 365

Met Met Arg Ala Glu Ser Ser Ala Arg Val Gln Glu Lys His Gly Ala
370                 375                 380

Arg Leu Leu Leu Gly Leu Val Gly Asp Cys Leu Val Glu Pro Phe Trp
385                 390                 395                 400

Pro Leu Gly Thr Gly Val Ala Arg Gly Phe Leu Ala Ala Phe Asp Ala
            405                 410                 415

Ala Trp Met Val Lys Arg Trp Ala Glu Gly Ala Glu Ser Leu Glu Val
                420                 425                 430

Leu Ala Glu Arg Glu Ser Leu Tyr Gln Leu Leu Ser Gln Thr Ser Pro
            435                 440                 445

Glu Asn Met His Arg Asn Val Ala Gln Tyr Gly Leu Asp Pro Ala Thr
            450                 455                 460

Arg Tyr Pro Asn Leu Asn Leu Arg Ala Val Thr Pro Asn Gln Val Arg
465                 470                 475                 480

Asp Leu Tyr Asp Val Leu Ala Lys Glu Pro Val Gln Arg Asn Asn Asp
                485                 490                 495

Lys Thr Asp Thr Gly Met Pro Ala Thr Gly Ser Ala Gly Thr Gln Glu
            500                 505                 510

Glu Leu Leu Arg Trp Cys Gln Glu Gln Thr Ala Gly Tyr Pro Gly Val
            515                 520                 525

His Val Ser Asp Leu Ser Ser Ser Trp Ala Asp Gly Leu Ala Leu Cys
            530                 535                 540

Ala Leu Val Tyr Arg Leu Gln Pro Gly Leu Leu Glu Pro Ser Glu Leu
545                 550                 555                 560

Gln Gly Leu Gly Ala Leu Glu Ala Thr Ala Trp Ala Leu Lys Val Ala
                565                 570                 575

Glu Asn Glu Leu Gly Ile Thr Pro Val Val Ser Ala Gln Ala Val Val
            580                 585                 590

Ala Gly Ser Asp Pro Leu Gly Leu Ile Ala Tyr Leu Ser His Phe His
            595                 600                 605

Ser Ala Phe Lys Ser Met Ala His Ser Pro Gly Pro Val Ser Gln Ala
            610                 615                 620

Ser Pro Gly Thr Ser Ser Ala Val Leu Phe Leu Ser Lys Leu Gln Arg
625                 630                 635                 640

Thr Leu Gln Arg Ser Arg Ala Lys Glu Asn Ala Glu Asp Ala Gly Gly
                645                 650                 655

Lys Lys Leu Arg Leu Glu Met Glu Ala Glu Thr Pro Ser Thr Glu Val
            660                 665                 670

Pro Pro Asp Pro Glu Pro Gly Val Pro Leu Thr Pro Pro Ser Gln His
            675                 680                 685

Gln Glu Ala Gly Ala Gly Asp Leu Cys Ala Leu Cys Gly Glu His Leu
690                 695                 700

Tyr Val Leu Glu Arg Leu Cys Val Asn Gly His Phe Phe His Arg Ser
705                 710                 715                 720

Cys Phe Arg Cys His Thr Cys Glu Ala Thr Leu Trp Pro Gly Gly Tyr
                725                 730                 735

Glu Gln His Pro Gly Asp Gly His Phe Tyr Cys Leu Gln His Leu Pro
            740                 745                 750

Gln Thr Asp His Lys Lys Glu Gly Ser Asp Arg Gly Pro Glu Ser Pro
            755                 760                 765
```

```
Glu Leu Pro Thr Pro Ser Glu Asn Ser Met Pro Pro Gly Leu Ser Thr
770                 775                 780

Pro Thr Ala Ser Gln Glu Gly Ala Gly Pro Val Pro Asp Pro Ser Gln
785                 790                 795                 800

Pro Thr Arg Arg Gln Ile Arg Leu Ser Ser Pro Glu Arg Gln Arg Leu
                805                 810                 815

Ser Ser Leu Asn Leu Thr Pro Asp Pro Glu Met Glu Pro Pro Pro Lys
            820                 825                 830

Pro Pro Arg Ser Cys Ser Ala Leu Ala Arg His Ala Leu Glu Ser Ser
        835                 840                 845

Phe Val Gly Trp Gly Leu Pro Val Gln Ser Pro Gln Ala Leu Val Ala
850                 855                 860

Met Glu Lys Glu Glu Lys Glu Ser Pro Phe Ser Ser Glu Glu Glu Glu
865                 870                 875                 880

Glu Asp Val Pro Leu Asp Ser Asp Val Glu Gln Ala Leu Gln Thr Phe
                885                 890                 895

Ala Lys Thr Ser Gly Thr Met Asn Asn Tyr Pro Thr Trp Arg Arg Thr
            900                 905                 910

Leu Leu Arg Arg Ala Lys Glu Glu Met Lys Arg Phe Cys Lys Ala
        915                 920                 925

Gln Thr Ile Gln Arg Arg Leu Asn Glu Ile Glu Ala Ala Leu Arg Glu
930                 935                 940

Leu Glu Ala Glu Gly Val Lys Leu Glu Leu Ala Leu Arg Arg Gln Ser
945                 950                 955                 960

Ser Ser Pro Glu Gln Gln Lys Lys Leu Trp Val Gly Gln Leu Leu Gln
                965                 970                 975

Leu Val Asp Lys Lys Asn Ser Leu Val Ala Glu Glu Ala Glu Leu Met
            980                 985                 990

Ile Thr Val Gln Glu Leu Asn Leu  Glu Glu Lys Gln Trp  Gln Leu Asp
                995                 1000                1005

Gln Glu  Leu Arg Gly Tyr Met  Asn Arg Glu Glu  Asn Leu Lys Thr
    1010                1015                1020

Ala Ala  Asp Arg Gln Ala Glu  Asp Gln Val Leu Arg  Lys Leu Val
    1025                1030                1035

Asp Leu  Val Asn Gln Arg Asp  Ala Leu Ile Arg Phe  Gln Glu Glu
    1040                1045                1050

Arg Arg  Leu Ser Glu Leu Ala  Leu Gly Thr Gly Ala  Gln Gly
    1055                1060                1065

<210> SEQ ID NO 78
<211> LENGTH: 257
<212> TYPE: PRT
<213> ORGANISM: Homo sapiens

<400> SEQUENCE: 78

Met Val Gln Leu Arg Pro Arg Ala Ser Arg Ala Pro Ala Ser Ala Glu
1               5                   10                  15

Ala Met Val Asp Glu Gly Gln Leu Ala Ser Glu Glu Glu Glu Ala Glu
            20                  25                  30

His Gly Leu Leu Leu Gly Gln Pro Ser Ser Gly Ala Ala Ala Glu Pro
        35                  40                  45

Leu Glu Glu Asp Glu Glu Gly Asp Asp Glu Phe Asp Asp Glu Ala Pro
    50                  55                  60

Glu Glu Leu Thr Phe Ala Ser Ala Gln Ala Glu Ala Arg Glu Glu Glu
65                  70                  75                  80
```

```
Arg Arg Val Arg Glu Thr Val Arg Arg Asp Lys Thr Leu Leu Lys Glu
                85                  90                  95
Lys Arg Lys Arg Arg Glu Glu Leu Phe Ile Glu Gln Lys Lys Arg Lys
            100                 105                 110
Leu Leu Pro Asp Thr Ile Leu Glu Lys Leu Thr Thr Ala Ser Gln Thr
        115                 120                 125
Asn Ile Lys Lys Ser Pro Gly Lys Val Lys Glu Val Asn Leu Gln Lys
    130                 135                 140
Lys Asn Glu Asp Cys Glu Lys Gly Asn Asp Ser Lys Lys Val Lys Val
145                 150                 155                 160
Gln Lys Val Gln Ser Val Ser Gln Asn Lys Ser Tyr Leu Ala Val Arg
                165                 170                 175
Leu Lys Asp Gln Asp Leu Arg Asp Ser Arg Gln Gln Ala Ala Gln Ala
            180                 185                 190
Phe Ile His Asn Ser Leu Tyr Gly Pro Gly Thr Asn Arg Thr Thr Val
        195                 200                 205
Asn Lys Phe Leu Ser Leu Ala Asn Lys Arg Leu Pro Val Lys Arg Ala
    210                 215                 220
Ala Val Gln Phe Leu Asn Asn Ala Trp Gly Ile Gln Lys Lys Gln Asn
225                 230                 235                 240
Ala Lys Arg Phe Lys Arg Arg Trp Met Val Arg Lys Met Lys Thr Lys
                245                 250                 255
Lys
```

<210> SEQ ID NO 79
<211> LENGTH: 569
<212> TYPE: DNA
<213> ORGANISM: Homo sapiens
<220> FEATURE:
<221> NAME/KEY: misc_feature
<222> LOCATION: (463)..(463)
<223> OTHER INFORMATION: n is a, c, g, or t

<400> SEQUENCE: 79

```
tttttttttt cctttttgga cttcttattc tctttctcac actctttctt tttaagaact    60
gcacaggaac caggacttgg aaaaatcata ttctgggaag cagctttgat agtagccaaa   120
gagatgtctt cccaaaaagc cactaaatgt tgtaaagtta agtgaagagg agacttagac   180
ttcattgtgt tatgcatgga catttcaaaa gtggtctcgg ttttcccatc ctcacatttt   240
tcatgcagag gtggttcctt aagcatagac aataccttgt ttttgttgat gctacccatc   300
ttagatatat ctggtccatg gggtgcaata ttaaacatat tcagtgcaga tgatatttct   360
aatgaatgtc tattttttaa cttggttcct ttttcctctg taggttgttg gctatttaaa   420
ctactcctta taggagcatg tcctttggaa agttcaggat ganactttag gaaagaagaa   480
caagccattg catcatgtac tatgccttca tggcagagga agggagccaa cacagctctg   540
gcacattcgg ccacagtagg agacatggc                                    569
```

<210> SEQ ID NO 80
<211> LENGTH: 4641
<212> TYPE: PRT
<213> ORGANISM: Homo sapiens

<400> SEQUENCE: 80

```
Met Pro Val Pro Asp Gly Ser Val Ala Ala Gly Leu Gly Leu Gly
1               5                   10                  15
```

```
Leu Pro Ala Ala Asp Ser Pro Gly His Tyr Gln Leu Leu Ser Gly
            20                  25                  30

Arg Ala Leu Ala Asp Arg Tyr Arg Ile Tyr Thr Ala Ala Leu Asn
        35                  40                  45

Asp Arg Asp Gln Gly Gly Ser Ala Gly His Pro Ala Ser Arg Asn
    50                  55                  60

Lys Lys Ile Leu Asn Lys Lys Leu Lys Arg Lys Gln Lys Ser Lys
65                  70                  75                  80

Ser Lys Val Lys Thr Arg Ser Lys Ser Glu Asn Leu Glu Asn Thr Val
                85                  90                  95

Ile Ile Pro Asp Ile Lys Leu His Ser Asn Pro Ser Ala Phe Asn Ile
            100                 105                 110

Tyr Cys Asn Val Arg His Cys Val Leu Glu Trp Gln Lys Lys Glu Ile
        115                 120                 125

Ser Leu Ala Ala Ala Ser Lys Asn Ser Val Gln Ser Gly Glu Ser Asp
    130                 135                 140

Ser Asp Glu Glu Glu Ser Lys Glu Pro Pro Ile Lys Leu Pro Lys
145                 150                 155                 160

Ile Ile Glu Val Gly Leu Cys Glu Val Phe Glu Leu Ile Lys Glu Thr
                165                 170                 175

Arg Phe Ser His Pro Ser Leu Cys Leu Arg Ser Leu Gln Ala Leu Leu
            180                 185                 190

Asn Val Leu Gln Gly Gln Pro Glu Val Leu Gln Ser Glu Pro Pro
        195                 200                 205

Glu Val Leu Glu Ser Leu Phe Gln Leu Leu Glu Ile Thr Val Arg
    210                 215                 220

Ser Thr Gly Met Asn Asp Ser Thr Gly Gln Ser Leu Thr Ala Leu Ser
225                 230                 235                 240

Cys Ala Cys Leu Phe Ser Leu Val Ala Ser Trp Gly Glu Thr Gly Arg
                245                 250                 255

Thr Leu Gln Ala Ile Ser Ala Ile Leu Thr Asn Asn Gly Ser His Ala
            260                 265                 270

Cys Gln Thr Ile Gln Val Pro Thr Ile Leu Asn Ser Leu Gln Arg Ser
        275                 280                 285

Val Gln Ala Val Leu Val Gly Lys Ile Gln Ile Gln Asp Trp Phe Ser
    290                 295                 300

Asn Gly Ile Lys Lys Ala Ala Leu Met His Lys Trp Pro Leu Lys Glu
305                 310                 315                 320

Ile Ser Val Asp Glu Asp Asp Gln Cys Leu Leu Gln Asn Asp Gly Phe
                325                 330                 335

Phe Leu Tyr Leu Leu Cys Lys Asp Gly Leu Tyr Lys Ile Gly Ser Gly
            340                 345                 350

Tyr Ser Gly Thr Val Arg Gly His Ile Tyr Asn Ser Thr Ser Arg Ile
        355                 360                 365

Arg Asn Arg Lys Glu Lys Lys Ser Trp Leu Gly Tyr Ala Gln Gly Tyr
    370                 375                 380

Leu Leu Tyr Arg Asp Val Asn Asn His Ser Met Thr Ala Ile Arg Ile
385                 390                 395                 400

Ser Pro Glu Thr Leu Glu Gln Asp Gly Thr Val Met Leu Pro Asp Cys
                405                 410                 415

His Thr Glu Gly Gln Asn Ile Leu Phe Thr Asp Gly Glu Tyr Ile Asn
            420                 425                 430

Gln Ile Ala Ala Ser Arg Asp Asp Gly Phe Val Val Arg Ile Phe Ala
```

```
                435                 440                 445
Thr Ser Thr Glu Pro Val Leu Gln Gln Glu Leu Gln Leu Lys Leu Ala
450                     455                 460
Arg Lys Cys Leu His Ala Cys Arg Ile Ser Leu Phe Asp Leu Glu Lys
465                         470                 475                 480
Asp Leu His Ile Ile Ser Thr Gly Phe Asp Glu Glu Ser Ala Ile Leu
                    485                 490                 495
Gly Ala Gly Arg Glu Phe Ala Leu Met Lys Thr Ala Asn Gly Lys Ile
                500                 505                 510
Tyr Tyr Thr Gly Lys Tyr Gln Ser Leu Gly Ile Lys Gln Gly Gly Pro
                515                 520                 525
Ser Ala Gly Lys Trp Val Glu Leu Pro Ile Thr Lys Ser Pro Lys Ile
530                     535                 540
Val His Phe Ser Val Gly His Asp Gly Ser His Ala Leu Leu Val Ala
545                     550                 555                 560
Glu Asp Gly Ser Ile Phe Phe Thr Gly Ser Ala Ser Lys Gly Glu Asp
                    565                 570                 575
Gly Glu Ser Ile Lys Ser Arg Arg Gln Ser Lys Pro Tyr Lys Pro Lys
                580                 585                 590
Lys Ile Ile Lys Met Glu Gly Lys Ile Val Val Tyr Thr Ala Cys Asn
            595                 600                 605
Asn Gly Ser Ser Ser Val Ile Ser Lys Asp Gly Glu Leu Tyr Met Phe
        610                 615                 620
Gly Lys Asp Ala Ile Tyr Ser Asp Ser Ser Leu Val Thr Asp Leu
625                     630                 635                 640
Lys Gly His Phe Val Thr Gln Val Ala Met Gly Lys Ala His Thr Cys
                    645                 650                 655
Val Leu Met Lys Asn Gly Glu Val Trp Thr Phe Gly Val Asn Asn Lys
                660                 665                 670
Gly Gln Cys Gly Arg Asp Thr Gly Ala Met Asn Gln Gly Lys Gly
            675                 680                 685
Phe Gly Val Glu Asn Met Ala Thr Ala Met Asp Glu Asp Leu Glu Glu
        690                 695                 700
Glu Leu Asp Glu Lys Asp Glu Lys Ser Met Met Cys Pro Pro Gly Met
705                     710                 715                 720
His Lys Trp Lys Leu Glu Gln Cys Met Val Cys Thr Val Cys Gly Asp
                    725                 730                 735
Cys Thr Gly Tyr Gly Ala Ser Cys Val Ser Ser Gly Arg Pro Asp Arg
                740                 745                 750
Val Pro Gly Gly Ile Cys Gly Cys Gly Ser Gly Glu Ser Gly Cys Ala
            755                 760                 765
Val Cys Gly Cys Cys Lys Ala Cys Ala Arg Glu Leu Asp Gly Gln Glu
        770                 775                 780
Ala Arg Gln Arg Gly Ile Leu Asp Ala Val Lys Glu Met Ile Pro Leu
785                     790                 795                 800
Asp Leu Leu Leu Ala Val Pro Val Pro Gly Val Asn Ile Glu Glu His
                    805                 810                 815
Leu Gln Leu Arg Gln Glu Glu Lys Arg Gln Arg Val Ile Arg Arg His
                820                 825                 830
Arg Leu Glu Glu Gly Arg Gly Pro Leu Val Phe Ala Gly Pro Ile Phe
            835                 840                 845
Met Asn His Arg Glu Gln Ala Leu Ala Arg Leu Arg Ser His Pro Ala
        850                 855                 860
```

-continued

His Val Lys His Lys Arg Asp Lys His Lys Asp Gly Ser Gly Glu Arg
865                 870                 875                 880

Gly Glu Lys Asp Ala Ser Lys Ile Thr Thr Tyr Pro Pro Gly Ser Val
            885                 890                 895

Arg Phe Asp Cys Glu Leu Arg Ala Val Gln Val Ser Cys Gly Phe His
        900                 905                 910

His Ser Val Val Leu Met Glu Asn Gly Asp Val Tyr Thr Phe Gly Tyr
            915                 920                 925

Gly Gln His Gly Gln Leu Gly His Gly Asp Val Asn Ser Arg Gly Cys
    930                 935                 940

Pro Thr Leu Val Gln Ala Leu Pro Gly Pro Ser Thr Gln Val Thr Ala
945                 950                 955                 960

Gly Ser Asn His Thr Ala Val Leu Leu Met Asp Gly Gln Val Phe Thr
            965                 970                 975

Phe Gly Ser Phe Ser Lys Gly Gln Leu Gly Arg Pro Ile Leu Asp Val
            980                 985                 990

Pro Tyr Trp Asn Ala Lys Pro Ala Pro Met Pro Asn Ile Gly Ser Lys
        995                 1000                1005

Tyr Gly Arg Lys Ala Thr Trp Ile Gly Ala Ser Gly Asp Gln Thr
    1010                1015                1020

Phe Leu Arg Ile Asp Glu Ala Leu Ile Asn Ser His Val Leu Ala
    1025                1030                1035

Thr Ser Glu Ile Phe Ala Ser Lys His Ile Ile Gly Leu Val Pro
    1040                1045                1050

Ala Ser Ile Ser Glu Pro Pro Phe Lys Cys Leu Leu Ile Asn
    1055                1060                1065

Lys Val Asp Gly Ser Cys Lys Thr Phe Asn Asp Ser Glu Gln Glu
    1070                1075                1080

Asp Leu Gln Gly Phe Gly Val Cys Leu Asp Pro Val Tyr Asp Val
    1085                1090                1095

Ile Trp Arg Phe Arg Pro Asn Thr Arg Glu Leu Trp Cys Tyr Asn
    1100                1105                1110

Ala Val Val Ala Asp Ala Arg Leu Pro Ser Ala Ala Asp Met Gln
    1115                1120                1125

Ser Arg Cys Ser Ile Leu Ser Pro Glu Leu Ala Leu Pro Thr Gly
    1130                1135                1140

Ser Arg Ala Leu Thr Thr Arg Ser His Ala Ala Leu His Ile Leu
    1145                1150                1155

Gly Cys Leu Asp Thr Leu Ala Ala Met Gln Asp Leu Lys Met Gly
    1160                1165                1170

Val Ala Ser Thr Glu Glu Thr Gln Ala Val Met Lys Val Tyr
    1175                1180                1185

Ser Lys Glu Asp Tyr Ser Val Val Asn Arg Phe Glu Ser His Gly
    1190                1195                1200

Gly Gly Trp Gly Tyr Ser Ala His Ser Val Glu Ala Ile Arg Phe
    1205                1210                1215

Ser Ala Asp Thr Asp Ile Leu Leu Gly Gly Leu Gly Leu Phe Gly
    1220                1225                1230

Gly Arg Gly Glu Tyr Thr Ala Lys Ile Lys Leu Phe Glu Leu Gly
    1235                1240                1245

Pro Asp Gly Gly Asp His Glu Thr Asp Gly Asp Leu Leu Ala Glu
    1250                1255                1260

-continued

| | | | | | | | | | | | | | | |
|---|---|---|---|---|---|---|---|---|---|---|---|---|---|---|
|Thr|Asp|Val|Leu|Ala|Tyr|Asp|Cys|Ala|Ala|Arg|Glu|Lys|Tyr|Ala|
| |1265| | | |1270| | | |1275| | | | | |

Thr Asp Val Leu Ala Tyr Asp Cys Ala Ala Arg Glu Lys Tyr Ala
    1265                1270                1275

Met Met Phe Asp Glu Pro Val Leu Leu Gln Ala Gly Trp Trp Tyr
    1280                1285                1290

Val Ala Trp Ala Arg Val Ser Gly Pro Ser Ser Asp Cys Gly Ser
    1295                1300                1305

His Gly Gln Ala Ser Ile Thr Thr Asp Asp Gly Val Val Phe Gln
    1310                1315                1320

Phe Lys Ser Ser Lys Lys Ser Asn Asn Gly Thr Asp Val Asn Ala
    1325                1330                1335

Gly Gln Ile Pro Gln Leu Leu Tyr Arg Leu Pro Thr Ser Asp Gly
    1340                1345                1350

Ser Ala Ser Lys Gly Lys Gln Gln Thr Ser Glu Pro Val His Ile
    1355                1360                1365

Leu Lys Arg Ser Phe Ala Arg Thr Val Ser Val Glu Cys Phe Glu
    1370                1375                1380

Ser Leu Leu Ser Ile Leu His Trp Ser Trp Thr Thr Leu Val Leu
    1385                1390                1395

Gly Val Glu Glu Leu Arg Gly Leu Lys Gly Phe Gln Phe Thr Ala
    1400                1405                1410

Thr Leu Leu Asp Leu Glu Arg Leu Arg Phe Val Gly Thr Cys Cys
    1415                1420                1425

Leu Arg Leu Leu Arg Val Tyr Thr Cys Glu Ile Tyr Pro Val Ser
    1430                1435                1440

Ala Thr Gly Lys Ala Val Val Glu Glu Thr Ser Lys Leu Ala Glu
    1445                1450                1455

Cys Ile Gly Lys Thr Arg Thr Leu Leu Arg Lys Ile Leu Ser Glu
    1460                1465                1470

Pro Leu Asp His Cys Met Val Lys Leu Asp Asn Asp Pro Gln Gly
    1475                1480                1485

Tyr Leu Ser Gln Pro Leu Ser Leu Leu Glu Ala Val Leu Gln Glu
    1490                1495                1500

Cys His Asn Thr Phe Thr Ala Cys Phe His Ser Phe Tyr Pro Thr
    1505                1510                1515

Pro Ala Leu Gln Trp Ala Cys Leu Cys Asp Leu Leu Asn Cys Leu
    1520                1525                1530

Asp Gln Asp Ile Gln Glu Ala Asn Phe Lys Thr Ser Ser Ser Arg
    1535                1540                1545

Leu Leu Ala Ala Val Met Ser Ala Leu Cys His Thr Ser Val Lys
    1550                1555                1560

Leu Thr Ser Ile Phe Pro Ile Ala Tyr Asp Gly Glu Val Leu Leu
    1565                1570                1575

Arg Ser Ile Val Lys Gln Val Ser Thr Glu Asn Asp Ser Thr Leu
    1580                1585                1590

Val His Arg Phe Pro Leu Leu Val Ala His Met Glu Lys Leu Ser
    1595                1600                1605

Gln Ser Glu Glu Asn Ile Ser Gly Met Thr Ser Phe Arg Glu Val
    1610                1615                1620

Leu Glu Lys Met Leu Val Ile Val Val Leu Pro Val Arg Asn Ser
    1625                1630                1635

Leu Arg Arg Glu Asn Glu Leu Phe Ser Ser His Leu Val Ser Asn
    1640                1645                1650

Thr Cys Gly Leu Leu Ala Ser Ile Val Ser Glu Leu Thr Ala Ser

```
            1655               1660                1665

Ala Leu Gly Ser Glu Val Asp Gly Leu Asn Ser Leu His Ser Val
        1670            1675                1680

Lys Ala Ser Ala Asn Arg Phe Thr Lys Thr Ser Gln Gly Arg Ser
        1685            1690                1695

Trp Asn Thr Gly Asn Gly Ser Pro Asp Ala Ile Cys Phe Ser Val
        1700            1705                1710

Asp Lys Pro Gly Ile Val Val Gly Phe Ser Val Tyr Gly Gly
        1715            1720                1725

Gly Gly Ile His Glu Tyr Glu Leu Glu Val Leu Val Asp Asp Ser
        1730            1735                1740

Glu His Ala Gly Asp Ser Thr His Ser His Arg Trp Thr Ser Leu
        1745            1750                1755

Glu Leu Val Lys Gly Thr Tyr Thr Thr Asp Ser Pro Ser Asp
        1760            1765                1770

Ile Ala Glu Ile Arg Leu Asp Lys Val Val Pro Leu Lys Glu Asn
        1775            1780                1785

Val Lys Tyr Ala Val Arg Leu Arg Asn Tyr Gly Ser Arg Thr Ala
        1790            1795                1800

Asn Gly Asp Gly Gly Met Thr Thr Val Gln Cys Pro Asp Gly Val
        1805            1810                1815

Thr Phe Thr Phe Ser Thr Cys Ser Leu Ser Ser Asn Gly Thr Asn
        1820            1825                1830

Gln Thr Arg Gly Gln Ile Pro Gln Ile Leu Tyr Tyr Arg Ser Glu
        1835            1840                1845

Phe Asp Gly Asp Leu Gln Ser Gln Leu Leu Ser Lys Ala Asn Glu
        1850            1855                1860

Glu Asp Lys Asn Cys Ser Arg Ala Leu Ser Val Val Ser Thr Val
        1865            1870                1875

Val Arg Ala Ser Lys Asp Leu Leu His Arg Ala Leu Ala Val Asp
        1880            1885                1890

Ala Asp Asp Ile Pro Glu Leu Leu Ser Ser Ser Leu Phe Ser
        1895            1900                1905

Met Leu Leu Pro Leu Ile Ile Ala Tyr Ile Gly Pro Val Ala Ala
        1910            1915                1920

Ala Ile Pro Lys Val Ala Val Glu Val Phe Gly Leu Val Gln Gln
        1925            1930                1935

Leu Leu Pro Ser Val Ala Ile Leu Asn Gln Lys Tyr Ala Pro Pro
        1940            1945                1950

Ala Phe Asn Pro Asn Gln Ser Thr Asp Ser Thr Thr Gly Asn Gln
        1955            1960                1965

Pro Glu Gln Gly Leu Ser Ala Cys Thr Thr Ser Ser His Tyr Ala
        1970            1975                1980

Val Ile Glu Ser Glu His Pro Tyr Lys Pro Ala Cys Val Met His
        1985            1990                1995

Tyr Lys Val Thr Phe Pro Glu Cys Val Arg Trp Met Thr Ile Glu
        2000            2005                2010

Phe Asp Pro Gln Cys Gly Thr Ala Gln Ser Glu Asp Val Leu Arg
        2015            2020                2025

Leu Leu Ile Pro Val Arg Thr Val Gln Asn Ser Gly Tyr Gly Pro
        2030            2035                2040

Lys Leu Thr Ser Val His Glu Asn Leu Asn Ser Trp Ile Glu Leu
        2045            2050                2055
```

```
Lys Lys Phe Ser Gly Ser Ser Gly Trp Pro Thr Met Val Leu Val
    2060                2065                2070

Leu Pro Gly Asn Glu Ala Leu Phe Ser Leu Glu Thr Ala Ser Asp
    2075                2080                2085

Tyr Val Lys Asp Asp Lys Ala Ser Phe Tyr Gly Phe Met Cys Phe
    2090                2095                2100

Ala Ile Gly Tyr Glu Phe Ser Pro Gly Pro Asp Glu Gly Val Ile
    2105                2110                2115

Gln Leu Glu Lys Glu Leu Ala Asn Leu Gly Val Cys Ala Ala
    2120                2125                2130

Ala Leu Met Lys Lys Asp Leu Ala Leu Pro Ile Gly Asn Glu Leu
    2135                2140                2145

Glu Glu Asp Leu Glu Ile Leu Glu Glu Ala Ala Leu Gln Val Cys
    2150                2155                2160

Lys Thr His Ser Gly Ile Leu Gly Lys Gly Leu Ala Leu Ser His
    2165                2170                2175

Ser Pro Thr Ile Leu Glu Ala Leu Glu Gly Asn Leu Pro Leu Gln
    2180                2185                2190

Ile Gln Ser Asn Glu Gln Ser Phe Leu Asp Asp Phe Ile Ala Cys
    2195                2200                2205

Val Pro Gly Ser Ser Gly Gly Arg Leu Ala Arg Trp Leu Gln Pro
    2210                2215                2220

Asp Ser Tyr Ala Asp Pro Gln Lys Thr Ser Leu Ile Leu Asn Lys
    2225                2230                2235

Asp Asp Ile Arg Cys Gly Trp Pro Thr Thr Ile Thr Val Gln Thr
    2240                2245                2250

Lys Asp Gln Tyr Gly Asp Val Val His Val Pro Asn Met Lys Val
    2255                2260                2265

Glu Val Lys Ala Val Pro Val Ser Gln Lys Lys Met Ser Leu Gln
    2270                2275                2280

Gln Asp Gln Ala Lys Lys Pro Gln Arg Ile Pro Gly Ser Pro Ala
    2285                2290                2295

Val Thr Ala Ala Ser Ser Asn Thr Asp Met Thr Tyr Gly Gly Leu
    2300                2305                2310

Ala Ser Pro Lys Leu Asp Val Ser Tyr Glu Pro Met Ile Val Lys
    2315                2320                2325

Glu Ala Arg Tyr Ile Ala Ile Thr Met Met Lys Val Tyr Glu Asn
    2330                2335                2340

Tyr Ser Phe Glu Glu Leu Arg Phe Ala Ser Pro Thr Pro Lys Arg
    2345                2350                2355

Pro Ser Glu Asn Met Leu Ile Arg Val Asn Asn Asp Gly Thr Tyr
    2360                2365                2370

Cys Ala Asn Trp Thr Pro Gly Ala Ile Gly Leu Tyr Thr Leu His
    2375                2380                2385

Val Thr Ile Asp Gly Ile Glu Ile Asp Ala Gly Leu Glu Val Lys
    2390                2395                2400

Val Lys Asp Pro Pro Lys Gly Met Ile Pro Pro Gly Thr Gln Leu
    2405                2410                2415

Val Lys Pro Lys Ser Glu Pro Gln Pro Asn Lys Val Arg Lys Phe
    2420                2425                2430

Val Ala Lys Asp Ser Ala Gly Leu Arg Ile Arg Ser His Pro Ser
    2435                2440                2445
```

-continued

```
Leu Gln Ser Glu Gln Ile Gly Ile Val Lys Val Asn Gly Thr Ile
2450                2455                2460

Thr Phe Ile Asp Glu Ile His Asn Asp Asp Gly Val Trp Leu Arg
2465                2470                2475

Leu Asn Asp Glu Thr Ile Lys Lys Tyr Val Pro Asn Met Asn Gly
2480                2485                2490

Tyr Thr Glu Ala Trp Cys Leu Ser Phe Asn Gln His Leu Gly Lys
2495                2500                2505

Ser Leu Leu Val Pro Val Asp Glu Ser Lys Thr Asn Thr Asp Asp
2510                2515                2520

Phe Phe Lys Asp Ile Asn Ser Cys Cys Pro Gln Glu Ala Thr Met
2525                2530                2535

Gln Glu Gln Asp Met Pro Phe Leu Arg Gly Gly Pro Gly Met Tyr
2540                2545                2550

Lys Val Val Lys Thr Gly Pro Ser Gly His Asn Ile Arg Ser Cys
2555                2560                2565

Pro Asn Leu Arg Gly Ile Pro Ile Gly Met Leu Val Leu Gly Asn
2570                2575                2580

Lys Val Lys Ala Val Gly Glu Val Thr Asn Ser Glu Gly Thr Trp
2585                2590                2595

Val Gln Leu Asp Gln Asn Ser Met Val Glu Phe Cys Glu Ser Asp
2600                2605                2610

Glu Gly Glu Ala Trp Ser Leu Ala Arg Asp Arg Gly Gly Asn Gln
2615                2620                2625

Tyr Leu Arg His Glu Asp Glu Gln Ala Leu Leu Asp Gln Asn Ser
2630                2635                2640

Gln Thr Pro Pro Pro Ser Pro Phe Ser Val Gln Ala Phe Asn Lys
2645                2650                2655

Gly Ala Ser Cys Ser Ala Gln Gly Phe Asp Tyr Gly Leu Gly Asn
2660                2665                2670

Ser Lys Gly Asp Arg Gly Asn Ile Ser Thr Ser Ser Lys Pro Ala
2675                2680                2685

Ser Thr Ser Gly Lys Ser Glu Leu Ser Ser Lys His Ser Arg Ser
2690                2695                2700

Leu Lys Pro Asp Gly Arg Met Ser Arg Thr Thr Ala Asp Gln Lys
2705                2710                2715

Lys Pro Arg Gly Thr Glu Ser Leu Ser Ala Ser Glu Ser Leu Ile
2720                2725                2730

Leu Lys Ser Asp Ala Ala Lys Leu Arg Ser Asp Ser His Ser Arg
2735                2740                2745

Ser Leu Ser Pro Asn His Asn Thr Leu Gln Thr Leu Lys Ser Asp
2750                2755                2760

Gly Arg Met Pro Ser Ser Ser Arg Ala Glu Ser Pro Gly Pro Gly
2765                2770                2775

Ser Arg Leu Ser Ser Pro Lys Pro Lys Thr Leu Pro Ala Asn Arg
2780                2785                2790

Ser Ser Pro Ser Gly Ala Ser Ser Pro Arg Ser Ser Pro His
2795                2800                2805

Asp Lys Asn Leu Pro Gln Lys Ser Thr Ala Pro Val Lys Thr Lys
2810                2815                2820

Leu Asp Pro Pro Arg Glu Arg Ser Lys Ser Asp Ser Tyr Thr Leu
2825                2830                2835

Asp Pro Asp Thr Leu Arg Lys Lys Lys Met Pro Leu Thr Glu Pro
```

2840                2845                2850

Leu Arg Gly Arg Ser Thr Ser Pro Lys Pro Lys Ser Val Pro Lys
        2855                2860                2865

Asp Ser Thr Asp Ser Pro Gly Ser Glu Asn Arg Ala Pro Ser Pro
        2870                2875                2880

His Val Val Gln Glu Asn Leu His Ser Glu Val Val Glu Val Cys
        2885                2890                2895

Thr Ser Ser Thr Leu Lys Thr Asn Ser Leu Thr Asp Ser Thr Cys
        2900                2905                2910

Asp Asp Ser Ser Glu Phe Lys Ser Val Asp Gly Ser Asn Lys
        2915                2920                2925

Val His Phe Ser Ile Gly Lys Ala Pro Leu Lys Asp Glu Gln Glu
        2930                2935                2940

Met Arg Ala Ser Pro Lys Ile Ser Arg Lys Cys Ala Asn Arg His
        2945                2950                2955

Thr Arg Pro Lys Lys Glu Lys Ser Ser Phe Leu Phe Lys Gly Asp
        2960                2965                2970

Gly Ser Lys Pro Leu Glu Pro Ala Lys Gln Ala Met Ser Pro Ser
        2975                2980                2985

Val Ala Glu Cys Ala Arg Ala Val Phe Ala Ser Phe Leu Trp His
        2990                2995                3000

Glu Gly Ile Val His Asp Ala Met Ala Cys Ser Ser Phe Leu Lys
        3005                3010                3015

Phe His Pro Glu Leu Ser Lys Glu His Ala Pro Ile Arg Ser Ser
        3020                3025                3030

Leu Asn Ser Gln Gln Pro Thr Glu Glu Lys Glu Thr Lys Leu Lys
        3035                3040                3045

Asn Arg His Ser Leu Glu Ile Ser Ser Ala Leu Asn Met Phe Asn
        3050                3055                3060

Ile Ala Pro His Gly Pro Asp Ile Ser Lys Met Gly Ser Ile Asn
        3065                3070                3075

Lys Asn Lys Val Leu Ser Met Leu Lys Glu Pro Pro Leu His Glu
        3080                3085                3090

Lys Cys Glu Asp Gly Lys Thr Glu Thr Thr Phe Glu Met Ser Met
        3095                3100                3105

His Asn Thr Met Lys Ser Lys Ser Pro Leu Pro Leu Thr Leu Gln
        3110                3115                3120

His Leu Val Ala Phe Trp Glu Asp Ile Ser Leu Ala Thr Ile Lys
        3125                3130                3135

Ala Ala Ser Gln Asn Met Ile Phe Pro Ser Pro Gly Ser Cys Ala
        3140                3145                3150

Val Leu Lys Lys Lys Glu Cys Glu Lys Gly Arg Asn Lys Lys Ser
        3155                3160                3165

Lys Lys Glu Lys Lys Lys Glu Lys Ala Glu Val Arg Pro Arg
        3170                3175                3180

Gly Asn Leu Phe Gly Glu Met Ala Gln Leu Ala Val Gly Gly Pro
        3185                3190                3195

Glu Lys Asp Thr Ile Cys Glu Leu Cys Gly Glu Ser His Pro Tyr
        3200                3205                3210

Pro Val Thr Tyr His Met Arg Gln Ala His Pro Gly Cys Gly Arg
        3215                3220                3225

Tyr Ala Gly Gly Gln Gly Tyr Asn Ser Ile Gly His Phe Cys Gly
        3230                3235                3240

```
Gly Trp Ala Gly Asn Cys Gly Asp Gly Ile Gly Gly Ser Thr
3245             3250             3255

Trp Tyr Leu Val Cys Asp Arg Cys Arg Glu Lys Tyr Leu Arg Glu
3260             3265             3270

Lys Gln Ala Ala Ala Arg Glu Lys Val Lys Gln Ser Arg Arg Lys
3275             3280             3285

Pro Met Gln Val Lys Thr Pro Arg Ala Leu Pro Thr Met Glu Ala
3290             3295             3300

His Gln Val Ile Lys Ala Asn Ala Leu Phe Leu Leu Ser Leu Ser
3305             3310             3315

Ser Ala Ala Glu Pro Ser Ile Leu Cys Tyr His Pro Ala Lys Pro
3320             3325             3330

Phe Gln Ser Gln Leu Pro Ser Val Lys Glu Gly Ile Ser Glu Asp
3335             3340             3345

Leu Pro Val Lys Met Pro Cys Leu Tyr Leu Gln Thr Leu Ala Arg
3350             3355             3360

His His His Glu Asn Phe Val Gly Tyr Gln Asp Asp Asn Leu Phe
3365             3370             3375

Gln Asp Glu Met Arg Tyr Leu Arg Ser Thr Ser Val Pro Ala Pro
3380             3385             3390

Tyr Ile Ser Val Thr Pro Asp Ala Ser Pro Asn Val Phe Glu Glu
3395             3400             3405

Pro Glu Ser Asn Met Lys Ser Met Pro Pro Ser Leu Glu Thr Ser
3410             3415             3420

Pro Ile Thr Asp Thr Asp Leu Ala Lys Arg Thr Val Phe Gln Arg
3425             3430             3435

Ser Tyr Ser Val Val Ala Ser Glu Tyr Asp Lys Gln His Ser Ile
3440             3445             3450

Leu Pro Ala Arg Val Lys Ala Ile Pro Arg Arg Arg Val Asn Ser
3455             3460             3465

Gly Asp Thr Glu Val Gly Ser Ser Leu Leu Arg His Pro Ser Pro
3470             3475             3480

Glu Leu Ser Arg Leu Ile Ser Ala His Ser Ser Leu Ser Lys Gly
3485             3490             3495

Glu Arg Asn Phe Gln Trp Pro Val Leu Ala Phe Val Ile Gln His
3500             3505             3510

His Asp Leu Glu Gly Leu Glu Ile Ala Met Lys Gln Ala Leu Arg
3515             3520             3525

Lys Ser Ala Cys Arg Val Phe Ala Met Glu Ala Phe Asn Trp Leu
3530             3535             3540

Leu Cys Asn Val Ile Gln Thr Thr Ser Leu His Asp Ile Leu Trp
3545             3550             3555

His Phe Val Ala Ser Leu Thr Pro Ala Pro Val Glu Pro Glu Glu
3560             3565             3570

Glu Glu Asp Glu Glu Asn Lys Thr Ser Lys Glu Asn Ser Glu Gln
3575             3580             3585

Glu Lys Asp Thr Arg Val Cys Glu His Pro Leu Ser Asp Ile Val
3590             3595             3600

Ile Ala Gly Glu Arg Ala His Pro Leu Pro His Thr Phe His Arg
3605             3610             3615

Leu Leu Gln Thr Ile Ser Asp Leu Met Met Ser Leu Pro Ser Gly
3620             3625             3630
```

```
Ser Ser Leu Gln Gln Met Ala Leu Arg Cys Trp Ser Leu Lys Phe
3635                3640                3645

Lys Gln Ser Asp His Gln Phe Leu His Gln Ser Asn Val Phe His
3650                3655                3660

His Ile Asn Asn Ile Leu Ser Lys Ser Asp Asp Gly Asp Ser Glu
3665                3670                3675

Glu Ser Phe Ser Ile Ser Ile Gln Ser Gly Phe Glu Ala Met Ser
3680                3685                3690

Gln Glu Leu Cys Ile Val Met Cys Leu Lys Asp Leu Thr Ser Ile
3695                3700                3705

Val Asp Ile Lys Thr Ser Ser Arg Pro Ala Met Ile Gly Ser Leu
3710                3715                3720

Thr Asp Gly Ser Thr Glu Thr Phe Trp Glu Ser Gly Asp Glu Asp
3725                3730                3735

Lys Asn Lys Thr Lys Asn Ile Thr Ile Asn Cys Val Lys Gly Ile
3740                3745                3750

Asn Ala Arg Tyr Val Ser Val His Val Asp Asn Ser Arg Asp Leu
3755                3760                3765

Gly Asn Lys Val Thr Ser Met Thr Phe Leu Thr Gly Lys Ala Val
3770                3775                3780

Glu Asp Leu Cys Arg Ile Lys Gln Val Asp Leu Asp Ser Arg His
3785                3790                3795

Ile Gly Trp Val Thr Ser Glu Leu Pro Gly Gly Asp Asn His Ile
3800                3805                3810

Ile Lys Ile Glu Leu Lys Gly Pro Glu Asn Thr Leu Arg Val Arg
3815                3820                3825

Gln Val Lys Val Leu Gly Trp Lys Asp Gly Glu Ser Thr Lys Ile
3830                3835                3840

Ala Gly Gln Ile Ser Ala Ser Val Ala Gln Gln Arg Asn Cys Glu
3845                3850                3855

Ala Glu Thr Leu Arg Val Phe Arg Leu Ile Thr Ser Gln Val Phe
3860                3865                3870

Gly Lys Leu Ile Ser Gly Asp Ala Glu Pro Thr Pro Glu Gln Glu
3875                3880                3885

Glu Lys Ala Leu Leu Ser Ser Pro Glu Gly Glu Glu Lys Val Tyr
3890                3895                3900

Asn Ala Thr Ser Asp Ala Asp Leu Lys Glu His Met Val Gly Ile
3905                3910                3915

Ile Phe Ser Arg Ser Lys Leu Thr Asn Leu Gln Lys Gln Val Cys
3920                3925                3930

Ala His Ile Val Gln Ala Ile Arg Met Glu Ala Thr Arg Val Arg
3935                3940                3945

Glu Glu Trp Glu His Ala Ile Ser Ser Lys Glu Asn Ala Asn Ser
3950                3955                3960

Gln Pro Asn Asp Glu Asp Ala Ser Ser Asp Ala Tyr Cys Phe Glu
3965                3970                3975

Leu Leu Ser Met Val Leu Ala Leu Ser Gly Ser Asn Val Gly Arg
3980                3985                3990

Gln Tyr Leu Ala Gln Gln Leu Thr Leu Leu Gln Asp Leu Phe Ser
3995                4000                4005

Leu Leu His Thr Ala Ser Pro Arg Val Gln Arg Gln Val Thr Ser
4010                4015                4020

Leu Leu Arg Arg Val Leu Pro Glu Val Thr Pro Ser Arg Leu Ala
```

```
                4025                4030                4035
Ser  Ile  Ile  Gly  Val  Lys  Ser  Leu  Pro  Pro  Ala  Asp  Ile  Ser  Asp
         4040                4045                4050

Ile  Ile  His  Ser  Thr  Glu  Lys  Gly  Asp  Trp  Asn  Lys  Leu  Gly  Ile
         4055                4060                4065

Leu  Asp  Met  Phe  Leu  Gly  Cys  Ile  Ala  Lys  Ala  Leu  Thr  Val  Gln
         4070                4075                4080

Leu  Lys  Ala  Lys  Gly  Thr  Thr  Ile  Thr  Gly  Thr  Ala  Gly  Thr  Thr
         4085                4090                4095

Val  Gly  Lys  Gly  Val  Thr  Thr  Val  Thr  Leu  Pro  Met  Ile  Phe  Asn
         4100                4105                4110

Ser  Ser  Tyr  Leu  Arg  Arg  Gly  Glu  Ser  His  Trp  Trp  Met  Lys  Gly
         4115                4120                4125

Ser  Thr  Pro  Thr  Gln  Ile  Ser  Glu  Ile  Ile  Ile  Lys  Leu  Ile  Lys
         4130                4135                4140

Asp  Met  Ala  Ala  Gly  His  Leu  Ser  Glu  Ala  Trp  Ser  Arg  Val  Thr
         4145                4150                4155

Lys  Asn  Ala  Ile  Ala  Glu  Thr  Ile  Ile  Ala  Leu  Thr  Lys  Met  Glu
         4160                4165                4170

Glu  Glu  Phe  Arg  Ser  Pro  Val  Arg  Cys  Ile  Ala  Thr  Thr  Arg  Leu
         4175                4180                4185

Trp  Leu  Ala  Leu  Ala  Ser  Leu  Cys  Val  Leu  Asp  Gln  Asp  His  Val
         4190                4195                4200

Asp  Arg  Leu  Ser  Ser  Gly  Arg  Trp  Met  Gly  Lys  Asp  Gly  Gln  Gln
         4205                4210                4215

Lys  Gln  Met  Pro  Met  Cys  Asp  Asn  His  Asp  Asp  Gly  Glu  Thr  Ala
         4220                4225                4230

Ala  Ile  Ile  Leu  Cys  Asn  Val  Cys  Gly  Asn  Leu  Cys  Thr  Asp  Cys
         4235                4240                4245

Asp  Arg  Phe  Leu  His  Leu  His  Arg  Arg  Thr  Lys  Thr  His  Gln  Arg
         4250                4255                4260

Gln  Val  Phe  Lys  Glu  Glu  Glu  Ala  Ile  Lys  Val  Asp  Leu  His
         4265                4270                4275

Glu  Gly  Cys  Gly  Arg  Thr  Lys  Leu  Phe  Trp  Leu  Met  Ala  Leu  Ala
         4280                4285                4290

Asp  Ser  Lys  Thr  Met  Lys  Ala  Met  Val  Glu  Phe  Arg  Glu  His  Thr
         4295                4300                4305

Gly  Lys  Pro  Thr  Thr  Ser  Ser  Glu  Ala  Cys  Arg  Phe  Cys  Gly
         4310                4315                4320

Ser  Arg  Ser  Gly  Thr  Glu  Leu  Ser  Ala  Val  Gly  Ser  Val  Cys  Ser
         4325                4330                4335

Asp  Ala  Asp  Cys  Gln  Glu  Tyr  Ala  Lys  Ile  Ala  Cys  Ser  Lys  Thr
         4340                4345                4350

His  Pro  Cys  Gly  His  Pro  Cys  Gly  Gly  Val  Lys  Asn  Glu  Glu  His
         4355                4360                4365

Cys  Leu  Pro  Cys  Leu  His  Gly  Cys  Asp  Lys  Ser  Ala  Thr  Ser  Leu
         4370                4375                4380

Lys  Gln  Asp  Ala  Asp  Asp  Met  Cys  Met  Ile  Cys  Phe  Thr  Glu  Ala
         4385                4390                4395

Leu  Ser  Ala  Ala  Pro  Ala  Ile  Gln  Leu  Asp  Cys  Ser  His  Ile  Phe
         4400                4405                4410

His  Leu  Gln  Cys  Cys  Arg  Arg  Val  Leu  Glu  Asn  Arg  Trp  Leu  Gly
         4415                4420                4425
```

```
Pro Arg Ile Thr Phe Gly Phe Ile Ser Cys Pro Ile Cys Lys Asn
    4430                4435                4440

Lys Ile Asn His Ile Val Leu Lys Asp Leu Leu Asp Pro Ile Lys
    4445                4450                4455

Glu Leu Tyr Glu Asp Val Arg Arg Lys Ala Leu Met Arg Leu Glu
    4460                4465                4470

Tyr Glu Gly Leu His Lys Ser Glu Ala Ile Thr Thr Pro Gly Val
    4475                4480                4485

Arg Phe Tyr Asn Asp Pro Ala Gly Tyr Ala Met Asn Arg Tyr Ala
    4490                4495                4500

Tyr Tyr Val Cys Tyr Lys Cys Arg Lys Ala Tyr Phe Gly Gly Glu
    4505                4510                4515

Ala Arg Cys Asp Ala Glu Ala Gly Arg Gly Asp Asp Tyr Asp Pro
    4520                4525                4530

Arg Glu Leu Ile Cys Gly Ala Cys Ser Asp Val Ser Arg Ala Gln
    4535                4540                4545

Met Cys Pro Lys His Gly Thr Asp Phe Leu Glu Tyr Lys Cys Arg
    4550                4555                4560

Tyr Cys Cys Ser Val Ala Val Phe Phe Cys Phe Gly Thr Thr His
    4565                4570                4575

Phe Cys Asn Ala Cys His Asp Asp Phe Gln Arg Met Thr Ser Ile
    4580                4585                4590

Pro Lys Glu Glu Leu Pro His Cys Pro Ala Gly Pro Lys Gly Lys
    4595                4600                4605

Gln Leu Glu Gly Thr Glu Cys Pro Leu His Val Val His Pro Pro
    4610                4615                4620

Thr Gly Glu Glu Phe Ala Leu Gly Cys Gly Val Cys Arg Asn Ala
    4625                4630                4635

His Thr Phe
    4640

<210> SEQ ID NO 81
<211> LENGTH: 595
<212> TYPE: PRT
<213> ORGANISM: Homo sapiens

<400> SEQUENCE: 81

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
        50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
```

```
              130                 135                 140
Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560
```

```
Glu Glu Thr Asp Gln Ser His Leu Ala Thr Ala Gly Ser Thr Ser Ser
            565                 570                 575

His Ser Leu Gln Lys Tyr Tyr Ile Thr Gly Glu Ala Glu Gly Phe Pro
        580                 585                 590

Ala Thr Val
        595

<210> SEQ ID NO 82
<211> LENGTH: 536
<212> TYPE: DNA
<213> ORGANISM: Homo sapiens

<400> SEQUENCE: 82
ttatagaaaa atacttttta ttttgtcatt gaaaaaccat tttaaaataa tatatcgtgt    60
agaataaaaa attccatgga tatatacatg caaattatac atatatgtga atttaatttt   120
gttaaaaggt aattggcatc tgcaatttca tgcagtctaa gtgaaaccca taaagaaatg   180
tgtatgaaat aggaaagcaa caaaagctca taacatttta aaattagaaa tcagattcaa   240
aacccatcat gatctattt aaatttatct ctataacatt tcaattgaga cataaaacac    300
actttataca acatgcctca ctattttatt aacagcatga cttcccttc cccaatcccc    360 aaaccatgtt cccatctaca ccccacccca cccaaatctc acctcttcca ttagcattat   420
tacaaacata ttttacaaat cttataccaa gcttttccag tctcttttca atgtagaaat   480
atcttatata taaacccaaa taccacaaat cttcacattt atattttcta aagcag       536

<210> SEQ ID NO 83
<211> LENGTH: 609
<212> TYPE: DNA
<213> ORGANISM: Homo sapiens

<400> SEQUENCE: 83
ttttgtacag atccttttta ttcagattta tataggcaat ttaccaacac agaaaaccag    60
tctagcagct ccaaagtaac tgtaaaaacg gtggtgctga cggtggtgtg ccccacacag   120
ggcaggtgac ctcagacgtg gagcagcatc tcccgtggga tactatttca gacgtgcact   180
agtgagtgta tactgagaag ggattataaa ccttccctgg cacaacagat acaaaaagag   240
atagaaccaa tgatattttg tctaggtaca atatctagat ttacagtatc tagtttactg   300
gcttcacttc gtatagcaat gcacaataga aaacggattt ctttcttcaa gggtattcaa   360
gaatatagta aatatgttac tatattgatg gctatgaaaa cagacagaga caaatgagtg   420
aggaggcacg ttctctcaca gagacaggac ttcattctat ttcacataaa tcattaaggg   480
tccattcaaa tataagacct ctcacaaagt ttcagtcatg tatgagggcg cttaccttta   540 agacccccatt tcaaaaccat tttgaaatag tgaaggggg aaaaagtcac actcaaatgt    600
gctactctt                                                           609

<210> SEQ ID NO 84
<211> LENGTH: 1527
<212> TYPE: DNA
<213> ORGANISM: Homo sapiens

<400> SEQUENCE: 84
aggaatattt tcaattgtgt atttgtatta caaagaactt gaaatttact ttcttagttg    60
attatattaa atgatgtata tattatatgt ggtttataag ctcaacactg gccattttt    120 tagttttatt gttaaatggt attttctat gtttaattat aatagatctg gcttttttctg   180
```

```
gatagcataa agatcactga actatatata tataagaaac aagagttcta ttttagcaca       240
aaggcatttt atattattta ttgaatccat aagtttgttt tcgtcaaaaa cattcaatat       300
tatttctgct ccttttttatt tgtatagttt gttatttaaa gaaatggcag tccttcctgt      360
tcttaataca ataaaattga aataatgcac ctagtaatgt ggccgacatc tcttctcacc       420
accatggact gttttcaaca acagttgatc ttctggtctg tgctgagagg cgcatgcatg       480
tctttcgtca cgtcgggcag cacacctgct gtgaaatact gctttcatct acctcttcag       540
aaggcttctt gcttgttgac aagtaccgca aaggctttat tctggactgg ctatctcata       600
aaaggatttc tgtaagactt tgcagtgtca ttccctcaga acctaggttt gtttctaaag       660
ccacggtatt gtccaggagc ccctgtgtgt ggggcaggta gctatccctc ccatgtcatt       720
agtaatcctt taggatttaa ggtacaactg gacagcatca ttccttcccc ttattgtgcc       780
aaatccccac catcagcctt gccattgcct taagatttga ttattgcacc caattaccta       840
accactaaac agaaaggcca ccttcattct ttgaaaaagg caagctgtgc ttagaaacac       900
tgcttttaag agtagcacat ttgagtgtga cttttttcccc ccttcactat ttcaaaatgg      960
ttttgaaatg gggtcttaaa ggtaagcgcc ctcatacatg actgaaactt tgtgagaggt       1020
cttatatttg aatggaccct taatgattta tgtgaaatag aatgaagtcc tgtctctgtg       1080
agagaacgtg cctcctcact catttgtctc tgtctgtttt catagccatc aatatagtaa       1140
catatttact atattcttga ataccttga agaaagaaat ccgttttcta ttgtgcattg        1200
ctatacgaag tgaagccagt aaactagata ctgtaaatct agatattgta cctagacaaa       1260
atatcattgg ttctatctct ttttgtatct gttgtgccag ggaaggttta taatcccttc       1320
tcagtataca ctcactagtg cacgtctgaa atagtatccc acgggagatg ctgctccacg       1380
tctgaggtca cctgccctgt gtggggcaca ccaccgtcag caccaccgtt tttacagtta       1440
ctttggagct gctagactgg ttttctgtgt tggtaaattg cctatataaa tctgaataaa       1500
aaggatctgt acaaaaaaaa aaaaaaa                                           1527

<210> SEQ ID NO 85
<211> LENGTH: 583
<212> TYPE: DNA
<213> ORGANISM: Homo sapiens

<400> SEQUENCE: 85
tcggttttat tagattacag agaatacttt ctctatccaa aatctgtgat tttaatctag       60
aacactgaat gtaggtcagt atccacccca tttcagaaa tctgggaaga tctttttttg        120
tttttcagct tctcagaata aatacttct aggatgttac aaacatggat gaagttcacc        180
agaacagatc cagggttaac cttttaaagt cattagatat ggctccagta aaaggcatga       240
gaaggcaccc gtgagaccct gcagaggaag cctcactcct gggcagcctt acggctgacg       300
agctacctta ctgagcatat tcctgcctct acaccagaga ctcactctgt ggtccggtgt       360
cacctcgatt ctaaattccc tgcttcctgg ggaatgatgc tatcacactt cagaaacctg      420
gccaataaat gctttgaaat ttaaggatcg ctatcctgaa aaatttaat ataacctaaa       480 ttgatagtct aatgacatca gtattcagaa gaagcattct atttcagcaa gtggttttca      540
gaaaataagt tgtaaaaatc tcaagggggg gcctggtacc caa                        583

<210> SEQ ID NO 86
<211> LENGTH: 359
<212> TYPE: PRT
```

<213> ORGANISM: Homo sapiens

<400> SEQUENCE: 86

```
Met Pro Asn Pro Ser Ser Thr Ser Ser Pro Tyr Pro Leu Pro Glu Glu
1               5                   10                  15

Ile Arg Asn Leu Leu Ala Asp Val Glu Thr Phe Val Ala Asp Ile Leu
            20                  25                  30

Lys Gly Glu Asn Leu Ser Lys Lys Ala Lys Glu Lys Arg Glu Ser Leu
        35                  40                  45

Ile Lys Lys Ile Lys Asp Val Lys Ser Ile Tyr Leu Gln Glu Phe Gln
50                  55                  60

Asp Lys Gly Asp Ala Glu Asp Gly Glu Glu Tyr Asp Asp Pro Phe Ala
65                  70                  75                  80

Gly Pro Pro Asp Thr Ile Ser Leu Ala Ser Glu Arg Tyr Asp Lys Asp
            85                  90                  95

Asp Glu Ala Pro Ser Asp Gly Ala Gln Phe Pro Pro Ile Ala Ala Gln
            100                 105                 110

Asp Leu Pro Phe Val Leu Lys Ala Gly Tyr Leu Glu Lys Arg Arg Lys
            115                 120                 125

Asp His Ser Phe Leu Gly Phe Glu Trp Gln Lys Arg Trp Cys Ala Leu
        130                 135                 140

Ser Lys Thr Val Phe Tyr Tyr Tyr Gly Ser Asp Lys Asp Lys Gln Gln
145                 150                 155                 160

Lys Gly Glu Phe Ala Ile Asp Gly Tyr Ser Val Arg Met Asn Asn Thr
            165                 170                 175

Leu Arg Lys Asp Gly Lys Lys Asp Cys Cys Phe Glu Ile Ser Ala Pro
            180                 185                 190

Asp Lys Arg Ile Tyr Gln Phe Thr Ala Ala Ser Pro Lys Asp Ala Glu
            195                 200                 205

Glu Trp Val Gln Gln Leu Lys Phe Val Leu Gln Asp Met Glu Ser Asp
        210                 215                 220

Ile Ile Pro Glu Asp Tyr Asp Glu Arg Gly Glu Leu Tyr Asp Asp Val
225                 230                 235                 240

Asp His Pro Leu Pro Ile Ser Asn Pro Leu Thr Ser Ser Gln Pro Ile
            245                 250                 255

Asp Asp Glu Ile Tyr Glu Glu Leu Pro Glu Glu Glu Asp Ser Ala
            260                 265                 270

Pro Val Lys Val Glu Glu Gln Arg Lys Met Ser Gln Asp Ser Val His
            275                 280                 285

His Thr Ser Gly Asp Lys Ser Thr Asp Tyr Ala Asn Phe Tyr Gln Gly
        290                 295                 300

Leu Trp Asp Cys Thr Gly Ala Phe Ser Asp Glu Leu Ser Phe Lys Arg
305                 310                 315                 320

Gly Asp Val Ile Tyr Ile Leu Ser Lys Glu Tyr Asn Arg Tyr Gly Trp
            325                 330                 335

Trp Val Gly Glu Met Lys Gly Ala Ile Gly Leu Val Pro Lys Ala Tyr
            340                 345                 350

Ile Met Glu Met Tyr Asp Ile
            355
```

<210> SEQ ID NO 87
<211> LENGTH: 537
<212> TYPE: DNA
<213> ORGANISM: Homo sapiens
<220> FEATURE:

<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (481)..(481)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t

<400> SEQUENCE: 87

```
acttattaaa atttattttt tctaactttt gttattattg cactaccagc tttgatccat    60
tataatcgta caggaccatc gtacacgcag tccactgttg actaaaatgt tatgtggcac   120
gtgactgtac ataccaggcc agactcaagg cctctgctct taatcacttt gctggactgc   180
ttcaatttcc actgtgctat tctgcttggt tttcccacct tatatttat gagttctacc    240
aataaaactt cttgtagttt gatacgtttg aagttctggg ttaccttctc catggttgtc   300
caggcctgac gtaatggagt tgtgaaacag ttggggagtg gccaccttcc ctgcagatat   360
tggattcaat ttctaatcgt acaacatcat caaatccaag aggatgtgtg cttgggagg    420
gagaagtact tgncatataa aatcatggca tcattctgng ccttctgtnc atcacattgg   480
nccttttgg cagcaagctg anactggaag ttatctgctg gccancagaa tgtnaga       537
```

<210> SEQ ID NO 88
<211> LENGTH: 662
<212> TYPE: PRT
<213> ORGANISM: Homo sapiens

<400> SEQUENCE: 88

```
Met Arg Gly Ala Gly Pro Ser Pro Arg Gln Ser Pro Arg Thr Leu Arg
1               5                   10                  15

Pro Asp Pro Gly Pro Ala Met Ser Phe Phe Arg Arg Lys Val Lys Gly
            20                  25                  30

Lys Glu Gln Glu Lys Thr Ser Asp Val Lys Ser Ile Lys Ala Ser Ile
        35                  40                  45

Ser Val His Ser Pro Gln Lys Ser Thr Lys Asn His Ala Leu Leu Glu
    50                  55                  60

Ala Ala Gly Pro Ser His Val Ala Ile Asn Ala Ile Ser Ala Asn Met
65                  70                  75                  80

Asp Ser Phe Ser Ser Arg Thr Ala Thr Leu Lys Lys Gln Pro Ser
            85                  90                  95

His Met Glu Ala Ala His Phe Gly Asp Leu Gly Arg Ser Cys Leu Asp
            100                 105                 110

Tyr Gln Thr Gln Glu Thr Lys Ser Ser Leu Ser Lys Thr Leu Glu Gln
        115                 120                 125
```

Val Leu His Asp Thr Ile Val Leu Pro Tyr Phe Ile Gln Phe Met Glu
130                 135                 140

Leu Arg Arg Met Glu His Leu Val Lys Phe Trp Leu Glu Ala Glu Ser
145                 150                 155                 160

Phe His Ser Thr Thr Trp Ser Arg Ile Arg Ala His Ser Leu Asn Thr
                165                 170                 175

Val Lys Gln Ser Ser Leu Ala Glu Pro Val Ser Pro Ser Lys Lys His
            180                 185                 190

Glu Thr Thr Ala Ser Phe Leu Thr Asp Ser Leu Asp Lys Arg Leu Glu
        195                 200                 205

Asp Ser Gly Ser Ala Gln Leu Phe Met Thr His Ser Glu Gly Ile Asp
210                 215                 220

Leu Asn Asn Arg Thr Asn Ser Thr Gln Asn His Leu Leu Leu Ser Gln
225                 230                 235                 240

Glu Cys Asp Ser Ala His Ser Leu Arg Leu Glu Met Ala Arg Ala Gly
                245                 250                 255

Thr His Gln Val Ser Met Glu Thr Gln Glu Ser Ser Ser Thr Leu Thr
            260                 265                 270

Val Ala Ser Arg Asn Ser Pro Ala Ser Pro Leu Lys Glu Leu Ser Gly
        275                 280                 285

Lys Leu Met Lys Ser Ile Glu Gln Asp Ala Val Asn Thr Phe Thr Lys
290                 295                 300

Tyr Ile Ser Pro Asp Ala Ala Lys Pro Ile Pro Ile Thr Glu Ala Met
305                 310                 315                 320

Arg Asn Asp Ile Ile Ala Arg Ile Cys Gly Glu Asp Gly Gln Val Asp
                325                 330                 335

Pro Asn Cys Phe Val Leu Ala Gln Ser Ile Val Phe Ser Ala Met Glu
            340                 345                 350

Gln Glu His Phe Ser Glu Phe Leu Arg Ser His His Phe Cys Lys Tyr
        355                 360                 365

Gln Ile Glu Val Leu Thr Ser Gly Thr Val Tyr Leu Ala Asp Ile Leu
370                 375                 380

Phe Cys Glu Ser Ala Leu Phe Tyr Phe Ser Glu Tyr Met Glu Lys Glu
385                 390                 395                 400

Asp Ala Val Asn Ile Leu Gln Phe Trp Leu Ala Ala Asp Asn Phe Gln
                405                 410                 415

Ser Gln Leu Ala Ala Lys Lys Gly Gln Tyr Asp Gly Gln Glu Ala Gln
            420                 425                 430

Asn Asp Ala Met Ile Leu Tyr Asp Lys Tyr Phe Ser Leu Gln Ala Thr
        435                 440                 445

His Pro Leu Gly Phe Asp Asp Val Val Arg Leu Glu Ile Glu Ser Asn
450                 455                 460

Ile Cys Arg Glu Gly Gly Pro Leu Pro Asn Cys Phe Thr Thr Pro Leu
465                 470                 475                 480

Arg Gln Ala Trp Thr Thr Met Glu Lys Val Phe Leu Pro Gly Phe Leu
                485                 490                 495

Ser Ser Asn Leu Tyr Tyr Lys Tyr Leu Asn Asp Leu Ile His Ser Val
            500                 505                 510

Arg Gly Asp Glu Phe Leu Gly Gly Asn Val Ser Leu Thr Ala Pro Gly
        515                 520                 525

Ser Val Gly Pro Pro Asp Glu Ser His Pro Gly Ser Ser Asp Ser Ser
530                 535                 540

```
Ala Ser Gln Ser Ser Val Lys Lys Ala Ser Ile Lys Ile Leu Lys Asn
545                 550                 555                 560

Phe Asp Glu Ala Ile Ile Val Asp Ala Ala Ser Leu Asp Pro Glu Ser
                565                 570                 575

Leu Tyr Gln Arg Thr Tyr Ala Gly Lys Met Thr Phe Gly Arg Val Ser
                580                 585                 590

Asp Leu Gly Gln Phe Ile Arg Glu Ser Glu Pro Glu Pro Asp Val Arg
                595                 600                 605

Lys Ser Lys Gly Ser Met Phe Ser Gln Ala Met Lys Lys Trp Val Gln
                610                 615                 620

Gly Asn Thr Asp Glu Ala Gln Glu Glu Leu Ala Trp Lys Ile Ala Lys
625                 630                 635                 640

Met Ile Val Ser Asp Ile Met Gln Gln Ala Gln Tyr Asp Gln Pro Leu
                645                 650                 655

Glu Lys Ser Thr Lys Leu
                660

<210> SEQ ID NO 89
<211> LENGTH: 21
<212> TYPE: PRT
<213> ORGANISM: Artificial Sequence
<220> FEATURE:
<223> OTHER INFORMATION: ETRB antagonist peptide, BQ-788 Synthetic
      peptide

<400> SEQUENCE: 89

Ser Lys Arg Gly Arg Pro Gly Ala Lys Ala Leu Ser Arg Val Arg
1               5                   10                  15

Glu Asp Ile Val Glu
                20
```